(12) United States Patent
Sogo et al.

(10) Patent No.: US 7,735,356 B2
(45) Date of Patent: Jun. 15, 2010

(54) MEASURING APPARATUS AND MEASURING METHOD FOR CONCRETE-FORMING MATERIALS

(75) Inventors: Shigeyuki Sogo, Kiyose (JP); Ryuichi Chikamatsu, Kiyose (JP); Koji Watanabe, Kiyose (JP); Hisayoshi Kikkawa, Natori (JP)

(73) Assignee: Obayashi Corporation, Osaka (JP)

( * ) Notice: Subject to any disclaimer, the term of this patent is extended or adjusted under 35 U.S.C. 154(b) by 409 days.

(21) Appl. No.: 11/710,419

(22) Filed: Feb. 26, 2007

(65) Prior Publication Data
US 2007/0163333 A1 Jul. 19, 2007

Related U.S. Application Data

(62) Division of application No. 10/470,044, filed as application No. PCT/JP02/00447 on Jan. 23, 2002, now Pat. No. 7,207,212.

(30) Foreign Application Priority Data

| Jan. 31, 2001 | (JP) | ............................. 2001-024968 |
| Feb. 1, 2001  | (JP) | ............................. 2001-026143 |
| Feb. 14, 2001 | (JP) | ............................. 2001-036770 |
| Feb. 14, 2001 | (JP) | ............................. 2001-036902 |
| Feb. 26, 2001 | (JP) | ............................. 2001-049751 |
| Mar. 6, 2001  | (JP) | ............................. 2001-062611 |
| Mar. 6, 2001  | (JP) | ............................. 2001-062622 |
| Mar. 6, 2001  | (JP) | ............................. 2001-062698 |
| Apr. 9, 2001  | (JP) | ............................. 2001-109466 |

(51) Int. Cl.
*G01N 5/02* (2006.01)

(52) U.S. Cl. ......................................................... 73/74
(58) Field of Classification Search ....................... None
See application file for complete search history.

(56) References Cited

U.S. PATENT DOCUMENTS 1,656,002 A    1/1928   Johnson (Continued)

FOREIGN PATENT DOCUMENTS

FR               2 431 016      *   3/1980

(Continued)

OTHER PUBLICATIONS

Shigeyuki Sogo et al., entitled "*Development of a High Reliability Concrete Production System (Part 1)*", -Proposal for New Batching Method by Immersing Sand in Water to Facilitate Accurate Measurement- pp. 57-64.

(Continued)

*Primary Examiner*—Robert R Raevis
(74) *Attorney, Agent, or Firm*—Wenderoth, Lind & Ponack, L.L.P.

(57) ABSTRACT

A measuring apparatus of submergence aggregate according to the present invention comprising a stock bin for storing fine aggregate, a fine aggregate feed hopper placed under the stock bin, a vibrating feeder placed under a discharge opening of the fine aggregate feed hopper, a screen device placed in the vicinity of an exit of the vibrating feeder, a measurement tank placed under the screen device, an electrode-type displacement sensor as means for measuring a water level placed above the measurement tank, and load cells as mass measuring means for measuring a mass of the measurement tank.

5 Claims, 77 Drawing Sheets

U.S. PATENT DOCUMENTS

| | | | |
|---|---|---|---|
| 1,733,410 A | 10/1929 | Johnson | |
| 3,800,694 A * | 4/1974 | Miller et al. | 100/45 |
| 4,176,965 A | 12/1979 | Ito et al. | |
| 4,895,450 A | 1/1990 | Holik | |
| 4,953,732 A * | 9/1990 | Cocks | 220/502 |
| 5,969,243 A | 10/1999 | Frey et al. | |
| 6,658,921 B2 | 12/2003 | Lavallee et al. | |

FOREIGN PATENT DOCUMENTS

| | | | |
|---|---|---|---|
| FR | 2777439 | * | 10/1999 |
| JP | 64-53902 | * | 3/1989 |
| JP | 03039115 | * | 2/1991 |
| JP | 3-183932 | * | 8/1991 |
| JP | 11-6828 | | 1/1999 |
| JP | 2000-61926 | | 2/2000 |
| JP | 2000-84921 | | 3/2000 |
| JP | 2000-84922 | | 3/2000 |

OTHER PUBLICATIONS

Supplementary European Search Report issued Jan. 19, 2007 in the Application No. EP 02 71 0325.

* cited by examiner

FIG. 32

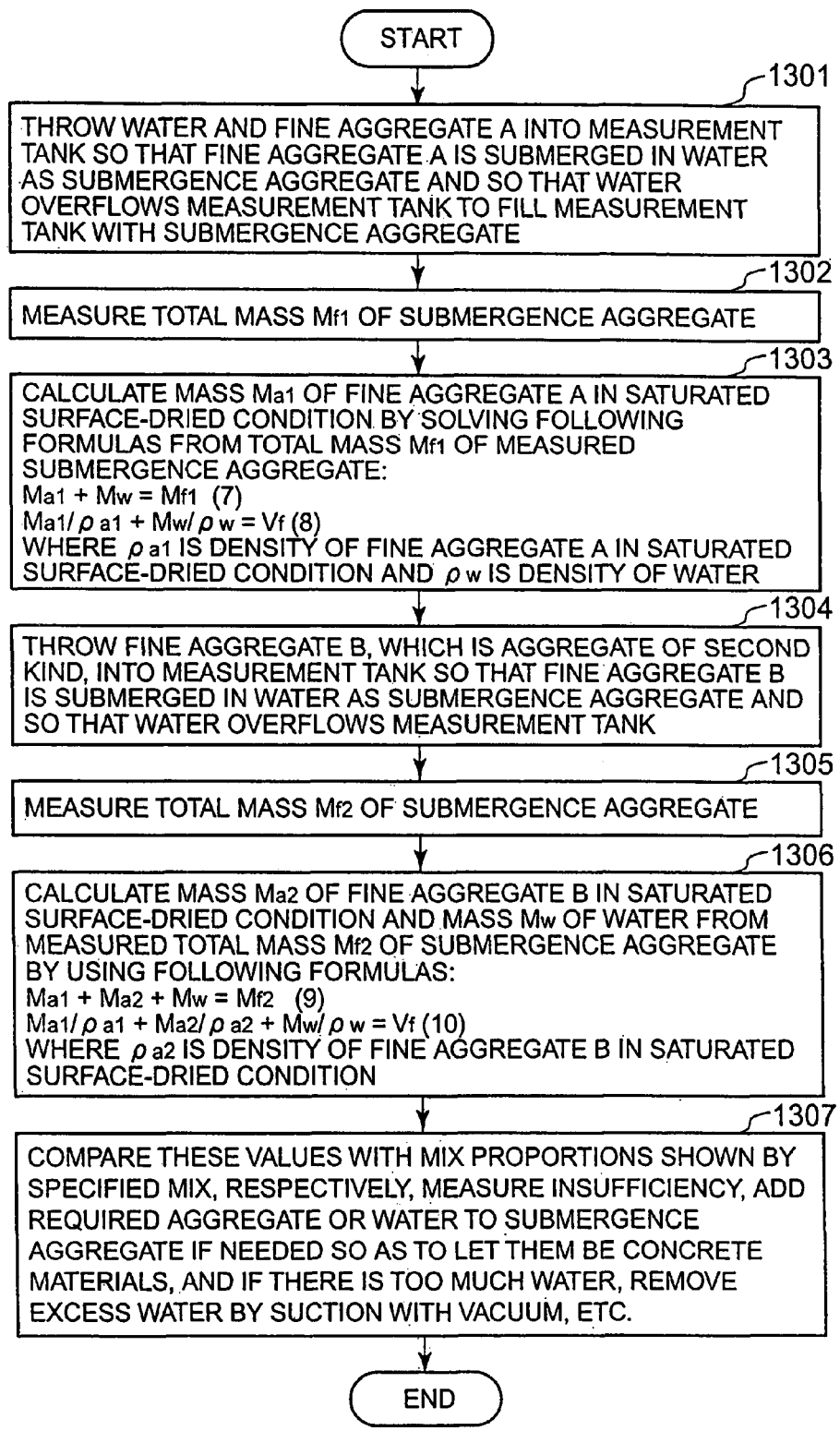

START
↓
1301 THROW WATER AND FINE AGGREGATE A INTO MEASUREMENT TANK SO THAT FINE AGGREGATE A IS SUBMERGED IN WATER AS SUBMERGENCE AGGREGATE AND SO THAT WATER OVERFLOWS MEASUREMENT TANK TO FILL MEASUREMENT TANK WITH SUBMERGENCE AGGREGATE
↓
1302 MEASURE TOTAL MASS $M_{f1}$ OF SUBMERGENCE AGGREGATE
↓
1303 CALCULATE MASS $M_{a1}$ OF FINE AGGREGATE A IN SATURATED SURFACE-DRIED CONDITION BY SOLVING FOLLOWING FORMULAS FROM TOTAL MASS $M_{f1}$ OF MEASURED SUBMERGENCE AGGREGATE:
$M_{a1} + M_w = M_{f1}$ (7)
$M_{a1}/\rho_{a1} + M_w/\rho_w = V_f$ (8)
WHERE $\rho_{a1}$ IS DENSITY OF FINE AGGREGATE A IN SATURATED SURFACE-DRIED CONDITION AND $\rho_w$ IS DENSITY OF WATER
↓
1304 THROW FINE AGGREGATE B, WHICH IS AGGREGATE OF SECOND KIND, INTO MEASUREMENT TANK SO THAT FINE AGGREGATE B IS SUBMERGED IN WATER AS SUBMERGENCE AGGREGATE AND SO THAT WATER OVERFLOWS MEASUREMENT TANK
↓
1305 MEASURE TOTAL MASS $M_{f2}$ OF SUBMERGENCE AGGREGATE
↓
1306 CALCULATE MASS $M_{a2}$ OF FINE AGGREGATE B IN SATURATED SURFACE-DRIED CONDITION AND MASS $M_w$ OF WATER FROM MEASURED TOTAL MASS $M_{f2}$ OF SUBMERGENCE AGGREGATE BY USING FOLLOWING FORMULAS:
$M_{a1} + M_{a2} + M_w = M_{f2}$ (9)
$M_{a1}/\rho_{a1} + M_{a2}/\rho_{a2} + M_w/\rho_w = V_f$ (10)
WHERE $\rho_{a2}$ IS DENSITY OF FINE AGGREGATE B IN SATURATED SURFACE-DRIED CONDITION
↓
1307 COMPARE THESE VALUES WITH MIX PROPORTIONS SHOWN BY SPECIFIED MIX, RESPECTIVELY, MEASURE INSUFFICIENCY, ADD REQUIRED AGGREGATE OR WATER TO SUBMERGENCE AGGREGATE IF NEEDED SO AS TO LET THEM BE CONCRETE MATERIALS, AND IF THERE IS TOO MUCH WATER, REMOVE EXCESS WATER BY SUCTION WITH VACUUM, ETC.
↓
END

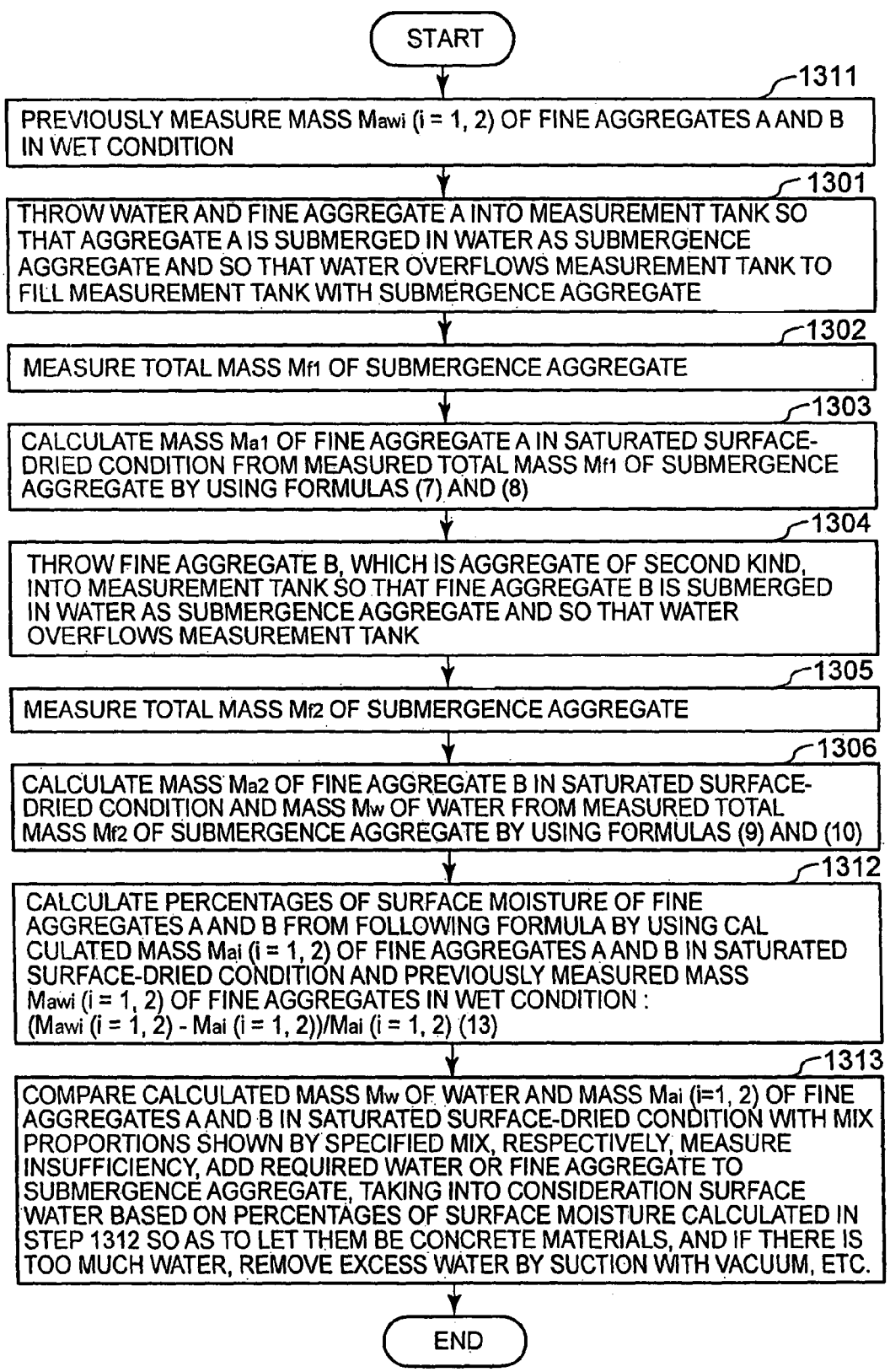

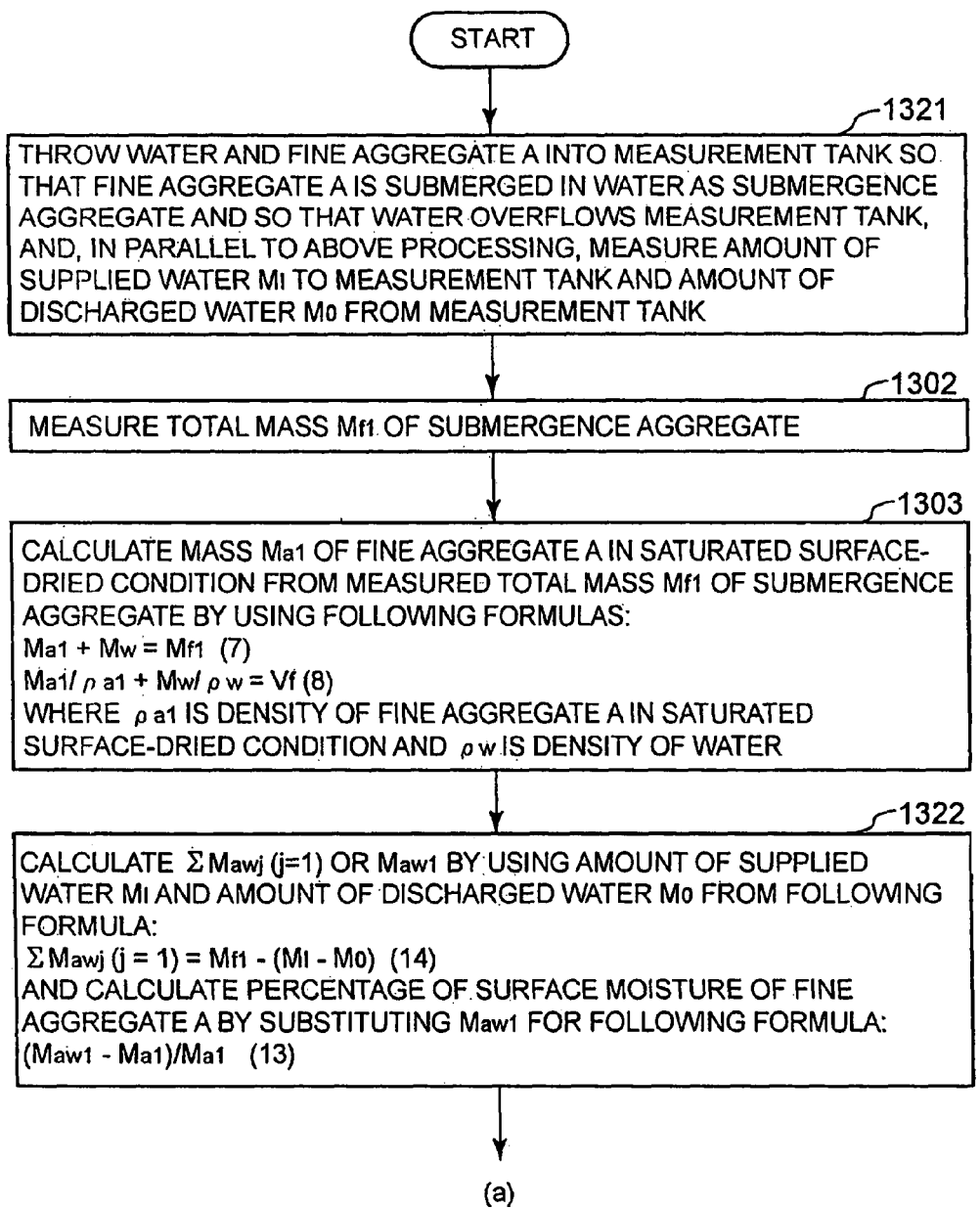

1335 — MEASURE MASS Maw2 OF FINE AGGREGATE B IN WET CONDITION

1336 — THROW FINE AGGREGATE B AND WATER INTO SUBMERGENCE AGGREGATE CONTAINER SO THAT FINE AGGREGATE B IS SUBMERGED IN WATER AND SO THAT WATER OVERFLOWS SUBMERGENCE AGGREGATE CONTAINER TO FILL IT WITH SUBMERGENCE AGGREGATE, AND MEASURE AMOUNT OF SUPPLIED WATER Mi AND AMOUNT OF DISCHARGE WATER Mo AS ACCUMULATION VALUES

1337 — CALCULATE MASS Ma2 OF FINE AGGREGATE B IN SATURATED SURFACE-DRIED CONDITION AND MASS Mw OF WATER IN SUBMERGENCE AGGREGATE FROM FOLLOWING TWO FORMULAS:
$Ma1 + Ma2 + Mw = Maw1 + Maw2 + (Mi - Mo)$ (19)
$Ma1/\rho a1 + Ma2/\rho a2 + Mw/\rho w = Vf$ (20)
WHERE $\rho a2$ IS DENSITY OF FINE AGGREGATE B IN SATURATED SURFACE-DRIED CONDITION AND $\rho w$ IS DENSITY OF WATER, AND CALCULATE PERCENTAGE OF SURFACE MOISTURE OF FINE AGGREGATE B FROM FOLLOWING FORMULA:
$(Maw2 - Ma2)/Ma2$ (21)

1338 — COMPARE THESE VALUES WITH MIX PROPORTIONS SHOWN BY SPECIFIED MIX, RESPECTIVELY, MEASURE INSUFFICIENCY, ADD REQUIRED WATER OR FINE AGGREGATE IF NEEDED TO SUBMERGENCE AGGREGATE, TAKING INTO CONSIDERATION SURFACE WATER BASED ON PERCENTAGES OF CALCULATED SURFACE MOISTURE, SO AS TO LET THEM BE CONCRETE MATERIALS, AND IF THERE IS TOO MUCH WATER, REMOVE EXCESS WATER BY SUCTION WITH VACUUM, ETC.

↓
( END )

(c)

(d)

(e)

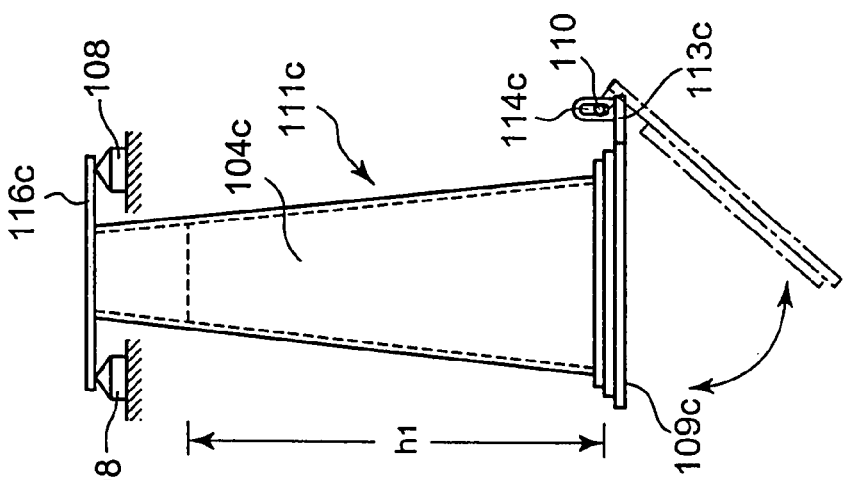
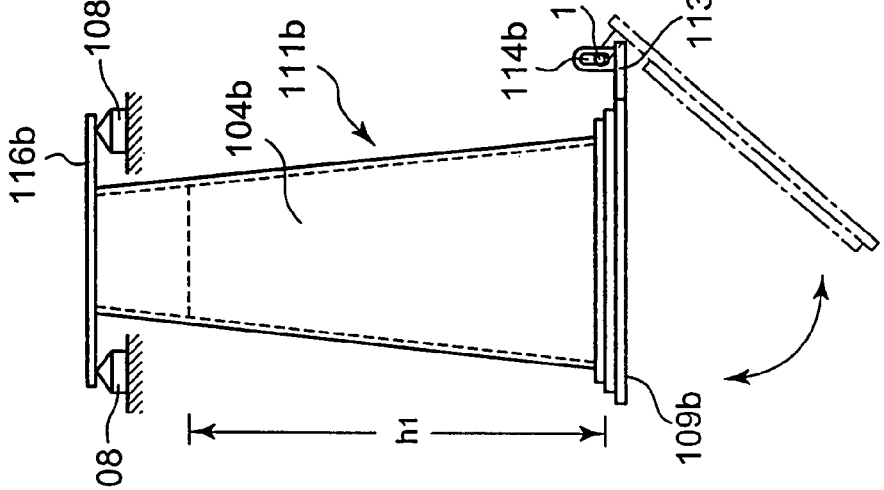
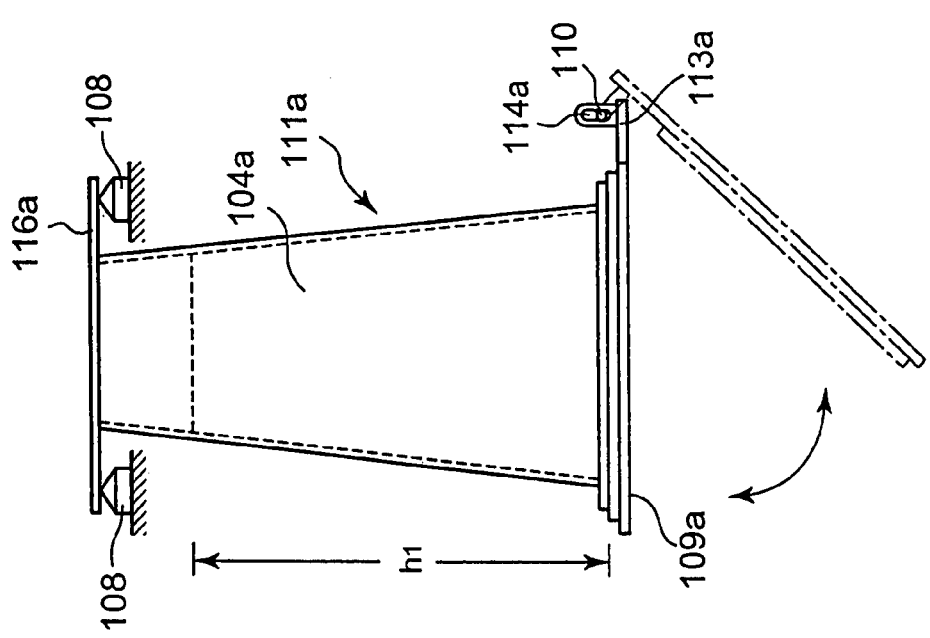

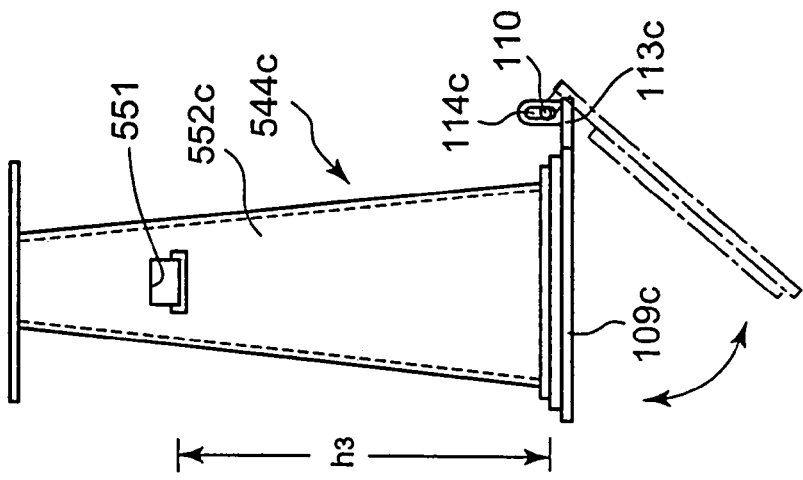
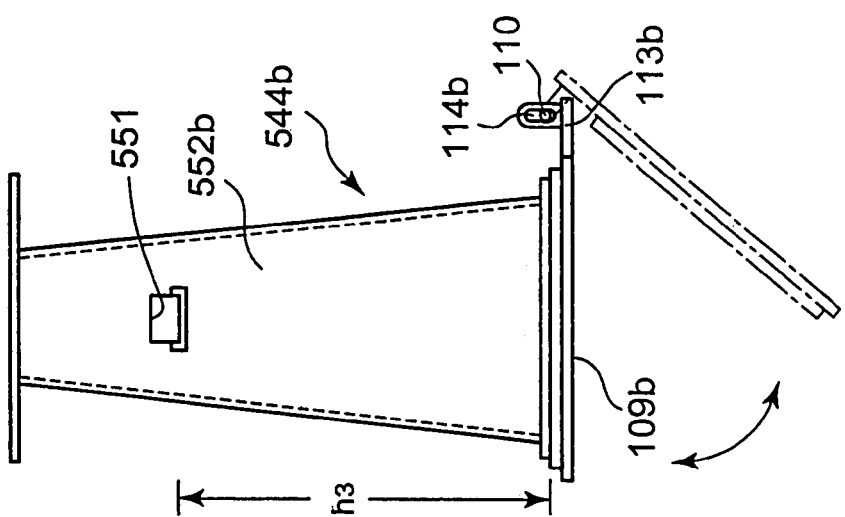
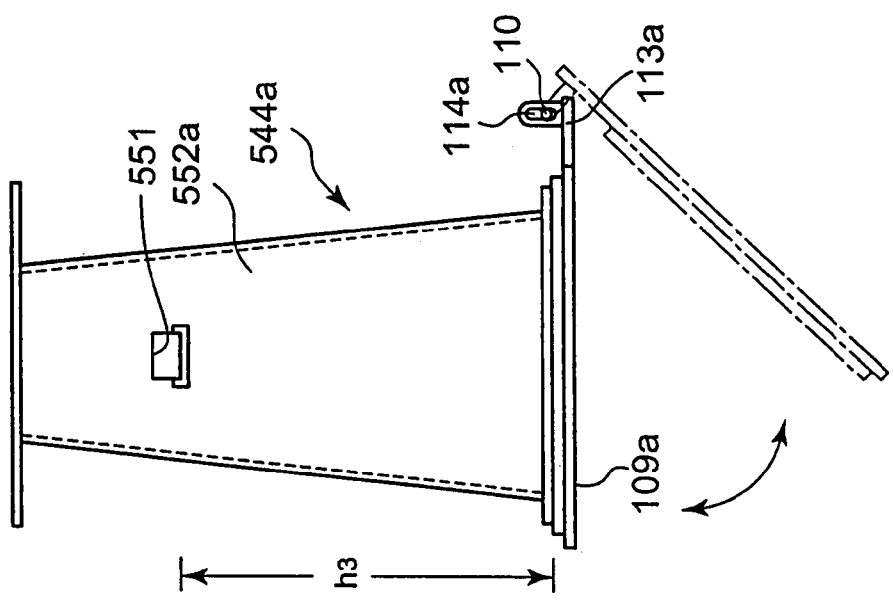

MEASURING APPARATUS AND MEASURING METHOD FOR CONCRETE-FORMING MATERIALS

This application is a divisional of U.S. application Ser. No. 10/470,044, filing date Feb. 2, 2004, now U.S. Pat. No. 7,207,212 which was the National Stage of International Application No. PCT/JP02/00447, filed Jan. 23, 2002.

BACKGROUND OF THE INVENTION

The present invention relates to a measuring apparatus and a measuring method for concrete-forming materials which measure water and aggregate whose moisture state is not uniform.

When kneading concrete-forming materials on site, it is necessary to manage appropriately an amount of water since it has a strong influence on strength of concrete and the like. However, a moisture state of the aggregate, which is a concrete-forming material, changes with storage situations, climatic conditions, and the like. Therefore, if aggregate in a wet condition is used, an amount of water in concrete will increase by an amount of surface water of the aggregate. On the other hand, if aggregate in a dry state is used, an amount of water in concrete will decrease by an amount of water absorbed into the aggregate according to an effective absorption of the aggregate.

Therefore, in order to make concrete as a specified mix, it becomes very important in a case of kneading of concrete-forming materials to correct the amount of water according to a dryness-and-moisture grade of aggregate.

Here, aggregate generally stored, especially fine aggregate is wet in many cases. Therefore, it is common to measure a percentage of surface moisture of aggregate beforehand, and to adjust the amount of water based on the percentage of surface moisture measured.

A percentage of surface moisture, which is an index pertaining to dryness and moisture of aggregate, is obtained by dividing a mass of surface water of the aggregate (water adhering to a front face of the aggregate in a wet condition) by mass of the aggregate in a saturated surface-dried condition. Here, the aggregate in the saturated surface-dried condition means aggregate whose front face is dry and whose core is saturated with water.

And conventionally, in measurement of such percentage of surface moisture, a small amount of sample is extracted from a storage container called a stock bin in which aggregate is stored for measuring the mass of the sample and the mass of the sample dried completely. Next, the percentage of surface moisture was computed by using these measured values and a coefficient of water absorption of the aggregate measured beforehand.

However, by such a measuring method, since a percentage of surface moisture of aggregate in the stock bin is guessed from few samples, accuracy is inferior. On the other hand, in order to measure the mass of aggregate dried completely, heating by a burner and the like is needed. Therefore, it is impractical to measure the mass of aggregate dried completely whose amount is near an actually used amount since much time and expense are needed.

In order to avoid such a problem, an operator checks a kneading situation visually or adjusts an amount of water by using an electric-current value of a mixer. However, these methods have low accuracy primarily. Therefore, as a result, in order to secure strength of concrete, it is necessary to expect nearly twenty superfluous factors of safety, and this leads to an uneconomical mix proportion.

Especially in mixing a plurality of aggregates, kinds of which are different in terms of density and grading, for example, the problem mentioned above becomes still more serious.

SUMMARY OF THE INVENTION

Accordingly, it is an object of the present invention to provide a measuring apparatus and a measuring method for concrete-forming materials which can measure mass of aggregate and water correctly even if a percentage of surface moisture of the aggregate is not measured.

It is a further object of the present invention to provide a measuring method for concrete-forming materials which can measure correctly mass of a plurality of aggregates, kinds of which are different, and mass of water.

It is another object of the present invention to provide a measuring method for concrete-forming materials which can measure mass of aggregate and water correctly taking into consideration a percentage of surface moisture of the aggregate.

It is another object of the present invention to provide a measuring method for concrete-forming materials, a measuring program for concrete-forming materials, and a recording medium of this measurement, which can measure mass of aggregate and water correctly taking into consideration a percentage of surface moisture of the aggregate.

It is another object of the present invention to provide a discharge mechanism of a measurement container which can prevent lowering of water-tightness and damage on a seal by aggregate intervening between a body of the measurement container and a bottom lid of the measurement container when measuring aggregate and water as submergence aggregate.

It is another object of the present invention to provide a discharge mechanism of a measurement container which can feed certainly water and aggregate into a kneading mixer, which are correctly measured as submergence aggregate, when measuring aggregate and water as submergence aggregate.

It is another object of the present invention to provide a measuring apparatus of concrete-forming materials which can maintain accuracy of aggregate measurement uniformly without making it dependent on an amount of aggregate.

(Measurement by a Submergence Method)

In order to measure aggregate and water using the measuring apparatus for concrete-forming materials according to one aspect of the present invention, aggregate in an arbitrary wet condition is first breathed out from a discharge opening of an aggregate feed hopper. Next, this breathed-out aggregate is put into a measurement tank with water. The aggregate is thoroughly sunk within the measurement tank as submergence aggregate.

Next, while measuring total mass $M_f$ of the submergence aggregate which consists of the aggregate and the water which are held in the measurement tank with means for measuring mass, total volume $V_f$ is measured with means for measuring a water level. For example, a load cell can be used as means for measuring mass, and an electrode-type displacement sensor, an ultrasonic sensor, a photosensor, or the like can be used as means for measuring a water level.

The total mass $M_f$ is obtained just by subtracting the mass of only the measurement tank from the value measured by the means for measuring mass as an example. In order to measure the total volume $V_f$, first, a relationship between a level and a corresponding capacity is previously measured at 1-mm intervals, for example, and a storage device in a computer, for example, is made to store the relationship in advance so as to read appropriately a capacity corresponding to the measured level from the storage device.

Next, mass $M_w$ of water and mass $M_a$ of the aggregate in a saturated surface-dried condition are computed by substituting the total mass $M_f$ and total volume $V_f$ into the following two formulas.

$$M_a + M_w = M_f \qquad (1)$$

$$M_a/\rho_a + M_w/\rho_w = V_f(1-a/100) \qquad (2\text{-}a)$$

Here, $\rho_a$ expresses density of the aggregate in the saturated surface-dried condition, $\rho_w$ expresses density of water, and "a" expresses air content (%) included in total volume $V_f$.

When air content can be disregarded, the mass $M_w$ of water and the mass $M_a$ of the aggregate in the saturated surface-dried condition are computed by solving the following two formulas.

$$M_a + M_w = M_f \qquad (1)$$

$$M_a/\rho_a + M_w/\rho_w = V_f \qquad (2)$$

Next, the mass $M_w$ of water and the mass $M_a$ of the aggregate in the saturated surface-dried condition are compared with a mix proportion shown by a specified mix. Subsequently, an insufficiency which should be remedied by filling is measured and then the submergence aggregate is supplemented by an amount of the insufficiency so as to allow the aggregate and the water to be concrete material.

Thus, surface water of aggregate is indirectly computed as a part of the mass $M_w$ of water, even if aggregate whose moisture state is not uniform is used, and the mass of aggregate is computed as mass $M_a$ in the saturated surface-dried condition. That is, since the mass of aggregate and water will be computed on the same conditions as the specified mix, even if aggregate whose moisture state is not uniform is used, concrete can be made by the amount of water as that of the specified mix.

Here, when a supplement of aggregate is needed, the surface water of the aggregate is not strictly taken into consideration. However, the amount of supplement is limited to be small by measuring an amount of aggregate and water whose ratio matches the ratio of the specified mix or is close to it. And since the surface water of aggregate adhering to supplement aggregate is a slight amount of a grade which can be disregarded when compared with required amount of water, a problem is not produced at all in terms of quality of concrete.

When putting aggregate and water into the measurement tank, it is good to supply them to the measurement tank, and perform water binding of the aggregate so that a top of the aggregate may be mostly in agreement with the water level. By so doing, the ratio of the aggregate and the water in the measurement tank becomes close to the specified mix, thereby reducing an amount of supplement of aggregate dramatically.

A volume of the measurement tank is arbitrary. That is, the volume of the measurement tank may be made in agreement with the entire quantity required for a unit of concrete mixing, i.e., one batch. Otherwise, the quantity required can be some amount in the measurement tank.

A particle diameter of the aggregate is arbitrary and fine aggregate and coarse aggregate are included in the term of the aggregate. Although it is arbitrary as to how the measurement tank is constituted, if the aggregate is fine aggregate, the submergence fine aggregate can be easily taken out after a measurement process by forming the measurement tank in a shape of a truncated cone so that a bore of the measurement tank may spread downwardly.

In throwing the fine aggregate and the water into the measurement tank, it is arbitrary as to which should be made to precede, but if the water is thrown in previously and the fine aggregate is thrown in there after, air bubble mixing in the submergence fine aggregate can be suppressed considerably.

The fine aggregate breathed out from the fine-aggregate feed hopper may be directly thrown into the measurement tank. Here, while placing a screen device above the measurement tank, a vibrating feeder can be placed so that a conveyance starting position is located in a discharge opening under the fine-aggregate feed hopper, and so that a conveyance end location is located in the screen device. In this case, the fine aggregate breathed out from the discharge opening of the fine-aggregate feed hopper is conveyed by the vibrating feeder to the screen device, while a predetermined vibration is given. Next, the fine aggregate is thrown into the measurement tank, into which water is thrown previously, via the vibrating feeder and the screen device. According to this constitution, granulation of the fine aggregate is prevented, by which it becomes possible to suppress nearly thoroughly mixing of air bubbles in the submergence fine aggregate, and an influence of air bubbles can be disregarded practically.

In order to prevent air bubble mixing by using the vibrating feeder and the screen device, the following procedures should be used for measurement.

First, water is previously thrown into the measurement tank. Next, a discharge of the fine aggregate in arbitrary wet conditions is performed from the discharge opening of the fine-aggregate feed hopper. Subsequently, the fine aggregate is conveyed by the vibrating feeder, preventing granulation of this breathed-out fine aggregate by vibration using the vibrating feeder. Next, the fine aggregate conveyed from the vibrating feeder is vibrated on the screen device, only the fine aggregate of a predetermined particle diameter is dropped from the screen device, and this is supplied to the measurement tank. The water and the fine aggregate which are thrown into the measurement tank in such a procedure turn into a submergence fine aggregate.

Next, total mass $M_f$ and total volume $V_f$ of the submergence fine aggregate held in the measurement tank are similarly measured as mentioned above, respectively, by the means for measuring mass and the means for measuring a water level.

Next, the mass $M_w$ of the water and the mass $M_a$ of the fine aggregate in a saturated surface-dried condition are computed by substituting the total mass $M_f$ and the total volume $V_f$ into the following two formulas.

$$M_a + M_w = M_f \qquad (1)$$

$$M_a/\rho_a + M_w/\rho_w = V_f \qquad (2)$$

Here, $\rho_a$ is the density of the fine aggregate in the saturated surface-dried condition, and $\rho_w$ is the density of water.

Thus, the mass $M_w$ of the water and the mass $M_a$ of the fine aggregate in the saturated surface-dried condition are computed, and then $M_w$ and $M_a$ are compared with the specified mix. Subsequently, an insufficiency is measured and then the submergence aggregate is supplemented by an amount of the insufficiency so as to allow the aggregate and the water be concrete material.

(Measurement by a Submergence Method which does not Need Capacity Measurement)

In a measuring apparatus and a measuring method for concrete-forming materials according to another aspect of the invention, an interior of a measurement tank is first changed into a water-tight state by closing a bottom opening of the measurement tank by a bottom lid. Next, aggregate is thrown in the measurement tank by means for supplying aggregate, and water is thrown in the measurement tank by means for supplying water, so that the interior of the measurement tank may be in a submergence state.

When throwing the aggregate and the water into the measurement tank, it is arbitrary as to which should be thrown first, but if the water is thrown in first and the aggregate is thrown in later, especially in the case of the fine aggregate, air bubble mixing in the submergence aggregate can be suppressed considerably.

Here, a predetermined opening for overflow, for making the water in the measurement tank overflow outside, is formed in a wall of the measurement tank at a predetermined height location of the measurement tank. The water and the aggregate are thrown into the measurement tank, and fill the interior of the measurement tank with submergence aggregate so that the aggregate may not come out from a water surface, and so that water may overflow from the opening for overflow.

Here, a water level at which water overflows from the opening for overflow is decided beforehand. Therefore, by filling the submergence aggregate in the procedure mentioned above, even if total volume Vf of the submergence aggregate is not measured, it becomes settled naturally.

Accordingly, if only total mass $M_f$ of the submergence aggregate is measured with means for measuring mass of submergence aggregate, the mass $M_a$ of the aggregate in the saturated surface-dried condition and the mass $M_w$ of the water can be easily calculated by solving the following two formulas.

$$M_a + M_w = M_f \quad (1)$$

$$M_a/\rho_a + M_w/\rho_w = V_f \quad (2)$$

Here, $\rho_a$ is the density of the aggregate in the saturated surface-dried condition, and $\rho_w$ is the density of the water. In order to measure the total mass $M_f$ of the submergence aggregate, the mass of only the measurement tank is subtracted from the value measured by the means for measuring mass of submergence aggregate.

Thus, after measuring and computing the mass $M_w$ of the water, and the mass $M_a$ of the aggregate in the saturated surface-dried condition, $M_w$ and $M_a$ are compared with those amounts of mix shown by the specified mix. Subsequently, insufficiency is measured and then the submergence aggregate is supplemented by an amount of the insufficiency so as to allow the aggregate and the water to be concrete material. When there is too much water, a surplus is sucked with a vacuum or the like.

Thus, surface water of aggregate is indirectly computed as a part of the mass $M_w$ of water, even if aggregate whose moisture state is not uniform is used, and mass of aggregate is computed as mass $M_a$ in the saturated surface-dried condition. That is, since the mass of the aggregate and the water will be grasped on conditions equivalent to the specified mix, even if an aggregate whose moisture state is not uniform is used, it becomes possible to make concrete by the amount of water as that of the specified mix.

Although fine aggregate is mainly targeted for aggregate, it is applicable to use coarse aggregate.

When a plurality of openings for overflow are provided in the measurement tank at different heights, it becomes unnecessary to prepare a measurement tank for each total volume $V_f$ individually, although it is arbitrary as to how each opening for overflow is formed in a measurement tank. In this constitution, only the opening for overflow corresponding to the total volume $V_f$ to measure is opened, and other openings for overflow are altogether sealed, for example, using seal plugs.

On the other hand, when an overflow height of a opening for overflow is constituted as being adjustable, it becomes unnecessary to prepare a measurement tank for each total volume $V_f$ individually, even if it does not provide a plurality of openings for overflow. In order to constitute the overflow height of the opening for overflow as adjustable, a predetermined cover plate is attached to the opening for overflow so that a water-tight state with the opening for overflow may be maintained, and so that the plate can be moved up and down along the measurement tank. Thus, since the cover plate can cover a part of the opening for overflow which exists below a desired overflow height, it becomes possible to adjust the water level at which water of the submergence aggregate in the measurement tank overflows.

Configuration of the measurement tank is arbitrary as long as the submergence aggregate can be held. For example, it is possible to constitute a measurement tank in a shape of a hollow cylinder. Here, if a measurement tank is formed in a shape of a hollow truncated cone, a bore of the measurement tank will become large, as it goes downward. Therefore, since it is prevented that the submergence aggregate remains in the measurement tank, when a measurement is finished, only by opening the bottom lid of the measurement tank, free fall of the submergence aggregate in the measurement tank occurs, and the submergence aggregate can be removed easily.

If free fall of the submergence aggregate cannot be performed thoroughly due to aggregate adhesion in the measurement tank, compaction of aggregate, and the like, this problem can be solved by attaching oscillating grant instruments, such as a vibrator and a knocker, exteriorly of the measurement tank.

Here, a predetermined vibrator can be installed above the measurement tank so that it can go up and down freely, and so that it may be buried in the submergence aggregate in the measurement tank at a downward location. In this case, during aggregate charge or after the charge, the vibrator is lowered and operated.

By so doing, the aggregate supplied in the measurement tank will become flat by vibration, and this aggregate will not come out on the water surface. A volume of the measurement tank is arbitrary and can be made equal to the entire quantity required for mixing of one batch. Otherwise, the quantity required can be divided into some amounts in the measurement tank.

The means for supplying aggregate is constituted so that the aggregate can be stored, and so that discharge of a necessary amount can be performed. The means for supplying aggregate can consist of a hopper, for example. If a means for measuring mass of aggregate which measures the mass of the aggregate in the means for supplying aggregate is provided, the mass $M_a$ of the aggregate in the saturated surface-dried condition and the mass $M_w$ of the water can be calculated easily. In addition, a percentage of surface moisture of the aggregate is also computable.

That is, if mass of the aggregate in the wet condition is set to $M_{aw}$, the percentage of surface moisture of the aggregate is computable by the following formula.

$$(M_{aw} - M_a)/M_a \quad (3)$$

If means for measuring mass of supplied water provided in the means for supplying water in order to measure the mass of the water in the measurement tank, and means for measuring mass of overflow water for measuring the mass of the water which overflowed from the opening for overflow, are provided, the mass $M_a$ of the aggregate in the saturated surface-dried condition and the mass $M_w$ of the water can be calculated easily. In addition, a percentage of surface moisture of the aggregate is computable. That is, when the amount of supplied water is set to $M_I$ and the amount of overflow is set to $M_O$, we have $$M_{aw}=M_I-(M_I-M_O) \tag{4}$$

Hence, if this is substituted for formula (3), the percentage of surface moisture of the aggregate is computable.

Thus, if the percentage of surface moisture is computed in advance, for the supplement of aggregate as mentioned above, the surface water of the aggregate can be appropriately taken into consideration also for a part for this supplement.

If air content (amount of air included in submergence aggregate) a (%) is taken into consideration, the total volume $V_f$ which is known will be multiplied by (1−a/100). Let this be total volume $V_f$ anew. If this is the case, still higher-precision measurement can be performed in the actual total volume except the air content.

(Measurement by a Submergence Method which does not Need Measurement of Capacity and Mass)

In a measuring apparatus and a measuring method of concrete-forming materials according to still another aspect of the invention, mass $M_{aw}$ of aggregate stored by an aggregate measurement container is first measured by means for measuring mass of aggregate.

Next, a bottom opening of the submergence aggregate container is closed by a bottom lid, and an interior of the submergence aggregate container is changed into a watertight state. Next, the above-mentioned aggregate is supplied to the submergence aggregate container with water, and the interior of the submergence aggregate container is filled with the submergence aggregate.

In feeding the aggregate and the water into the submergence aggregate container, it is arbitrary as to which should be made to precede, but it is good to supply the water first and to supply the aggregate subsequently. If this is done, it will become possible to suppress air bubble mixing in the submergence aggregate considerably, especially in a case of the fine aggregate.

Here, a predetermined opening for overflow is formed at the predetermined height location of the wall of this submergence aggregate container so that the water in the submergence aggregate container may overflow outside. In order to supply the water and the aggregate as submergence aggregate in such a submergence aggregate container, the water and the aggregate are fed into the submergence aggregate container so that the aggregate may not come out from the water surface, and so that the water may overflow from the opening for overflow. And while measuring the amount of supplied water $M_I$ as an accumulation value, the amount $M_O$ of overflow which overflowed from the opening for overflow is measured as an accumulation value by a means for measuring mass of overflow water.

Since a level of the water which overflows from the opening for overflow is beforehand decided, it becomes unnecessary to measure total volume $V_f$, and this level serves as a known value.

Next, while calculating mass $M_a$ of the aggregate in the saturated surface-dried condition and mass $M_w$ of the water in the submergence aggregate from the following formulas (5) and formulas (2), a percentage of surface moisture of the aggregate is computed by formula (3).

$$M_a+M_w=M_{aw}+(M_I-M_O) \tag{5}$$

$$M_a/\rho_a+M_w/\rho_w=V_f \tag{2}$$

$$(M_{aw}-M_a)/M_a \tag{3}$$

Here, $\rho_a$ is the density of the aggregate in the saturated surface-dried condition, and $\rho_w$ is the density of water.

Thus, the mass $M_w$ of the water, the mass $M_a$ of the aggregate in the saturated surface-dried condition, and the percentage of surface moisture are measured and computed, and then these values are compared with a mix proportion shown by a specified mix. An insufficiency is then measured. If the insufficiency is the water, the above-mentioned submergence aggregate is supplemented with the water equal to the amount of the insufficiency so as to let the aggregate and the water be concrete material. On the other hand, taking the surface water of the aggregate into consideration using the computed percentage of surface moisture, if the insufficiency is the aggregate, the above-mentioned submergence aggregate is supplemented with the aggregate equal to the amount of the insufficiency so as to let the aggregate and the water be concrete material. When there is too much water, the surplus is sucked with a vacuum or the like.

Thus, surface water of aggregate is indirectly computed as a part of mass $M_w$ of water, even if aggregate whose moisture state is not uniform is used. On the other hand, mass of the aggregate is computed as mass $M_a$ in the saturated surface-dried condition. That is, since mass of the aggregate and water will be computed on conditions equivalent to the specified mix, even if a humidity grade of aggregate is not fixed at every measurement, it becomes possible to make concrete by the amount of water as that of the specified mix.

Although fine aggregate is mainly targeted for aggregate, it is applicable also to use coarse aggregate.

It is arbitrary as to how the amount of supplied water $M_I$ of the water fed into the submergence aggregate container, is measured. For example, the amount of supplied water $M_I$ of the water can be known by feeding water into the submergence aggregate container previously, and causing the water to overflow therefrom. That is, since a water level at which water overflows from the opening for overflow is decided beforehand, as mentioned above, the amount of supplied water $M_I$ of the supplied water serves as a known value, even if it is not measured.

Since the water level does not fall even if water may overflow by subsequent aggregate throwing in this case, an accumulation value of the amount of supplied water $M_I$ becomes fixed during measurement.

Here, means for measuring mass of supplied water can be provided in means for supplying water. In this case, the water supply amount from the means for supplying water is measured as an accumulation value by the means for measuring mass of supplied water. Let this accumulation value be an amount of supplied water $M_I$.

When a plurality of openings for overflow are provided in the submergence aggregate container at different heights, it becomes unnecessary to prepare a measurement tank for each total volume $V_f$ individually, although it is arbitrary as to how an opening for overflow is formed in a submergence aggregate container. In this constitution, only the opening for overflow corresponding to the total volume $V_f$ to measure is opened, and other openings for overflow are altogether sealed, for example, using seal plugs.

When the overflow height of the opening for overflow is constituted as being adjustable, it becomes unnecessary to prepare a measurement tank for each total volume $V_f$ individually, even if the measurement tank does not provide a plurality of openings for overflow.

In order to constitute the overflow height of the opening for overflow as being adjustable, a predetermined cover plate is attached to the opening for overflow so that a water-tight state with the opening for overflow may be maintained, and so that the cover plate can go up and down along the submergence aggregate container. Thus, since the cover plate can cover a part of the opening for overflow which exists below the desired overflow height, it becomes possible to adjust the water to a level at which water of the submergence aggregate in the submergence aggregate container overflows.

Configuration of the submergence aggregate container is arbitrary as long as submergence aggregate can be held therein. For example, it is possible to constitute a measurement tank in a shape of a hollow cylinder. Here, if a submergence aggregate container is formed in a shape of a hollow truncated cone, a bore of the submergence aggregate container will become large in a downward direction. Therefore, since it is prevented that the submergence aggregate remains in the submergence aggregate container, when a measurement is finished, only by opening the bottom lid of the submergence aggregate container, free fall of the submergence aggregate in the submergence aggregate container can be performed, and the submergence aggregate can be removed easily.

If free fall of the submergence aggregate cannot be performed thoroughly due to aggregate adhesion in the measurement tank, compaction of aggregate, and the like, this can be resolved by attaching oscillating grant instruments, such as a vibrator and a knocker, exteriorly of the submergence aggregate container.

Here, a predetermined vibrator can be installed above the submergence aggregate container so that the vibrator can move up and down freely, and so that it may be buried in the submergence aggregate in the submergence aggregate container at a downward location. In this case, during the aggregate charge or after the charge, the vibrator is lowered and operated.

By so doing, the aggregate supplied in the submergence aggregate container will become flat by vibration, and the aggregate will not come out on the water surface.

A volume of a submergence aggregate container is arbitrary. That is, the volume of the submergence aggregate container may be made in agreement with an entire quantity required for a unit of concrete mixing, i.e., one batch. Otherwise, the required quantity can be divided into some amounts in the submergence aggregate container.

(Measurement by a Submergence Method in a Case of Supplying Cumulatively a Plurality of Aggregates, Kinds of which are Different)

In a measuring method of concrete-forming materials according to still another aspect of the invention, first, aggregate of a first kind and water are supplied to a predetermined measurement tank so that the water and aggregate may become submergence aggregate in which the aggregate of the first kind does not appear from the water surface.

When throwing the aggregate and the water into the measurement tank, it is arbitrary as to which should be thrown first, but if the water is thrown in first and the aggregate is thrown in later, especially in a case of fine aggregate, air bubble mixing of the submergence aggregate can be suppressed considerably.

Next, total mass $M_{f1}$ of the submergence aggregate is measured. In order to measure the total mass $M_{f1}$ of the submergence aggregate, the mass of only the measurement tank is subtracted from the mass of the measurement tank filled with the submergence aggregate.

Here, in order to measure total volume $V_{f1}$ of the submergence aggregate, means for measuring a water level for measuring a level of the submergence aggregate, such as an electrode-type displacement sensor, can be used.

Next, mass $M_{a1}$ of the aggregate of the first kind in a saturated surface-dried condition is calculated by solving the following two formulas.

$$M_{a1} + M_w = M_{f1} \quad (7)$$

$$M_{a1}/\rho_{a1} + M_w/\rho_w = V_{f1} \quad (8)$$

Here, $\rho_{a1}$ is the density of the aggregate of the first kind in the saturated surface-dried condition, and $\rho_w$ is the density of water.

Next, aggregate of a second kind and required water are supplied to the measurement tank so that the aggregate of the second kind may not come out from the water surface, namely, so that it may become part of submergence aggregate. Here, when throwing the aggregate of the second kind, as long as a state of submergence aggregate, i.e., a state where the aggregate of the second kind does not come out from the water surface, is maintained, it is not necessary to perform additional throwing of water. Required water means water required for holding the state of submergence aggregate.

Next, total mass $M_{f2}$ of the submergence aggregate is measured, and subsequently mass $M_{a2}$ of the aggregate of the second kind in a saturated surface-dried condition is calculated from the following two formulas.

$$M_{a1} + M_{a2} + M_w = M_{f2} \quad (9)$$

$$M_{a1}/\rho_{a1} + M_{a2}/\rho_{a2} + M_w/\rho_w = V_{f2} \quad (10)$$

Here, $V_{f2}$ is the total volume of the submergence aggregate, and $\rho_{a2}$ is the density of the aggregate of the second kind in the saturated surface-dried condition.

Hereafter, by repeating the above-mentioned procedure, $M_{a1}, M_{a2}, M_{a3}, \ldots, M_{ia}, \ldots, M_{a(N-1)}$, each of which is the mass of aggregate of an (N−1)th kind in the saturated surface-dried condition, are calculated one after another. Finally, aggregate of the Nth kind and required water are supplied to the measurement tank so that the aggregate of the Nth kind does not come out from the water surface, namely, so that it may become part of submergence aggregate.

Here, with required water, if the aggregate of the i-th kind does not come out from the water surface as mentioned above, it means that water may not be supplied. In this case, only the aggregate of the i-th kind is thrown into the measurement tank.

Next, total mass $M_{fN}$ of the submergence aggregate is measured, and next mass $M_{aN}$ of aggregate of the Nth kind in the saturated surface-dried condition and mass $M_w$ of water are calculated from the following two formulas.

$$\Sigma M_{ai}(i=1 \text{ to } (N-1)) + M_{aN} + M_w = M_{fN} \quad (11)$$

$$\Sigma M_{ai}/\rho_{ai}(i=1 \text{ to } (N-1)) + M_{aN}/\rho_{aN} + M_w/\rho_w = V_{fN} \quad (12)$$

Here, $V_{fN}$ is a total volume of the submergence aggregate and $\rho_{aN}$ is a density of the aggregate of the Nth kind in the saturated surface-dried condition.

When the mass $M_w$ of water and the mass $M_{ai}$ (i=1 to N) of the aggregate in the saturated surface-dried condition are measured and calculated, these calculated values will be compared with a mix proportion shown by a specified mix, respectively. Subsequently, an insufficiency is measured and then the submergence aggregate is supplemented by an amount of the insufficiency so as to let the aggregate and the water be concrete material. When there is too much water, a surplus is sucked with a vacuum or the like.

Thus, the surface water of aggregate is indirectly computed as a part of mass $M_w$ of water, even if an aggregate whose moisture state is not uniform is used, and the mass of aggregate is computed as the mass $M_{ai}$ (i=1 to N) of the aggregate in the saturated surface-dried condition. That is, since the mass of the aggregate and the water will be computed on conditions equivalent to the specified mix, even if a humidity grade of the aggregate is not fixed at every measurement, it becomes possible to make concrete with the amount of water as the specified mix.

In addition, a plurality of aggregates whose kinds, such as density and grading, are different are measured in high effectiveness and accuracy within one measurement tank in the procedure mentioned above.

The total volume $V_{fi}$ (i=1 to N) of the submergence aggregate may be measured using an electrode-type displacement sensor or the like, as mentioned above. Here, if the total volume $V_{fi}$ (i=1 to N) of the submergence aggregate is maintained at a steady value $V_f$ when throwing water and the aggregate of the i-th kind (i=1 to N) into the measurement tank, even if the total volume $V_f$ of the submergence aggregate is not measured, this volume will serve as a known value.

The total volume $V_{fi}$ (i=1 to N) of the submergence aggregate is maintainable at the steady value $V_f$ by making the water in the submergence aggregate overflow from the measurement tank, or sucking the water in the submergence aggregate at a predetermined depth location in the measurement tank.

As mentioned above, the mass $M_{ai}$ (i=1 to N) of the aggregate of the Nth kind in the saturated surface-dried condition and the mass $M_w$ of water can be calculated if the total mass $M_{fi}$ (i=1 to N) of the submergence aggregate is measured at least. On the other hand, if the mass $M_{awi}$ of the aggregate of the i-th kind (i=1 to N) in a wet condition are measured, respectively, a percentage of surface moisture of the aggregate of the i-th kind (i=1 to N) is computable with the following formula, respectively.

$$(M_{awi}-M_{ai})/M_{ai} \quad (13)$$

As another approach, the amount of water $M_I$ supplied to the measurement tank and the amount of water $M_O$ discharged from the measurement tank are measured as accumulation values, and these measurement values are substituted into the following formula, and $M_{awj}$ (j=1, 2, 3, ... i) is calculated.

$$\Sigma M_{awj}(j=1 \text{ to } i)=M_{fi}-(M_I-M_O) \quad (14)$$

Next, $M_{awi}$ is calculated by the following formula.

$$\Sigma M_{awj}(j=1 \text{ to } i)-\Sigma M_{awj}(j=1 \text{ to } (i-1)) \quad (15)$$

Next, the percentage of surface moisture of the aggregate of the i-th kind (i=1 to N) is computable by substituting $M_{awi}$ into the following formula.

$$(M_{awi}-M_{ai})/M_{ai} \quad (13)$$

Here, the accumulation value of the amount of water $M_I$ supplied to the measurement tank does not necessarily increase, but can be the amount of water thrown first, in other words, the accumulation value can be fixed without change. Similarly, water is not necessarily drained by the amount of water $M_O$ discharged from the measurement tank, but the accumulation value can remain zero. On the other hand, in order to maintain the total volume $V_{fi}$ (i=1 to N) of the submergence aggregate at a steady value $V_f$, when making the water in the submergence aggregate overflow from the measurement tank or sucking the water in the submergence aggregate at the predetermined depth location in the measurement tank, the accumulation value of amount of discharged water $M_O$ increases.

In order to calculate the mass $M_{awi}$ of the aggregate of the i-th kind (i=1 to N) in a wet condition, it is necessary to calculate one by one from the aggregate of the first kind. That is, first, the mass of the aggregate of the first kind in a wet condition is calculated, the mass of the aggregate of the second kind in a wet condition is calculated using this value, and next the mass of the third aggregate in a wet condition is calculated using these two values.

Here, as mentioned above, not only fine aggregate but coarse aggregate is contained in the aggregate described in the specification and claims. In addition, both fine aggregate and coarse aggregate are required for the material which constitutes concrete-forming material. Accordingly, there is assumed a case of using a plurality of fine aggregates and coarse aggregates whose kinds such as density and grading are different. Especially, by mixing a plurality of aggregates that differ from one another in terms of grading, aggregate with desired grading (particle size distribution) must be made anew in many cases.

The measuring method of concrete-forming materials concerning the present invention is a very effective measuring method, when mainly measuring a plurality of aggregates that differ from one another in at least one of density or grading. It is the same for other aspects of the invention applied to a plurality of aggregates whose kinds are different.

A plurality of aggregates concerning the present invention mean aggregates which comprise only fine aggregate, aggregates which comprise only coarse aggregate, and aggregates in which fine aggregate and coarse aggregate are arbitrarily mixed. As mentioned above, a plurality of aggregates mean the aggregates whose kinds are different, and all classification indices about aggregate are contained in the kind of aggregate. The classification indices include density, grading, a place of production, reinforcement, a Young's modulus, durability, distinction of nature, artificiality or by production, distinction of beach sand or pit sand, and the like.

In addition, when it is written as $\Sigma M_i$ (i=1 to N), it is a summation, i.e., $(M_1+M_2+ \ldots +M_N)$ is meant. When it is written as aggregate of the i-th kind (i=1 to N), aggregate of the first kind, aggregate of the second kind, aggregate of the third kind, ... , and aggregate of the Nth kind shall be meant.

(Measurement by a Submergence Method which does not Need Measurement of Capacity and Mass in a Case of Supplying Cumulatively a Plurality of Aggregates Whose Kinds are Different)

In a measuring method of concrete-forming materials according to still another aspect of the invention, mass $M_{awi}$ (i=1 to N) of an aggregate of the i-th kind (i=1 to N) in a wet condition is measured first.

Next, water and aggregate of the first kind are thrown into a predetermined submergence aggregate container so that the aggregate of the first kind may not come out from the water surface, and so that the total volume of submergence aggregate may be maintained at a steady value $V_f$.

The total volume of the submergence aggregate is maintainable at the steady value $V_f$ by making the water in the submergence aggregate overflow from the submergence aggregate container, or sucking the water in the submergence aggregate at a predetermined depth location in the submergence aggregate container.

When throwing the aggregate and the water into the submergence aggregate container, it is arbitrary as to which should be thrown first, but if the water is thrown in first and the aggregate is thrown in later, especially in a case of fine aggregate, air bubble mixing in the submergence aggregate can be suppressed considerably.

When throwing the water and aggregate into the submergence aggregate container, an amount of water $M_I$ supplied to the submergence aggregate container and an amount of water $M_O$ discharged from the submergence aggregate container are measured as accumulation values.

Next, mass $M_{a1}$ of the aggregate of the first kind in a saturated surface-dried condition is calculated from the following two formulas.

$$M_{a1}+M_w=M_{aw1}+(M_I-M_O) \tag{16}$$

$$M_{a1}/\rho_a+M_w/\rho_w=V_f \tag{17}$$

Here, $\rho_{a1}$ is the density of the aggregate of the first kind in the saturated surface-dried condition and $\rho_w$ is the density of water.

In addition, a percentage of surface moisture of the aggregate of the first kind is calculated by the following formula.

$$(M_{aw1}-M_{a1})/M_{a1} \tag{18}$$

Next, aggregate of a second kind and required water are fed into the submergence aggregate container so that the aggregate of the second kind may not come out from the water surface, and so that the total volume of submergence aggregate may be maintained at the steady value $V_f$. In addition, an amount of supplied water $M_I$ and an amount of discharged water $M_O$ are measured as accumulation values. Here, with required water, if the aggregate of the second kind does not come out from the water surface, it means that water may not be supplied. In this case, only the aggregate of the second kind is thrown into the submergence aggregate container.

Next, the mass $M_{a2}$ of the aggregate of the second kind in a saturated surface-dried condition is calculated from the following two formulas.

$$M_{a1}+M_{a2}+M_w=M_{aw1}+M_{aw2}+(M_I-M_O) \tag{19}$$

$$M_{a1}/\rho_{a1}+M_{a2}/\rho_{a2}+M_w/\rho_w=V_f \tag{20}$$

Here, $\rho_{a2}$ is the density of the aggregate of the second kind in the saturated surface-dried condition. In addition, the percentage of surface moisture of the aggregate of the second kind is calculated by the following formula.

$$(M_{aw2}-M_{a2})/M_{a2} \tag{21}$$

Hereafter, by repeating the above-mentioned procedure, $M_{a1}$, $M_{a2}$, $M_{a3}$ - - - , $M_{ai}$, - - - , $M_{a(N-1)}$, each of which is the mass of the aggregate of the (N-1)th kind in the saturated surface-dried condition, are calculated one after another. The above-mentioned procedure is repeated similarly and it calculates one by one the percentage of surface moisture of the aggregate of the (N-1)th kind. Finally, aggregate of the Nth kind and required water are supplied to the submergence aggregate container so that the aggregate of the Nth kind may not come out from the water surface, and so that the total volume of the submergence aggregate may be maintained at the steady value $V_f$. In addition, an amount of supplied water $M_I$ and an amount of discharged water $M_O$ are measured as accumulation values.

Here, with required water, if the aggregate of the i-th kind does not come out from the water surface as mentioned above, it means that water may not be supplied. In this case, only the aggregate of the i-th kind is thrown into the submergence aggregate container.

Next, the mass $M_{aN}$ of the aggregate of the Nth kind in the saturated surface-dried condition and the mass $M_w$ of the water in the submergence aggregate are calculated from the following two formulas.

$$\Sigma M_{ai}(i=1\ to\ (N-1))+M_{aN}+M_w=\Sigma(M_{awi}(i=1\ to\ (N-1))+M_{awN}+(M_I-M_O) \tag{22}$$

$$\Sigma(M_{ai}/\rho_{ai})(i=1\ to\ (N-1))+M_{aN}/\rho_{aN}+M_w/\rho_w=V_f \tag{23}$$

Here, $\rho_{aN}$ is the density of the aggregate of the Nth kind in the saturated surface-dried condition. In addition, the percentage of surface moisture of the aggregate of the Nth kind is calculated by the following formula.

$$(M_{awN}-M_{aN})/M_{aN} \tag{24}$$

Thus, the mass $M_w$ of water, the mass $M_{ai}$ (i=1 to N) of the aggregate in the saturated surface-dried condition, and the percentage of surface moisture of each aggregate are measured and calculated. Next, the mass $M_w$ of water and the mass $M_{ai}$ (i=1 to N) of the aggregate in the saturated surface-dried condition are compared with a mix proportion shown by a specified mix, respectively. An insufficiency is then measured. If the insufficiency is water, the above-mentioned submergence aggregate is supplemented with water equal to the amount of the insufficiency so as to let the aggregate and the water be concrete material. On the other hand, taking the surface water of the aggregate into consideration using the computed percentage of surface moisture, if the insufficiency is the aggregate, the above-mentioned submergence aggregate is supplemented with aggregate equal to the amount of the insufficiency so as to let the aggregate and the water become concrete material. When there is too much water, the surplus is sucked with the vacuum and the like.

Thus, the surface water of aggregate is indirectly computed as a part of mass $M_w$ of water, even if an aggregate whose moisture state is not uniform is used, and the mass of aggregate is computed as the mass $M_{ai}$ (i=1 to N) of the aggregate in the saturated surface-dried condition. That is, since the mass of the aggregate and the water will be computed on conditions equivalent to the specified mix, even if the humidity grade of the aggregate is not fixed at every measurement, it becomes possible to make concrete from the amount of water as the specified mix.

In addition, a plurality of aggregates whose kinds, such as density and grading, are different are measured in high effectiveness and accuracy within one submergence aggregate container in the procedure mentioned above.

The volume of the measurement tank and the submergence aggregate container may be made equal to the entire quantity required for the unit of concrete mixing, i.e., one batch, or the volume may be made equal to the amount of one batch divided into some amounts.

When taking into consideration air content in submergence aggregate (a (%)), still higher-precision measurement can be performed with the actual total volume except the air content by replacing $V_{fi}$ (i=1 to N) or Vf with $V_{fi}$ (i=1 to N)·(1−a/100) or $V_f$·(1−a/100). However, in a case of the method for supplying a plurality of aggregates cumulatively, an aggregate rate in submergence aggregate increases gradually. Therefore, the air content in total volume should be considered in this connection.

(Measurement by a Submergence Method in a Case of Supplying Simultaneously a Plurality of Aggregates Whose Kinds are Different)

In a measuring method of concrete-forming materials according to still another aspect of the invention, mean-density $\rho_{ave}$ of an entire aggregate is first calculated from a mass ratio when mixing a plurality of aggregates whose kinds are different, and then calculated is density $\rho_{ai}$ (i=1 to N) of the aggregate of the i-th kind in a saturated surface-dried condition.

Next, the aggregates of the i-th kind (i=1 to N) and water are supplied to a predetermined measurement tank. Here, the aggregates are supplied simultaneously so that the aggregates and water may become submergence aggregate in which the aggregates of the i-th kind (i=1 to N) do not appear from the water surface.

When throwing the aggregates and the water into the measurement tank, it is arbitrary as to which should be thrown first, but if the water is thrown in first and the aggregates are thrown in later, especially in a case of fine aggregates, air bubble mixing of the submergence aggregate can be suppressed considerably.

Next, total mass $M_f$ of the submergence aggregate is measured. In order to measure the total mass $M_f$ of the submergence aggregate, the mass of only the measurement tank is subtracted from the mass of the measurement tank filled with the submergence aggregate.

Here, in order to measure total volume $V_f$ of the submergence aggregate, means for measuring a water level for measuring a level of the submergence aggregate, such as an electrode-type displacement sensor, can be used.

Next, summation $\Sigma M_{ai}$ (i=1 to N), that is, total mass of the aggregates of the i-th kind (i=1 to N) in a saturated surface-dried condition and the mass $M_w$ of water are calculated by solving the following two formulas.

$$\Sigma M_{ai}(i=1 \text{ to } N) + M_w = M_f \quad (25)$$

$$\Sigma M_{ai}(i=1 \text{ to } N)/\rho_{ave} + M_w/\rho_w = V_f \quad (26)$$

Here, $\rho_w$ is the density of water.

When the mass $M_w$ of water and summation $\Sigma M_{ai}$ (i=1 to N) are measured and calculated, these calculated values will be compared with a mix proportion shown by a specified mix, respectively. Subsequently, an insufficiency is measured and then the submergence aggregate is supplemented by an amount of the insufficiency so as to let the aggregate and the water become concrete material. When there is too much water, the surplus is sucked with a vacuum or the like.

Thus, the surface water of aggregate is indirectly computed as a part of mass $M_w$ of water, even if an aggregate whose moisture state is not uniform is used, and the mass of aggregate is computed as summation $\Sigma M_{ai}$ (i=1 to N). That is, since the mass of the aggregate and the water will be computed on conditions equivalent to the specified mix, even if a humidity grade of the aggregate is not fixed at every measurement, it becomes possible to make concrete from the amount of water as the specified mix.

In addition, a plurality of aggregates whose kinds, such as density and grading, are different are measured in terms of high effectiveness and accuracy within one measurement tank in the procedure mentioned above.

Here, if the total volume $V_f$ of the submergence aggregate is maintained at a steady value $V_f$ when throwing water and the aggregates of the i-th kind (i=1 to N) into the measurement tank, even if the total volume $V_f$ of the submergence aggregate is not measured, it will serve as a known value.

The total volume of the submergence aggregate is maintainable at a steady value $V_f$ by making the water in the submergence aggregate overflow from the measurement tank, or sucking the water in the submergence aggregate at a predetermined depth location in the measurement tank.

If the total mass $M_f$ of the submergence aggregate is measured at least as mentioned above, summation $\Sigma M_{ai}$ (i=1 to N), that is, total mass of a plurality of aggregates of the i-th kind (i=1 to N) in the saturated surface-dried condition and the mass $M_w$ of water can be calculated. In addition, if summation $\Sigma M_{awi}$ (i=1 to N), that is, total mass of a plurality of aggregates of the i-th kind (i=1 to N) in a wet condition is measured, the average percentage of surface moisture is computable with the following formula.

$$(\Sigma M_{awi}(i=1 \text{ to } N) - \Sigma M_{ai}(i=1 \text{ to } N))/\Sigma M_{ai}(i=1 \text{ to } N) \quad (27)$$

As another approach, the amount of water $M_I$ supplied to the measurement tank and the amount of water $M_O$ discharged from the measurement tank are measured as accumulation values, which measurement values are substituted for the following formula, and $\Sigma M_{awi}$ (i=1 to N) is calculated.

$$\Sigma M_{awi}(i=1 \text{ to } N) = M_f - (M_I - M_O) \quad (28)$$

Next, the average percentage of surface moisture can be calculated by the following formula.

$$(\Sigma M_{awi}(i=1 \text{ to } N) - \Sigma M_{ai}(i=1 \text{ to } N))/\Sigma M_{ai}(i=1 \text{ to } N) \quad (27)$$

Here, an accumulation value of the amount of water $M_I$ supplied to the measurement tank does not necessarily increase, but can be the amount of water thrown first; in other words, the accumulation value can be fixed without change. Similarly, water is not necessarily drained by the amount of water $M_O$ discharged from the measurement tank, but the accumulation value can remain zero. On the other hand, in order to maintain the total volume of the submergence aggregate at a steady value $V_f$, when making the water in the submergence aggregate overflow from the measurement tank or sucking the water in the submergence aggregate at the predetermined depth location in the measurement tank, the accumulation value of amount of discharged water $M_O$ increases.

(Measurement by a Submergence Method which does not Need Measurement of a Capacity and Mass in a Case of Supplying Simultaneously a Plurality of Aggregates Whose Kinds are Different)

In a measuring method of concrete-forming materials according to still another aspect of the invention, first, summation $\Sigma M_{wai}$ (i=1 to N), that is, total mass of a plurality of aggregates in a wet condition whose kinds are different are measured.

Next, mean-density $\rho_{ave}$ of the entire aggregate is calculated from a mass ratio when mixing the aggregates and density $\rho_{ai}$ (i=1 to N) of the aggregate of the i-th kind (i=1 to N) in a saturated surface-dried condition.

Next, the aggregates and water are supplied to a predetermined submergence aggregate container. Here, the aggregates are supplied simultaneously so that the aggregates and water may become submergence aggregate in which the aggregates do not appear from the water surface, and so that the total volume of the submergence aggregate may be maintained at a steady value $V_f$.

The total volume of the submergence aggregate is maintainable at the steady value $V_f$ by making the water in the submergence aggregate overflow from the submergence aggregate container, or sucking the water in the submergence aggregate at a predetermined depth location in the submergence aggregate container.

When throwing the aggregates and the water into the submergence aggregate container, it is arbitrary as to which should be thrown first, but if the water is thrown in first and the aggregates are thrown in later, especially in a case of fine aggregates, air bubble mixing in the submergence aggregate can be suppressed considerably.

When throwing the water and aggregate into the submergence aggregate container, an amount of water $M_I$ supplied to the submergence aggregate container and an amount of water $M_O$ discharged from the submergence aggregate container are measured as accumulation values.

Next, summation $\Sigma M_{ai}$ (i=1 to N), that is, total mass of a plurality of aggregates of the i-th kind (i=1 to N) in a saturated surface-dried condition and the mass $M_w$ of water are calculated by solving the following two formulas.

$$\Sigma M_{ai}(i=1 \text{ to } N) + M_w = \Sigma M_{awi}(i=1 \text{ to } N) + (M_I - M_O) \quad (29)$$

$$\Sigma M_{ai}(i=1 \text{ to } N)/\rho_{ave} + M_w/\rho_w = V_f \quad (30)$$

Here, $\rho_w$ is the density of water.

In addition, the average percentage of surface moisture of the aggregates of the i-th kind (i=1 to N) is calculated from the following formula.

$$(\Sigma M_{awi}(i=1 \text{ to } N) - \Sigma M_{ai}(i=1 \text{ to } N))/\Sigma M_{ai}(i=1 \text{ to } N) \quad (31)$$

When the mass $M_w$ of water, summation $\Sigma M_{ai}$ (i=1 to N) and the average percentage of surface moisture are measured and calculated, these calculated values will be compared with a mix proportion shown by a specified mix, respectively. An insufficiency is then measured. If the insufficiency is water, the above-mentioned submergence aggregate is supplemented with water in an amount equal to the insufficiency so as to let the aggregate and the water become concrete material. On the other hand, taking the surface water of the aggregates into consideration using the computed average percentage of surface moisture, if the insufficiency is the aggregate, the above-mentioned submergence aggregate is supplemented with the aggregate in an amount equal to the insufficiency so as to let the aggregate and the water become concrete material. When there is too much water, the surplus is sucked with a vacuum or the like.

Thus, the surface water of aggregate is indirectly computed as a part of mass $M_w$ of water, even if an aggregate whose moisture state is not uniform is used, and the mass of aggregate is computed as summation $\Sigma M_{ai}$ (i=1 to N). That is, since the mass of the aggregate and the water will be computed on conditions equivalent to the specified mix, even if a humidity grade of the aggregate is not fixed at every measurement, it becomes possible to make concrete with the amount of water as that of the specified mix.

In addition, a plurality of aggregates whose kinds, such as density and grading, are different are measured in terms of high effectiveness and accuracy within one measurement tank in the procedure mentioned above.

The volume of the measurement tank and the submergence aggregate container may be made equal to the entire quantity required for a unit of concrete mixing, i.e., one batch, or may be made equal to the amount of one batch divided into some amounts.

When taking into consideration air content in submergence aggregate (a (%)), still higher-precision measurement can be performed with the actual total volume except the air content by replacing $V_f$ with $V_{fi} \cdot (1-a/100)$.

(Real-Time Measurement by a Submergence Method)

In a measuring method of concrete-forming materials according to still another aspect of the invention, first, aggregate and water are supplied to a predetermined measurement tank so that they may become submergence aggregate in which the aggregate does not appear from the water surface.

When throwing the aggregate and the water into the measurement tank, it is arbitrary as to which should be thrown first, but if the water is thrown in first and the aggregate is thrown in later, especially in a case of fine aggregate, air bubble mixing in the submergence aggregate can be suppressed considerably.

Next, total mass $M_f$ of the submergence aggregate is measured.

In order to measure the total mass $M_f$ of the submergence aggregate, the mass of only the measurement tank is subtracted from the mass of the measurement tank filled with the submergence aggregate.

Here, in order to measure total volume $V_f$ of the submergence aggregate, means for measuring a water level for measuring a level of the submergence aggregate, such as an electrode-type displacement sensor, can be used.

Next, the mass $M_a$ of the aggregate in the saturated surface-dried condition and the mass $M_w$ of the water in the submergence aggregate are calculated from the following two formulas.

$$M_a + M_w = M_f \quad (1)$$

$$M_a/\rho_a + M_w/\rho_w = V_f \quad (2)$$

Here, $\rho_a$ is the density of the aggregate in the saturated surface-dried condition, and $\rho_w$ is the density of water.

Here, in order to calculate the mass $M_a$ of the aggregate in the saturated surface-dried condition in the procedure mentioned above, the aggregate to the measurement tank is supplied continuously or intermittently at a predetermined rate. And when total mass $M_f$ of the submergence aggregate is measured in real time or at predetermined time intervals and the mass $M_a$ in the saturated surface-dried condition of the aggregate reaches a scheduled input, ds throwing the aggregate is stopped.

Real-time measurement means a measurement performed at predetermined time intervals, supplying aggregate, and it is contained also when measuring continuously.

Next, the mass $M_w$ of the water when finishing throwing the aggregate is compared with a mix proportion of the water shown by a specified mix. If the mass $M_w$ of water is insufficient, it is supplemented with water in an amount equal to this insufficiency, and when there is too much mass $M_w$ of water, the excess water is removed by a vacuum or the like. Then, the aggregate and the water are allowed to become concrete material.

Thus, the surface water of aggregate is indirectly computed as a part of mass $M_w$ of water, even if an aggregate whose moisture state is not uniform is used, and the mass of aggregate is computed as mass $M_a$ in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

In addition, as mentioned above, since the throwing of the aggregate into the measurement tank is ended when the mass $M_a$ of the aggregate in the saturated surface-dried condition reaches a scheduled input, while measuring total mass $M_f$ of the submergence aggregate in real time or at predetermined time intervals, a possibility that excess and deficiency may arise in terms of measurement of aggregate disappears, and effectiveness of aggregate measurement improves.

The total volume $V_f$ of the submergence aggregate is measurable during aggregate measurement using an electrode-type displacement sensor or the like, as mentioned above. At this point, if the total volume $V_f$ of the submergence aggregate is maintained at a steady value when water and aggregate are supplied to the measurement tank, the total volume $V_f$ of the submergence aggregate will serve as a known value, and it will become unnecessary to measure it.

The total volume of the submergence aggregate is maintainable at a steady value $V_f$ by making the water in the submergence aggregate overflow from the measurement tank or by sucking the water in the submergence aggregate at a predetermined depth location in the measurement tank.

Moreover, if the total mass $M_f$ of the submergence aggregate is measured at least as mentioned above, the mass $M_a$ of the aggregate in the saturated surface-dried condition and the mass $M_w$ of water can be calculated. That is, first, the amount of water $M_I$ supplied to the measurement tank and the amount of water $M_O$ discharged from the measurement tank are measured as accumulation values, and, subsequently $M_{aw}$ is calculated by the following formula.

$$M_{aw} = M_f - (M_I - M_O) \tag{4}$$

Next, the percentage of surface moisture of the aggregate is computable by substituting $M_{aw}$ for the following formula.

$$(M_{aw} - M_a)/M_a \tag{3}$$

Here, an accumulation value of the amount of water $M_I$ supplied to the measurement tank does not necessarily increase, but can be the amount of water thrown first; in other words, the accumulation value can be fixed without change. Similarly, water is not necessarily drained by the amount of water $M_O$ discharged from the measurement tank, but the accumulation value can remain zero. On the other hand, in maintaining the total volume $V_f$ of the submergence aggregate at a steady value by making the water in the submergence aggregate overflow from the measurement tank and sucking the water in the submergence aggregate at the predetermined depth location in the measurement tank, the accumulation value of amount of discharged water $M_O$ increases.

The volume of the measurement tank may be made equal to the entire quantity required for a unit of concrete mixing, i.e., one batch, or may be made equal to an amount of one batch divided into some amounts.

(Real-Time Measurement by a Submergence Method in a Case of Supplying Cumulatively a Plurality of Aggregates Whose Kinds are Different)

In a measuring method of concrete-forming materials according to still another aspect of the invention, first, aggregate of a first kind and water are supplied to a predetermined measurement tank so that the water and aggregate may become submergence aggregate in which the aggregate of the first kind does not appear from the water surface.

When throwing the aggregate and the water into the measurement tank, it is arbitrary as to which should be thrown first, but if the water is thrown in first and the aggregate is thrown in later, especially in a case of fine aggregate, air bubble mixing in the submergence aggregate can be suppressed considerably.

Next, total mass $M_{f1}$ of the submergence aggregate is measured. In order to measure the total mass $M_{f1}$ of the submergence aggregate, the mass of only the measurement tank is subtracted from the mass of the measurement tank filled with the submergence aggregate.

Here, in order to measure total volume $V_{f1}$ of the submergence aggregate, means for measuring a water level for measuring a level of the submergence aggregate, such as an electrode-type displacement sensor, can be used.

Next, mass $M_{a1}$ of the aggregate of the first kind in a saturated surface-dried condition is calculated by solving the following two formulas.

$$M_{a1} + M_w = M_{f1} \tag{7}$$

$$M_{a1}/\rho_{a1} + M_w/\rho_w = V_{f1} \tag{8}$$

Here, $\rho_{a1}$ is the density of the aggregate of the first kind in the saturated surface-dried condition, and $\rho_w$ is the density of water.

Next, aggregate of a second kind and required water are supplied to the measurement tank so that the aggregate of the second kind may not come out from the water surface, namely, so that it may become submergence aggregate. Here, when throwing the aggregate of the second kind, as long as a state of submergence aggregate, i.e., a state where the aggregate of the second kind does not come out from the water surface is maintained, it is not necessary to perform additional throwing of water. Required water means water required for maintaining a state of submergence aggregate.

Next, total mass $M_{f2}$ of the submergence aggregate is measured, and, subsequently mass $M_{a2}$ of the aggregate of the second kind in the saturated surface-dried condition is calculated from the following two formulas.

$$M_{a1} + M_{a2} + M_w = M_{f2} \tag{9}$$

$$M_{a1}/\rho_{a1} + M_{a2}/\rho_{a2} + M_w/\rho_w = V_{f2} \tag{10}$$

Here, $V_{f2}$ is a total volume of the submergence aggregate and $\rho_{a2}$ is a density of the aggregate of the second kind in the saturated surface-dried condition.

Hereafter, by repeating the above-mentioned procedure, $M_{a1}, M_{a2}, M_{a3} - - -, M_{ai}, - - -, M_{a(N-1)}$, each of which is the mass of aggregate of the (N-1)th kind in the saturated surface-dried condition, are calculated one after another. Finally aggregate of the Nth kind and required water are supplied to the measurement tank so that the aggregate of the Nth kind does not come out from the water surface, namely, so that it may become submergence aggregate.

Here, with required water, if the aggregate of the i-th kind does not come out from the water surface as mentioned above, it means that water may not be supplied. In this case, only the aggregate of the i-th kind is thrown into the measurement tank.

Next, total mass $M_{fN}$ of the submergence aggregate is measured. Subsequently, mass $M_{aN}$ of the aggregate of the Nth kind in the saturated surface-dried condition and mass $M_w$ of water are calculated from the following two formulas.

$$\Sigma M_{ai}(i=1 \text{ to } (N-1)) + M_{aN} + M_w = M_{fN} \tag{11}$$

$$\Sigma M_{ai}/\rho_{ai}(i=1 \text{ to } (N-1)) + M_{aN}/\rho_{aN} + M_w/\rho_w = V_{fN} \tag{12}$$

Here, $V_{fN}$ is a total volume of the submergence aggregate and $\rho_{aN}$ is a density of the aggregate of the Nth kind in the saturated surface-dried condition.

Here, in order to calculate the mass $M_{ai}$ (i=1 to N) of the aggregate of the Nth kind in the saturated surface-dried condition in the procedure mentioned above, the aggregate is supplied to the measurement tank continuously or intermittently at a predetermined rate. And when total mass $M_{fi}$ (i=1 to N) of the submergence aggregate is measured in real time or at predetermined time intervals and the mass $M_{ai}$ (i=1 to N) of the aggregate of the Nth kind in the saturated surface-dried condition reaches a scheduled input, the throwing of the aggregate is ended.

In a process which throws cumulatively the aggregates of the i-th kind (i=1 to N) one by one, after ending throwing of aggregate during throwing the j-th aggregate or after such throwing, the mass $M_w$ of the water at that time is compared with a mix proportion of the water shown by a specified mix. And if the mass $M_w$ of water is insufficient, it is supplemented with water equal to an amount of this insufficiency, and when there is too much mass $M_w$ of water, the excess water is removed by a vacuum or the like, whereby the aggregate and the water are allowed to become concrete material.

Thus, the surface water of aggregate is indirectly computed as a part of mass $M_w$ of water, even if the aggregate whose moisture state is not uniform is used, and the mass of aggregate is computed as the mass $M_{ai}$ (i=1 to N) of the aggregate in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

In addition, as mentioned above, since the throwing of the aggregate into the measurement tank continuously at a predetermined rate or intermittently is ended when the mass $M_{ai}$ (i=1 to N) of the aggregate in the saturated surface-dried condition reaches a scheduled input, while measuring total mass $M_{fi}$ (i=1 to N) of the submergence aggregate in real time or at predetermined time intervals, a possibility that excess and deficiency may arise in measurement of aggregate disappears, and effectiveness of aggregate measurement improves.

Real-time measurement means a measurement performed at predetermined time intervals, while supplying aggregate, and it also includes measuring continuously.

In addition, a plurality of aggregates whose kinds, such as density and grading, are different are measured in terms of high effectiveness and accuracy within one measurement tank in the procedure mentioned above.

The total volume $V_{fi}$ (i=1 to N) of the submergence aggregate is measurable during aggregate measurement using an electrode-type displacement sensor or the like, as mentioned above. Here, if the total volume $V_{fi}$ (i=1 to N) of the submergence aggregate is maintained at a steady value $V_f$ when throwing water and the aggregates of the i-th kind (i=1 to N) into the measurement tank, even if the total volume $V_f$ of the submergence aggregate is not measured, this volume will serve as a known value.

The total volume of the submergence aggregate is maintainable at a steady value $V_f$ by making the water in the submergence aggregate overflow from the measurement tank or by sucking the water in the submergence aggregate at the predetermined depth location in the measurement tank.

If the total mass $M_{fi}$ (i=1 to N) of the submergence aggregate is measured at least as mentioned above, $M_{ai}$ (i=1 to N) of the mass of the aggregates of the i-th kind (i=1 to N) in the saturated surface-dried condition and the mass $M_w$ of water, can be calculated.

That is, the amount of water $M_I$ supplied to the measurement tank and the amount of water $M_O$ discharged from the measurement tank are first measured as accumulation values.

Next, $\Sigma M_{awj}$ (j=1, 2, 3, . . . i) is calculated by the following formula.

$$\Sigma M_{awj}(j=1 \text{ to } i) = M_{fi} - (M_I - M_O) \tag{14}$$

$$\Sigma M_{awj}(j=1 \text{ to } i) - \Sigma M_{awj}(j=1 \text{ to } (i-1)) \tag{15}$$

Next, the percentage of surface moisture of the aggregates of the i-th kind (i=1 to N) are computable by substituting $M_{awi}$ for the following formula.

$$(M_{awi} - M_{ai})/M_{ai} \tag{13}$$

Here, the accumulation value of the amount of water $M_I$ supplied to the measurement tank does not necessarily increase, but can be the amount of water thrown first; in other words, the accumulation value can be fixed without change. Similarly, water is not necessarily drained by the amount of water $M_O$ discharged from the measurement tank, but the accumulation value can remain zero. On the other hand, in maintaining the total volume $V_{fi}$ (i=1 to N) of the submergence aggregate at a steady value $V_f$ by making the water in the submergence aggregate overflow from the measurement tank or by sucking the water in the submergence aggregate at the predetermined depth location in the measurement tank, the accumulation value of amount of discharged water $M_O$ increases.

In order to calculate the mass $M_{awi}$ of the aggregates of the i-th kind (i=1 to N) in a wet condition, it is necessary to calculate one by one from the aggregate of the first kind. That is, first, the mass of the aggregate of the first kind in a wet condition is calculated, the mass of the aggregate of the second kind in a wet condition is calculated using this value, and then the mass of a third aggregate in wet condition is calculated using these two values.

The volume of the measurement tank may be made equal to the entire quantity required for a unit of concrete mixing, i.e., one batch, or may be made equal to the amount of one batch divided into some amounts.

(Real-Time Measurement by a Submergence Method in a Case of Supplying Simultaneously a Plurality of Aggregates Whose Kinds are Different)

In a measuring method of concrete-forming materials according to still another aspect of the invention, first, mean-density $\rho_{ave}$ of the entire aggregate is calculated from a mass ratio when mixing a plurality of aggregates whose kinds are different, and then calculated is density $\rho_{ai}$ (i=1 to N) of the aggregate of the i-th kind in a saturated surface-dried condition.

Next, the aggregates and water are supplied to a predetermined measurement tank. Here, the aggregates are supplied simultaneously so that the aggregates and water may become submergence aggregate in which the aggregates do not appear from the water surface.

When throwing the aggregate and the water into the measurement tank, it is arbitrary as to which should be thrown first, but if the water is thrown in first and the aggregates are thrown in later, especially in a case of fine aggregate, air bubble mixing in the submergence aggregate can be suppressed considerably.

Next, total mass $M_f$ of the submergence aggregate is measured. In order to measure the total mass $M_f$ of the submergence aggregate, the mass of only the measurement tank is subtracted from the mass of the measurement tank filled with the submergence aggregate.

Here, in order to measure total volume $V_f$ of the submergence aggregate, means for measuring a water level for measuring a level of the submergence aggregate, such as an electrode-type displacement sensor, can be used.

Next, summation $\Sigma M_{ai}$ (i=1 to N), that is, total mass of a plurality of aggregates whose kinds are different in a saturated surface-dried condition, and the mass $M_w$ of water, is calculated by solving the following two formulas.

$$\Sigma M_{ai}(i=1 \text{ to } N) + M_w = M_f \tag{25}$$

$$\Sigma M_{ai}(i=1 \text{ to } N)/\rho_{ave} + M_w/\rho_w = V_f \tag{26}$$

Here, $\rho_w$ is the density of water.

Here, in order to calculate $\Sigma M_{ai}$ (i=1 to N), that is, total mass of the aggregate of the i-th kind (i=1 to N) in the saturated surface-dried condition in the procedure mentioned above, the aggregates are supplied to the measurement tank continuously or intermittently at a predetermined rate. And when $M_f$ of the submergence aggregate is measured in real time or at predetermined time intervals and the mass $\Sigma M_{ai}$ (i=1 to N) reaches a scheduled input, the throwing of the aggregates is ended.

Next, the mass $M_w$ of the water when finishing throwing the aggregate is compared with a mix proportion of the water shown by a specified mix. And if the mass $M_w$ of water is insufficient, it is supplemented with water of an amount equal to that of this insufficiency, and when there is too much mass $M_w$ of water, the excess water is removed by a vacuum or the like, whereby the aggregate and the water become concrete material.

Thus, the surface water of aggregate is indirectly computed as a part of mass $M_w$ of water, even if an aggregate whose moisture state is not uniform is used, and the mass of aggregate is computed as $\Sigma M_{ai}$ (i=1 to N), that is, total mass of the aggregate of the i-th kind (i=1 to N) in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

In addition, as mentioned above, since the throwing of the aggregate into the measurement tank continuously at a predetermined rate or intermittently is ended when $\Sigma M_{ai}$ (i=1 to N) reaches a scheduled input, while measuring total mass $M_f$ of the submergence aggregate in real time or at predetermined time intervals, a possibility that excess and deficiency may arise in measurement of aggregate disappears, and effectiveness of aggregate measurement improves.

Real-time measurement means a measurement performed at predetermined time intervals, while supplying aggregate, and it also includes measuring continuously.

In addition, a plurality of aggregates whose kinds, such as density and grading, are different are measured in terms of high effectiveness and accuracy within one measurement tank in the procedure mentioned above.

Here, if the total volume $V_f$ of the submergence aggregate is maintained at a steady value $V_f$ when throwing water and the aggregates of the i-th kind (i=1 to N) into the measurement tank, even if the total volume $V_f$ of the submergence aggregate is not measured, this volume will serve as a known value.

The total volume of the submergence aggregate is maintainable at a steady value $V_f$ by making the water in the submergence aggregate overflow from the measurement tank or by sucking the water in the submergence aggregate at a predetermined depth location in the measurement tank.

If the total mass $M_f$ of the submergence aggregate is measured at least as mentioned above, summation $\Sigma M_{ai}$ (i=1 to N) of the mass of the aggregate of the i-th kind (i=1 to N) in the saturated surface-dried condition, and the mass $M_w$ of water, can be calculated. That is, the amount of water $M_I$ supplied to the measurement tank and the amount of water $M_O$ discharged from the measurement tank are first measured as accumulation values. Next, $\Sigma M_{awi}$ (i=1 to N) is calculated by the following formula.

$$\Sigma M_{awi}(i=1 \text{ to } N) = M_f - (M_I - M_O) \qquad (28)$$

Next, the average percentage of surface moisture of the aggregate of the i-th kind (i=1 to N) is computable by substituting $\Sigma M_{awi}$ for the following formula.

$$(\Sigma M_{awi}(i=1 \text{ to } N) - \Sigma M_{ai}(i=1 \text{ to } N))/\Sigma M_{ai}(i=1 \text{ to } N) \qquad (27)$$

Here, an accumulation value of the amount of water $M_I$ supplied to the measurement tank does not necessarily increase, but can be the amount of water thrown first; in other words, the accumulation value can be fixed without change. Similarly, water is not necessarily drained by the amount of water $M_O$ discharged from the measurement tank, but the accumulation value can remain zero.

On the other hand, in maintaining the total volume $V_f$ of the submergence aggregate at a steady value by making the water in the submergence aggregate overflow from the measurement tank or by sucking the water in the submergence aggregate at the predetermined depth location in the measurement tank, the accumulation value of amount of discharged water $M_O$ increases.

The volume of the measurement tank may be made equal to the entire quantity required for a unit of concrete mixing, i.e., one batch, or may be made equal to the amount of one batch divided into some amounts.

When taking into consideration air content in submergence aggregate (a (%)), still higher-precision measurement can be performed with the actual total volume except the air content by replacing Vf with $V_{fi} \cdot (1-a/100)$.

(Another Measurement by a Submergence Method in a Case of Supplying a Plurality of Aggregates Whose Kinds are Different)

In another measuring method of concrete-forming materials concerning the present invention, first, target mass Mdi (i=1 to N) of submergence aggregate at a time of ending throwing the i-th (i=1 to N) aggregate is set up, respectively.

Next, aggregate of a first kind and water are supplied to the measurement tank so that the aggregate of the first kind may not come out from the water surface; namely, so that the water and aggregate may become submergence aggregate.

When throwing the aggregate and the water into the measurement tank, it is arbitrary as to which should be thrown first, but if the water is thrown in first and the aggregate is thrown in later, especially in a case of fine aggregate, air bubble mixing in the submergence aggregate can be suppressed considerably.

Next, total mass $M_{f1}$ of the submergence aggregate is measured. In order to measure the total mass $M_{f1}$ of the submergence aggregate, the mass of only the measurement tank is subtracted from the mass of the measurement tank filled with the submergence aggregate.

Next, total volume $V_{f1}$ of the submergence aggregate is measured. Here, in order to measure total volume $V_{f1}$ of the submergence aggregate, means for measuring a water level for measuring a level of the submergence aggregate, such as an electrode-type displacement sensor, can be used.

Next, when the total mass $M_{f1}$ of the submergence aggregate reaches the target mass $M_{d1}$, throwing the aggregate of the first kind into the measurement tank is ended. Subsequently, the total mass $M_{f1}$ and total volume $V_{f1}$ of the submergence aggregate at that time are substituted for the following formula, and mass $M_{a1}$ in a saturated surface-dried condition of the aggregate of the first kind is calculated.

$$M_{a1} = \rho_{a1}(M_{f1} - \rho_w V_{f1})/(\rho_{a1} - \rho_w) \qquad (32)$$

Here, $\rho_{a1}$ is the density of the aggregate of the first kind in the saturated surface-dried condition, and $\rho_w$ is the density of water.

Next, like the aggregate of the first kind, the aggregate of a second kind is thrown into the measurement tank so that it may become submergence aggregate in which the aggregate of the second kind does not appear from the water surface, the total mass $M_{f2}$ of the submergence aggregate is measured, and, subsequently the total volume $V_{f2}$ of the submergence aggregate is measured.

Next, when the total mass $M_{f2}$ of the submergence aggregate reaches the target mass $M_{d2}$, throwing the aggregate of the second kind into the measurement tank is ended. Subsequently, the total mass $M_{f2}$ and total volume $V_{f2}$ of the submergence aggregate at that time are substituted for the following formula, and mass $M_{a2}$ in the saturated surface-dried condition of the aggregate of the second kind is calculated.

$$M_{a2} = \rho_{a2}((M_{f2} - M_{a1}) - \rho_w(V_{f2} - M_{a1}/\rho_{a1}))/(\rho_{a2} - \rho_w) \quad (33)$$

Here, $\rho_{a1}$ is the density of the aggregate of the first kind in the saturated surface-dried condition, $\rho_{a2}$ is the density of the aggregate of the second kind in the saturated surface-dried condition, and $\rho_w$ is the density of water.

Hereafter, the above-mentioned procedure is repeated, aggregate measurement is calculated one by one for the mass $M_{a(N-1)}$ in the saturated surface-dried condition of the aggregate of (N−1)th kind, and finally, the aggregate of the Nth kind is thrown into the measurement tank so that it and water may become submergence aggregate in which the aggregate of the Nth kind does not appear from the water surface.

Next, as mentioned above, similarly, the total mass $M_{fN}$ of the submergence aggregate is measured, and the total volume $V_{fN}$ of the submergence aggregate is measured further.

Next, when the total mass $M_{fN}$ of the submergence aggregate reaches a target mass $M_{dN}$, throwing the aggregate of the Nth kind into the measurement tank is ended. Subsequently, the total mass $M_{fN}$ and total volume $V_{fN}$ of the submergence aggregate at that time are substituted for the following formulas, and mass $M_{aN}$ in the saturated surface-dried condition of the aggregate of the Nth kind is calculated. The mass $M_w$ of water is also calculated simultaneously.

$$M_{aN} = \rho_{aN}((M_{fN} - \Sigma M_{ai}(i=1 \text{ to } (N-1))) - \rho_w(V_{fN} - \Sigma(M_{ai}/\rho_{ai})(i=1 \text{ to } (N-1))))/(\rho_{aN} - \rho_w) \quad (34)$$

$$M_w = \rho_w(\rho_{aN}(V_{fN} - \Sigma(M_{ai}/\rho_{ai})(i=1 \text{ to } (N-1))) - (M_{fN} - \Sigma M_{ai}(i=1 \text{ to } (N-1))))/(\rho_{aN} - \rho_w) \quad (35)$$

Here, $\rho_{ai}$ (i=1 to N) is the density of the aggregate of the i-th kind in the saturated surface-dried condition, and $\rho_w$ is the density of water.

The total mass $M_{fi}$ (i=1 to N) of the submergence aggregate is measured in real time or at predetermined time intervals while supplying the aggregate of the i-th kind (i=1 to N) continuously or intermittently at a predetermined rate, when throwing cumulatively the aggregate into the measurement tank, respectively. In addition, when the total mass $M_{fj}$ of the submergence aggregate reaches the target mass $M_{dj}$ while supplying the j-th aggregate, as mentioned above, the j-th aggregate throwing is ended. If aggregate which should be cumulatively supplied further exists (i.e., if a plurality of aggregates should be supplied cumulatively and the j-th aggregate is not the last aggregate), the (j+1)-th aggregate is similarly supplied continuously as mentioned above.

When the mass $M_w$ of water and $M_{ai}$ (i=1 to N) are measured and calculated, original field mixes set up according to a specified mix are compared with these calculated results, and a field mix is corrected if needed. That is, the mass of the measured aggregate and the aggregate mass of the field mix are compared, and the mixing volume of one batch is corrected according to a ratio obtained as a result of this comparison. And according to this ratio, the submergence aggregate is supplemented with water, of an amount equal to an insufficiency, as secondary water, or excess water is drained.

Furthermore, according to the ratio mentioned above, each amount of other concrete-forming materials in the field mix, such as cement and a chemical admixture, is corrected. Next, above-mentioned concrete-forming materials are measured according to a corrected field mix. Finally, these concrete-forming materials are thrown into a kneading mixer, and are kneaded.

Thus, the surface water of aggregate is indirectly computed as a part of mass $M_w$ of water, even if an aggregate whose moisture state is not uniform is used, and the mass of aggregate is computed as the mass Mai (i=1 to N) of the aggregate in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

Furthermore, the total mass $M_{fi}$ (i=1 to N) of the submergence aggregate is measured in real time or at predetermined time intervals while supplying the aggregate of the i-th kind (i=1 to N) to the measurement tank continuously, or intermittently at a predetermined rate. Since the j-th aggregate throwing is ended when the total mass $M_{fj}$ of the submergence aggregate reaches the target mass $M_{dj}$ during the j-th aggregate throwing in the aggregate of the i-th kind mentioned above, it becomes possible to manage correctly the amount of the i-th (i=1 to N) aggregate, and to correct the field mix, consequently to make concrete as the specified mix.

In addition, a plurality of aggregates whose kinds, such as density and grading, are different can be measured in terms of high effectiveness and accuracy within one measurement tank in the procedure mentioned above.

(Another Measurement by a Submergence Method in a Case of Supplying a Plurality of Aggregates Whose Kinds are Different)

In another measuring method of concrete-forming materials concerning the present invention, first, target mass Mdi (i=1 to N) of submergence aggregate at a time of ending throwing the i-th (i=1 to N) aggregate is set up respectively.

Next, aggregate of a first kind and water are supplied to the measurement tank so that the aggregate of the first kind may not come out from the water surface; namely, so that the water and aggregate may become submergence aggregate.

When throwing the aggregate and the water into the measurement tank, it is arbitrary as to which should be thrown first, but if the water is thrown in first and the aggregate is thrown in later, especially in a case of fine aggregate, air bubble mixing in the submergence aggregate can be suppressed considerably.

Next, total mass $M_{f1}$ of the submergence aggregate is measured. In order to measure the total mass $M_{f1}$ of the submergence aggregate, the mass of only the measurement tank is subtracted from the mass of the measurement tank filled with the submergence aggregate.

Next, the total mass $M_{f1}$ of the submergence aggregate and the total volume $V_{f1}$ of the submergence aggregate are substituted for formula (32), and the mass $M_{a1}$ in a saturated surface-dried condition of the aggregate of a first kind is calculated. $V_{f1}$ is determined from a first water level set up beforehand. Here, $\rho_{a1}$ is the density of the aggregate of the first kind in the saturated surface-dried condition, and $\rho_w$ is the density of water.

The first water level can be beforehand set up by making the water in the submergence aggregate overflow from the measurement tank at a predetermined depth location in the measurement tank, or by performing suction drainage of the water in the submergence aggregate at the predetermined depth location.

Next, like the aggregate of the first kind, aggregate of a second kind is thrown into the measurement tank so that it may become part of the submergence aggregate, which does not come out from the water surface, and subsequently the total mass $M_{f2}$ of the submergence aggregate is measured.

Next, the total mass $M_{f2}$ of the submergence aggregate and the total volume $V_{f2}$ of the submergence aggregate are substituted for formula (33), and the mass $M_{a2}$ in the saturated surface-dried condition of the aggregate of the second kind is calculated. $V_{f2}$ is determined from a second water level set up beforehand. Here, $\rho_{a1}$ is the density of the aggregate of the first kind in the saturated surface-dried condition, $\rho_{a2}$ is the density of the aggregate of the second kind in the saturated surface-dried condition, and $\rho_w$ is the density of water.

Like the first water level, the second water level can be beforehand set up by making the water in the submergence aggregate overflow from the measurement tank at a predetermined depth location in the measurement tank, or by performing suction drainage of the water in the submergence aggregate at the predetermined depth location.

Hereafter, by repeating the above-mentioned procedure, the mass of the aggregate in the saturated surface-dried condition is calculated one by one to the mass $M_{a(N-1)}$ of the aggregate of (N−1)th kind in the saturated surface-dried condition, and finally, aggregate of the Nth kind is thrown into the measurement tank so that it may become part of the submergence aggregate, which does not come out from the water surface.

Next, the total mass $M_{fN}$ of the submergence aggregate is similarly measured as mentioned above.

Next, the total mass $M_{fN}$ and the total volume $V_{fN}$ of the submergence aggregate are substituted for formulas (34) and (35), and the mass $M_{aN}$ of the aggregate of the Nth kind in the saturated surface-dried condition and the mass $M_w$ of water are calculated. Here, $\rho_{ai}$ (i=1 to N) is the density of the aggregate of the i-th kind in the saturated surface-dried condition, and $\rho_w$ is the density of water. In addition, the total volume $V_{fN}$ of the submergence aggregate can be calculated from Nth water level, and the Nth water level can be set up like the first water level and the second water level which were mentioned above.

The total mass $M_{fi}$ (i=1 to N) of the submergence aggregate is measured in real time or at predetermined time intervals while supplying the aggregate of i-th kind (i=1 to N) continuously, or intermittently at a predetermined rate, when throwing cumulatively the aggregate into the measurement tank, respectively. While draining redundant water from the measurement tank so that the water level of the submergence aggregate may not exceed the j-th water level during the j-th aggregate throwing, the j-th aggregate throwing is ended when the total mass $M_{fj}$ of the submergence aggregate reaches the target mass $M_{dj}$ of the submergence aggregate.

On the other hand, if the water level of the submergence aggregate does not reach the j-th water level, when there is no redundant water, it is supplemented with water so that it may reach the j-th water level, and, subsequently re-measurement of the total mass $M_{fj}$ of the submergence aggregate, recalculation of the mass $M_{aj}$ of the j-th aggregate in the saturated surface-dried condition, and recalculation of the mass $M_w$ of water are performed.

If aggregate which should be cumulatively supplied further exists (i.e., if a plurality of aggregates should be supplied cumulatively and the j-th aggregate is not the last aggregate), the (j+1)-th aggregate is similarly supplied continuously as mentioned above.

Thus, after measuring the i-th (i=1 to N) aggregate and water, other concrete-forming materials, such as cement and a chemical admixture, are appropriately measured. With these concrete-forming materials, the i-th (i=1 to N) aggregate and water are fed into a kneading mixer and are kneaded.

Here, when the total mass $M_{fj}$ of the submergence aggregate reaches the target mass $M_{dj}$ of the submergence aggregate, while draining redundant water so that the water level of the submergence aggregate may not exceed the j-th water level set up beforehand, the mass $M_{aj}$ of the j-th aggregate in the saturated surface-dried condition becomes equal to the value set up first. Therefore, it is not necessary to correct the field mix.

On the other hand, when the water level of the submergence aggregate has not reached the j-th water level set up beforehand, it is supplemented with water so that it may reach this j-th water level. Therefore, the calculated value of the mass $M_{aj}$ of the j-th aggregate in the saturated surface-dried condition differs from the value set up first. In this case, the value measured and calculated is compared with the value of the field mix set up first according to the specified mix, and, subsequently corrects the field mix if needed. That is, the measured aggregate mass and the aggregate mass of the field mix setup first are compared, and the mixing volume of one batch is corrected according to a ratio obtained by this comparison. In addition, according to this ratio, the submergence aggregate is supplemented with water, equal in amount to that of an insufficiency, as secondary water, or excess water is drained. Similarly, with regard to the amount of other concrete-forming materials, such as cement and a chemical admixture, the original field mix is corrected according to the ratio mentioned above, other concrete-forming materials are measured according to this correction, and these are thrown into the kneading mixer and kneaded.

Thus, the surface water of aggregate is indirectly computed as a part of mass $M_w$ of water, even if an aggregate whose moisture state is not uniform is used, and the mass of aggregate is computed as the mass $M_{ai}$ (i=1 to N) of the aggregate in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

As mentioned above, when the total mass $M_{fj}$ of the submergence aggregate reaches the target mass $M_{dj}$ of the submergence aggregate, j-th aggregate throwing is ended, and when the water level of the submergence aggregate at that time has not reached the j-th water level set up beforehand, it is supplemented with water so that it may reach this j-th water level. And re-measurement of mass $M_{fj}$, recalculation of mass $M_{aj}$, and recalculation of mass $M_w$ are performed. Therefore, the total volume $V_{fi}$ (i=1 to N) of the submergence aggregate serves as a known value, by which it becomes unnecessary to measure this volume, and the input of the i-th (i=1 to N) aggregate can be managed correctly. And it becomes possible as a result to make concrete as the specified mix.

In addition, a plurality of aggregates whose kinds, such as density and grading, are different are measured in terms of high effectiveness and accuracy within one measurement tank in the procedure mentioned above.

The percentage of surface moisture of the i-th (i=1 to N) aggregate can be calculated in the following procedure. That is, the amount of supplied to water $M_f$ the measurement tank and the amount of water $M_O$ discharged from the measurement tank are first measured as accumulation values. Next, the amount of supplied water $M_f$, the amount of discharged water $M_O$, and the total mass $M_{fi}$ (i=1 to N) are substituted for the following formula, and $\Sigma M_{awj}$ (j=1, 2, 3, . . . i) is calculated.

$$\Sigma M_{awj}(j=1 \text{ to } i)=M_{fi}-(M_f-M_O) \quad (14)$$

Next, $M_{awi}$ is calculated from the following formula.

$$\Sigma M_{awj}(j=1 \text{ to } i)-\Sigma M_{awj}(j=1 \text{ to } (i-1)) \quad (15)$$

Next, $M_{awi}$ is substituted for the following formula and a percentage of surface moisture is calculated.

$$(M_{awi}-M_{ai})/M_{ai} \quad (13)$$

Here, the accumulation value of the amount of water $M_I$ supplied to the measurement tank does not necessarily increase, but can be the amount of water thrown first, in other words, the accumulation value can be fixed without change. Similarly, water is not necessarily drained by the amount of water $M_O$ discharged from the measurement tank, but the accumulation value can remain zero.

When taking into consideration the air content in submergence aggregate (a (%)), still higher-precision measurement can be performed with the actual total volume except the air content by replacing $V_{fi}$ (i=1 to N) with $V_{fi}$(i=1 to N)·(1−a/100).

(Program for Measurement by a Submergence Method in a Case of Supplying a Plurality of Aggregates Whose Kinds are Different)

In order to measure and calculate concrete-forming materials using a program concerning the present invention, it is possible to make the program run with a personal computer. That is, density $\rho_{ai}$ (i=1 to N) of the aggregate of the i-th kind (i=1 to N) in the saturated surface-dried condition, density $\rho_w$ of water, and the target mass $M_{di}$ (i=1 to N) of submergence aggregate are first inputted using means for inputting data, such as a keyboard and a mouse. Here, the target mass $M_{di}$ (i=1 to N) of submergence aggregate is the target mass of submergence aggregate when the process for throwing the aggregate of the i-th kind (i=1 to N) is completed. Next, the inputted value is stored in means for storing data comprising a hard disk or the like.

Next, the aggregate of the first kind and water are supplied to the measurement tank so that the aggregate of the first kind may not come out from the water surface, namely, so that this aggregate and water may become submergence aggregate.

When throwing the aggregate and the water into the measurement tank, it is arbitrary as to which should be thrown first, but if the water is thrown in first and the aggregate is thrown in later, especially in a case of fine aggregate, air bubble mixing in the submergence aggregate can be suppressed considerably.

Next, total mass $M_{f1}$ of the submergence aggregate is measured. In order to measure the total mass $M_{f1}$ of the submergence aggregate, the mass of only the measurement tank is subtracted from the mass of the measurement tank filled with the submergence aggregate.

Next, total volume $V_{f1}$ of the submergence aggregate is measured. Here, in order to measure total volume $V_{f1}$ of the submergence aggregate, means for measuring a water level for measuring a level of the submergence aggregate, such as an electrode-type displacement sensor, can be used.

Next, the density $\rho_{a1}$ of the aggregate of the first kind and the density $\rho_w$ of water are read from the means for storing data. Subsequently, the mass $M_{a1}$ of the aggregate of the first kind in the saturated surface-dried condition is calculated by means for calculating by substituting these read values for formula (32) with the total mass $M_{f1}$ of the submergence aggregate, and the total volume $V_{f1}$ of the submergence aggregate. Next, this calculated result is stored in the means for storing data.

Next, like the aggregate of the first kind, the aggregate of the second kind is thrown into the measurement tank so that it may become submergence aggregate which does not come out from the water surface, and subsequently the total mass $M_{f2}$ of the submergence aggregate is measured. In addition, the total volume $V_{f2}$ of the submergence aggregate is also measured.

Next, the density $\rho_{a1}$ in the saturated surface-dried condition of the aggregate of the first kind, the density $\rho_{a2}$ of the aggregate of the second kind, and the density $\rho_w$ of water are read from the means for storing data. Subsequently, the mass $M_{a2}$ of the aggregate of the second kind in the saturated surface-dried condition is calculated by the means for calculating by substituting these read values into formula (33) with the total mass $M_{f2}$ of the submergence aggregate, and the total volume $V_{f2}$ of the submergence aggregate. Next, this calculated result is stored in the means for storing data.

Hereafter, the above-mentioned procedure is repeated, aggregate measurement is calculated one by one to the mass $M_{a(N-1)}$ in the saturated surface-dried condition of the aggregate of the (N−1)th kind by the means for calculating, and this calculated result is stored in the means for storing data. Finally, the aggregate of the Nth kind is thrown into the measurement tank so that it may become part of submergence aggregate in which the aggregate of the Nth kind does not appear from the water surface.

Next, similarly as mentioned above, the total mass $M_{fN}$ of the submergence aggregate is measured, and the total volume $V_{fN}$ of the submergence aggregate is measured.

Next, the density $\rho_{ai}$ (i=1 to N) in the saturated surface-dried condition of the aggregate of the i-th kind (i=1 to N), and the density $\rho_w$ of water are read from the means for storing data. Subsequently, the mass $M_{aN}$ of the aggregate of the Nth kind in the saturated surface-dried condition and the mass $M_w$ of water are calculated by the means for calculating by substituting these read values into formulas (34) and (35) with the total mass $M_{fN}$ of the submergence aggregate and the total volume $V_{fN}$ of the submergence aggregate.

The total mass $M_{fi}$ (i=1 to N) of the submergence aggregate is measured in real time or at predetermined time intervals while supplying the aggregate of the i-th kind (i=1 to N) continuously or intermittently at a predetermined rate, when throwing cumulatively the aggregate into the measurement tank. And when the total mass $M_{fj}$ of the submergence aggregate reaches the target mass $M_{dj}$ of the submergence aggregate, throwing the j-th aggregate is ended.

If aggregate which should be cumulatively supplied further exists (i.e., if a plurality of aggregates should be supplied cumulatively and the j-th aggregate is not the last aggregate), the (j+1)-th aggregate is similarly supplied continuously as mentioned above.

When the mass $M_w$ of water and $M_{ai}$ (i=1 to N) are measured and calculated, the original field mixes set up according to the specified mix are compared with these calculated results, and the field mix is corrected if needed. That is, the measured aggregate mass and the aggregate mass of the field mix set up first are compared, and a ratio obtained by this comparison is stored in the means for storing data. Next, the ratio is read from the means for storing data at any time, and the mixing volume of one batch is corrected according to the ratio. In addition, according to this ratio, the submergence aggregate is supplemented with water, equal in amount to that of an insufficiency, as secondary water, or excess water is drained. Similarly, with regard to the amount of other concrete-forming materials, such as cement and a chemical admixture, the original field mix is corrected according to the ratio mentioned above, other concrete-forming materials are measured according to this correction, and these are thrown into a kneading mixer and kneaded.

Thus, the surface water of aggregate is indirectly computed as a part of mass $M_w$ of water, even if an aggregate whose moisture state is not uniform is used, and the mass of aggregate is computed as the mass $M_{ai}$ (i=1 to N) of the aggregate in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

Furthermore, the total mass $M_{fi}$ (i=1 to N) of the submergence aggregate is measured in real time or at predetermined time intervals while supplying the aggregate of the i-th kind (i=1 to N) into the measurement tank continuously or intermittently at a predetermined rate. Since the j-th aggregate throwing is ended when the total mass $M_{fj}$ of the submergence aggregate reaches the target mass $M_{dj}$ during the j-th aggregate throwing in the aggregate of the i-th kind mentioned above, it becomes possible to manage correctly the amount of the i-th (i=1 to N) aggregate, and to correct the field mix, consequently to make concrete as the specified mix.

In addition, a plurality of aggregates whose kinds, such as density and grading, are different can be measured in terms of high effectiveness and accuracy within one measurement tank in the procedure mentioned above.

(Another Program for Measurement by a Submergence Method in a Case of Supplying a Plurality of Aggregates Whose Kinds are Different)

In order to measure and calculate concrete-forming materials using another program concerning the present invention, as mentioned above, it is possible to make the program run with a personal computer. That is, density ρai (i=1 to N) of the aggregate of the i-th kind (i=1 to N) in the saturated surface-dried condition, density $ρ_w$ of water, and the target mass $M_{di}$ (i=1 to N) of submergence aggregate are first inputted using means for inputting data, such as a keyboard and a mouse. Here, the target mass $M_{di}$ (i=1 to N) of submergence aggregate is the target mass of submergence aggregate when the process for throwing the aggregate of the i-th kind (i=1 to N) is completed. Next, this inputted value is stored in means for storing data comprising a hard disk or the like.

Next, aggregate of a first kind and water are supplied to the measurement tank so that the aggregate of the first kind may not come out from the water surface, namely, so that this aggregate and water may become submergence aggregate.

When throwing the aggregate and the water into the measurement tank, it is arbitrary as to which should be thrown first, but if the water is thrown in first and the aggregate is thrown in later, especially in a case of fine aggregate, air bubble mixing in the submergence aggregate can be suppressed considerably.

Next, total mass $M_{f1}$ of the submergence aggregate is measured. In order to measure the total mass $M_{f1}$ of the submergence aggregate, the mass of only the measurement tank is subtracted from the mass of the measurement tank filled with the submergence aggregate.

Next, the density $ρ_{a1}$ of the aggregate of the first kind and the density $ρ_w$ of water are read from the means for storing data. Subsequently, the mass $M_{a1}$ of the aggregate of the first kind in the saturated surface-dried condition is calculated by means for calculating by substituting these read values into formulas (32) with the total mass $M_{f1}$ of the submergence aggregate, and the total volume $V_{f1}$ of the submergence aggregate. Next, this calculated result is stored in the means for storing data.

$V_{f1}$ is determined from a first water level set up beforehand.

The first water level can be beforehand set up by making the water in the submergence aggregate overflow from the measurement tank at a predetermined depth location in the measurement tank, or by performing suction drainage of the water in the submergence aggregate at the predetermined depth location.

Next, like the aggregate of the first kind, aggregate of a second kind is thrown into the measurement tank so that it may become part of submergence aggregate, which does not come out from the water surface, and subsequently the total mass $M_{f2}$ of the submergence aggregate is measured.

Next, the density $ρ_{a1}$ in the saturated surface-dried condition of the aggregate of the first kind, the density $ρ_{a2}$ of the aggregate of the second kind, and the density $ρ_w$ of water are read from the means for storing data. Subsequently, the mass $M_{a2}$ of the aggregate of the second kind in the saturated surface-dried condition is calculated by the means for calculating by substituting these read values into formula (33) with the total mass $M_{f2}$ of the submergence aggregate, and the total volume $V_{f2}$ of the submergence aggregate. Next, this calculated result is stored in the means for storing data.

$V_{f2}$ is determined from a second water level set up beforehand.

Hereafter, the above-mentioned procedure is repeated, aggregate measurement is calculated one by one to the mass $M_{a(N-1)}$ in the saturated surface-dried condition of the aggregate of (N−1)th kind by the means for calculating, and this calculated result is stored in the means for storing data. Finally, the aggregate of the Nth kind is thrown into the measurement tank so that it may become part of submergence aggregate in which the aggregate of the Nth kind does not appear from the water surface.

Next, similarly as mentioned above, the total mass $M_{fN}$ of the submergence aggregate is measured.

Next, the density $ρ_{ai}$ (i=1 to N) in the saturated surface-dried condition of the aggregate of the i-th kind (i=1 to N), and the density $ρ_w$ of water are read from the means for storing data. Subsequently, the mass $M_{aN}$ of the aggregate of the Nth kind in the saturated surface-dried condition and the mass $M_w$ of water are calculated by the means for calculating by substituting these read values into formulas (34) and (35) with the total mass $M_{fN}$ of the submergence aggregate and the total volume $V_{fN}$ of the submergence aggregate.

$V_{fN}$ is determined from the Nth water level set up beforehand.

The total mass $M_{fi}$ (i=1 to N) of the submergence aggregate is measured in real time or at predetermined time intervals while supplying the aggregate of the i-th kind (i=1 to N) continuously or intermittently at a predetermined rate, when throwing cumulatively the aggregate into the measurement tank. While draining redundant water from the measurement tank so that the water level of the submergence aggregate may not exceed the j-th water level during the j-th aggregate throwing, the j-th aggregate throwing is ended when the total mass $M_{fj}$ of the submergence aggregate reaches the target mass $M_{dj}$ of the submergence aggregate.

On the other hand, when the water level of the submergence aggregate at that time has not reached the j-th water level set up beforehand, the submergence aggregate is supplemented with water so that it may reach this j-th water level. And re-measurement of mass $M_{fj}$, recalculation of mass $M_{aj}$, and recalculation of mass $M_w$ are performed.

If aggregate which should be cumulatively supplied further exists (i.e., if a plurality of aggregates should be supplied cumulatively and the j-th aggregate is not the last aggregate), the (j+1)-th aggregate is similarly supplied continuously as mentioned above.

Thus, after measuring the i-th (i=1 to N) aggregate and water, other concrete-forming materials, such as cement and a chemical admixture, are measured, and with these concrete-forming materials, the i-th (i=1 to N) aggregate and water are fed into a kneading mixer, and are kneaded. Here, when the total mass $M_{fj}$ of the submergence aggregate reaches the target mass $M_{dj}$ of the submergence aggregate in draining redundant water so that the water level of the submergence aggregate may not exceed the j-th water level set up beforehand, the mass $M_{aj}$ of the j-th aggregate in the saturated surface-dried condition becomes equal to the value set up first. Therefore, it is not necessary to correct the field mix.

On the other hand, when the water level of the submergence aggregate has not reached the j-th water level set up beforehand, the submergence aggregate is supplemented with water so that it may reach this j-th water level. Therefore, the calculated value of the mass Maj of the j-th aggregate in the saturated surface-dried condition differs from the value set up first. In this case, the value measured and calculated is compared with the value of the field mix set up first according to the specified mix, and the field mix is then corrected if needed. That is, the measured aggregate mass and the aggregate mass of the field mix set up first are compared, and a ratio obtained by this comparison is stored in the means for storing data. Next, the ratio is read from the means for storing data at any time, and the mixing volume of one batch is corrected according to the ratio. In addition, according to this ratio, the submergence aggregate is supplemented with water, equal in amount to that of an insufficiency, as secondary water, or excess water is drained. Similarly, with regard to the amount of other concrete-forming materials, such as cement and a chemical admixture, the original field mix is corrected according to the ratio mentioned above, other concrete-forming materials are measured according to this correction, and these are thrown into the kneading mixer and kneaded.

Thus, the surface water of aggregate is indirectly computed as a part of mass $M_w$ of water, even if an aggregate whose moisture state is not uniform is used, and the mass of aggregate is computed as the mass Mai (i=1 to N) of the aggregate in the saturated surface-dried condition. That is, since the mass of the aggregate and the water will be computed on conditions equivalent to the specified mix, even if a humidity grade of the aggregate is not fixed at every measurement, it becomes possible to make concrete from an amount of water as that of the specified mix.

Furthermore, when the total mass $M_{fj}$ of the submergence aggregate reaches the target mass $M_{dj}$ of the submergence aggregate, the j-th aggregate throwing is ended, and when the water level of the submergence aggregate at that time has not reached the j-th water level set up beforehand, the submergence aggregate is supplemented with water so that it may reach this j-th water level. And re-measurement of mass $M_{fj}$, recalculation of mass $M_{aj}$, and recalculation of mass $M_w$ are performed. Therefore, the total volume $V_{fi}$ (i=1 to N) of the submergence aggregate serves as a known value, and it becomes unnecessary to measure this volume, and the input of the i-th (i=1 to N) aggregate can be managed correctly. And it becomes possible as a result to make concrete as the specified mix.

In addition, a plurality of aggregates whose kinds, such as density and grading, are different can be measured in terms of high effectiveness and accuracy within one measurement tank in the procedure mentioned above.

The percentage of surface moisture of the i-th (i=1 to N) aggregate can be calculated in the following procedure. That is, the amount of water $M_I$ supplied to the measurement tank and the amount of water $M_O$ discharged from the measurement tank are first measured as accumulation values, and this measured data are stored in the means for storing data. Next, the amount of supplied water $M_I$, the amount of discharged water $M_O$, and the total mass $M_{fi}$ (i=1 to N) are read from the means for storing data, these data are substituted into the following formula, and $\Sigma M_{awj}$ (j=1, 2, 3, ... i) is calculated by the means for calculating.

$$\Sigma M_{awj}(j=1 \text{ to } i) = M_{fi} - (M_I - M_O) \quad (14)$$

Next, the measured data are stored in the means for storing data. Next, Mawi is calculated from the following formula by the means for calculating.

$$\Sigma M_{awj}(j=1 \text{ to } i) - \Sigma M_{awj}(j=1 \text{ to } (i-1)) \quad (15)$$

Next, $M_{awi}$ is substituted for the following formula and a percentage of surface moisture is calculated by the means for calculating.

$$(M_{awi} - M_{ai})/M_{ai} \quad (13)$$

Here, the accumulation value of the amount of water $M_I$ supplied to the measurement tank does not necessarily increase, but can be the amount of water thrown first; in other words, the accumulation value can be fixed without change. Similarly, water is not necessarily drained by the amount of water $M_O$ discharged from the measurement tank, but the accumulation value can remain zero.

When taking into consideration air content in submergence aggregate (a (%)), still higher-precision measurement can be performed with the actual total volume except the air content by replacing $V_{fi}$ (i=1, 2, 3, ... N) with $V_{fi}$ (i=1, 2, 3, ... N)·(1−a/100).

The computer-readable recording medium of the present invention can be of any type such as FD, CD-ROM, CD-R, or MD naturally.

(Discharge Mechanism of a Measurement Container)

In a discharge mechanism of a measurement container of the present invention, after completing measurement of submergence aggregate, a fall discharge of the submergence aggregate is performed by opening a bottom lid. Thereafter, a top face of the bottom lid is sprayed with a gas flow by means of a gas spraying mechanism provided near the bottom lid with the bottom lid opened.

With this, aggregate adhering to the top face of the bottom lid at a time of discharge of the submergence aggregate will be blown away by the gas flow. Therefore, even if the bottom lid is closed for preparation for a subsequent measurement, the aggregate is not caught between a body of the measurement container and the bottom lid.

Therefore, the mechanism prevents an occurrence of an error in the measurement which may be caused by a leakage of water from a clearance by the aggregate being caught. Furthermore, a seal member provided in the body of the measurement container or the bottom lid is not damaged.

In the discharge mechanism of the measurement container concerning the present invention, after completing the measurement of the submergence aggregate, the fall discharge of the submergence aggregate is performed by opening the bottom lid. The bottom lid is not rotated around a horizontal axis as has been conventional, but the bottom lid is moved in a translation direction or rotated in a predetermined plane.

Thus, in the prior art, if the bottom lid is opened, it will hang down. Therefore, an opening-and-closing space of the bottom lid must be secured in a height direction in the prior art. However, it is not necessary to secure the opening-and-closing space of the bottom lid in the height direction in the present invention, but it is only necessary to secure the space in the plane.

Therefore, a bottom opening of the body of the measurement container can be lowered by the indispensable opening-and-closing height in the prior art, and certain throwing into a kneading mixer is possible.

An arbitrary constitution may be used for moving the bottom lid in the translation or rotating direction in the plane. For example, there can be a constitution having a pair of guide rails parallel to each other attached at a bottom end of the body of the measurement container so as to translate the bottom lid along the guide rails. Otherwise, there can be a constitution having a rotational axis installed in a protrusion extending from a rim of the bottom lid, with the rotational axis attached rotatably by inserting the axis into a hollow of a hinge member on a circumferential surface of the body of the measurement container, so that the bottom lid can rotate.

In the discharge mechanism of the measurement container of the present invention, after completing the measurement of the submergence aggregate, the fall discharge of the submergence aggregate is performed by opening the bottom lid. Thereafter, the top face of the bottom lid is sprayed with a gas flow by means of the gas spraying mechanism provided near the bottom lid with the bottom lid opened.

With this, the aggregate adhering to the top face of the bottom lid at the time of discharging the submergence aggregate will be blown away by the gas flow. Therefore, even if the bottom lid is closed for a preparation for a subsequent measurement, the aggregate is not caught between the body of the measurement container and the bottom lid.

Therefore, the mechanism prevents an occurrence of an error in the measurement which may be caused by a leakage of water from the clearance by the aggregate being caught. Furthermore, the seal member provided in the body of the measurement container or the bottom lid is not damaged.

In the discharge mechanism of the measurement container of the present invention, it is arbitrary as to how the gas spraying mechanism should be configured and where it should be installed. For example, the gas spraying mechanism can be an air spray nozzle connected in communication with an air compressor.

Furthermore, in the discharge mechanism of the measurement container of the present invention, after completing the measurement of the submergence aggregate, the fall discharge of the submergence aggregate is performed by opening the bottom lid. The bottom lid is not rotated around a horizontal axis as has been conventional, but it is moved in the translation direction or rotated in the predetermined plane.

Thus, in the prior art, if the bottom lid is opened, it will hang down. Therefore, the opening-and-closing space of the bottom lid must be secured in the height direction in the prior art. However, it is not necessary to secure the opening-and-closing space of the bottom lid in the height direction in the present invention, but it only needs to secure the space only in the plane.

Therefore, the bottom opening of the body of the measurement container can be lowered by the indispensable opening-and-closing height in the prior art, and certain throwing into a kneading mixer is possible.

The constitution is arbitrarily chosen to move the bottom lid between mechanisms for the translation and the rotation in the level surface. For example, there can be a constitution having a pair of guide rails parallel to each other attached at a bottom end of the body of the measurement container so as to translate the bottom lid along the guide rails. Otherwise, there can be a constitution having a rotational axis installed in a protrusion extending from the rim of the bottom lid, with the rotational axis attached rotatably by inserting the axis into the hollow of a hinge member on the circumferential surface of the body of the measurement container, so that the bottom lid can rotate.

In the measuring apparatus of the present invention, a plurality of measurement containers have volumes different from each other at a normal water level where they have the same depths. In measurement, measurement containers are selected out of the plurality of measurement containers mentioned above according to each mass of aggregate required for kneading the concrete-forming materials. Furthermore, water levels are measured and monitored by means for measuring a water level, while driving and controlling means for regulating a water level so as to maintain the water levels of submergence aggregates in the measurement containers at a normal water level.

With this, measured water levels match the normal water level where they have the same depth even if any measurement containers are used for the measurement. Therefore, an accuracy of the water level measurement, and thus an accuracy of conversion to the total volume of the submergence aggregate, is uniform throughout all the measurement containers.

Accordingly, even if a required mass of aggregate differs, it is possible to uniformize the accuracy of a total volume, and thus accuracy of an aggregate measurement.

The means for regulating the water level can be a suction unit for sucking and removing water, for example. If the water level of the submergence aggregate in the measurement container exceeds the normal water level, the suction unit should be driven to control the water level with a measured value from the means for measuring the water level as a controlled variable.

The mass of aggregate required for kneading the concrete-forming materials depends upon the specified mix proportion of the concrete-forming materials or upon a given amount determined by a specification of a kneading mixer. It also depends upon whether the mixing volume should be a given amount or an amount smaller than the given amount. Furthermore, naturally each mass of aggregate differs with each proportion when a plurality of aggregates are mixed to obtain a desired grading, for example.

The above is considered by giving a concrete example. It is assumed that there are the following cases: aggregates are kneaded with a given amount by the kneading mixer as one batch, with two-thirds of the given amount as one batch, and with one-half of the given amount as one batch. In these circumstances, measurement is conducted by using three measurement containers whose volumes are the given amount, the given amount multiplied by two-thirds, and the given amount multiplied by one-half, respectively, at a normal water level where they have the same depth.

(Measuring Apparatus Using a Plurality of Measurement Containers)

A measuring apparatus for concrete-forming materials of the present invention comprises means for maintaining water levels of submergence aggregates in a plurality of measurement containers at a normal water level at which they have the same depth. In measurement, measurement containers are selected out of the plurality of measurement containers according to each mass of aggregate required for kneading the concrete-forming materials. Furthermore, the water levels of the submergence aggregates are kept at the normal water level by the means for maintaining water levels mentioned above.

With this, the water levels of the submergence aggregates always match the normal water level where they have the same depth even if any measurement containers are used for the measurement. Therefore, an accuracy of the water level measurement, and thus an accuracy of conversion to the total volume of the submergence aggregate is uniform throughout all the measurement containers.

Accordingly, even if a required mass of aggregate differs, it is possible to uniformize the accuracy of the total volume, and thus the accuracy of the aggregate measurement.

The mass of aggregate required for kneading the concrete-forming materials depends upon the specified mix proportion of the concrete-forming materials or upon a given amount determined by a specification of a kneading mixer. It also depends upon whether the mixing volume should be the given amount or an amount smaller than the given amount. Furthermore, naturally each mass of aggregate differs with each proportion when a plurality of aggregates are mixed to obtain desired grading, for example.

The above is considered by giving a concrete example. It is assumed that there are the following cases: aggregates are kneaded with a given amount by the kneading mixer as one batch, with two-thirds of the given amount as one batch, and with one-half of the given amount as one batch. In these circumstances, measurement is conducted by using three measurement containers whose volumes are the given amount, the given amount multiplied by two-thirds, and the given amount multiplied by one-half, respectively, at a normal water level where they have the same depth.

Furthermore, the measuring apparatus of concrete-forming materials of the present invention comprises the means for maintaining water levels, which maintains the water levels of the submergence aggregates in the plurality of measurement containers at the normal water level where they have the same depth. In the measurement, measurement containers are selected out of the plurality of measurement containers according to each mass of aggregate required for kneading the concrete-forming materials. Furthermore, the water levels of the submergence aggregates are kept at the normal water level by the means for maintaining water levels mentioned above.

With this, the water levels of the submergence aggregates always match the normal water level where they have the same depth even if any measurement containers are used for the measurement. Therefore, an accuracy of the water level measurement, and thus an accuracy of conversion to the total volume of the submergence aggregate, is uniform throughout all the measurement containers.

Accordingly, even if a required mass of aggregate differs, it is possible to uniformize the accuracy of the total volume, and thus the accuracy of the aggregate measurement.

In this specification, the term "means for measuring an amount of supplied or discharged water" does not mean means for measuring an amount of supplied water or an amount of discharged water individually, but it means one capable of measuring an amount of water obtained by subtracting an amount of discharged water from an amount of supplied water to the measurement container as an accumulation value. In a case where no water is supplied after throwing water into the measurement container first, for example, only the amount of discharged water need be measured.

The mass of aggregate required for kneading the concrete-forming materials depends upon the specified mix proportion of the concrete-forming materials or upon a given amount determined by a specification of the kneading mixer. It also depends upon whether a mixing volume should be a given amount or an amount smaller than the given amount. Furthermore, naturally each mass of aggregate differs with each proportion when a plurality of aggregates are mixed to obtain a desired grading, for example.

The above is considered by giving a concrete example. It is assumed that there are the following cases: aggregates are kneaded with a given amount by a kneading mixer as one batch, with two-thirds of the given amount as one batch, and with one-half of the given amount as one batch. In these circumstances, measurement is conducted by using three measurement containers whose volumes are the given amount, the given amount multiplied by two-thirds, and the given amount multiplied by one-half, respectively, at a normal water level where they have the same depth.

As long as a fixed water level is maintained in the measurement containers, the constitution of the means for maintaining water levels is arbitrary. For example, the means can be a suction unit preventing the water level from increasing to exceed the normal water level or can be an opening for overflow formed in a wall of a measurement container so that water in the measurement container overflows to outside of the measurement container when the water reaches the normal water level.

BRIEF DESCRIPTION OF THE DRAWINGS

FIG. 32 is a flowchart of a preferable measuring method for concrete-forming materials according to the present invention;

FIG. 33 is a flowchart of another preferable measuring method for concrete-forming materials according to the present invention;

FIGS. 34 and 35 are a series of flowcharts of still another preferable measuring method for concrete-forming materials according to the present invention;

FIGS. 36 and 37 are a series of flowcharts of still another preferable measuring method for concrete-forming materials according to the present invention;

FIGS. 67A-67C are side views of measurement containers;

FIGS. 75A-75C are side views of measurement containers;

DETAILED DESCRIPTION OF THE PREFERRED EMBODIMENTS

Preferred embodiments of a measuring apparatus and a measuring method for concrete-forming materials according to the present invention will now be described in detail hereinafter with reference to the accompanying drawings.

First Embodiment

Figure 1:
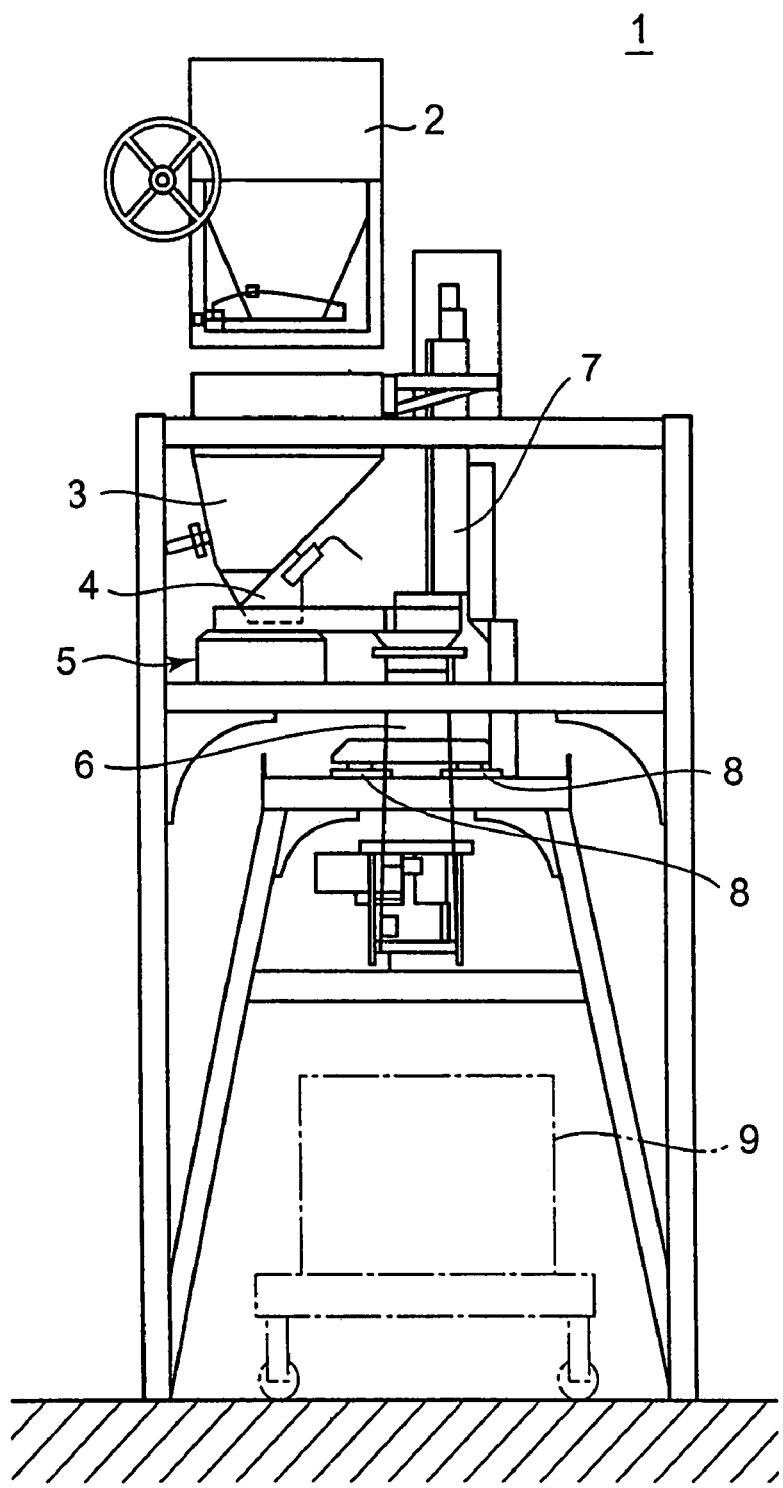
FIG. 1 is a general side view of a preferable measuring apparatus for concrete-forming materials according to the present invention.
Figure 2:
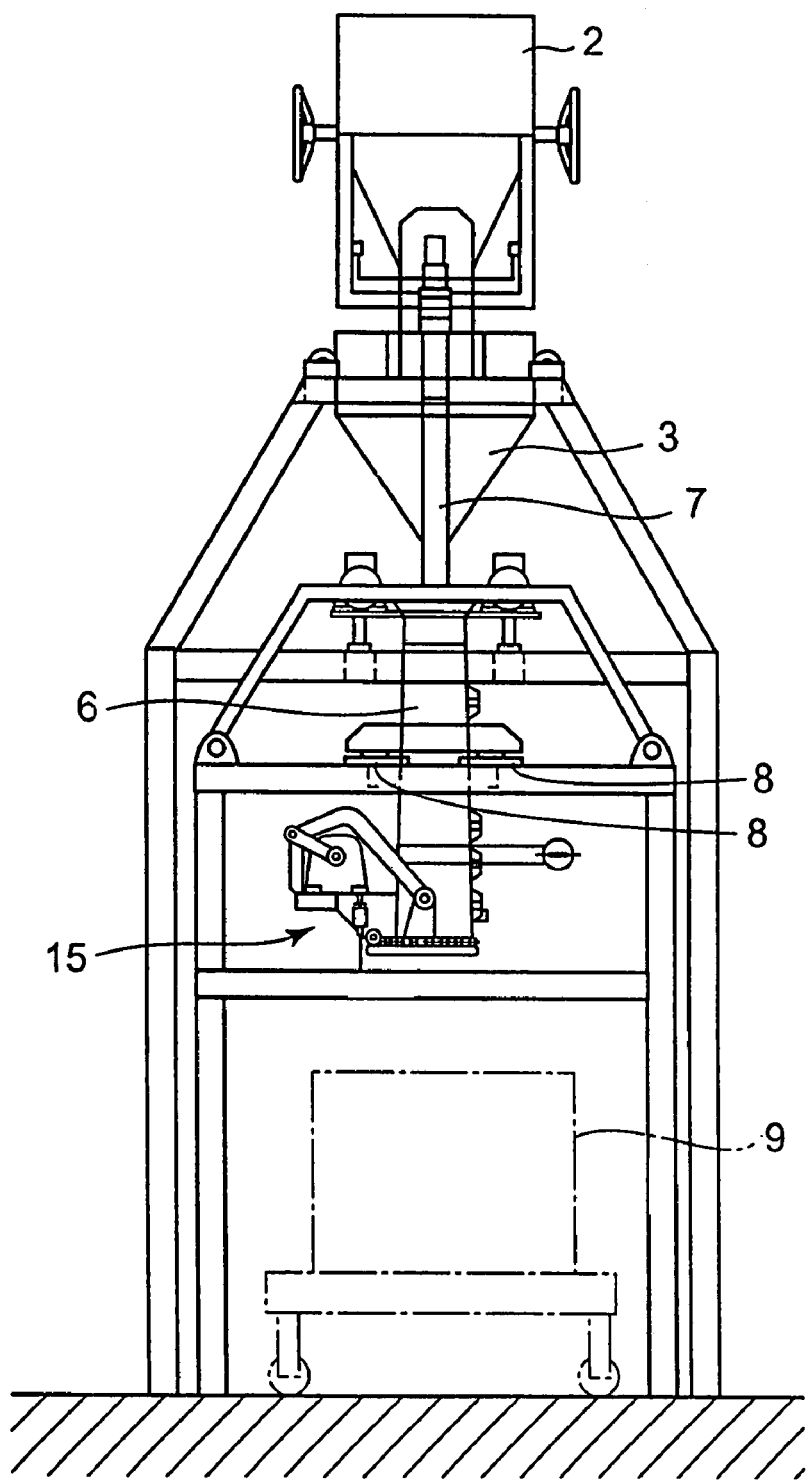
FIG. 2 is another general side view of the preferable measuring apparatus for concrete-forming materials according to the present invention.
Figure 3:
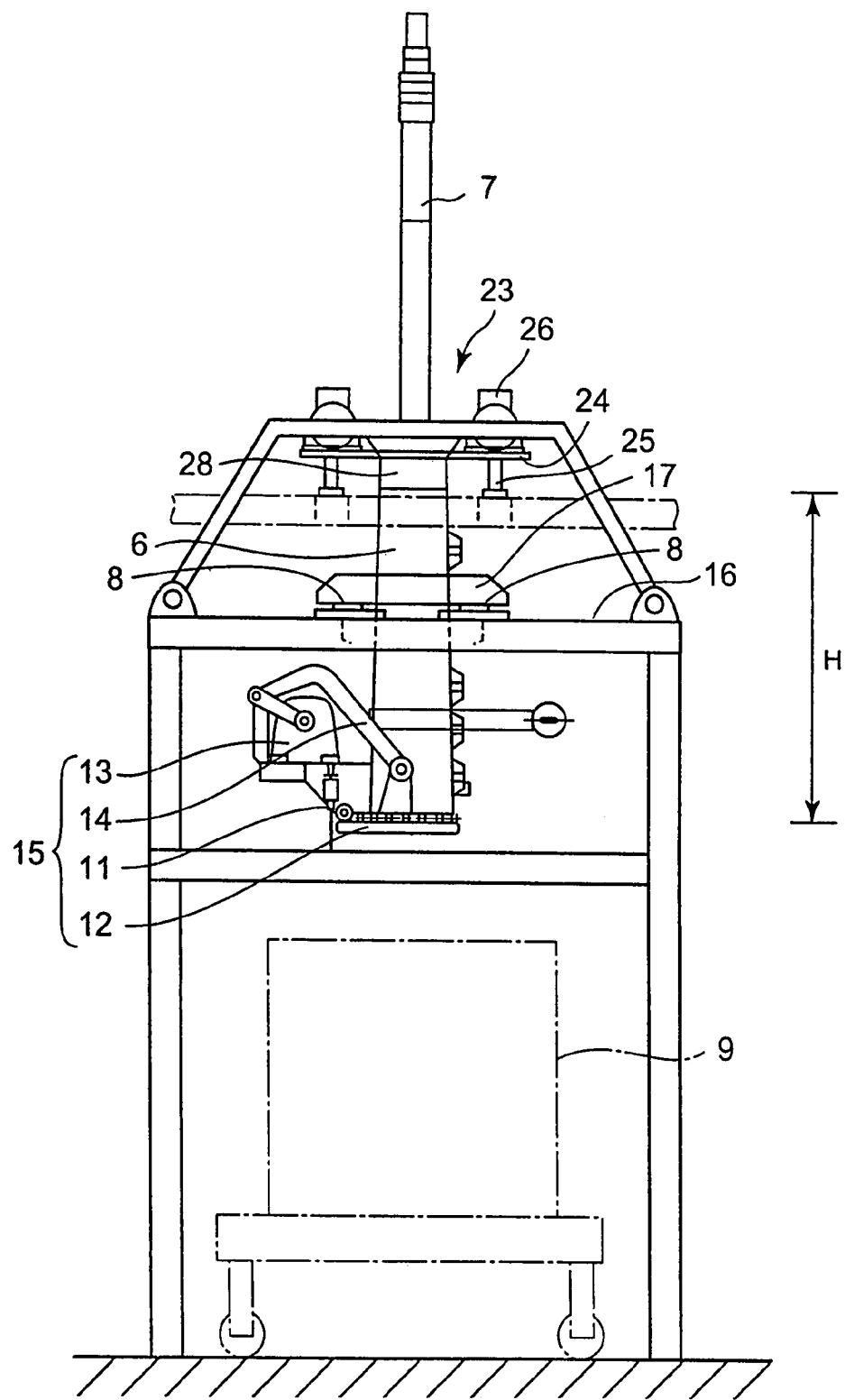
FIG. 3 is an expanded side view of the measuring apparatus in FIG. 2.

Referring to FIGS. 1 and 2, there are shown general side views of a measuring apparatus for concrete-forming materials according to a first embodiment, viewed from two sides at right angles to each other. Referring to FIG. 3, there is shown an expanded side view of FIG. 2. As shown in these diagrams, a measuring apparatus 1 of concrete-forming materials according to this embodiment generally comprises a stock bin 2 for storing fine aggregate, a fine aggregate feed hopper 3 placed under the stock bin 2, a vibrating feeder 5 placed under a discharge opening 4 of the fine aggregate feed hopper 3, a screen device 23 placed in the vicinity of an exit of the vibrating feeder 5, a measurement tank 6 placed under the screen device 23, an electrode-type displacement sensor 7 as means for measuring a water level placed above the measurement tank 6, and load cells 8 as mass measuring means for measuring a mass of submergence fine aggregate contained in the measurement tank 6.

The measurement tank 6 is formed substantially in a shape of a cylinder having a height H as apparent from FIG. 3 so that it can contain submergence fine aggregate made of fine aggregate and water. Furthermore, it is formed in a shape in which a bore becomes larger in a downward direction, in other words, in a shape of a hollow truncated cone so that the submergence fine aggregate can be easily taken out after measurement.

At a lower end of the measurement tank 6, there is provided an opening-and-closing mechanism 15 comprising an opening-and-closing lid 12 attached to an opening at the lower end of the measurement tank 6 so as to be free to rotate around a pin 11, and a driving motor 13 connected to the opening-and-closing lid via an accouplement 14. By driving to operate the driving motor, the opening-and-closing lid 12 can be kept closed during the measurement and the inside submergence fine aggregate can be dropped to a mixer 9 by opening the opening-and-closing lid 12 on completion of the measurement.

Figure 4:
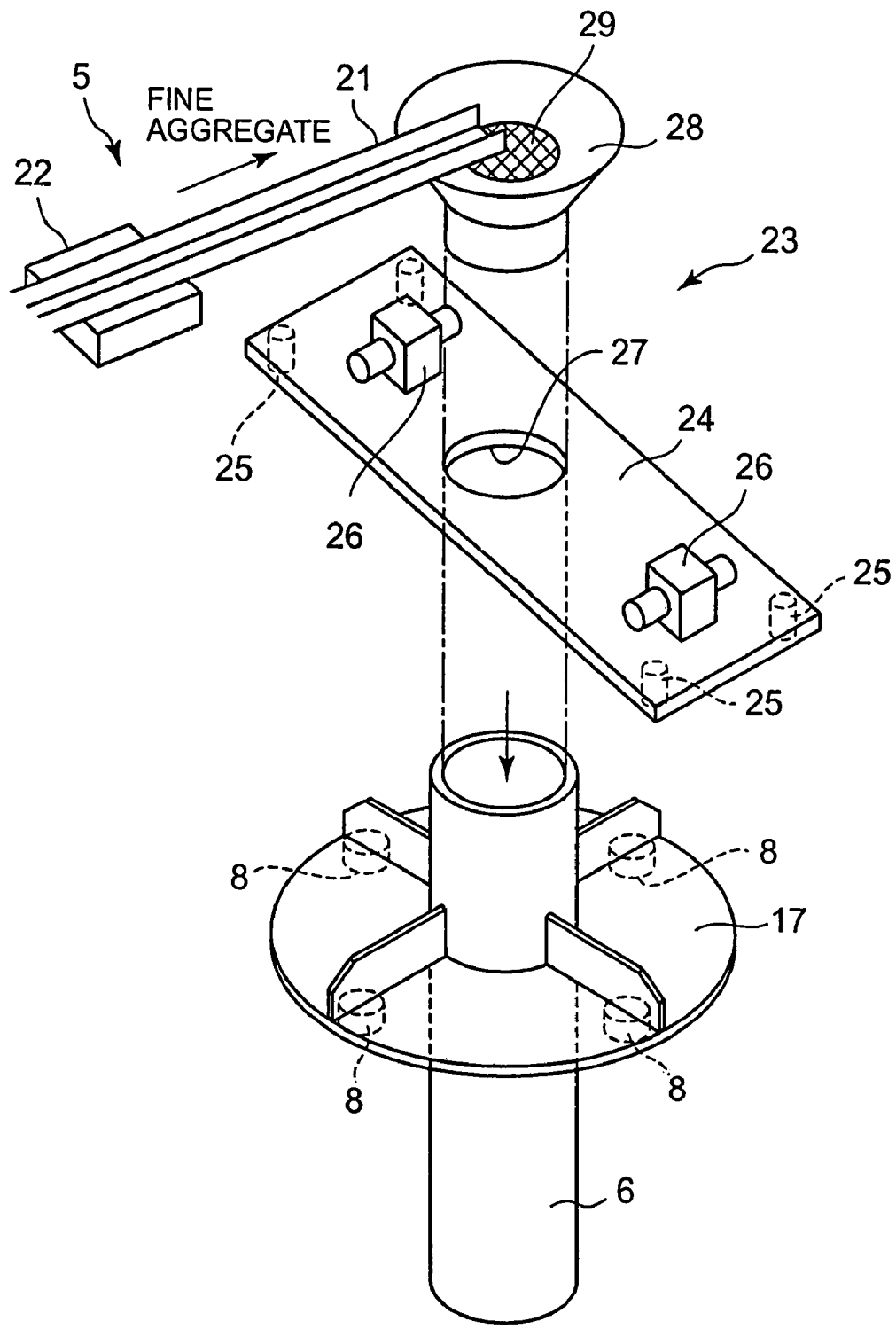
FIG. 4 is an exploded perspective view showing an arrangement condition of a vibrating feeder 5, a screen device 23, and a measurement tank 6.

Referring to FIG. 4, there is shown an exploded perspective view illustrating an arrangement condition of the vibrating feeder 5, the screen device 23, and the measurement tank 6. As apparent from FIG. 4, load cell 8 is arranged in four places between a load bearing bracket 17 attached to the measurement tank 6 at a middle height and an upper surface of a stand 16.

The vibrating feeder 5 comprises a U-shaped conveyor 21 for conveying fine aggregate discharged from the discharge opening 4 of the fine aggregate feed hopper 3, and an electromagnetic vibrator 22 for vibrating the conveyor. By operating the electromagnetic vibrator 22, fine aggregate can be conveyed in a direction indicated by an arrow in FIG. 4 without granulation of the fine aggregate on the conveyor 21.

The screen device 23 is located near the exit of the vibrating feeder 5 and in an upper portion of the measurement tank 6. The screen device comprises a rectangular vibrating plate 24 elastically supported by a stand (not shown) via four coil springs 25, a motor 26 for vibrating the vibrating plate, a funnel form guide chute 28 engaged in a circular opening 27 provided in a center of the vibrating plate 24, and a screen 29 attached to the guide chute 28, by which fine particles of aggregate can be thrown into the measurement tank 6 by vibrating the conveyed fine aggregate with the vibrating feeder 5 on the screen 29.

Figure 5:
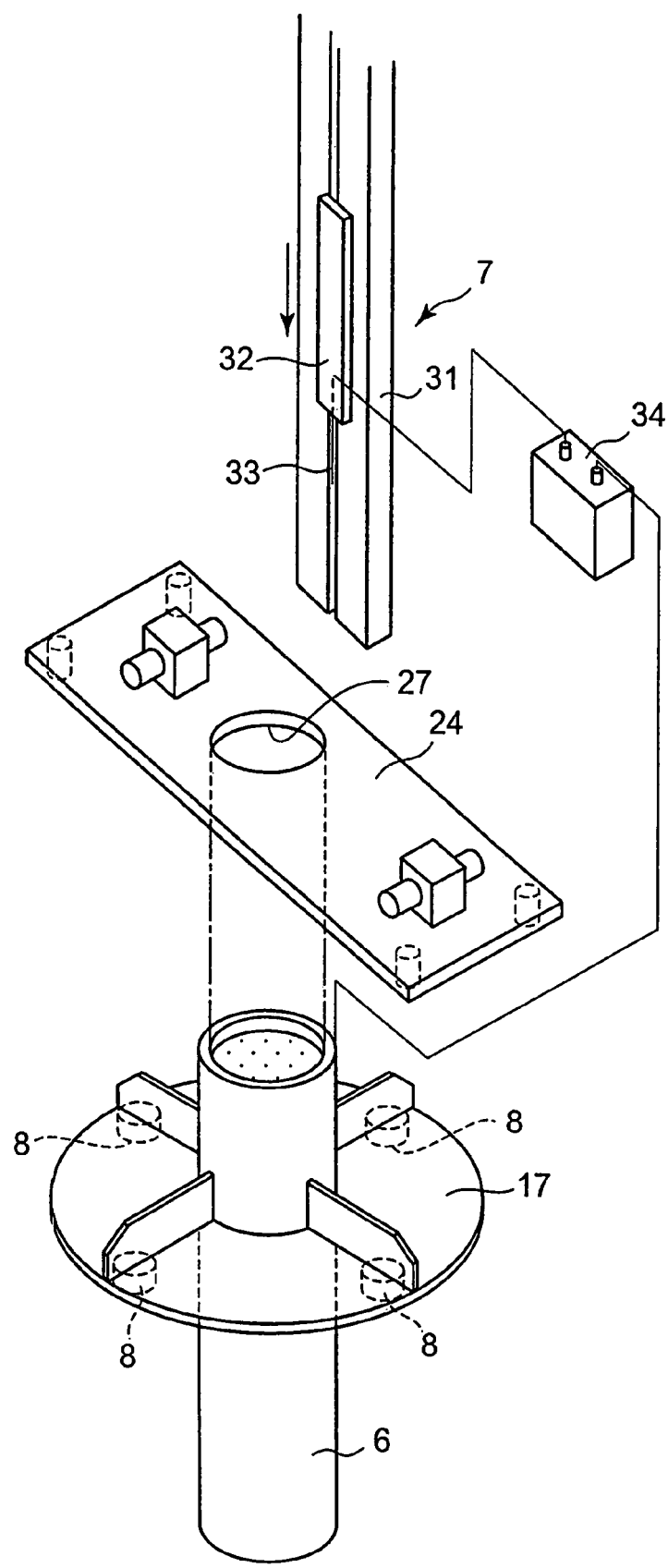
FIG. 5 is an exploded perspective view showing an arrangement condition of an electrode-type displacement sensor 7 and the measurement tank 6.

Referring to FIG. 5, there is shown an exploded perspective view illustrating an arrangement condition of the electrode-type displacement sensor 7 and the measurement tank 6. As apparent from FIG. 5, the electrode-type displacement sensor 7 comprises a guide 31 attached to a stand (not shown), an elevator 32 free to move up and down along the guide 31, a detection electrode 33 provided in a hanging condition at a lower end of the elevator 32, and a power supply 34 for energizing the detection electrode 33, so that a water level of submergence fine aggregate can be measured by monitoring a change in an energized condition when the lower end of the detection electrode 33 contacts the water surface of the submergence fine aggregate in the measurement tank 6. At this point, one electrode terminal of the power supply 34 is electrically connected to the detection electrode 33, while the other electrode terminal may be electrically connected to the measurement tank 6 made of steel, for example, as shown in FIG. 5.

To measure the submergence fine aggregate in the measuring apparatus of concrete-forming materials according to this embodiment, water is previously thrown into the measurement tank 6, first.

Figure 6A:
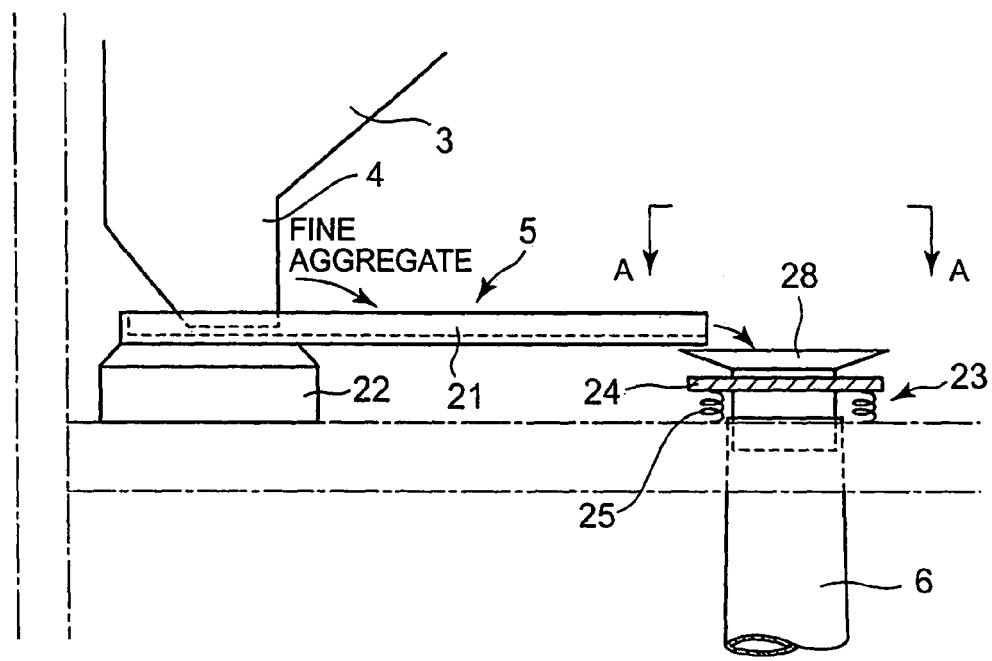
FIGS. 6A and 6B are diagrams showing a condition where fine aggregate is thrown into the measurement tank 6 by using the preferable measuring apparatus for concrete-forming materials according to the present invention, with FIG. 6A being a side view and FIG. 6B being a view along line A-A of FIG. 6A.
Figure 6B:
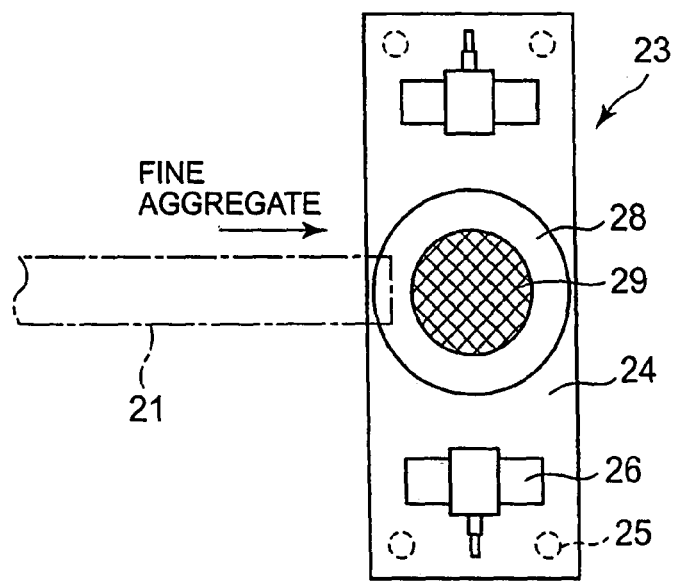

Subsequently, as shown in FIGS. 6A and 6B, fine aggregate in an arbitrary wet condition is first discharged from a discharge opening 4 of the aggregate feed hopper 3 and it is conveyed while preventing granulation by using the vibrating feeder 5. The fine aggregate conveyed by the vibrating feeder 5 is then thrown into the guide chute 28, so that it is put on the screen 29. The motor 26 is driven in this condition to vibrate the screen 29, by which only the fine aggregate having a given particle diameter is dropped from the screen to be thrown into the measurement tank 6 to make submergence fine aggregate.

Figure 7:
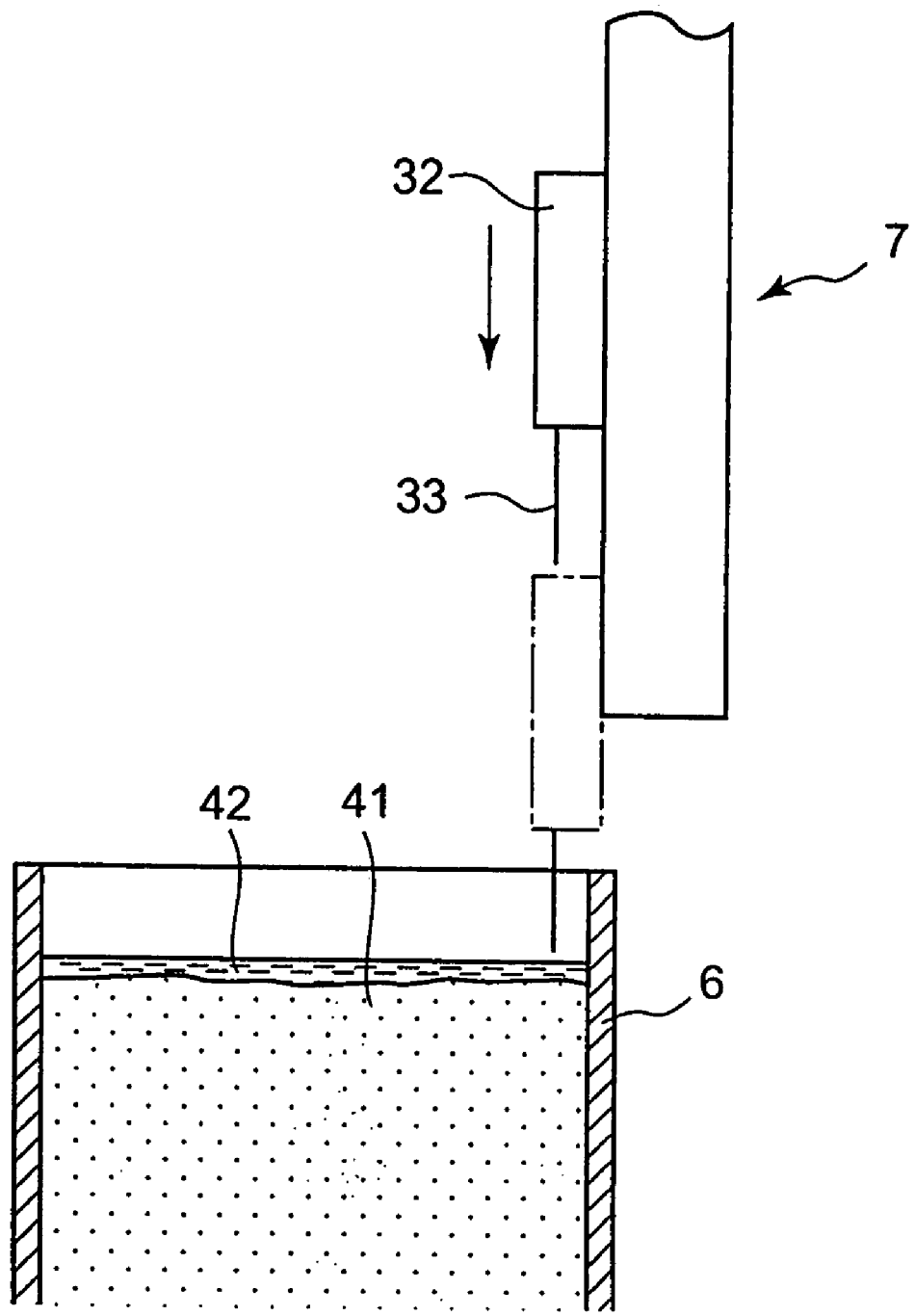
FIG. 7 is a side view showing a condition where a measurement is made on a water level of submergence fine aggregate thrown into the measurement tank 6 by using the preferable measuring apparatus for concrete-forming materials according to the present invention.

Subsequently, while measuring total mass $M_f$ of the submergence fine aggregate, which consists of the fine aggregate and the water, held in the measurement tank 6 in this condition by using the load cell 8, its total volume $V_f$ is measured by using the electrode-type displacement sensor 7 as shown in FIG. 7. Before measuring a water level with the electrode-type displacement sensor 7, the screen device 23 is detached, if necessary, to prevent it from affecting the measurement. For example, after throwing the fine aggregate into the measurement tank 6, the guide chute 28 to which the screen is attached may be removed from the circular opening 27 and put into the condition shown in FIG. 5.

The total mass $M_f$ is obtained just by measuring the mass of only the measurement tank before the measurement of the submergence fine aggregate and then subtracting the mass from a measured value in a condition where the submergence fine aggregate is held in the measurement tank.

To measure the total volume $V_f$, a relationship between a water level and a capacity is measured before the measurement of the submergence fine aggregate at 1-mm intervals, for example, first. This relationship is then stored in a storage device of a computer, for example, and a capacity corresponding to the measured water level is read from the storage device.

At this point, to measure the water level of the submergence fine aggregate in the measurement tank 6 with the electrode-type displacement sensor 7, the elevator 32 is moved down along the guide 31 as shown in FIG. 7 so that a stopping deviation of 1 mm, for example, is secured while monitoring an energization condition between the detection electrode 33 and the measurement tank 6. Thereafter, the moment a tip of the detection electrode 33 touches a surface 42 of the submergence fine aggregate 41, energization is confirmed. Therefore, the moving-down operation of the guide 31 is controlled as to stoppage with the energization condition as a controlled variable to measure the water level of the submergence fine aggregate 41.

Subsequently, mass $M_w$ of water and mass $M_a$ of the fine aggregate in a saturated surface-dried condition are calculated by substituting the total mass $M_f$ and the total volume $V_f$ for the following two formulas.

$$M_a + M_w = M_f \quad (1)$$

$$M_a/\rho_a + M_w/\rho_w = V_f \quad (2)$$

where $\rho_a$ is the density of the fine aggregate in a saturated surface-dried condition and $\rho_w$ is density of water.

After measuring and calculating the mass $M_w$ of water and the mass $M_a$ of the fine aggregate in the saturated surface-dried condition in this manner, they are compared with a mix proportion shown by a specified mix. Subsequently, an insufficiency, which should be remedied by filling, is measured and then the submergence fine aggregate is supplemented with additional water or aggregate when needed so as to let the fine aggregate and the water be concrete material.

At this point, if a supplement of fine aggregate is needed, surface water of the fine aggregate is not strictly taken into consideration. The amount of supplement, however, is limited to be small by measuring an amount of fine aggregate and water whose ratio matches the ratio of the specified mix or is close to it. Since the surface water adhering to the supplement fine aggregate is a slight amount of a grade that can be disregarded compared with a required amount of water, there is no problem in terms of quality of concrete.

When putting fine aggregate and water into the measurement tank 6, it is preferable to supply them to the measurement tank 6, performing water binding of the fine aggregate so that a top of the fine aggregate may be mostly in agreement with the water level. Thereby, the ratio of the fine aggregate to the water in the measurement tank 6 becomes close to the specified mix, thereby reducing an amount of supplement of fine aggregate dramatically.

As described above, according to the measuring apparatus 1 for concrete-forming materials of this embodiment, surface water of fine aggregate is indirectly calculated as a pat of the mass $M_w$ of water, even if the fine aggregate whose moisture state is not uniform is used, taking into consideration this variation, and the mass of fine aggregate is calculated as mass $M_a$ in the saturated surface-dried condition. More specifically, since the mass of fine aggregate and water will be calculated on the same conditions as the specified mix, even if fine aggregate whose moisture state is not uniform is used, concrete can be made with the amount of water as in the specified mix without measuring a percentage of surface moisture of the fine aggregate.

Furthermore, according to the measuring apparatus 1 of concrete-forming materials of this embodiment, the vibrating feeder 5 and the screen device 23 are provided, by which fine aggregate can be conveyed without granulation and this conveyed fine aggregate can be thrown into the measurement tank 6 as fine particles. Therefore, it becomes possible to suppress nearly thoroughly mixing of air bubbles into the submergence fine aggregate and to disregard an influence of air bubbles practically.

While the detection electrode 33 is electrically connected to one electrode terminal of the power supply 34, which is a component of the electrode-type displacement sensor 7, and the steel measurement tank 6 is electrically connected to the other electrode terminal in this embodiment, a reference electrode longer than the detection electrode 33 can be arranged almost parallel to the detection electrode instead.

In this constitution, when moving down the elevator 32, a tip of the reference electrode penetrates to the submergence fine aggregate 41, first. At this point, however, the electrode is not yet energized. Only after the tip of the detection electrode contacts the water surface of the submergence fine aggregate 41, the electrode is energized.

If a stopping accuracy cannot be secured sufficiently without decreasing a descending speed of the elevator 32, by which it takes long time in the measurement, it is also possible to further provide a speed-control electrode longer than the detection electrode 33 and shorter than the reference electrode.

In this constitution, energization between the speed-control electrode and the reference electrode is monitored. When the speed-control electrode contacts the water surface of the submergence fine aggregate 41, energization therebetween is achieved. Therefore, the descending speed of the elevator 32 can be controlled therewith.

According to this constitution, the descending speed of the elevator 32 can be previously decreased when the detection electrode 33 approaches the water surface of the submergence fine aggregate 41 to some extent. Therefore, the elevator 32 can be stopped with sufficient accuracy.

Furthermore, air content measurement can be omitted by preventing air bubbles from being mixed into the submergence fine aggregate in this embodiment. If the air content is measured separately, however, the vibrating feeder 5 and the screen device 23 can be omitted.

In this case, to measure the submergence fine aggregate, fine aggregate in an arbitrary wet condition is first discharged from the discharge opening 4 of the fine aggregate feed hopper 3. It is then put into the measurement tank 6 with water to form a submergence fine aggregate. The fine aggregate is thoroughly submerged in the water within the measurement tank as submergence aggregate.

Subsequently, the total mass $M_f$ and the total $V_f$ of the submergence fine aggregate, in other words, the fine aggregate and the water held in the measurement tank 6 in this condition are measured with the load cell 8 and the electrode-type displacement sensor 7, respectively, in the same manner as described above.

Then, the mass $M_w$ of water and the mass $M_a$ of the fine aggregate in a saturated surface-dried condition are calculated by substituting the total mass $M_f$ and the total volume $V_f$ for the following two formulas.

$$M_a + M_w = M_f \quad (1)$$

$$M_a/\rho_a + M_w/\rho_w = V_f(1 - a/100) \quad (2\text{-}a)$$

where $\rho_a$ is the density of the fine aggregate in the saturated surface-dried condition, $\rho_w$ is the density of water, and "a" is an air content (%) included in the total volume $V_f$.

After measuring and calculating the mass $M_w$ of water and the mass $M_a$ of the fine aggregate in the saturated surface-dried condition in this manner, they are compared with a mix proportion shown by a specified mix. Subsequently, an insufficiency, which should be remedied by filling, is measured and then the submergence fine aggregate is supplemented with additional water or aggregate when needed so as to allow the fine aggregate and the water to form concrete material.

Second Embodiment

Figure 8:
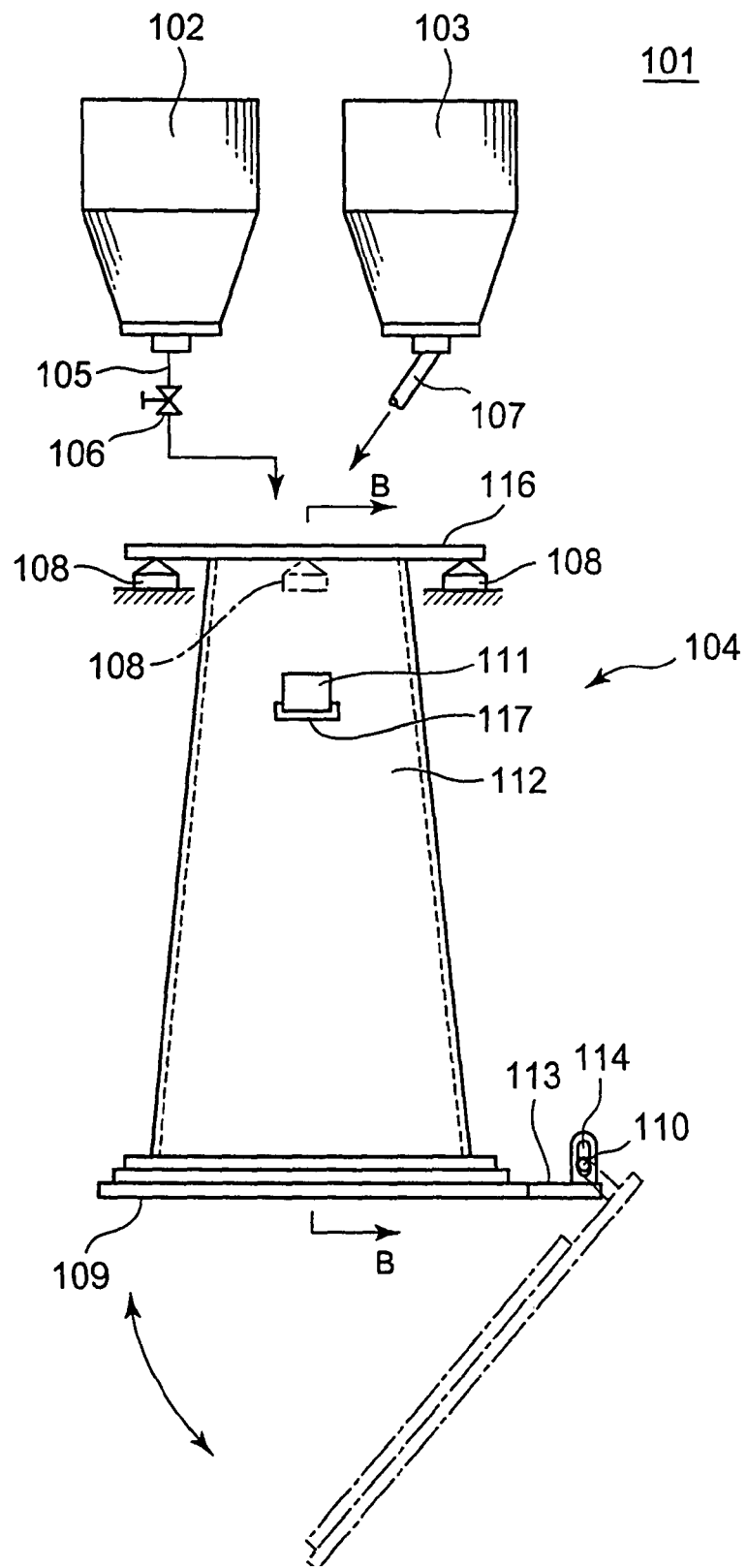
FIG. 8 is a general view of the preferable measuring apparatus for concrete-forming materials according to the present invention.

Referring to FIG. 8, there is shown a general view illustrating a measuring apparatus for concrete-forming materials according to a second embodiment. As shown in FIG. 8, measuring apparatus 101 for concrete-forming materials according to this embodiment comprises a water storage hopper 102 for storing water, a fine aggregate storage hopper 103 for storing fine aggregate used as aggregate, a measurement tank 104 for containing water and fine aggregate supplied from the water storage hopper 102 and the fine aggregate storage hopper 103 as submergence aggregate, and load cells 108 as submergence aggregate mass measuring means for measuring a mass of the submergence aggregate in the measurement tank 104. The water storage hopper 102 forms means for supplying water in conjunction with a water feed pipe 105 connected to the water storage hopper 102 at a bottom thereof, whose discharge opening is located above the measurement tank 104, and a closing valve 106 arranged in a predetermined position of the water feed pipe 105. The fine aggregate storage hopper 103 forms aggregate supply means in conjunction with a fine aggregate feed pipe 107 whose discharge opening is located above the measurement tank 104.

In this arrangement, the water storage hopper 102, the fine aggregate storage hopper 103, and the load cells 108 are mounted on a stand, which is not shown, and a collar circular ring 116 of the measurement tank 104 is put on the load cells to hold the measurement tank 104 in a suspended condition. Thereby, the mass of the measurement tank can be measured with the load cells 108. The load cells 108 are preferably placed, for example, in three places at 120° intervals on the same horizontal surface so that the measurement tank 104 can be held stably in a suspended condition during measurement.

Figure 9:
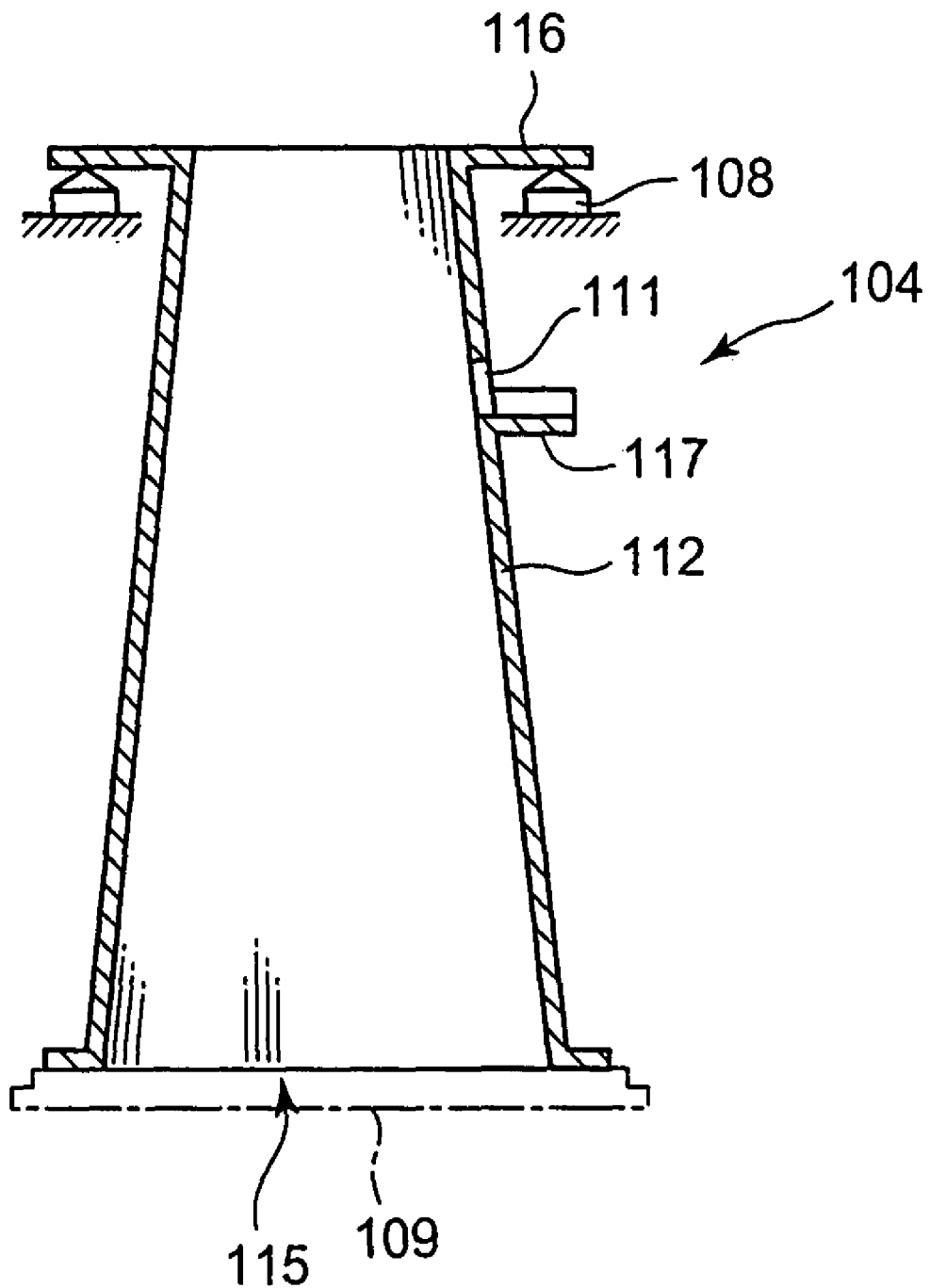
FIG. 9 is a cross section of the measurement tank taken along line B-B of FIG. 8.

Referring to FIG. 9, there is shown a longitudinal sectional view of the measurement tank 104. As apparent from FIGS. 8 and 9, it is possible to attach a bottom lid 109 capable of maintaining watertightness inside the measurement tank at a bottom opening 115 of the measurement tank 104 in such a way that the bottom lid 109 is free to open or close. In other words, the bottom lid 109 is made of a circular plate having an outside diameter substantially equivalent to or slightly larger than an outside diameter of the bottom opening of the measurement tank 104. Furthermore, a long hole 114 is formed at a tip of an L-shaped mounting arm 113 provided as an extension from a rim of the circular plate, and a pin 110 fixed to a stand not shown is passed through the long hole 114, by which it becomes possible to rotate the bottom lid 109 around the pin 110 so as to open or close the bottom opening 115 of the measurement tank 104. Furthermore, in a condition where the bottom lid 109 is closed, the long hole 114 is oriented vertically, thereby preventing a reaction force from being generated at the pin 110 by a load of the measurement tank 104. In fixing the bottom lid 109 to the bottom opening 115 of the measurement tank 104, an appropriate method can be selected out of known methods such as fastening with a bolt or a clamp.

The measurement tank 104 is formed in a shape of a hollow truncated cone so that a bore of the measurement tank 104 gets larger in a downward direction. Therefore, when the measurement is finished, a free fall of the submergence aggregate in measurement tank 104 can be achieved only by opening the bottom lid 109 without a blockage of submergence aggregate in the measurement tank even if no vibrating instrument such as a vibrator is used. Thereafter, the submergence aggregate can be thrown into a kneading mixer, which is not shown, together with cement and coarse aggregate measured separately.

As apparent from the sectional view in FIG. 9, a rectangular opening for overflow 111 is formed in a wall 112 of the measurement tank 104 at a predetermined height of the measurement tank 104 so that water of the submergence aggregate in the measurement tank 104 overflows outside. In addition, a grooved guide 117 is provided in a horizontally protruding condition along a lower edge of the opening for overflow 111. Overflow water flows on the guide and runs down from a tip thereof, thereby enabling water to overflow smoothly from the opening for overflow 111 without a flow on a circumferential surface of the measurement tank 104.

A volume of the measurement tank 104 is arbitrary. The volume of the measurement tank may be made in agreement with a total amount required for a unit of concrete mixing, i.e., one batch. Otherwise, the amount required can be divided into some amounts in the measurement tank.

Figure 10:
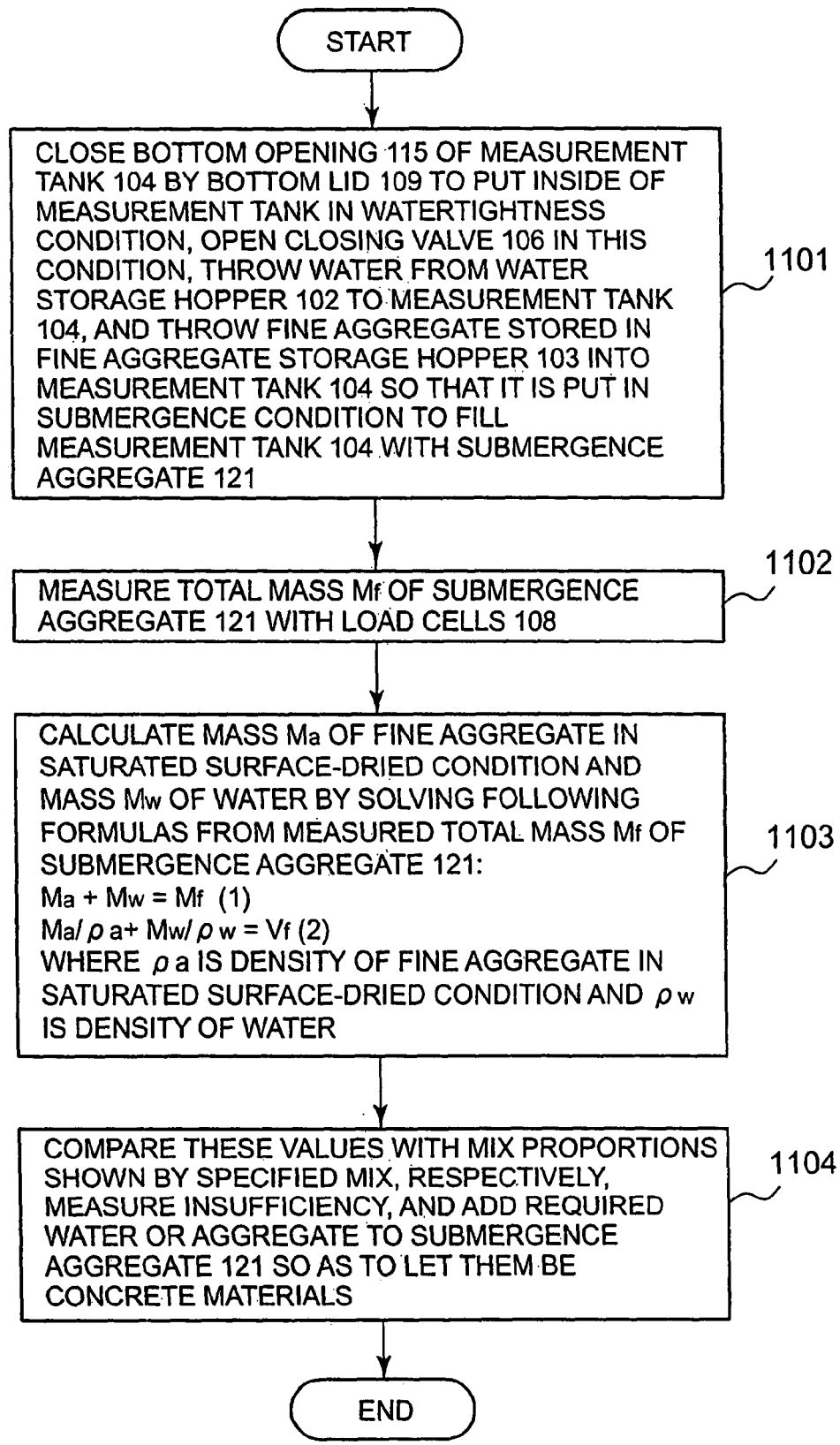
FIG. 10 is a flowchart showing a preferable measuring method for concrete-forming materials according to the present invention.
Figure 11:
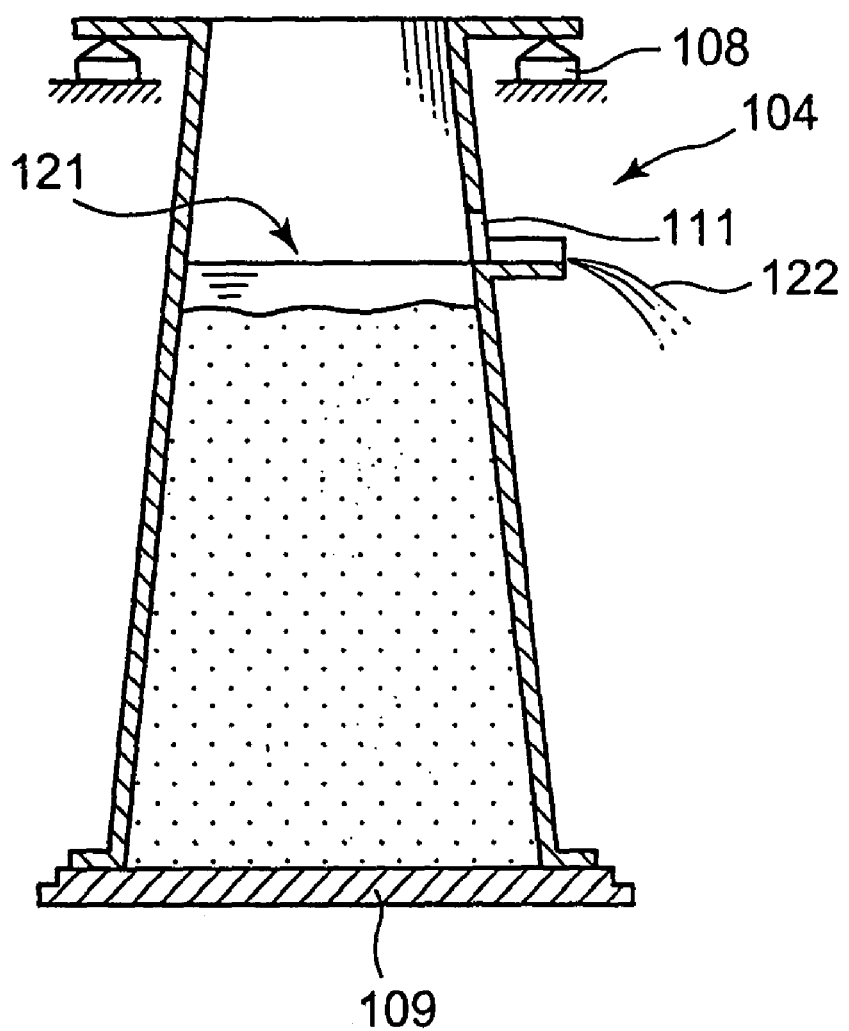
FIG. 11 is a diagram showing an action of the preferable measuring apparatus for concrete-forming materials according to the present invention.

A flowchart in FIG. 10 shows a measurement procedure for measuring water and fine aggregate by using the measuring apparatus 101 for concrete-forming materials according to this embodiment. As shown in FIG. 10, the bottom opening 115 of the measurement tank 104 is closed by the bottom lid 109 to put the inside of the measurement tank in the water-tightness condition, first. The closing valve 106 is opened in the above condition. Water is then thrown from the water storage hopper 102 to the measurement tank 104, and the fine aggregate stored in the fine aggregate storage hopper 103 is thrown into the measurement tank 104 so that it is put in a submergence condition to fill the measurement tank 104 with submergence aggregate 121 as shown in FIG. 11 (step 1101).

When throwing the aggregate and the water into the measurement tank 104, preferably the water is thrown earlier and the fine aggregate is thrown later to prevent the submergence aggregate from being mixed with air bubbles. In addition, if the fine aggregate is not directly thrown from the fine aggregate storage hopper 103 to the measurement tank 104, but the fine aggregate is conveyed from a portion beneath the fine aggregate storage hopper 103 to an upper opening of the measurement tank 104 by using a vibrating feeder having an electromagnetic vibrator, for example, it becomes possible to prevent granulation of the fine aggregate, and thus prevent air bubble mixing.

When throwing water and the fine aggregate into the measurement tank 104 to fill it with the submergence aggregate 121, care should be taken so that the fine aggregate is submerged in water and the water overflows the opening for overflow 111.

With this, a water level at which the water 122 overflows the opening for overflow 111 is predetermined. Therefore, if the measurement tank 104 is filled with the submergence aggregate 121 as mentioned above, the total volume $V_f$ of the submergence aggregate 121 equal to a known value is obtained without measurement.

Subsequently, the total mass $M_f$ of the submergence aggregate 121 is measured with the load cells 108 (step 1102). The total mass $M_f$ of the submergence aggregate 121 can be obtained by subtracting a mass of an empty measurement tank 104, containing no submergence aggregate 121, from a value measured by the load cells 108.

Subsequently, mass $M_a$ of the fine aggregate in a saturated surface-dried condition and mass $M_w$ of the water are calculated by solving the following two formulas from the measured total mass $M_f$ of the submergence aggregate 121 (step 1103).

$$M_a + M_w = M_f \quad (1)$$

$$M_a/\rho_a + M_w/\rho_w = V_f \quad (2)$$

where $\rho_a$ is the density of the fine aggregate in the saturated surface-dried condition and $\rho_w$ is the density of the water.

After measuring and calculating the mass $M_w$ of the water and the mass $M_a$ of the fine aggregate in the saturated surface-dried condition as mentioned above, these values are compared with mix proportions shown by a specified mix, respectively. Thereafter, an insufficiency is measured and then the submergence aggregate 121 is supplemented with additional water or aggregate when needed so as to let the aggregate and the water become concrete materials (step 1104). If there is too much water, excess water is sucked with a vacuum or the like.

As set forth hereinabove, according to the measuring apparatus and the measuring method for concrete-forming materials of this embodiment, the surface water of the fine aggregate is indirectly calculated as a part of the mass $M_w$ of the water, even if a fine aggregate whose moisture state is not uniform is used, and the mass of fine aggregate is calculated as the mass $M_a$ of the fine aggregate in the saturated surface-dried condition. In other words, since the mass of the fine aggregate and the mass of the water are calculated on conditions equivalent to the specified mix, even if a humidity grade of the fine aggregate is not fixed at every measurement, it becomes possible to make concrete with water of the amount as shown by the specified mix.

While the load cells 108 of compression type are used, and they are placed in three places in this embodiment, it is arbitrary as to what type of load cells are used as means for measuring a mass of submergence aggregate. For example, load cells of a tension type can be used or they can be placed in four or more places. If the measurement tank 104 can be held stably in a suspended condition, only one or two load cells can be used.

A correction of air content has not been described particularly in this embodiment. If air content a (%) of the submergence aggregate is considered, however, the already-known total volume $V_f$ should be multiplied by (1−a/100). For example, the following formula may be used instead of formula (2).

$$M_a/\rho_a + M_w/\rho_w = V_f(1-a/100) \quad (2\text{-}a)$$

This enables more accurate measurement since actual total volume is used for the measurement with the air content excluded. In other cases, the air content can be corrected similarly, if necessary.

Figure 12:
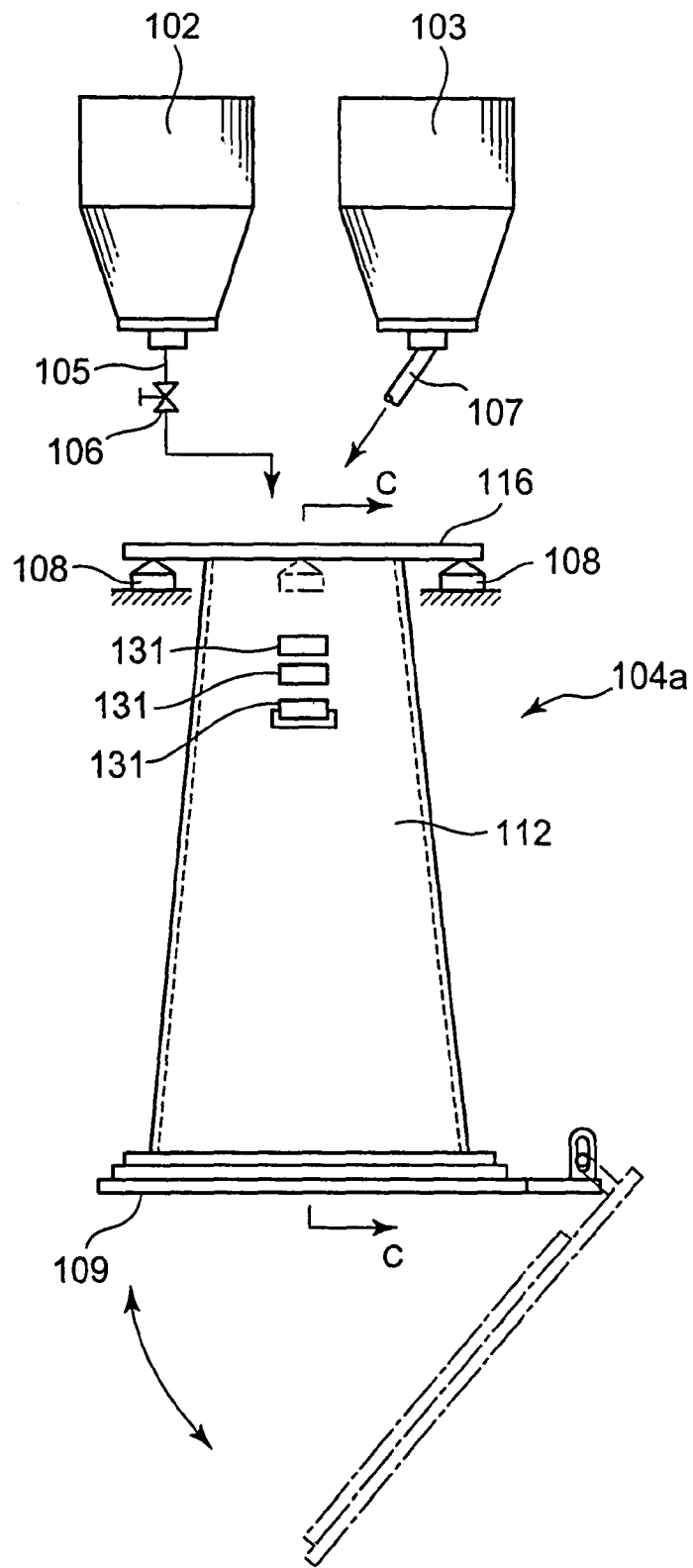
FIG. 12 is a general view showing a measuring apparatus for concrete-forming materials according to a modification of the invention.
Figure 13:
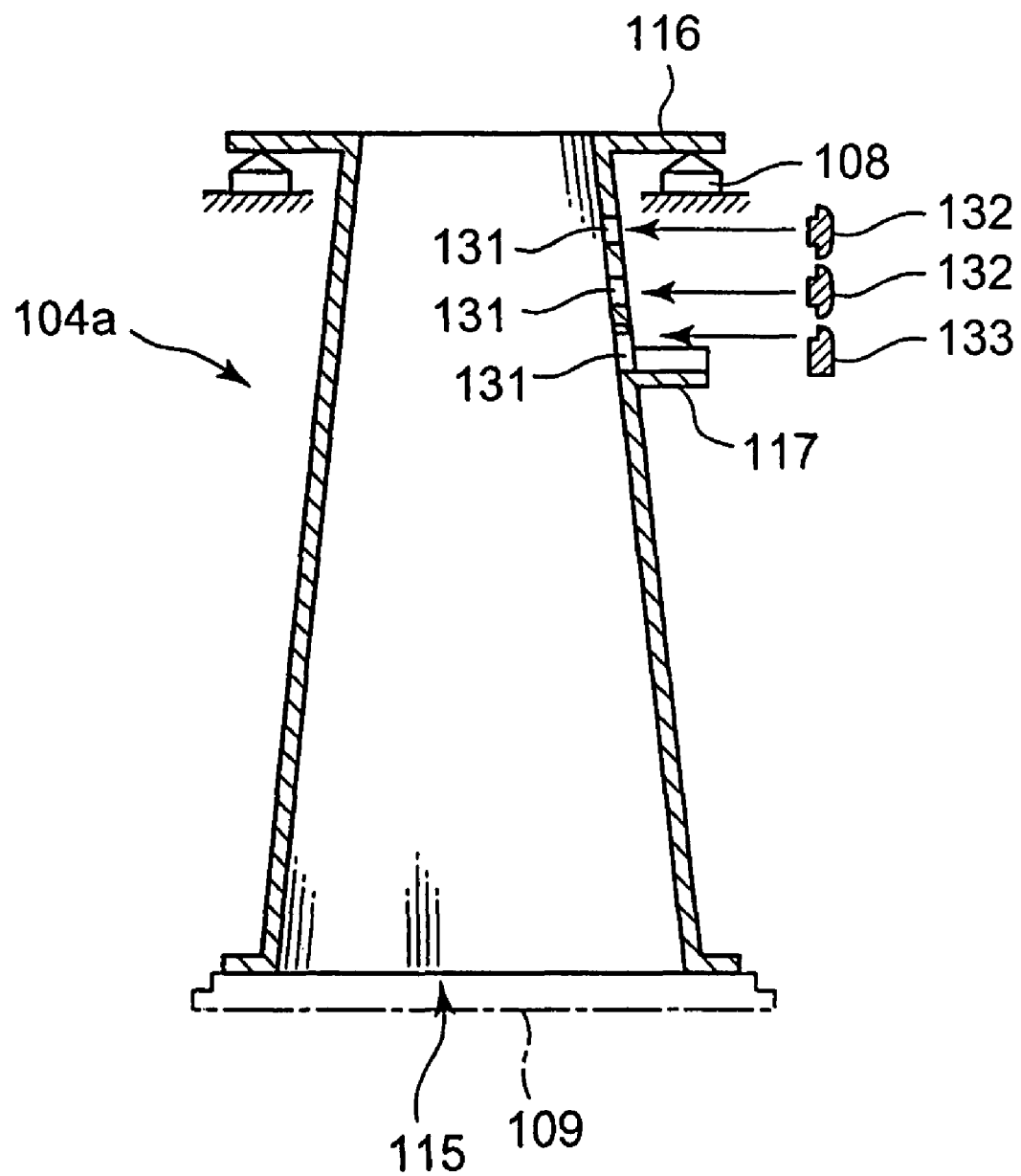
FIG. 13 is a cross section of a measurement tank taken along line C-C of FIG. 12.

Furthermore, the rectangular opening for overflow 111 is formed in the wall 112 of the measurement tank 104 at the predetermined height of the measurement tank 104, and the guide 117 is provided in a horizontally protruding condition along the lower edge of the opening for overflow 111 in this embodiment. As shown in FIGS. 12 and 13, however, three openings for overflow 131 can be provided at different heights in the wall 112 of the measurement tank 104 instead of the opening for overflow 111, and the guide 117 can be provided in a horizontally protruding condition along a lowest edge of the opening for overflow 131.

In this constitution, only the opening for overflow 131 corresponding to a required total volume Vf is opened, and all other openings for overflow 131 are sealed by using seal plugs 132 and 133 as shown in FIG. 13.

According to the constitution, it becomes unnecessary to prepare a measurement tank for each total volume $V_f$.

In the measuring apparatus for concrete-forming materials shown in FIGS. 12 and 13, a measurement tank 104a having three openings for overflow 131 is used instead of the measurement tank 104 having the opening for overflow 111. The measurement tank 104a is the same as the measurement tank 104 in components except for the difference in the openings for overflow, and it is the same as the above embodiment in its entire constitution. Therefore, description of these points will be omitted here.

Figure 14:
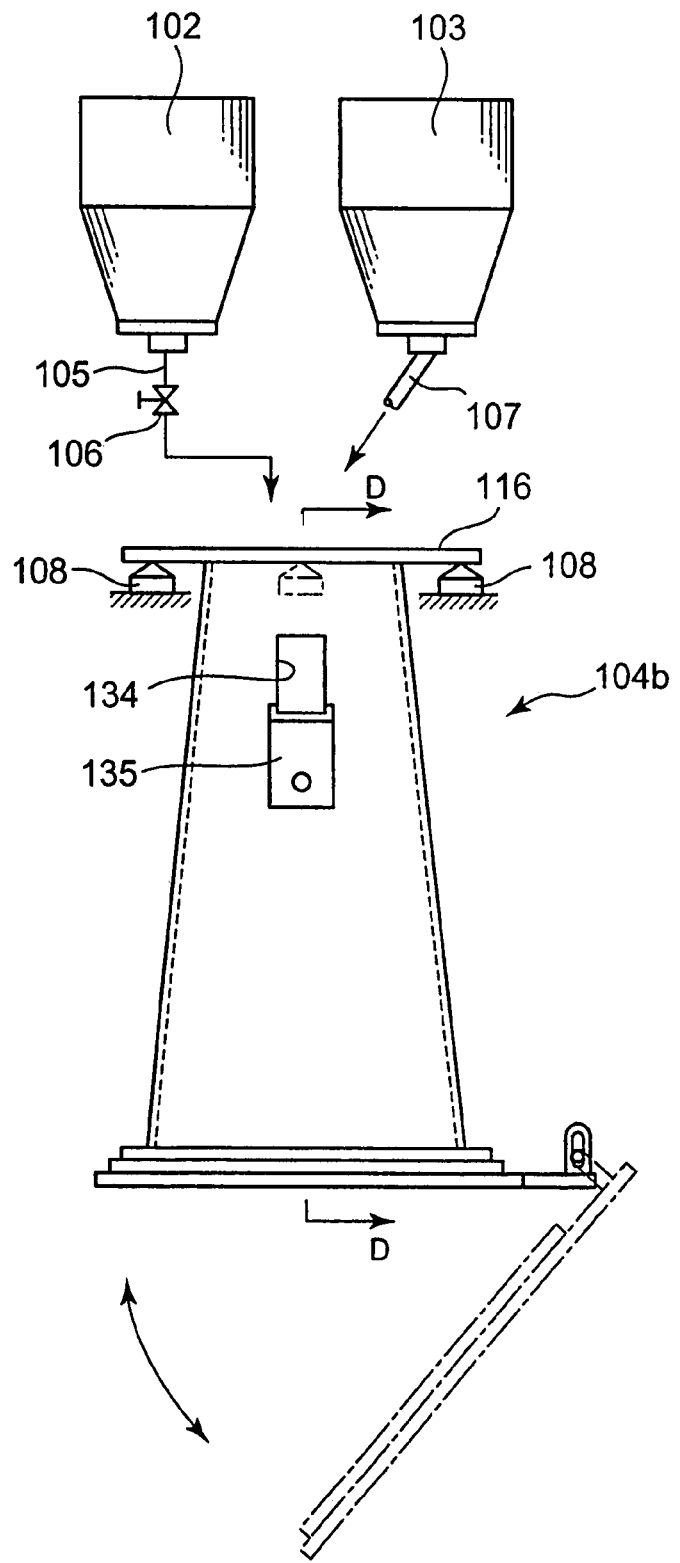
FIG. 14 is a general view showing a measuring apparatus for concrete-forming materials according to another modification of the invention.
Figure 15:
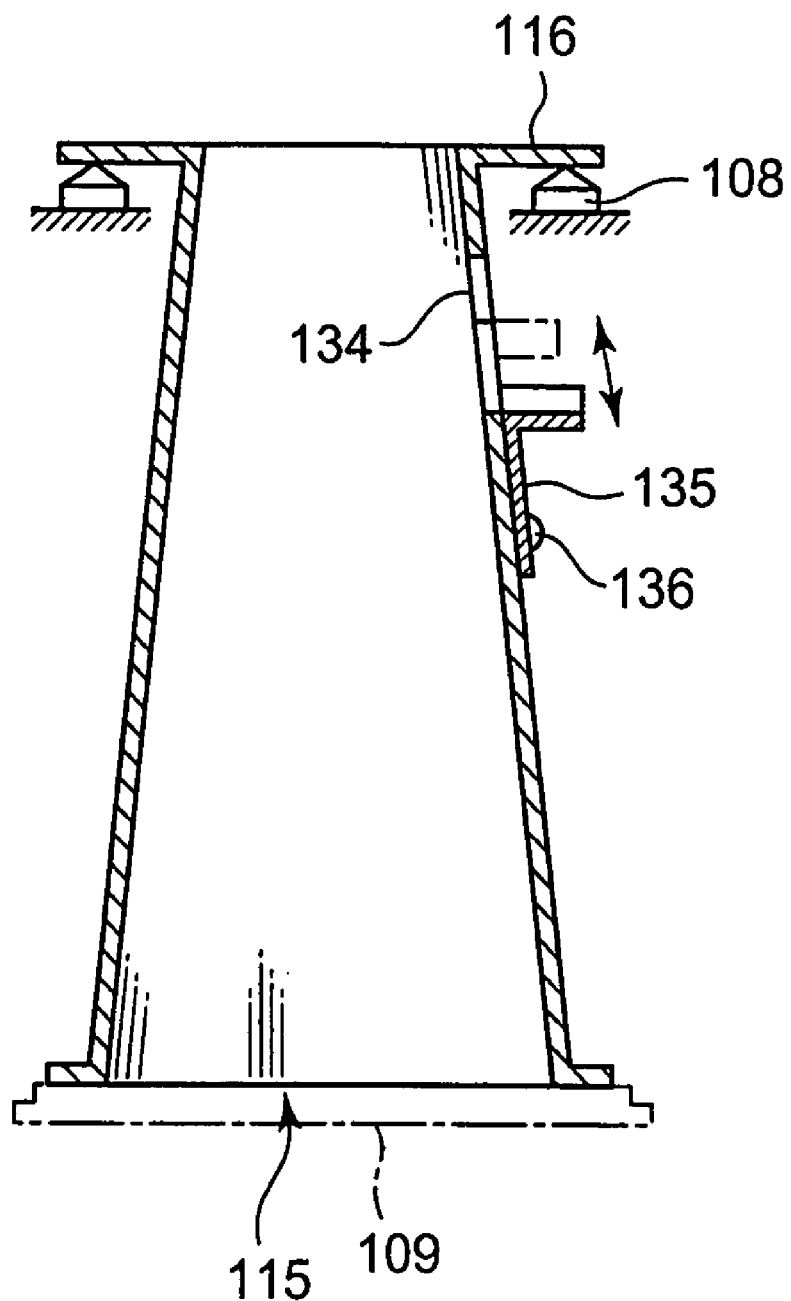
FIG. 15 is a cross section of a measurement tank taken along line D-D of FIG. 14.

Furthermore, in this embodiment, the rectangular opening for overflow 111 is formed in the wall 112 of the measurement tank 104 at the predetermined height of the measurement tank 104 and the guide 117 is provided in the horizontally protruding condition along the lower edge of the opening for overflow. As shown in FIGS. 14 and 15, an opening for overflow 134 having an increased height thereof can be formed in the wall 112 instead of the opening for overflow 111, with the opening for overflow 134 covered with a bracket cover 135 free to move up and down. Furthermore, an overflow height can be variable according to a position where the bracket cover 135 moves up and down.

The bracket cover 135 comprises a guide, which is similar to the guide 117, provided in a horizontally protruding condition from an upper edge of a curved cover plate moving up and down along a circumferential surface of measurement tank 104b. The bracket cover 135 is fixed to the wall of the measurement tank 104b with a screw 136, by which it can be positioned at a desired height. A rubber gasket or the like may be used appropriately so that predetermined watertightness is secured between a curved cover plate and the wall of the measurement tank 104b.

In this constitution, the bracket cover 135 is moved up and down so that the guide of the bracket cover 135 is located at the desired height and then it is fixed with the screw 136. With this, the curved cover plate of the bracket cover 135 closes a part of the opening for overflow 134 lower than the guide, by which it becomes possible to variably adjust a water level at which water of submergence aggregate in the measurement tank 104b overflows. Therefore, there is no need to prepare a measurement tank for each total volume $V_f$.

In the measuring apparatus of concrete materials shown in FIGS. 14 and 15, a measurement tank 104b having the opening for overflow 134 and the bracket cover 135 for variably adjusting the overflow height of the opening for overflow 134 is used instead of the measurement tank 104 having the opening for overflow 111. The measurement tank 104b is the same as the measurement tank 104 in components except for the difference in the opening for overflow and its related member, and it is the same as the above embodiment in its entire constitution. Therefore, description of these points will be omitted here.

The following should be noted though it has not been particularly noted in this embodiment. If there is a possibility that the aggregate thrown into the measurement tank 104 will emerge from the water and will not be submergence aggregate, a vibrator is used to level a top of the aggregate.

Figure 16:
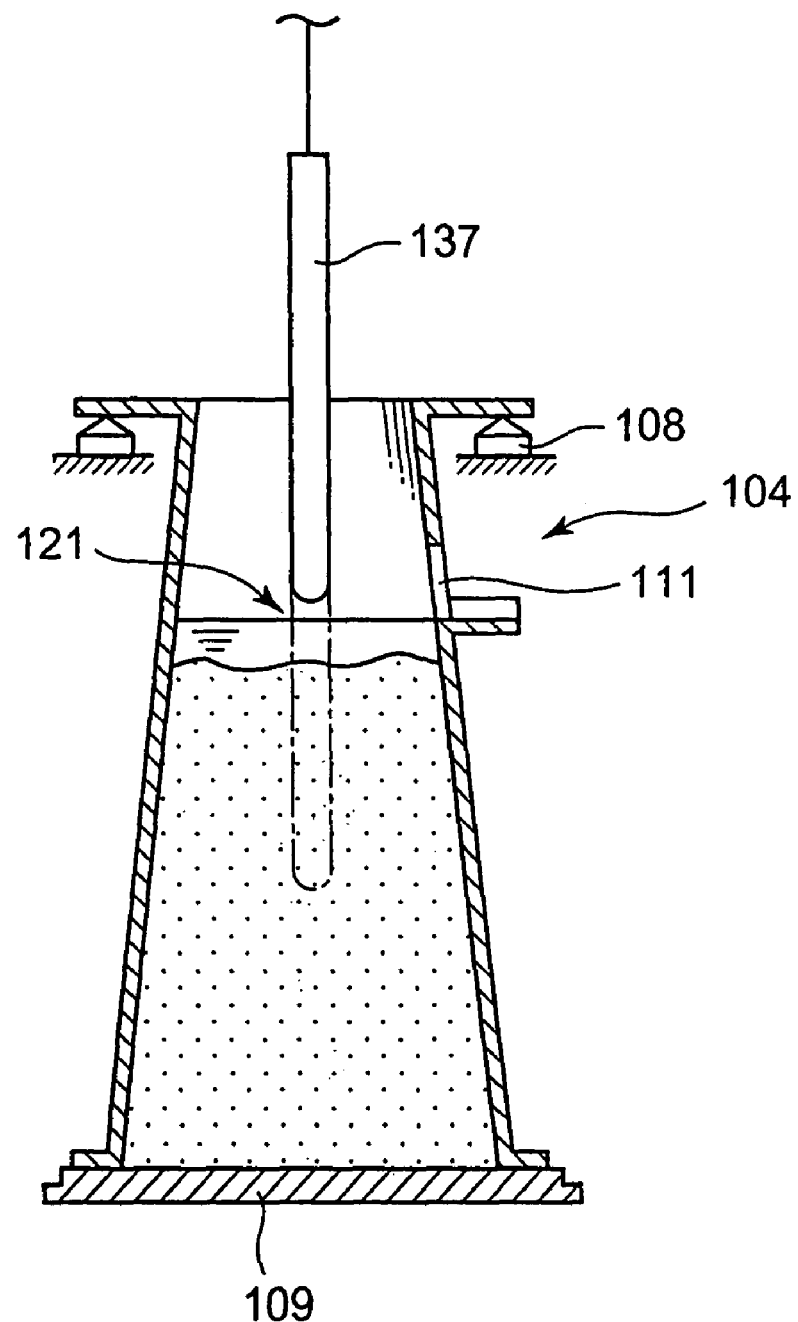
FIG. 16 is a cross section of a measuring apparatus for concrete-forming materials according to another modification of the invention.

Referring to FIG. 16, there is shown a modification as mentioned above. In FIG. 16, a rod vibrator 137 is installed above the measurement tank 104 so that the rod vibrator is free to move up and down and so that it may be buried in the submergence aggregate 121 in a downward location (indicated by a dash-single-dot line in FIG. 16).

In this constitution, during or after throwing fine aggregate, the vibrator 137 is lowered and operated in the shown condition.

With this, the fine aggregate thrown into the measurement tank 104 is leveled by vibration of the vibrator 137, by which the fine aggregate will be submerged in the water. Before measuring a mass of the submergence aggregate 121, the vibrator 137 is raised and put in a standby state, until a next measurement, in an upward location.

Third Embodiment

Figure 17:
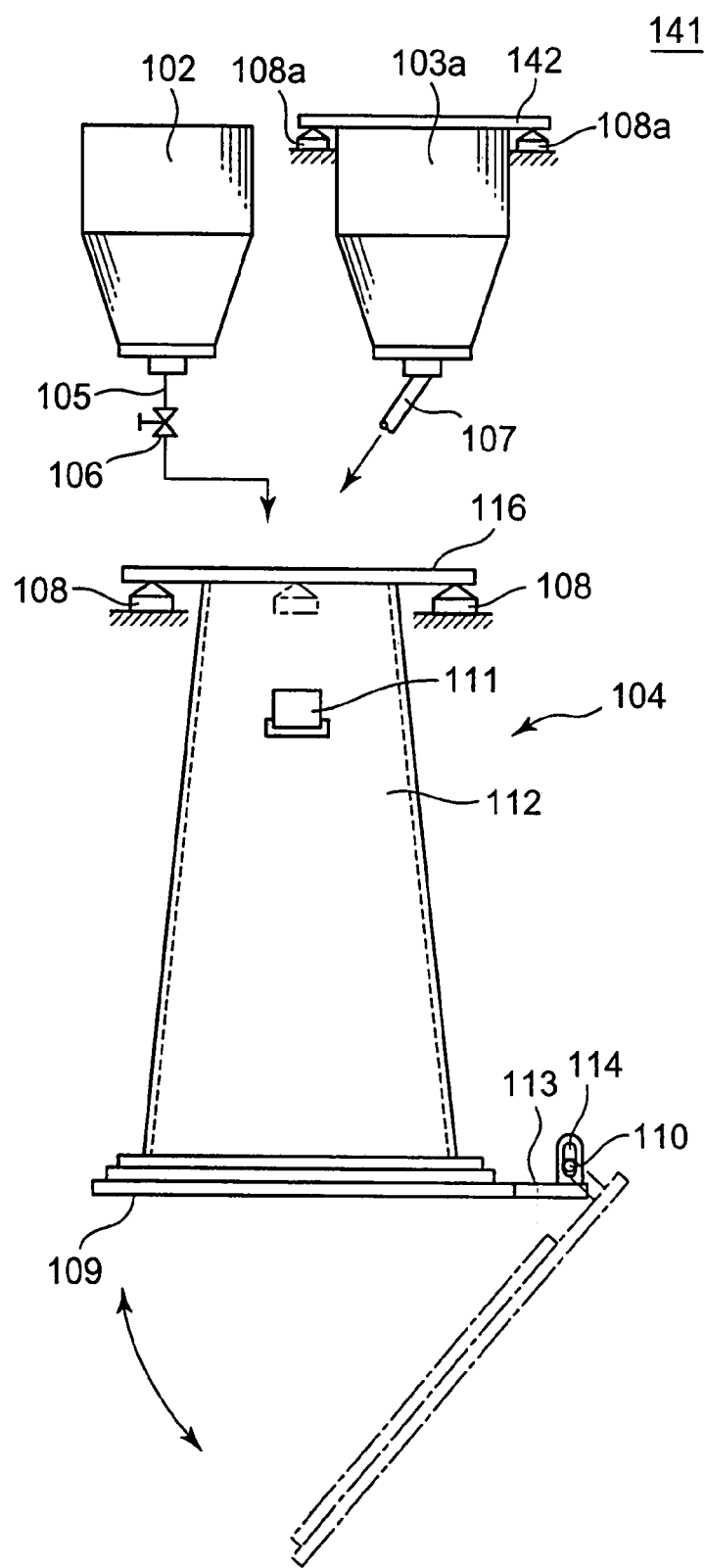
FIG. 17 is a general view of a measuring apparatus for concrete-forming materials according to still another modification of the invention.

Referring to FIG. 17, there is shown a general view illustrating a measuring apparatus of concrete materials according to a third embodiment. As shown in FIG. 17, measuring apparatus 141 of concrete-forming materials according to this embodiment comprises a water storage hopper 102 for storing water, a fine aggregate storage hopper 103a for storing fine aggregate used as aggregate, a measurement tank 104 for containing water and fine aggregate supplied from the water storage hopper 102 and the fine aggregate storage hopper 103a as submergence aggregate, and load cells 108 as submergence aggregate mass measuring means for measuring a mass of the submergence aggregate in the measurement tank 104. The water storage hopper 102 forms means for supplying water in conjunction with a water feed pipe 105 connected to the water storage hopper 102 at a bottom thereof and whose discharge opening is located above the measurement tank 104, and a closing valve 106 arranged in a predetermined position of the water feed pipe 105. The fine aggregate storage hopper 103a forms means for feeding aggregate in conjunction with a fine aggregate feed pipe 107 whose discharge opening is located above the measurement tank 104.

In this arrangement, the water storage hopper 102 and the load cells 108 are attached to a stand, which is not shown, and a collar circular ring 116 of the measurement tank 104 is put on the load cells 108 to hold the measurement tank 104 in a suspended condition. Thereby, the mass of the measurement tank 104 can be measured with the load cells 108. The load cells 108 are preferably placed, for example, in three places at 120° intervals on the same horizontal surface so that the measurement tank 104 can be held stably in a suspended condition during measurement.

Furthermore, in this embodiment, load cells 108a as means for measuring a mass of aggregate are attached to a stand (not shown), and a collar circular ring 142 of the fine aggregate storage hopper 103a is put on the load cells 108a to hold the fine aggregate storage hopper 103a in a suspended condition, by which a mass of the fine aggregate storage hopper 103a can be measured by the load cells 108a. The load cells 108a are preferably placed in three places at 120° intervals on the same horizontal surface in the same manner as for the load cells 108 so that the fine aggregate storage hopper 103a can be held stably in a suspended condition during measurement.

The arrangements of the measurement tank 104, bottom lid 109, and other components are the same as those of the second embodiment. Therefore, their description will be omitted here.

Figure 18:
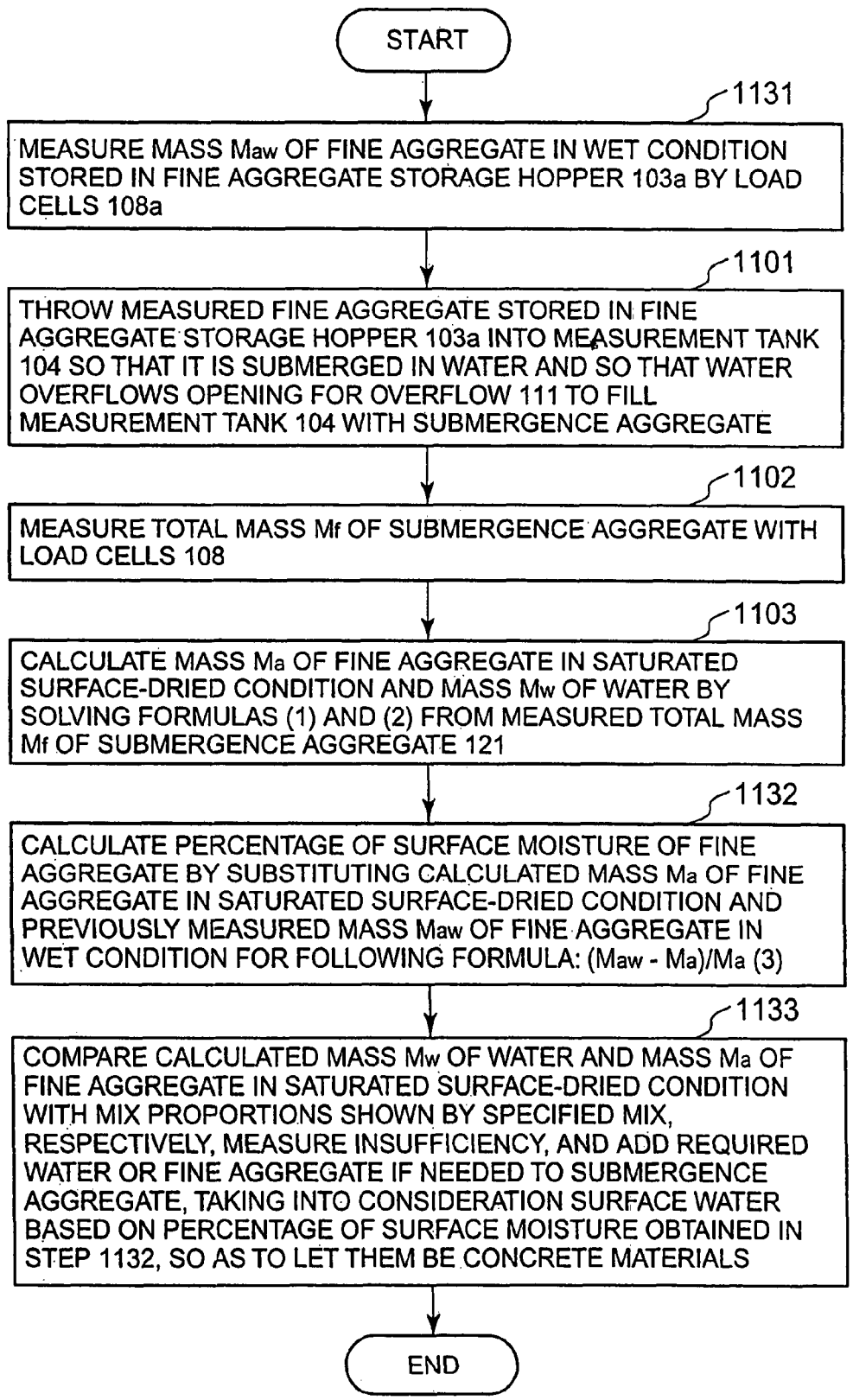
FIG. 18 is a flowchart showing a measuring method for concrete-forming materials according to another modification of the invention.

A flowchart in FIG. 18 shows a measurement procedure for measuring water and fine aggregate by using the measuring apparatus 141 for concrete-forming materials according to this embodiment. As shown in FIG. 18, mass $M_{aw}$ of fine aggregate in a wet condition stored in the fine aggregate storage hopper 103a is measured by the load cells 108a, first (step 1131).

On the other hand, the inside of the measurement tank 104 is put into a watertightness condition in the same manner as in the second embodiment. The closing valve 106 is opened in the above condition. Water is then thrown from the water storage hopper 102 to the measurement tank 104, and the measured fine aggregate stored in the fine aggregate storage hopper 103a is thrown into the measurement tank 104 so that it is submerged in water and so that water overflows an opening for overflow 111 to fill the measurement tank 104 with submergence aggregate (step 1101).

Hereinafter, in the same manner as in the second embodiment, total mass $M_f$ of the submergence aggregate is measured with the load cells 108 (step 1102). Thereafter, mass $M_a$ of the fine aggregate in the saturated surface-dried condition and mass $M_w$ of the water are calculated by solving the formulas (1) and (2) from the measured total mass $M_f$ of the submergence aggregate 121 (step 1103).

Subsequently, a percentage of surface moisture of the fine aggregate is calculated by substituting the calculated mass $M_a$ of the fine aggregate in the saturated surface-dried condition, and the previously measured mass $M_{aw}$ of the fine aggregate in the wet condition into the following formula (step 1132).

$$(M_{aw} - M_a)/M_a \tag{3}$$

Subsequently, the calculated mass $M_w$ of the water and the mass $M_a$ of the fine aggregate in the saturated surface-dried condition are compared with mix proportions shown by a specified mix, respectively, and an insufficiency is measured. Thereafter, the submergence aggregate is supplemented with additional water if water is needed or with additional fine aggregate if fine aggregate is needed as a result of referencing the percentage of surface moisture obtained in step 1132 while taking into consideration the percentage of surface moisture. Then, the aggregate and the water become concrete materials (step 1133). If there is too much water, excess water is sucked with a vacuum or the like.

As set forth hereinabove, according to the measuring apparatus and the measuring method for concrete-forming materials of this embodiment, surface water of the fine aggregate can be indirectly calculated as a part of the mass $M_w$ of the water, even if a fine aggregate whose moisture state is not uniform is used, and the mass of fine aggregate can be calculated as the mass $M_a$ of the fine aggregate in the saturated surface-dried condition in the same manner as in the second embodiment. In other words, since the mass of the fine aggregate and the mass of the water are calculated on conditions equivalent to the specified mix, even if a humidity grade of the fine aggregate is not fixed at every measurement, it becomes possible to make concrete with water of the amount as shown by the specified mix.

Furthermore, according to the measuring apparatus and the measuring method for concrete-forming materials of this embodiment, the percentage of surface moisture can be measured in parallel in addition to the action and effect mentioned above.

While load cells 108 of compression type are used and they are placed in three places in this embodiment, it is arbitrary as to what type of load cells are used as means for measuring a mass of submergence aggregate. For example, load cells of a tension type can be used or they can be placed in four or more places. If the measurement tank 104 can be held stably in a suspended condition, only one or two load cells can be used.

A correction of air content has not been described particularly in this embodiment. If the air content a (%) of the submergence aggregate is considered, however, the already-known total volume $V_f$ should be multiplied by (1−a/100). For example, the following formula may be used instead of formula (2).

$$M_a/\rho_a + M_w/\rho_w = V_f(1-a/100) \tag{2-a}$$

This enables more accurate measurement since actual total volume is used for the measurement with the air content excluded.

While the modifications of the second embodiment described by referring to FIGS. 12 to 16 are directly applicable to the third embodiment, their constitution and their action and effect are the same as those of the second embodiment. Therefore, their description will be omitted here.

Fourth Embodiment

Figure 19:
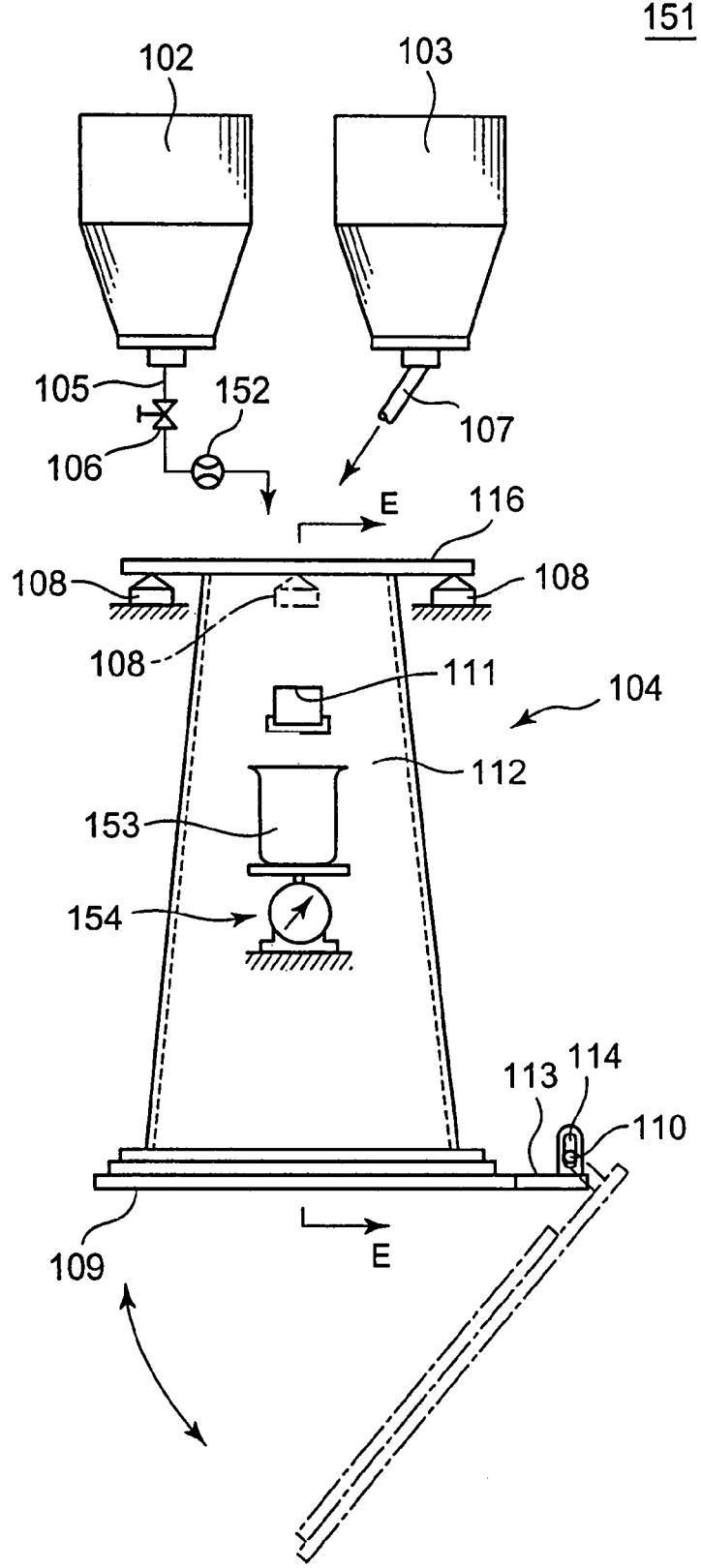
FIG. 19 is a general view of a measuring apparatus for concrete-forming materials according to another modification of the invention.

Referring to FIG. 19, there is shown a general view illustrating a measuring apparatus for concrete-forming materials according to a fourth embodiment. As shown in FIG. 19, measuring apparatus 151 for concrete-forming materials according to this embodiment comprises a water storage hopper 102 for storing water, a fine aggregate storage hopper 103 for storing fine aggregate used as aggregate, a measurement tank 104 for containing water and fine aggregate supplied from the water storage hopper 102 and the fine aggregate storage hopper 103 as submergence aggregate, and load cells 108 as submergence aggregate mass measuring means for measuring a mass of the submergence aggregate in the measurement tank 104. The water storage hopper 102 forms means for supplying water in conjunction with a water feed pipe 105 connected to the water storage hopper 102 at a bottom thereof and whose discharge opening is located above the measurement tank 104, a closing valve 106 arranged in a predetermined position of the water feed pipe 105, and a flowmeter 152 as means for measuring feed water. The fine aggregate storage hopper 103 forms means for feeding aggregate in conjunction with a fine aggregate feed pipe 107 whose discharge opening is located above the measurement tank 104.

In this arrangement, the water storage hopper 102, the fine aggregate storage hopper 103, and the load cells 108 are attached to a stand, which is not shown, and a collar circular ring 116 of the measurement tank 104 is put on the load cells 108 to hold the measurement tank 104 in a suspended condition. Thereby, the mass of the measurement tank 104 can be measured with the load cells 108. The load cells 108 are preferably placed, for example, in three places at 120° intervals on the same horizontal surface so that the measurement tank 104 can be held stably in a suspended condition during measurement.

Figure 20:
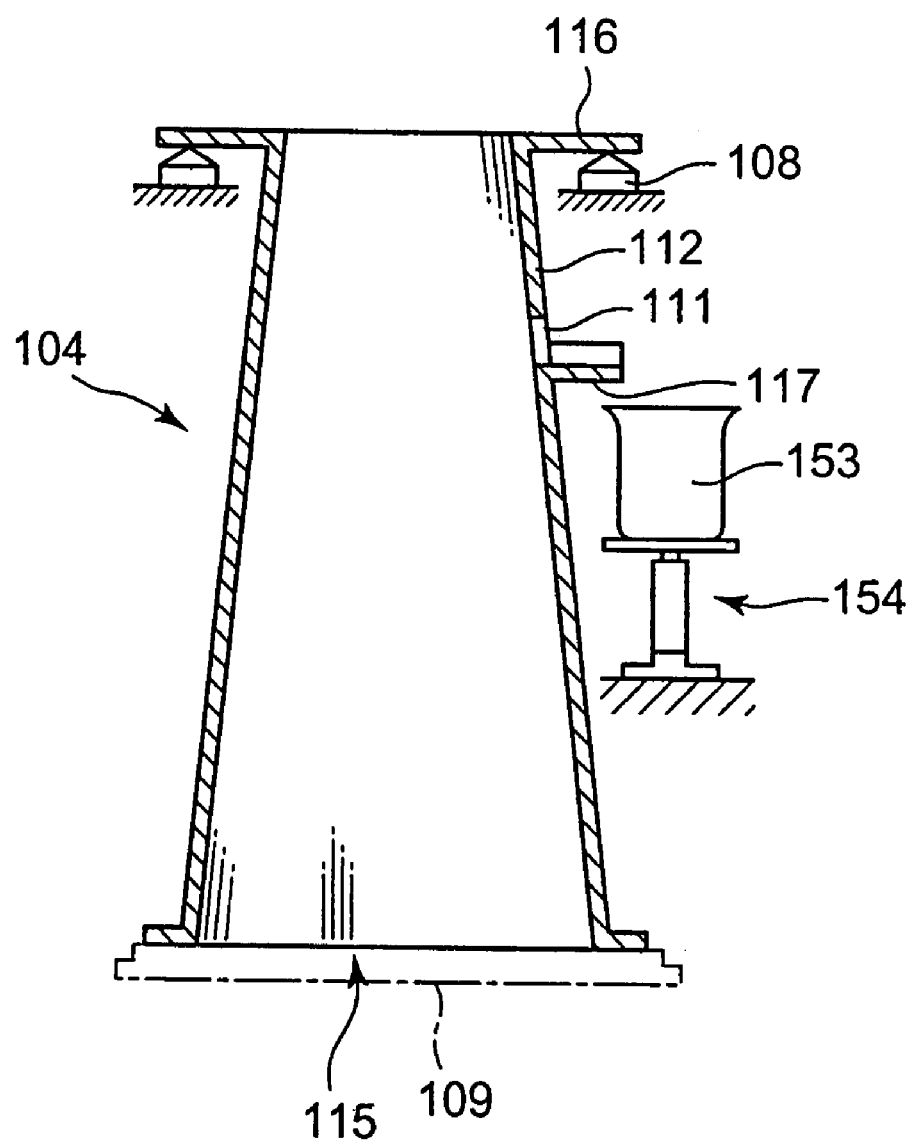
FIG. 20 is a cross section of a measurement tank taken along line E-E of FIG. 19.

Furthermore, in this embodiment, as apparent from the sectional view in FIG. 20, the measuring apparatus comprises a storage container 153 for storing water overflowing an opening for overflow 111 and running down from a tip of a guide 117, and a massmeter 154 as means for measuring a mass of overflow water together with the storage container 153. This measuring apparatus is capable of measuring the mass of water thrown into the measurement tank 104 by means of the above flowmeter 152, and the mass of overflow water from the measurement tank 104 by means of the massmeter 154.

The arrangement of the measurement tank 104, bottom lid 109, and other components are the same as those of the second embodiment. Therefore, their description will be omitted here.

Figure 21:
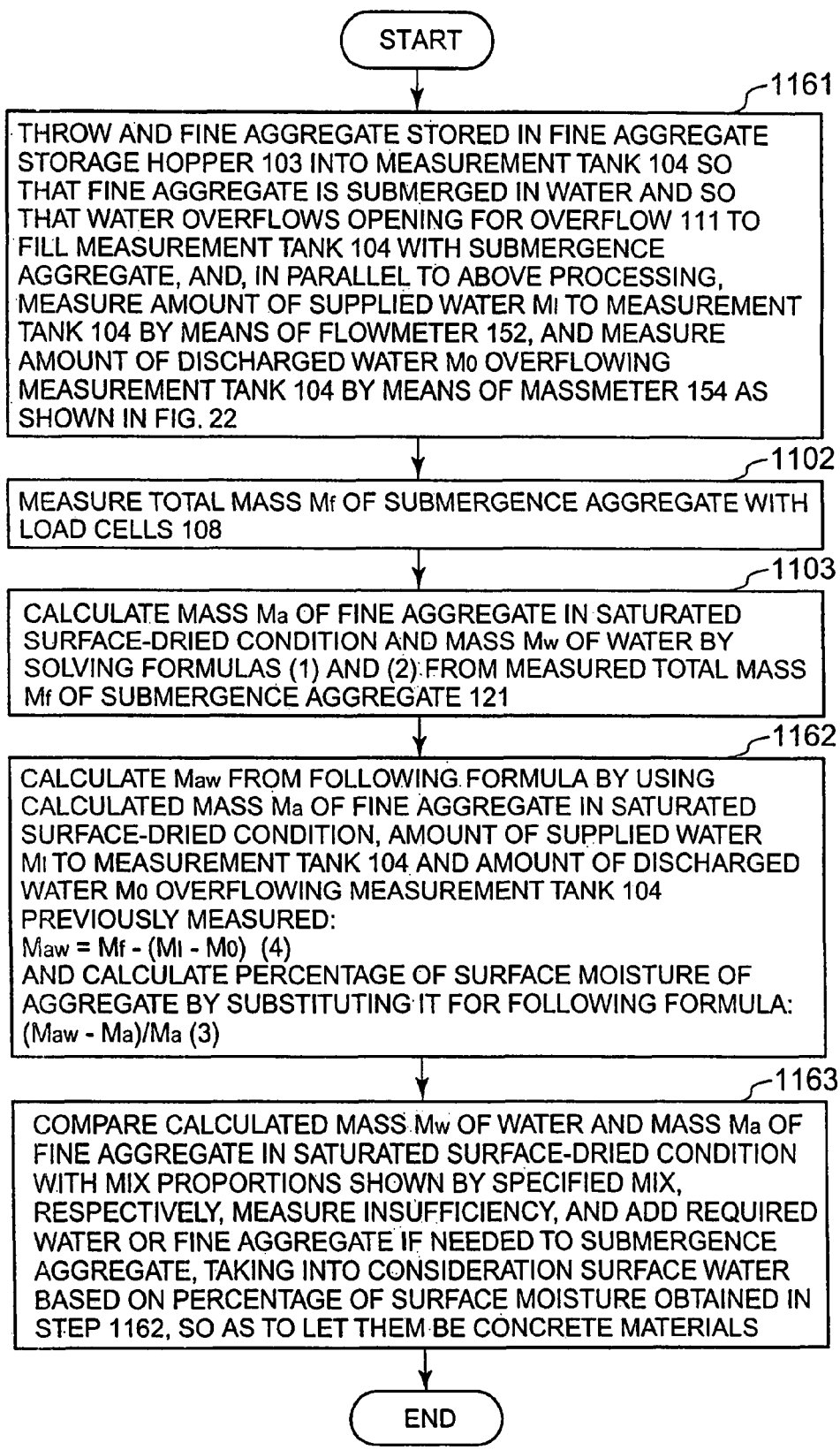
FIG. 21 is a flowchart of a preferable measuring method for concrete-forming materials according to the present invention.
Figure 22:
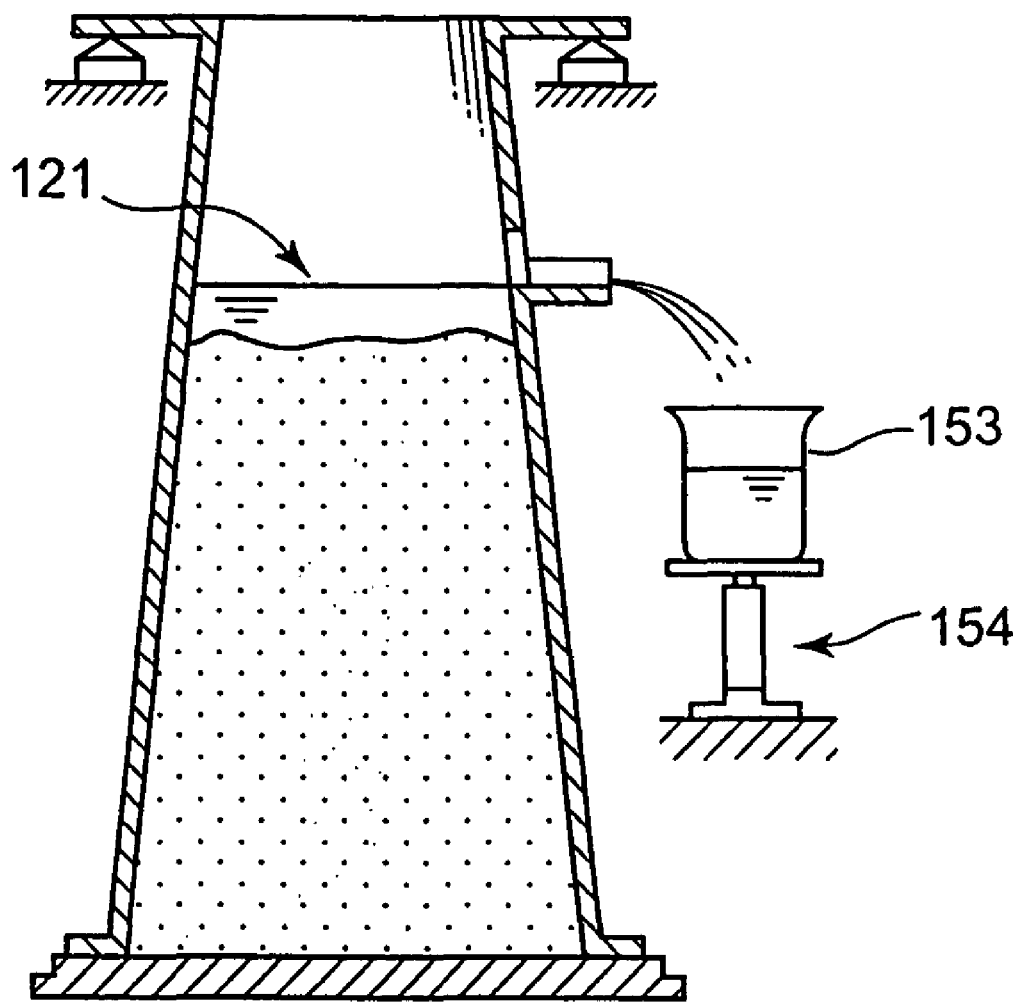
FIG. 22 is a diagram showing an action of a preferable measuring apparatus for concrete-forming materials according to the present invention.

A flowchart in FIG. 21 shows a measurement procedure for measuring water and fine aggregate by using measuring apparatus 151 for concrete-forming materials according to this embodiment. As shown in FIG. 21, the inside of the measurement tank 104 is put into a watertightness condition in the same manner as in the second embodiment. The closing valve 106 is opened in the above condition. Water is then thrown from the water storage hopper 102 to the measurement tank 104 and the fine aggregate stored in the fine aggregate storage hopper 103 is thrown into the measurement tank 104 so that it is submerged in water and so that water overflows the opening for overflow 111 to fill the measurement tank 104 with submergence aggregate. In parallel to the above processing, the measuring apparatus measures the amount of water $M_I$ supplied to the measurement tank 104 by means of the flowmeter 152, and measures the amount of water $M_O$ discharged overflowing the measurement tank 104 by means of the massmeter 154 as shown in FIG. 22 (step 1161).

Hereinafter, in the same manner as in the second embodiment, total mass $M_f$ of the submergence aggregate is measured with the load cells 108 (step 1102). Thereafter, mass $M_a$ of the fine aggregate in a saturated surface-dried condition and mass $M_w$ of the water are calculated by solving the formulas (1) and (2) from the measured total mass $M_f$ of the submergence aggregate 121 (step 1103).

Subsequently, $M_{aw}$ is calculated from the following formula by using the calculated mass $M_a$ of the fine aggregate in the saturated surface-dried condition, the amount of water $M_I$ supplied to the measurement tank 104 and the amount of discharged water $M_O$ overflowing the measurement tank 104 previously measured:

$$M_{aw} = M_f - (M_I - M_O) \tag{4}$$

A percentage of surface moisture of the fine aggregate is then calculated by substituting the calculated mass $M_{aw}$ into the following formula (step 1162).

$$(M_{aw} - M_a)/M_a \tag{3}$$

Furthermore, the calculated mass $M_w$ of the water and the mass $M_a$ of the fine aggregate in the saturated surface-dried condition are compared with mix proportions shown by a specified mix, respectively, and an insufficiency is measured. Thereafter, the submergence aggregate is supplemented with additional water if water is needed, or with additional fine aggregate if fine aggregate is needed, as a result of referencing the percentage of surface moisture obtained in step 1162 while taking into consideration the percentage of surface moisture. Then, the aggregate and the water are allowed to become concrete materials (step 1163). If there is too much water, excess water is sucked with a vacuum or the like.

As set forth hereinabove, according to the measuring apparatus and the measuring method of concrete materials of this embodiment, surface water of the fine aggregate can be indirectly calculated as a part of the mass $M_w$ of the water, even if a fine aggregate whose moisture state is not uniform is used, and the mass of fine aggregate can be calculated as the mass $M_a$ of the fine aggregate in the saturated surface-dried condition in the same manner as in the second embodiment. In other words, since the mass of the fine aggregate and the mass of the water are calculated on conditions equivalent to the specified mix, even if a humidity grade of the fine aggregate is not fixed at every measurement, it becomes possible to make concrete with water of the amount as shown by the specified mix.

Furthermore, according to the measuring apparatus and the measuring method for concrete-forming materials of this embodiment, the percentage of surface moisture can be measured in parallel in addition to the action and effect mentioned above.

While load cells 108 of a compression type are used and placed in three places in this embodiment, it is arbitrary as to what type of load cells are used as means for measuring a mass of submergence aggregate. For example, load cells of a tension type can be used or they can be placed in four or more places. If the measurement tank 104 can be held stably in a suspended condition, only one or two load cells can be used.

A correction of air content has not been described particularly in this embodiment. If air content a (%) of the submergence aggregate is considered, however, the known total volume $V_f$ should be multiplied by $(1-a/100)$. For example, the following formula may be used instead of formula (2).

$$M_a/\rho_a + M_w/\rho_w = V_f(1-a/100) \quad (2\text{-}a)$$

This enables more accurate measurement since actual total volume is used for the measurement with the air content excluded.

While the modifications of the second embodiment described by referring to FIGS. 12 to 16 are directly applicable to the fourth embodiment, their constitution and their action and effect are the same as those of the second embodiment. Therefore, their description will be omitted here.

Fifth Embodiment

Figure 23:
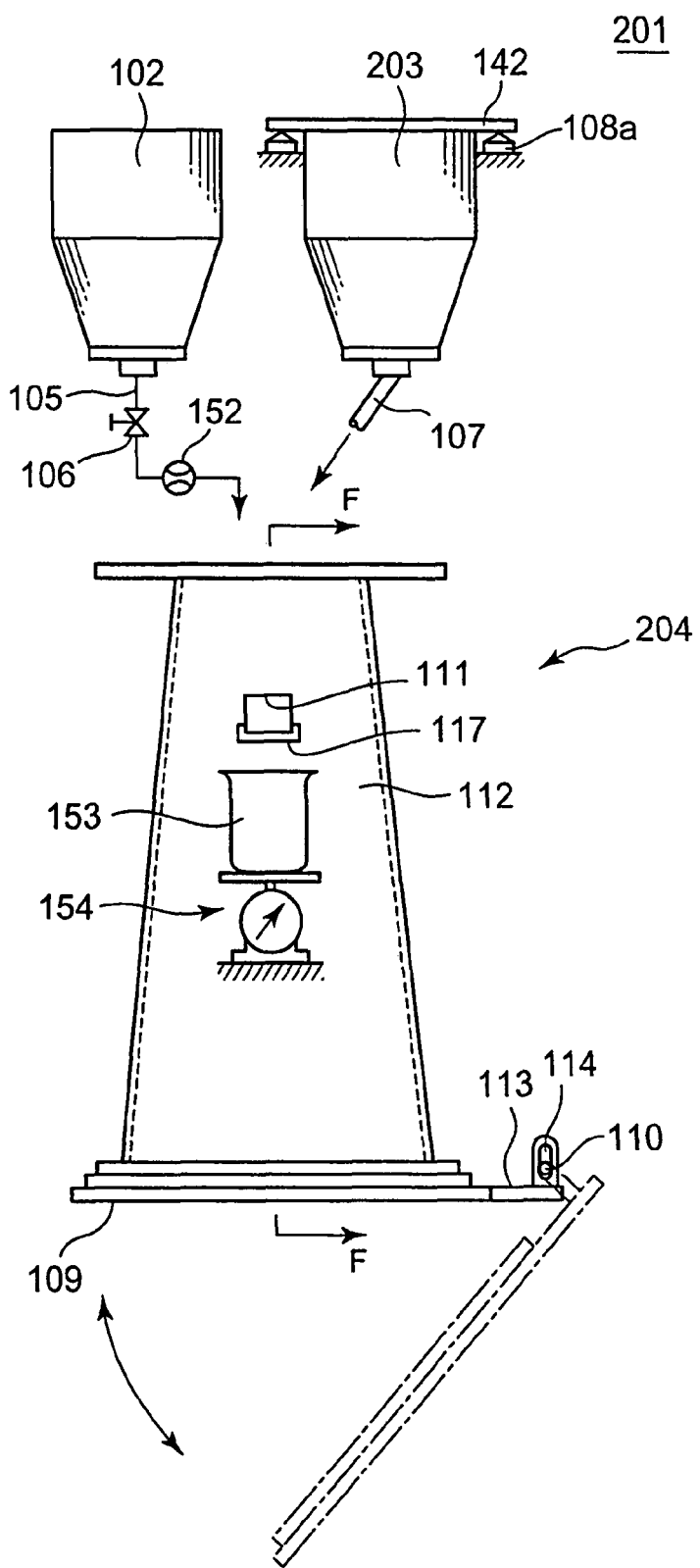
FIG. 23 is a general view of a preferable measuring apparatus for concrete-forming materials according to the present invention.

Referring to FIG. 23, there is shown a general view illustrating a measuring apparatus for concrete-forming materials according to a fifth embodiment. A shown in FIG. 23, measuring apparatus 201 for concrete-forming materials of this embodiment comprises a water storage hopper 102 for storing water, a fine aggregate measurement container 203 as an aggregate measurement container storing fine aggregate as aggregate to be measured, a submergence aggregate container 204 for containing water and fine aggregate supplied from the water storage hopper 102 and the fine aggregate measurement container 203, respectively, as submergence aggregate, and load cells 108a as submergence aggregate mass measuring means for measuring a mass of the fine aggregate in the fine aggregate measurement container 203. The water storage hopper 102 forms means for supplying water in conjunction with a water feed pipe 105 connected to the water storage hopper 102 at a bottom thereof and whose discharge opening is located above the submergence aggregate container 204, a closing valve 106 arranged in a predetermined position of the water feed pipe 105, and a flowmeter 152 as means for measuring feed water.

Fine aggregate is supplied as needed from a stock bin not shown to the fine aggregate measurement container 203, and this container is connected to a fine aggregate feed pipe 107 whose discharge opening is located above the submergence aggregate container 204.

In this arrangement, the water storage hopper 102, the submergence aggregate container 204, and the load cells 108a are attached to a stand, which is not shown, and a collar circular ring 142 attached to a top opening edge of the fine aggregate measurement container 203 is mounted on the load cells 108a to hold the fine aggregate measurement container 203 in a suspended condition. Thereby, the mass of the fine aggregate stored in the fine aggregate measurement container 203 can be measured with the load cells 108a. The load cells 108a are preferably placed, for example, in three places at 120° intervals on the same horizontal surface so that the fine aggregate measurement container 203 can be held stably in the suspended condition during measurement.

Figure 24:
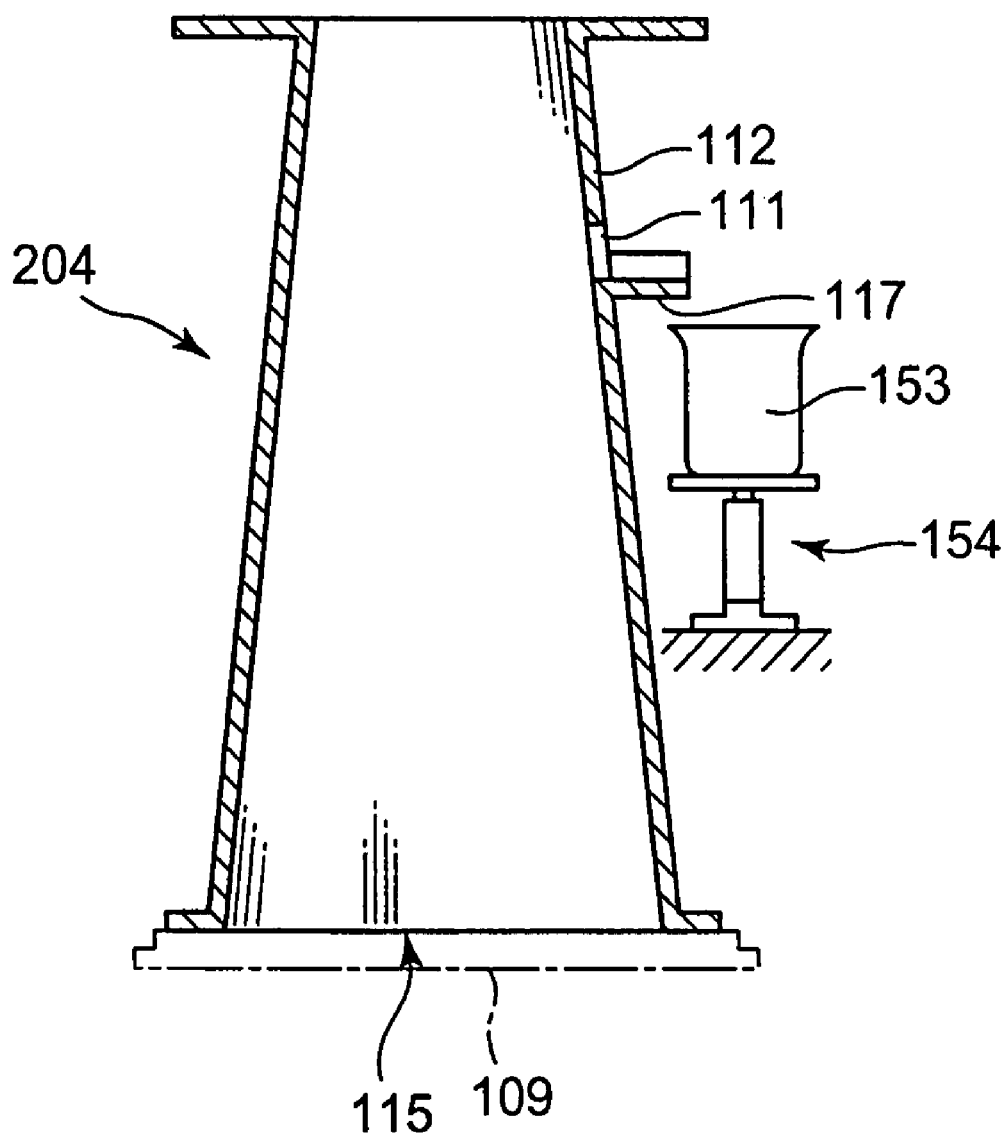
FIG. 24 is a cross section of a submergence aggregate container taken along line F-F of FIG. 23.

Referring to FIG. 24, there is shown a longitudinal sectional view of the submergence aggregate container 204. As apparent from FIGS. 23 and 24, it is possible to attach a bottom lid 109 capable of maintaining watertightness inside the submergence aggregate container 204 at a bottom opening 115 of the submergence aggregate container 204 in such a way that the bottom lid 109 is free to open or close. In other words, the bottom lid 109 is made of a circular plate having an outside diameter substantially equivalent to or slightly larger than an outside diameter of the bottom opening of the submergence aggregate container 204. Furthermore, a long hole 114 is formed at a tip of an L-shaped mounting arm 113 provided as an extension from a rim of the circular plate, and a pin 110 fixed to a stand not shown is passed through the long hole 114, by which it becomes possible to rotate the bottom lid 109 around the pin 110 so as to open or close the bottom opening 115 of the submergence aggregate container 204. In fixing the bottom lid 109 to the bottom opening 115 of the submergence aggregate container 204, an appropriate method can be selected out of known methods such as fastening with a bolt or a clamp.

The submergence aggregate container 204 is formed in a shape of a hollow truncated cone so that a bore of the submergence aggregate container 204 gets larger in a downward direction. Therefore, when a measurement is finished, a free fall of the submergence aggregate in the submergence aggregate container 204 can be achieved only by opening the bottom lid 109 without a blockage of submergence aggregate in the submergence aggregate container 204 even if no vibrating instrument such as a vibrator is used. Thereafter, the submergence aggregate can be thrown into a kneading mixer, which is not shown, together with cement and coarse aggregate measured separately.

As apparent from the sectional view in FIG. 24, a rectangular opening for overflow 111 is formed in a wall 112 of the submergence aggregate container 204 at a predetermined height of the submergence aggregate container 204 so that water of the submergence aggregate in the submergence aggregate container 204 overflows outside. In addition, a grooved guide 117 is provided in a horizontally protruding condition along a lower edge of the opening for overflow 111. Overflow water flows on the guide and falls from a tip thereof, thereby enabling water to overflow smoothly from the opening for overflow 111 without a flow on a circumferential surface of the submergence aggregate container 204.

A volume of the submergence aggregate container 204 is arbitrary. The volume of the submergence aggregate container 204 may be made in agreement with a total amount required for a unit of concrete mixing, i.e., one batch. Otherwise, the amount required can be divided into some amounts in the submergence aggregate container 204.

On the other hand, as apparent from a sectional view in FIG. 24, the measuring apparatus 201 for concrete-forming materials according to this embodiment comprises a storage container 153 for storing water overflowing the opening for overflow 111 and running down from the tip of the guide 117, and a massmeter 154 as means for measuring a mass of overflow water. This measuring apparatus is capable of measuring the mass of water thrown into the submergence aggregate container 204 by means of the above flowmeter 152, and the mass of overflow water from the submergence aggregate container 204 by means of the massmeter 154.

Figure 25:
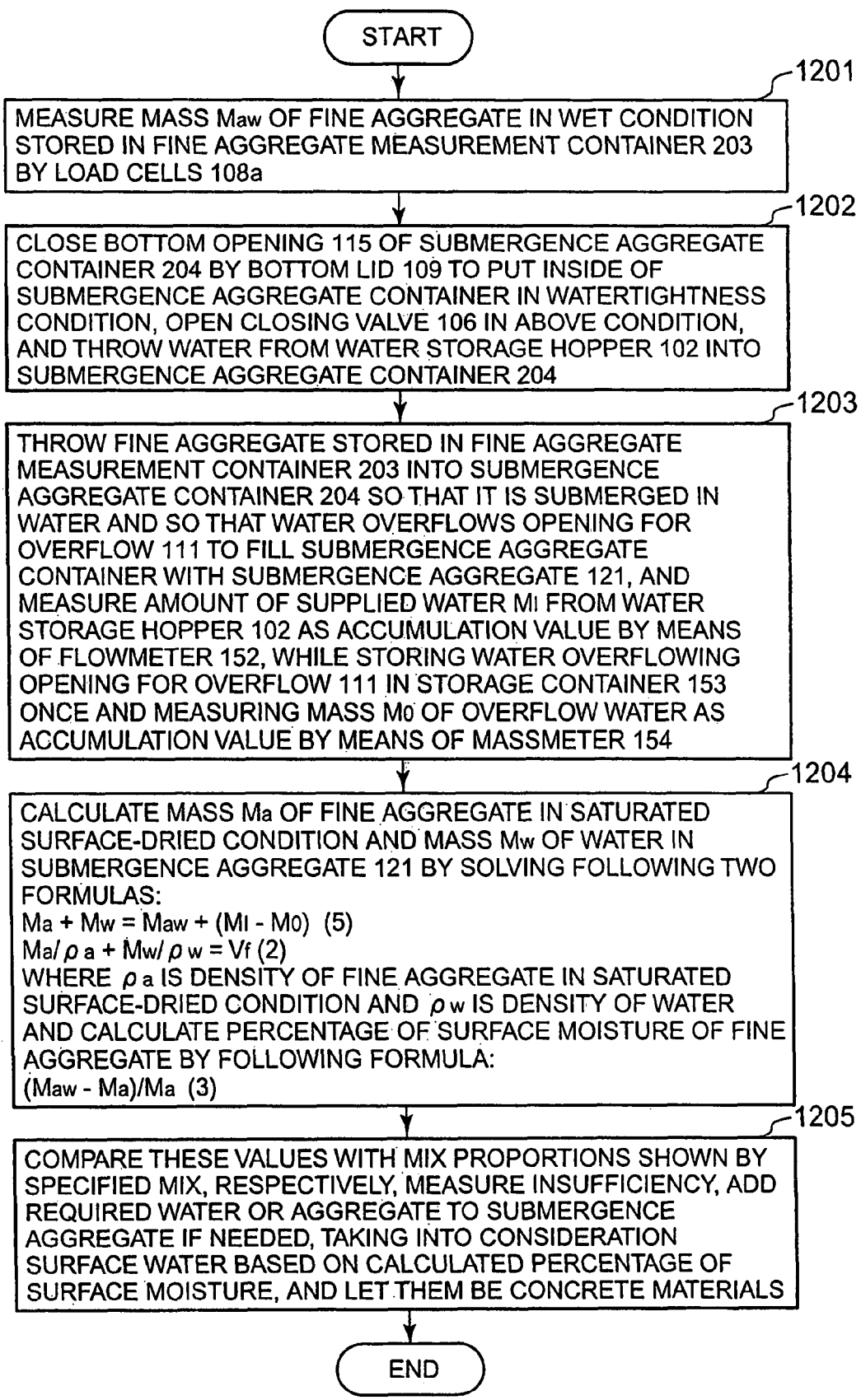
FIG. 25 is a flowchart of a preferable measuring method for concrete-forming materials according to the present invention.

A flowchart in FIG. 25 shows a measurement procedure for measuring water and fine aggregate by using the measuring apparatus 201 for concrete-forming materials according to this embodiment. As shown in FIG. 25, mass $M_{aw}$ of fine aggregate in a wet condition stored in the fine aggregate measurement container 203 is measured by the load cells 108a, first (step 1201).

The mass $M_{aw}$ of the fine aggregate in the fine aggregate measurement container 203 can be obtained by subtracting a mass of an empty fine aggregate measurement container 203 containing no fine aggregate from the value measured by the load cells 108a. In this connection, fine aggregate is generally in a wet condition.

Subsequently, the bottom opening 115 of the submergence aggregate container 204 is closed by the bottom lid 109 to put the inside of the submergence aggregate container 203 in a watertightness condition. The closing valve 106 is opened in the above condition. Water is then thrown from the water storage hopper 102 to the submergence aggregate container 204 (step 1202).

Figure 26:
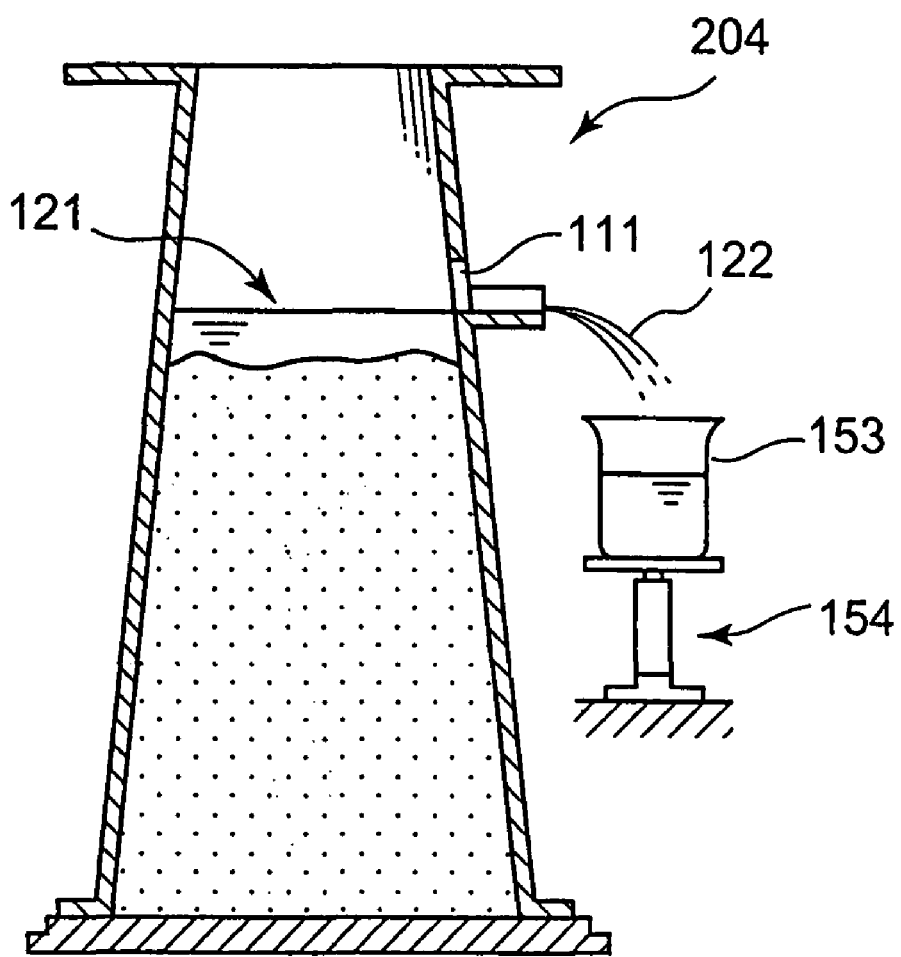
FIG. 26 is a diagram showing an action of the preferable measuring apparatus for concrete-forming materials according to the present invention.

As shown in FIG. 26, the fine aggregate stored in the fine aggregate measurement container 203 is thrown into the submergence aggregate container 204 so that it is submerged in water and so that the water overflows the opening for overflow 111 to fill the submergence aggregate container with submergence aggregate 121. In parallel to the above processing, the measuring apparatus measures the amount of water $M_I$ supplied from the water storage hopper 102 as an accumulation value by means of the flowmeter 152, while storing water overflowing the opening for overflow 111 in the storage container 153 once, and then measuring mass $M_O$ of the overflow water as an accumulation value by means of the massmeter 154 (step 1203).

In this manner, if the submergence aggregate 121 is allowed to overflow the opening for overflow 111, a water level at which the water 122 overflows the opening for overflow 111 is predetermined. Therefore, if the submergence aggregate container is filled with the submergence aggregate 121 as mentioned above, the total volume $V_f$ of the submergence aggregate 121 equal to a known value is obtained without measurement.

If the fine aggregate is not directly thrown from the fine aggregate measurement container 203 to the submergence aggregate container 204, but the fine aggregate is conveyed from a portion beneath the fine aggregate measurement container 203 to an upper opening of the submergence aggregate container 204 by using a vibrating feeder having an electromagnetic vibrator, for example, it becomes possible to prevent granulation of the fine aggregate, and thus prevent air bubble mixing.

Subsequently, mass $M_a$ of the fine aggregate in the saturated surface-dried condition and mass $M_w$ of the water in the submergence aggregate 121 are calculated by solving the following two formulas.

$$M_a + M_w = M_{aw} + (M_I - M_O) \quad (5)$$

$$M_a/\rho_a + M_w/\rho_w = V_f \quad (2)$$

where $\rho_a$ is the density of the fine aggregate in the saturated surface-dried condition and $\rho_w$ is the density of the water. In addition, a percentage of surface moisture of the fine aggregate is calculated by the following formula (step 1204).

$$(M_{aw} - M_a)/M_a \quad (3)$$

After measuring and calculating the mass $M_w$ of the water and the mass $M_a$ of the fine aggregate in the saturated surface-dried condition as mentioned above, these values are compared with mix proportions shown by the specified mix, respectively. Thereafter, an insufficiency is measured and then the submergence aggregate is supplemented with additional aggregate if aggregate is needed, or with additional water if water is needed, so as to let the aggregate and the water become concrete materials, taking into consideration surface water by using the calculated percentage of surface moisture (step 1205). If there is too much water, excess water is sucked with a vacuum or the like.

As set forth hereinabove, according to the measuring apparatus and the measuring method for concrete-forming materials of this embodiment, surface water of the fine aggregate is indirectly calculated as a part of the mass $M_w$ of the water, even if a fine aggregate whose moisture state is not uniform is used, and the mass of fine aggregate is calculated as the mass $M_a$ of the fine aggregate in the saturated surface-dried condition. In other words, since the mass of the fine aggregate and the mass of the water are calculated on conditions equivalent to the specified mix, even if a humidity grade of the fine aggregate is not fixed at every measurement, it becomes possible to make concrete with water of the amount as shown by the specified mix.

While load cells 108a of a compression type are used and placed in three places in this embodiment, it is arbitrary as to what type of load cells are used as means for measuring a mass of submergence aggregate. For example, load cells of a tension type can be used or they can be placed in four or more places. If the submergence aggregate container 204 can be held stably in a suspended condition, only one or two load cells can be used.

A correction of air content has not been described particularly in this embodiment. If the air content a (%) of the submergence aggregate is considered, however, the already-known total volume $V_f$ should be multiplied by (1−a/100). For example, the following formula may be used instead of formula (2).

$$M_a/\rho_a + M_w/\rho_w = V_f(1 - a/100) \quad (2\text{-a})$$

This enables more accurate measurement since actual total volume is used for the measurement with the air content excluded. In other cases, the air content can be corrected similarly, if necessary.

The amount of supplied water $M_I$ thrown into the submergence aggregate container 204 is measured as an accumulation value by using the flowmeter 152 in this embodiment. If the water is thrown into the submergence aggregate container previously so that it overflows instead, however, a water level at which the water overflows the opening for overflow is predetermined as mentioned above, and therefore, the amount of supplied water $M_I$ becomes equal to a known value even if it is not measured. Accordingly, this constitution does not need means for supplying water comprising the flowmeter 152 as means for measuring feed water, the water storage hopper 102, the water feed pipe 105, and the closing valve 106.

Since the water level does not fall even if water may overflow due to subsequent aggregate throwing in this case, the accumulation value of the amount of supplied water $M_I$ becomes fixed during measurement.

Figure 27:
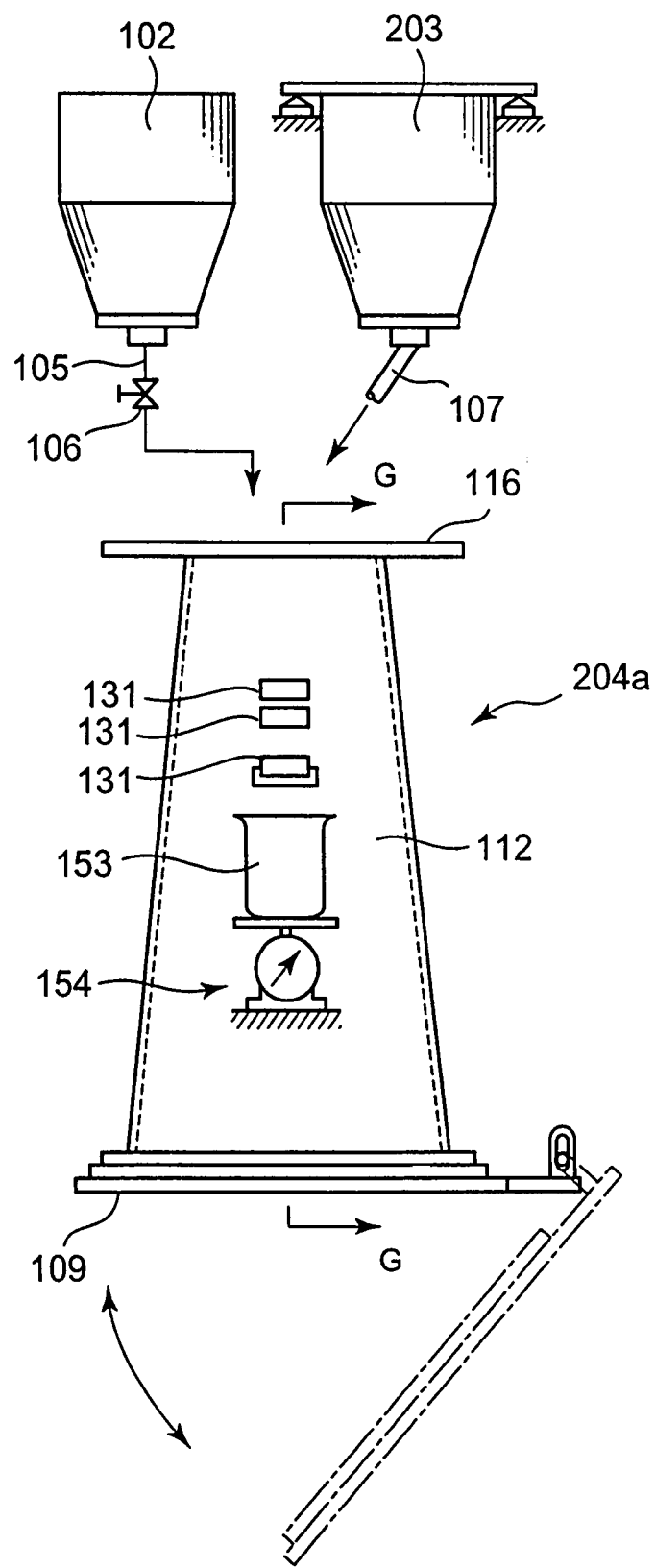
FIG. 27 is a general view of a measuring apparatus for concrete-forming materials according to a modification of the invention.
Figure 28:
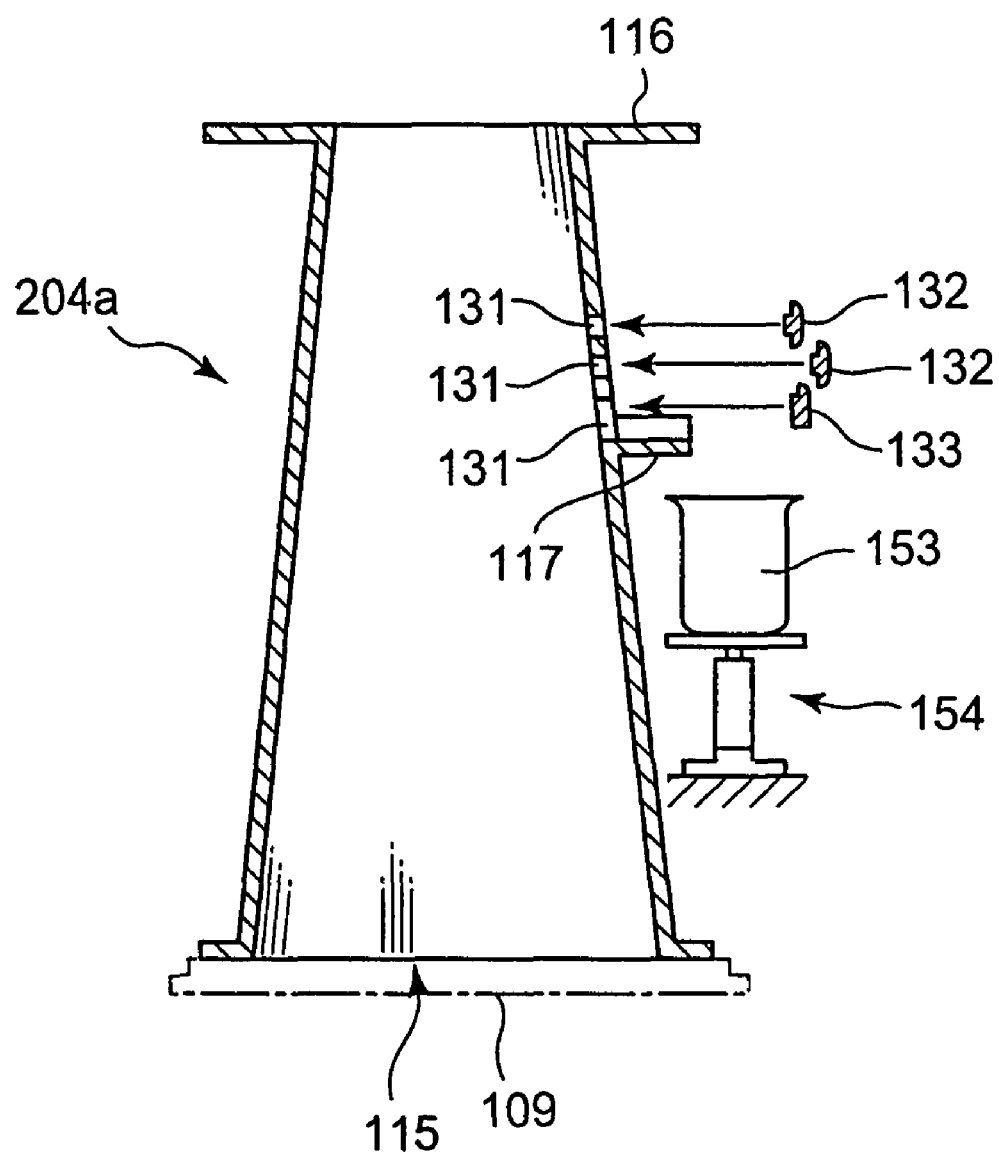
FIG. 28 is a cross section of a submergence aggregate container taken along line G-G of FIG. 27.

Furthermore, a rectangular opening for overflow 111 is formed in the wall 112 of the submergence aggregate container 204 at a predetermined height of the submergence aggregate container 204, and guide 117 is provided in a horizontally protruding condition along the lower edge of the opening for overflow 111 in this embodiment. As shown in FIGS. 27 and 28, however, three openings for overflow 131 can be provided at different heights in the wall 112 of the submergence aggregate container 204 instead of the opening for overflow 111, and the guide 117 can be provided in a horizontally protruding condition along a lowest edge of the opening for overflow 131.

In this constitution, only the opening for overflow 131 corresponding to a required total volume $V_f$ is opened, and all other openings for overflow 131 are sealed by using seal plugs 132 and 133 as shown in FIG. 28.

According to this constitution, it becomes unnecessary to prepare a submergence aggregate container for each total volume $V_f$.

In the measuring apparatus for concrete-forming materials shown in FIGS. 27 and 28, a submergence aggregate container 204a having three openings for overflow 131 is used instead of the submergence aggregate container 204 having the opening for overflow 111. The submergence aggregate container 204a is the same as the submergence aggregate container 204 in components except for the difference in the openings for overflow, and it is the same as the above embodiment in its entire constitution. Therefore, description of these points will be omitted here.

Figure 29:
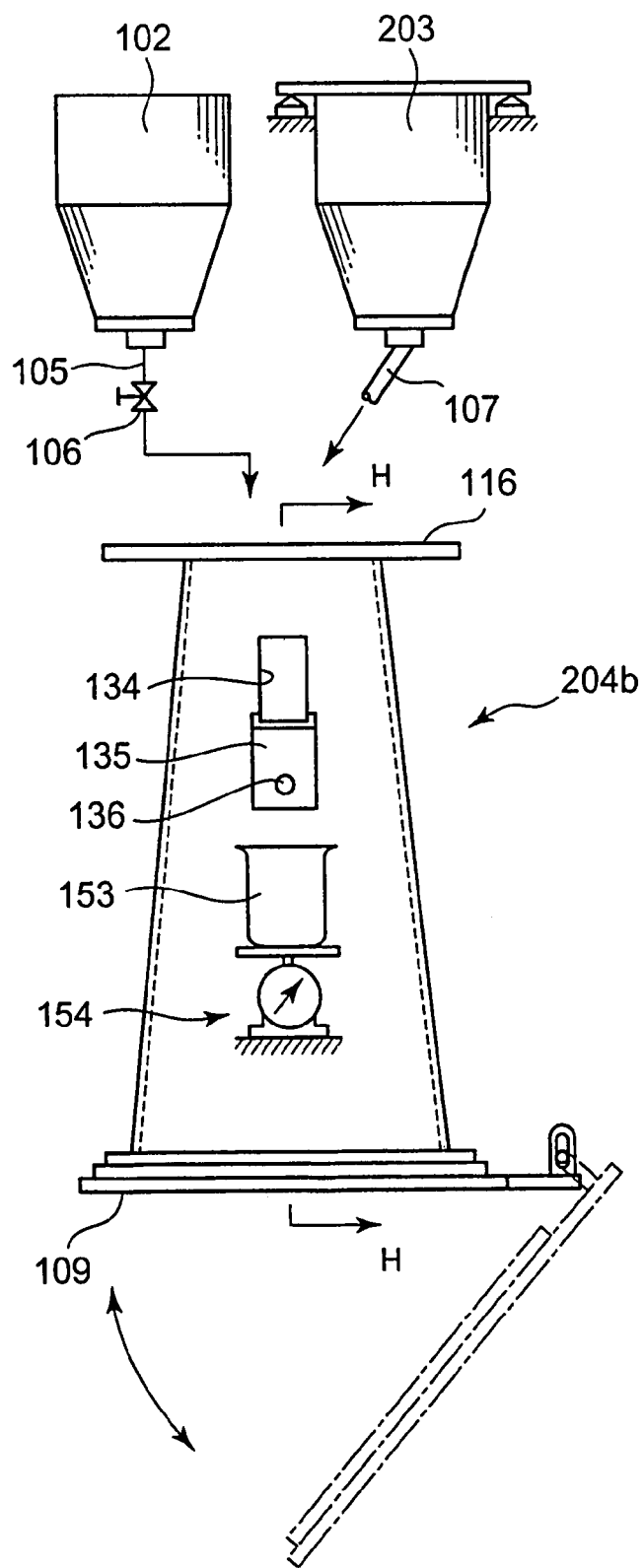
FIG. 29 is a general view of a measuring apparatus for concrete-forming materials according to another modification of the invention.
Figure 30:
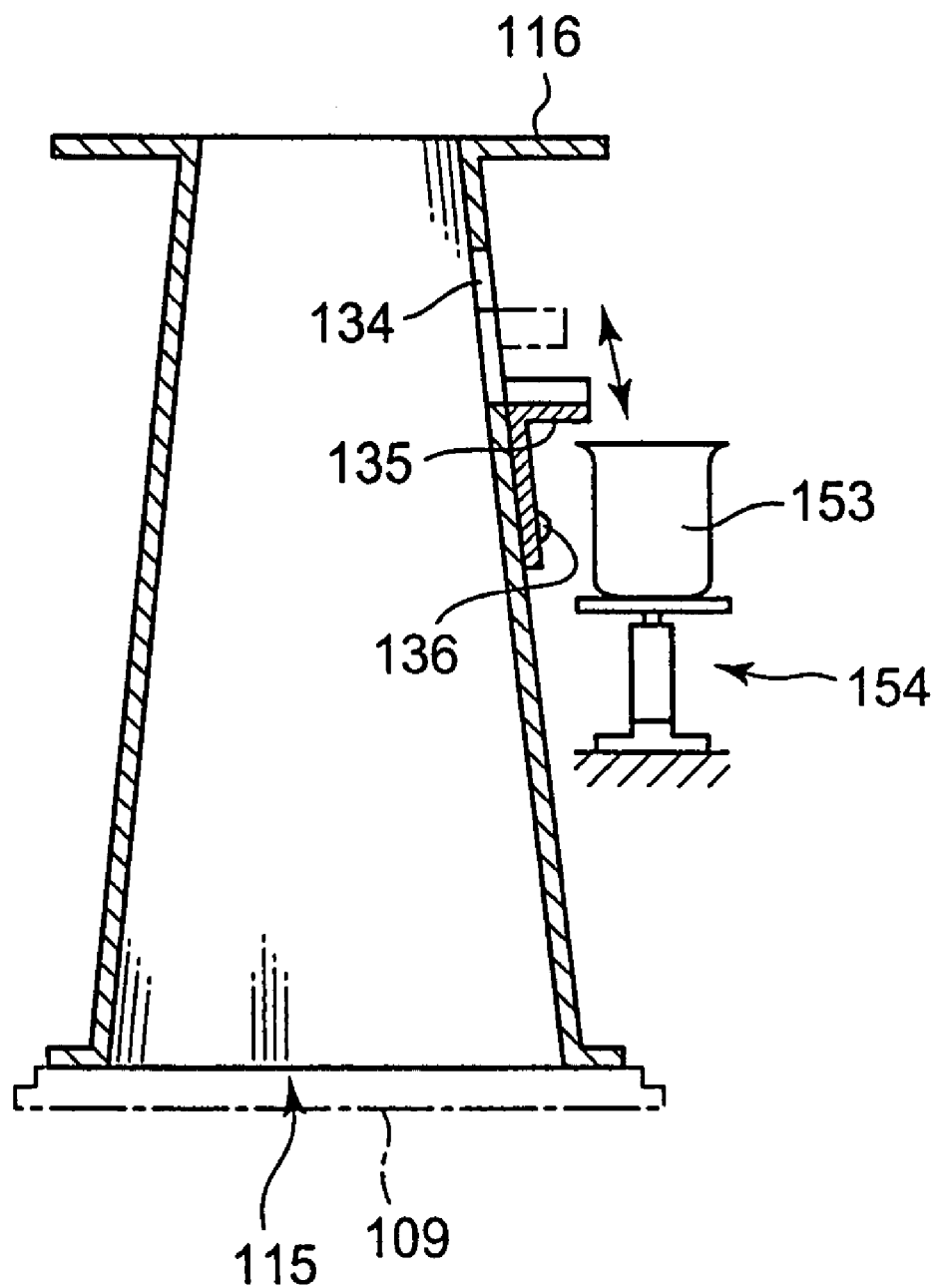
FIG. 30 is a cross section of a submergence aggregate container taken along line H-H of FIG. 29.

Furthermore, in this embodiment, the rectangular opening for overflow 111 is formed on the wall 112 of the submergence aggregate container 204 at the predetermined height of the submergence aggregate container 204 and the guide 117 is provided in the horizontally protruding condition along the lower edge of the opening for overflow. As shown in FIGS. 29 and 30, an opening for overflow 134 with an increased height may be formed in the wall 112, instead of the opening for overflow 111, in a condition where the opening for overflow 134 is covered with a bracket cover 135 free to move up and down. Furthermore, an overflow height can be variable according to a position where the bracket cover 135 moves up and down.

The bracket cover 135 comprises a guide, which is similar to the guide 117, provided in a horizontally protruding condition from an upper edge of a curved cover plate moving up and down along a circumferential surface of submergence aggregate container 204b. The bracket cover 135 is fixed to the wall of the submergence aggregate container 204b with a screw 136, by which it can be positioned at a desired height. A rubber gasket or the like may be used appropriately so that predetermined watertightness is secured between the curved cover plate and the wall of the submergence aggregate container 204b.

In this constitution, the bracket cover 135 is moved up and down so that the guide of the bracket cover 135 is located at a desired height and then it is fixed with the screw 136. With this, the curved cover plate of the bracket cover 135 closes a part of the opening for overflow 134 lower than the guide, by which it becomes possible to variably adjust a water level at which water of the submergence aggregate in the submergence aggregate container 204b overflows. Therefore, there is no need to prepare a submergence aggregate container for each total volume $V_f$.

In the measuring apparatus for concrete-forming materials shown in FIGS. 29 and 30, a submergence aggregate container 204b having the opening for overflow 134 and the bracket cover 135 for variably adjusting the overflow height of the opening for overflow 134 is used instead of the submergence aggregate container 204 having the opening for overflow 111. The submergence aggregate container 204b is the same as the submergence aggregate container 204 in terms of components except for the difference in the opening for overflow and its related member, and it is otherwise the same as the above embodiment in its entire constitution. Therefore, description of these points will be omitted here.

The following should be noted though it has not been particularly noted in this embodiment. If there is a possibility that the aggregate thrown into the submergence aggregate container 204 will emerge from the water and will not be submergence aggregate, a vibrator is used to level a top of the aggregate.

Figure 31:
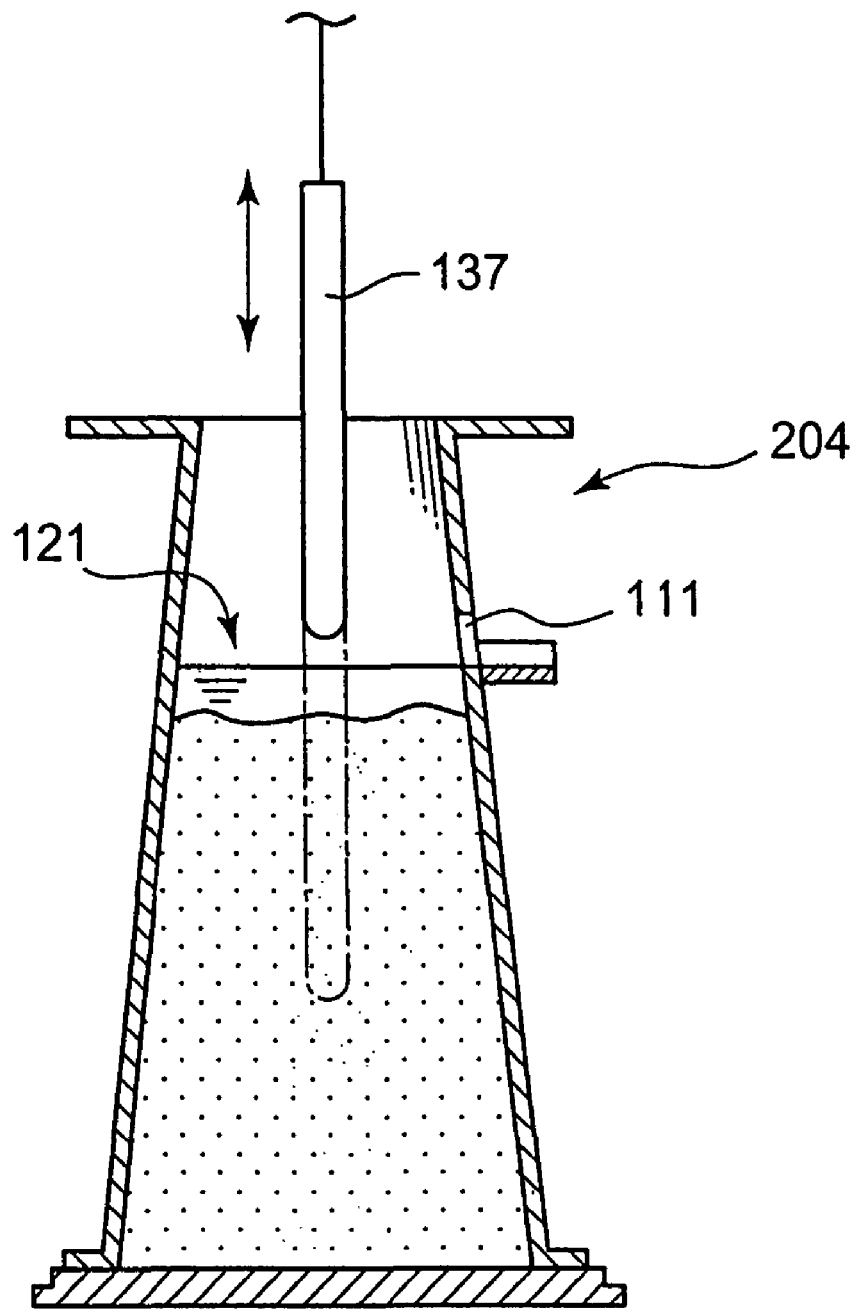
FIG. 31 is a cross section of a measuring apparatus for concrete-forming materials according to another modification of the invention.

Referring to FIG. 31, there is shown a modification as mentioned above. In FIG. 31, a rod vibrator 137 is installed above the submergence aggregate container 204 so that it is free to move up and down and so that it may be buried in the submergence aggregate 121 in a downward location (indicated by a dash-single-dot line in FIG. 31).

In this constitution, during or after throwing fine aggregate, the vibrator 137 is lowered and operated in the shown condition.

With this, the fine aggregate thrown into the submergence aggregate container 204 is leveled by vibration of the vibrator 137, by which the fine aggregate will be submerged in the water. Before measuring a mass of the submergence aggregate 121, the vibrator 137 is raised and put in a standby state, until a next measurement, in an upward location.

Sixth Embodiment

Referring to FIG. 32, there is shown a flowchart of a procedure for a measuring method for concrete-forming materials according to a sixth embodiment. The embodiment will now be described by giving an example of using fine aggregate of two kinds A and B. The measuring method for concrete-forming materials according to this embodiment can be implemented by selecting an appropriate one from the above measuring apparatuses.

As apparent from FIG. 32, in the measuring method for concrete-forming materials according to this embodiment, first, water and fine aggregate A are thrown into a measurement tank so that the fine aggregate A is submerged in water as submergence aggregate and so that the water overflows the measurement tank to fill the measurement tank with the submergence aggregate (step 1301).

The measurement tank may be formed, for example, in a shape of a hollow truncated cone so that a bore of the measurement tank gets larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

If the water and the fine aggregate A are thrown into the measurement tank in this manner, a water level at which the water overflows the measurement tank is predetermined. Therefore, if the measurement tank is filled with the submergence aggregate as mentioned above, total volume $V_f$ of the submergence aggregate equal to a known value is obtained without measurement.

Subsequently, the total mass $M_{f1}$ of the submergence aggregate is measured (step 1302). The total mass $M_{f1}$ of the submergence aggregate can be obtained by subtracting a measurement value of an empty measurement tank, containing no submergence aggregate, from a measurement value of the measurement tank filled with the submergence aggregate.

Subsequently, mass $M_{a1}$ of the fine aggregate A in the saturated surface-dried condition is calculated by solving the following formulas from the total mass $M_{f1}$ of the measured submergence aggregate (step 1303).

$$M_{a1}+M_w=M_{f1} \tag{7}$$

$$M_{a1}/\rho_{a1}+M_w/\rho_w=V_f \tag{8}$$

where $\rho_{a1}$ is the density of the fine aggregate A in the saturated surface-dried condition and $\rho_w$ is the density of the water.

After measuring and calculating the mass $M_{a1}$ of the fine aggregate A in the saturated surface-dried condition as mentioned above, the fine aggregate B, which is aggregate of the second kind, is thrown into the measurement tank so that the fine aggregate B is submerged in water as part of submergence aggregate and so that the water overflows the measurement tank (step 1304).

When throwing the aggregates A and B and the water into the measurement tank, preferably the water is thrown earlier and the fine aggregates are thrown later to prevent the submergence aggregate from being mixed with air bubbles. In addition, if the fine aggregates A and B are not directly thrown into the measurement tank, but the fine aggregates are conveyed to the measurement tank by using a vibrating feeder having an electromagnetic vibrator, for example, it becomes possible to prevent granulation of the fine aggregates, and thus prevent air bubble mixing.

Subsequently, total mass $M_{f2}$ of the submergence aggregate is measured (step 1305).

Thereafter, mass $M_{a2}$ of the fine aggregate B in a saturated surface-dried condition and mass $M_w$ of the water are calculated from the measured total mass $M_{f2}$ of the submergence aggregate by using the following formulas (step 1306).

$$M_{a1}+M_{a2}+M_w=M_{f2} \tag{9}$$

$$M_{a1}/\rho_{a1}+M_{a2}/\rho_{a2}+M_w/\rho_w=V_f \tag{10}$$

where $\rho_{a2}$ is the density of the fine aggregate B in the saturated surface-dried condition.

After measuring and calculating the mass $M_w$ of the water, the mass $M_{a1}$ of the fine aggregate A in the saturated surface-dried condition, and the mass $M_a2$ of the fine aggregate B in the saturated surface-dried condition in this manner, these values are compared with mix proportions shown by a specified mix, respectively. Thereafter, an insufficiency is measured and then the submergence aggregate is supplemented by an amount equal to that of the insufficiency so as to let the aggregate and the water become concrete materials. If there is too much water, excess water is sucked with a vacuum or the like (step 1307).

As set forth hereinabove, according to the measuring method for concrete-forming materials of this embodiment, surface water of the fine aggregates A and B can be indirectly calculated as a part of the mass $M_w$ of the water, even if a fine aggregate whose moisture state is not uniform is used, and the mass of the fine aggregate A and that of the fine aggregate B can be calculated as the mass $M_{ai}$ (i=1, 2) of the fine aggregate in the saturated surface-dried condition. In other words, since the mass of the fine aggregates and the mass of the water are calculated on conditions equivalent to the specified mix, even if a humidity grade of the fine aggregate is not fixed at every measurement, it becomes possible to make concrete with water of the amount as shown by the specified mix.

In addition, even if the fine aggregates A and B differ from each other in density, grading, or the like, they can be measured in a single measurement tank efficiently and very accurately.

Furthermore, according to the measuring method for concrete-forming materials of this embodiment, the fine aggregates A and B are thrown into the measurement tank so that the water overflows the measurement tank, by which the total volume $V_{fi}$ (i=1, 2) of the submergence aggregate is maintained at a steady value $V_f$ that is an internal volume of the measurement tank in the overflow condition, and therefore the total volume $V_{fi}$ (i=1, 2) of the submergence aggregate need not be measured every time.

While the total volume $V_{fi}$ (i=1, 2) of the submergence aggregate is maintained at the steady value $V_f$ by causing the water to overflow the measurement tank in this embodiment as mentioned above, the total volume $V_{fi}$ (i=1, 2) of the submergence aggregate can be measured by using an electrode-type displacement sensor or the like, instead.

The electrode-type displacement sensor can be one capable of measuring a water level of the submergence aggregate by monitoring a change in an energized condition when a lower end of a detection electrode contacts a water surface of submergence fine aggregate in the measurement tank, for example.

Furthermore, while this embodiment has been described by giving the example of fine aggregate of two kinds, naturally aggregate of an arbitrary number of kinds can be used. This method is applicable to a measurement of coarse aggregate and also applicable to a combination of fine aggregate and coarse aggregate.

A correction of air content has not been described particularly in this embodiment. If the air content a (%) of the submergence aggregate is considered, however, the known total volume $V_f$ should be multiplied by (1−a/100). For example, the following formula may be used instead of formula (8).

$$M_{a1}/\rho_{a1}+M_w/\rho_w=V_f(1-a/100)$$

This enables more accurate measurement since actual total volume is used for the measurement with the air content excluded.

Furthermore, the following should be noted though it has not been particularly noted in this embodiment. If there is a possibility that the aggregates thrown into the measurement tank will emerge from the water and will not be submergence aggregate, a vibrator is lowered during or after throwing the fine aggregates A and B and operated in this condition. Thereby, the fine aggregates A and B thrown into the measurement tank can be leveled by vibration of the vibrator, so that the fine aggregates A and B are submerged in the water. Before measuring a mass of the submergence aggregate, the vibrator is raised and put in a standby state, until a next measurement, in an upward location.

While the following has not been particularly noted in this embodiment, percentages of surface moisture of the fine aggregates A and B can be calculated from the following formula by previously measuring the mass $M_{awi}$ (i=1, 2) of the fine aggregates A and B in a wet condition.

$$(M_{awi}-M_{ai})/M_{ai} \tag{13}$$

Referring to FIG. 33, there is shown a flowchart of a procedure of the measuring method according to this modification.

This modification is described by giving an example of using two fine aggregates A and B in the same manner as for the above embodiment. First, measurements are made previously on the mass $M_{awi}$ (i=1, 2) of the fine aggregates A and B in a wet condition (step 1311).

On the other hand, in the same manner as for the above embodiment, water is thrown into the measurement tank and the measured fine aggregate A is thrown into the measurement tank so that the aggregate A is submerged in water as submergence aggregate, and so that the water overflows the measurement tank (step 1301).

Hereinafter, in the same manner as for the above embodiment, the total mass $M_{f1}$ of the submergence aggregate is measured (step 1302), the mass $M_{a1}$ of the fine aggregate A in the saturated surface-dried condition is calculated from the measured total mass $M_{f1}$ of the submergence aggregate by using the formulas (7) and (8) (step 1303). Subsequently, the measured fine aggregate B is thrown into the measurement tank so that the fine aggregate B is submerged in water as submergence aggregate and so that the water overflows the measurement tank (step 1304). Thereafter, the total mass $M_{f2}$ of the submergence aggregate is measured (step 1305) and the mass $M_{a2}$ of the fine aggregate B in the saturated surface-dried condition and the mass $M_w$ of the water are calculated from the measured total mass $M_{f2}$ of the submergence aggregate by using the formulas (9) and (10) (step 1306).

Percentages of surface moisture of the fine aggregates A and B are then calculated from the following formula by using the calculated mass $M_{ai}$ (i=1, 2) of the fine aggregates A and B in the saturated surface-dried condition and the previously measured mass $M_{awi}$ (i=1, 2) of the fine aggregates in a wet condition (step 1312).

$$(M_{awi}(i=1, 2)-M_{ai}(i=1, 2)/M_{ai}(i=1, 2) \tag{13}$$

Subsequently, the calculated mass $M_w$ of the water and the mass $M_{ai}$ (i=1, 2) of the fine aggregates A and B in the saturated surface-dried condition are compared with mix proportions shown by a specified mix, respectively, and an insufficiency is measured. The submergence aggregate is supplemented with additional water if water is needed or with additional aggregate if aggregate is needed, taking into consideration the surface water on the basis of the percentages of surface moisture calculated in step 1312. The aggregates and the water are then treated as concrete materials. If there is too much water, excess water is sucked and removed with a vacuum or the like (step 1313).

Furthermore, if the amount of water $M_I$ supplied to the measurement tank and the amount of water $M_O$ discharged from the measurement tank are previously measured as accumulation values similarly, $\Sigma M_{awj}$ (j=1 to i) can be calculated from the following formula.

$$\Sigma M_{awj}(j=1 \text{ to } i)=M_{fi}-(M_I-M_O) \tag{14}$$

$M_{awi}$ is then calculated from the following formula.

$$\Sigma M_{awj}(j=1 \text{ to } i)-\Sigma M_{awj}(j=1 \text{ to } (i-1)) \tag{15}$$

Thereafter, the percentages of surface moisture of the aggregate of the i-th kind (i=1 to N) can be calculated by substituting the $M_{awi}$ into the following formula.

$$(M_{awi}-M_{ai})/M_{ai} \tag{13}$$

Figure 35:
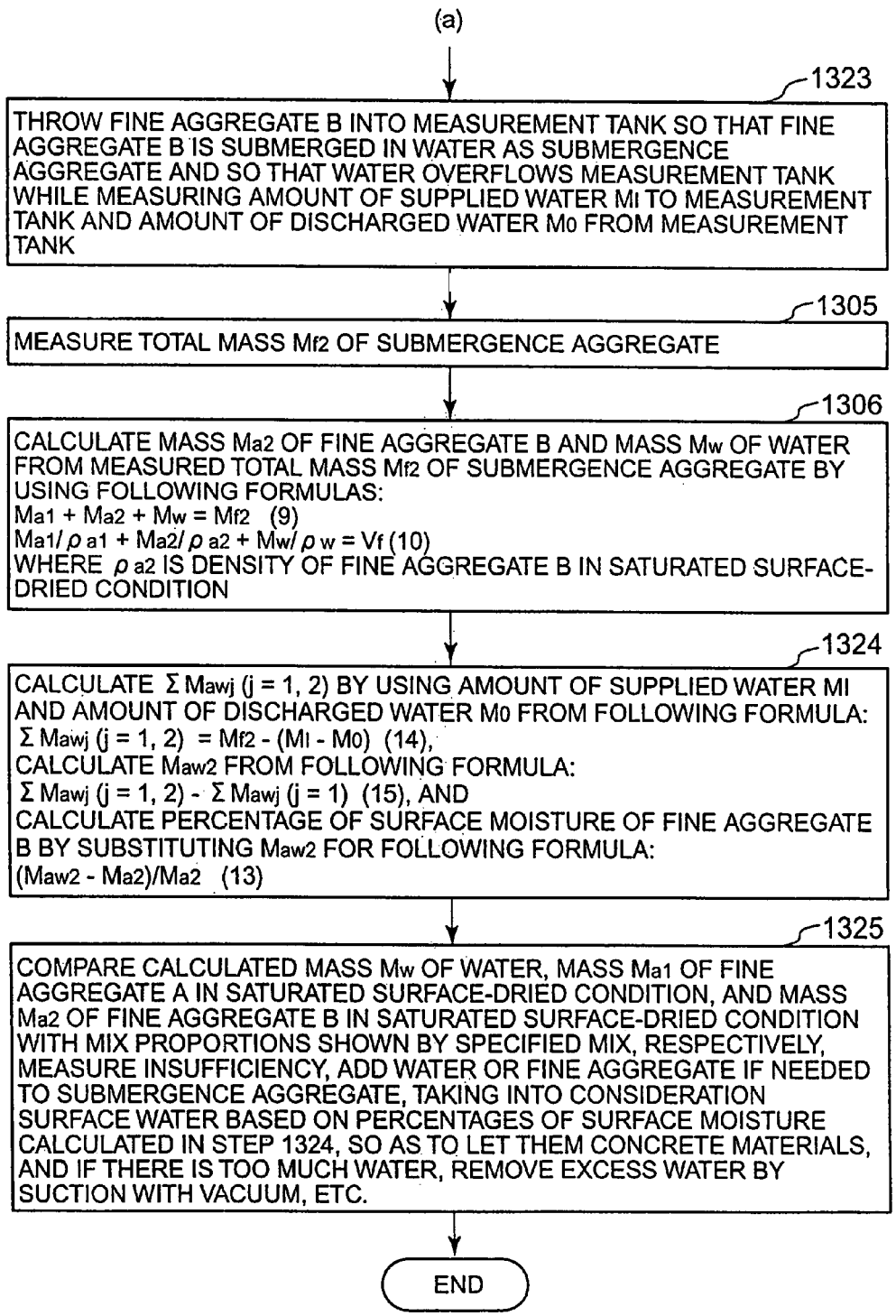

Referring to FIGS. 34 and 35, there is shown a flowchart of a procedure for a measuring method according to the modification. In this measuring method, two fine aggregates A and B are used, for example. Water is thrown first into the measurement tank in the same manner as for the above embodiment, and then the fine aggregate A is thrown into the measurement tank so that it is submerged in water as submergence aggregate and so that the water overflows the measurement tank to fill the measurement tank with submergence aggregate. In parallel to the above processing, the amount of water $M_I$ supplied to the measurement tank and the amount of water $M_O$ discharged from the measurement tank are measured (step 1321).

Thereafter, total mass $M_{f1}$ of the submergence aggregate is measured in the same manner as for the above embodiment (step 1302) and mass $M_{a1}$ of the fine aggregate A in a saturated surface-dried condition is calculated from the measured total mass $M_{f1}$ of the submergence aggregate by using the formulas (7) and (8) (step 1303).

Subsequently, $\Sigma M_{awj}$ (j=1) or $M_{aw1}$ is calculated by using the amount of supplied water $M_I$ and the amount of discharged water $M_O$ from the following formula.

$$\Sigma M_{awj}(j=1)=M_{f1}-(M_I-M_O) \tag{14}$$

A percentage of surface moisture of the fine aggregate A is calculated by substituting the $M_{aw1}$ into the following formula (step 1322).

$$(M_{aw1}-M_{a1})/M_{a1} \tag{13}$$

Subsequently, the fine aggregate B is thrown into the measurement tank so that the fine aggregate B is submerged in water as submergence aggregate and so that the water overflows the measurement tank while measuring the amount of water $M_I$ supplied to the measurement tank and the amount of water $M_O$ discharged from the measurement tank (step 1323). Total mass $M_{f2}$ of the submergence aggregate is then measured (step 1305) and mass $M_{a2}$ of the fine aggregate B and mass $M_w$ of the water are calculated from the measured total mass $M_{f2}$ of the submergence aggregate by using the formulas (9) and (10) (step 1306).

Thereafter, $\Sigma M_{awj}$ (j=1, 2) is calculated by using the amount of supplied water $M_I$ and the amount of discharged water $M_O$ from the following formula.

$$\Sigma M_{awj}(j=1, 2)=M_{f2}-(M_I-M_O) \tag{14}$$

$M_{aw2}$ is then calculated from the following formula.

$$\Sigma M_{awj}(j=1, 2)-\Sigma M_{awj}(j=1) \tag{15}$$

A percentage of surface moisture of the fine aggregate B is calculated by substituting the above $M_{aw2}$ into the following formula (step 1324).

$$(M_{aw2}-M_{a2})/M_{a2} \tag{13}$$

Subsequently, the mass $M_w$ of the water, the mass $M_{a1}$ of the fine aggregate A in the saturated surface-dried condition, and the mass $M_{a2}$ of the fine aggregate B in the saturated surface-dried condition calculated in the above are compared with mix proportions shown by the specified mix, respectively, and an insufficiency is measured. The submergence aggregate is supplemented with additional water if water is needed or with additional fine aggregate if fine aggregate is needed, taking into consideration the surface water on the basis of the percentages of surface moisture calculated in step 1324. The aggregates and the water are then treated as concrete materials. If there is too much water, excess water is sucked and removed with a vacuum or the like (step 1325).

Seventh Embodiment

Figure 36:
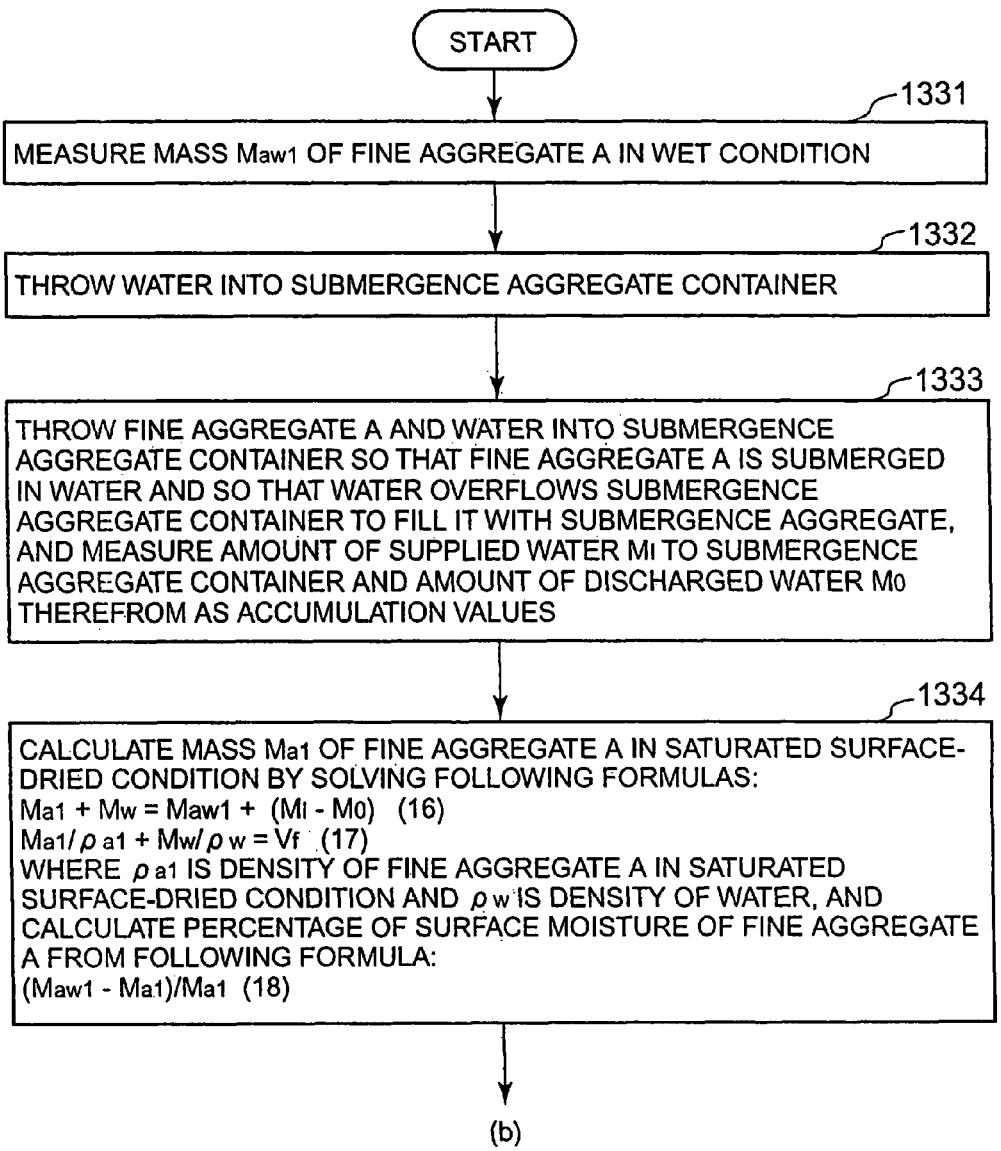

Referring to FIGS. 36 and 37, there is shown a flowchart of a procedure for a measuring method for concrete-forming materials according to a seventh embodiment. This embodiment will now be described by giving an example of using fine aggregate of two kinds A and B as aggregate of a first kind and aggregate of a second kind, respectively. The measuring method for concrete-forming materials according to this embodiment can be implemented by selecting an appropriate one from the above measuring apparatuses.

As apparent from FIGS. 36 and 37, in the measuring method for concrete-forming materials according to this embodiment, mass $M_{aw1}$ of the fine aggregate A in a wet condition is measured, first (step 1331).

Water is then thrown into a submergence aggregate container (step 1332).

The submergence aggregate container can be formed in a shape of a hollow truncated cone so that a bore of the submergence aggregate container gets larger in a downward direction. With this, when measurement is finished, a free fall of submergence aggregate in the submergence aggregate container can be achieved only by opening a bottom lid without a blockage of submergence aggregate in the submergence aggregate container even if no vibrating instrument such as a vibrator is used. Thereafter, the submergence aggregate can be thrown into a kneading mixer together with cement and coarse aggregate measured separately.

Subsequently, the fine aggregate A and water are thrown into the submergence aggregate container so that the fine aggregate A is submerged in water and so that the water overflows the submergence aggregate container to fill it with submergence aggregate. Then, an amount of water $M_I$ supplied to the submergence aggregate container and an amount of water $M_O$ discharged from the submergence aggregate container are measured as accumulation values (step 1333).

If the water and the fine aggregate A are thrown into the submergence aggregate container in this manner, a water level at which the water overflows the submergence aggregate container is predetermined. Therefore, if the submergence aggregate container is filled with the submergence aggregate as mentioned above, total volume $V_f$ of the submergence aggregate equal to a known value is obtained without measurement.

When throwing the aggregates A into the submergence aggregate container or throwing the aggregate B in post-processing, preferably the fine aggregates A and B are conveyed to the submergence aggregate container by using a vibrating feeder having an electromagnetic vibrator, for example.

Subsequently, mass $M_{a1}$ of the fine aggregate A in a saturated surface-dried condition is calculated by solving the following formulas.

$$M_{a1}+M_w=M_{aw1}+(M_I-M_O) \tag{16}$$

$$M_{a1}/\rho_{a1}+M_w/\rho_w=V_f \tag{17}$$

where $\rho_{a1}$ is the density of the fine aggregate A in the saturated surface-dried condition and $\rho_w$ is the density of the water. In addition, a percentage of surface moisture of the fine aggregate A is calculated from the following formula (step 1334).

$$(M_{aw1}-M_{a1})/M_{a1} \tag{18}$$

Mass $M_{aw2}$ of the fine aggregate B in a wet condition is measured (step 1335).

The fine aggregate B and water are then thrown into the submergence aggregate container so that the fine aggregate B is submerged in water and so that the water overflows the submergence aggregate container to fill it with submergence aggregate. In addition, an amount of supplied water $M_I$ and an amount of discharge water $M_O$ are measured as accumulation values (step 1336).

Subsequently, mass $M_{a2}$ of the fine aggregate B in a saturated surface-dried condition and mass $M_w$ of the water in the submergence aggregate are calculated from the following two formulas (step 1337).

$$M_{a1}+M_{a2}+M_w=M_{aw1}+M_{aw2}+(M_I-M_O) \tag{19}$$

$$M_{a1}/\rho_{a1}+M_{a2}/\rho_{a2}+M_w/\rho_w=V_f \tag{20}$$

where $\rho_{a2}$ is the density of the fine aggregate B in the saturated surface-dried condition and $\rho_w$ is the density of the water. In addition, a percentage of surface moisture of the fine aggregate B is calculated from the following formula (step 1337).

$$(M_{aw2}-M_{a2})/M_{a2} \tag{21}$$

After measuring and calculating the mass $M_w$ of the water, the mass $M_{ai}$ (i=1, 2) of the fine aggregate A and the fine aggregate B in the saturated surface-dried condition, and percentages of surface moisture of the fine aggregates A and B, these values are compared with mix proportions shown by a specified mix, respectively, and an insufficiency is measured. The submergence aggregate is supplemented with additional water if water is needed or with additional fine aggregate if fine aggregate is needed, taking into consideration the surface water on the basis of the percentages of surface moisture calculated in the above. The aggregates and the water are then treated as concrete materials. If there is too much water, excess water is sucked and removed with a vacuum or the like (step 1338).

As set forth hereinabove, according to the measuring method for concrete-forming materials of this embodiment, the surface water of the fine aggregates A and B can be indirectly calculated as a part of the mass $M_w$ of the water, even if a fine aggregate whose moisture state is not uniform is used, and the mass of the fine aggregates A and that of the fine aggregates B can be calculated as the mass $M_{ai}$ (i=1, 2) of the fine aggregate in the saturated surface-dried condition. In other words, since the mass of the fine aggregate and the mass of the water are calculated on conditions equivalent to the specified mix, even if a humidity grade of the fine aggregates is not fixed at every measurement, it becomes possible to make concrete with water of the amount as shown by the specified mix.

In addition, even if the fine aggregates A and B differ from each other in density, grading, or the like, they can be measured in a single measurement tank efficiently and very accurately.

Furthermore, the percentages of the fine aggregates A and B can be calculated, by which the surface water can be considered on the basis of the calculated percentages of surface moisture when the fine aggregates are added for supplement.

While this embodiment has been described by giving the example fine aggregate of two kinds, naturally aggregates of an arbitrary number of kinds can be used. This method is applicable to a measurement of coarse aggregate and also applicable to a combination of fine aggregate and coarse aggregate.

A correction of air content has not been described particularly in this embodiment. If the air content a (%) of the submergence aggregate is considered, however, the known total volume $V_f$ should be multiplied by $(1-a/100)$ in the same manner as for the above embodiment.

This constitution enables more accurate measurement since actual total volume is used for the measurement with the air content excluded.

Furthermore, the following should be noted though it has not been particularly noted in this embodiment. If there is a possibility that the aggregates thrown into the submergence aggregate container will emerge from the water and will not be submergence aggregate, a vibrator is lowered during or after throwing the fine aggregates A and B and operated in this condition. Thereby, the fine aggregates A and B thrown into the submergence aggregate container can be leveled by vibration of the vibrator, so that the fine aggregates A and B are submerged in the water. Before measuring a mass of the submergence aggregate, the vibrator is raised and put in a standby state, until a next measurement, in an upward location.

Eighth Embodiment

Figure 38:
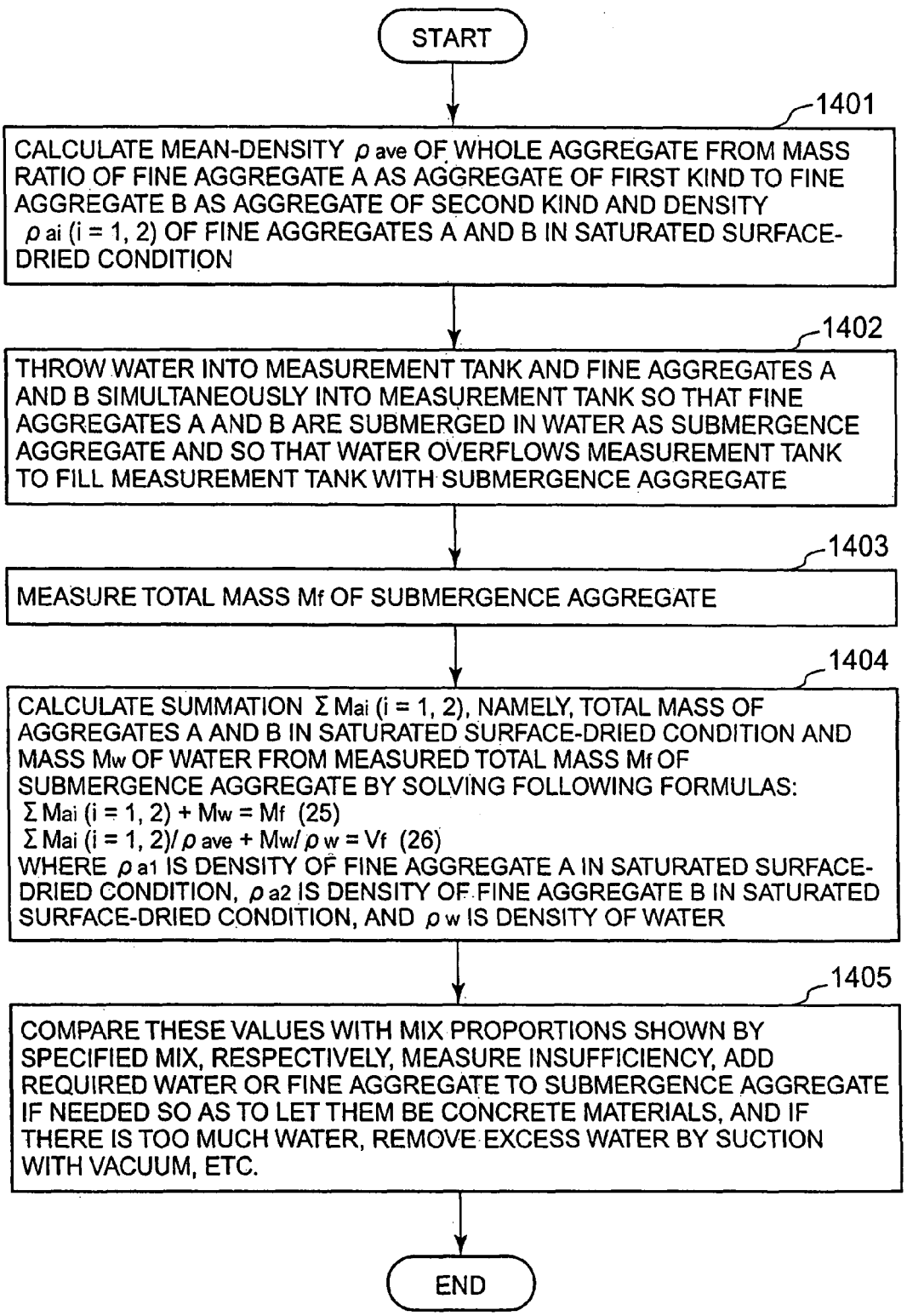
FIG. 38 is a flowchart of a preferable measuring method for concrete-forming materials according to the present invention.

Referring to FIG. 38, there is shown a flowchart of a procedure for a measuring method for concrete-forming materials according to an eighth embodiment. This embodiment will now be described by giving an example of using fine aggregate of two kinds A and B. The measuring method for concrete-forming materials according to this embodiment can be implemented by selecting an appropriate one from the above measuring apparatuses.

As apparent from FIG. 38, in the measuring method for concrete-forming materials according to this embodiment, mean-density $\rho_{ave}$ of an entire aggregate is first calculated from a mass ratio of the fine aggregate A as aggregate of a first kind to the fine aggregate B as aggregate of a second kind and density $\rho_{ai}$ (i=1, 2) of the fine aggregates A and B in a saturated surface-dried condition (step 1401).

The fine aggregates A and B can be stored in a predetermined storage hopper collectively in a condition where the mass ratio is known. Otherwise, two storage hoppers can be prepared individually to calculate the mass ratio from a speed at which the aggregates are conveyed from a location beneath these storage hoppers to a measurement tank. Contrarily, this conveyance speed can be adjusted so as to achieve a target mass ratio.

Subsequently, water is thrown into the measurement tank, and the fine aggregates A and B are thrown at the same time into the measurement tank so that the fine aggregates A and B are submerged in the water as submergence aggregate and so that the water overflows the measurement tank to fill the measurement tank with the submergence aggregate (step 1402).

The measurement tank may be formed, for example, in a shape of a hollow truncated cone so that a bore of the measurement tank gets larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

When throwing the fine aggregates A and B at the same time into the measurement tank, preferably the water is thrown earlier and the fine aggregates A and B are thrown later to prevent the submergence aggregate from being mixed with air bubbles. In addition, if the fine aggregates A and B are conveyed to the measurement tank by using a vibrating feeder having an electromagnetic vibrator, for example, it becomes possible to prevent granulation of the fine aggregates, and thus prevent air bubble mixing.

If the water and the fine aggregate A and B are thrown into the measurement tank in this manner, a water level at which the water overflows the measurement tank is predetermined. Therefore, if the measurement tank is filled with the submergence aggregate as mentioned above, total volume $V_f$ of the submergence aggregate equal to a known value is obtained without measurement.

Subsequently, the total mass $M_f$ of the submergence aggregate is measured (step 1403). The total mass $M_f$ of the submergence aggregate can be obtained by subtracting a measurement value of an empty measurement tank, containing no submergence aggregate, from a measurement value of the measurement tank filled with the submergence aggregate.

Subsequently, summation $\Sigma M_{ai}$ (i=1, 2), that is, total mass of the aggregates A and B in the saturated surface-dried condition and mass $M_w$ of water are calculated from the measured total mass $M_f$ of the submergence aggregate by solving the following formulas (step 1404).

$$\Sigma M_{ai}(i=1, 2)+M_w=M_f \quad (25)$$

$$\Sigma M_{ai}(i=1, 2)/\rho_{ave}+M_w/\rho_w=V_f \quad (26)$$

where $\rho_{a1}$ is the density of the fine aggregate A in the saturated surface-dried condition, $\rho_{a2}$ is the density of the fine aggregate B in the saturated surface-dried condition, and $\rho_w$ is the density of the water.

After measuring and calculating the mass $M_w$ of the water and the summation $\Sigma M_{ai}$ (i=1, 2), that is, the total mass of the fine aggregates A and B in the saturated surface-dried condition as mentioned above, these values are compared with mix proportions shown by a specified mix, respectively. Thereafter, an insufficiency is measured and then the submergence aggregate is supplemented with additional water or aggregate when needed so as to let the aggregates and the water become concrete materials. If there is too much water, excess water is sucked and removed with a vacuum or the like (step 1405).

As set forth hereinabove, according to the measuring method for concrete-forming materials of this embodiment, the surface water of the fine aggregates A and B can be indirectly calculated as a part of the mass $M_w$ of the water, even if a fine aggregate whose moisture state is not uniform is used, and the mass of the fine aggregate A and that of the fine aggregate B can be calculated as the summation $\Sigma M_{ai}$ (i=1, 2); that is, the total mass of the fine aggregates in the saturated surface-dried condition. In other words, since the mass of the fine aggregates and the mass of the water are calculated on conditions equivalent to the specified mix, even if a humidity grade of the fine aggregate is not fixed at every measurement, it becomes possible to make concrete with water of the amount as shown by the specified mix.

In addition, even if the fine aggregates A and B differ from each other in density, grading, or the like, they can be measured in a single measurement tank efficiently and very accurately.

Furthermore, according to the measuring method of concrete materials of this embodiment, the fine aggregates A and B are thrown into the measurement tank at the same time so that the water overflows the measurement tank, by which the total volume $V_f$ of the submergence aggregate is maintained at a steady value that is an internal volume of the measurement tank in an overflow condition, and therefore, the total volume $V_f$ of the submergence aggregate need not be measured every time.

While the total volume $V_f$ of the submergence aggregate is maintained at the steady value by causing the water to overflow the measurement tank in this embodiment as mentioned above, the total volume $V_f$ of the submergence aggregate can be measured by using an electrode-type displacement sensor or the like, instead.

The electrode-type displacement sensor can be one capable of measuring a water level of the submergence aggregate by monitoring a change in an energized condition when a lower end of a detection electrode contacts a water surface of the submergence aggregate in the measurement tank, for example.

Furthermore, while this embodiment has been described by giving the example of fine aggregate of two kinds, naturally aggregates of an arbitrary number of kinds can be used. This method is applicable to a measurement of coarse aggregate and also applicable to a combination of fine aggregate and coarse aggregate.

A correction of air content has not been described particularly in this embodiment. If the air content a (%) of the submergence aggregate is considered, however, the known total volume $V_f$ should be multiplied by (1−a/100). For example, the following formula may be used instead of formula (26).

$$\Sigma M_{ai}(i=1 \text{ to } N)/\rho_{ave} + M_w/\rho_w = V_f(1-a/100)$$

This enables more accurate measurement since actual total volume is used for the measurement with the air content excluded.

Furthermore, the following should be noted though it has not been particularly noted in this embodiment. If there is a possibility that the aggregates thrown into the measurement tank will emerge from the water and will not be submergence aggregate, a vibrator is lowered during or after throwing the fine aggregates A and B and operated in this condition. Thereby, the fine aggregates A and B thrown into the measurement tank can be leveled by vibration of the vibrator, so that the fine aggregates A and B are submerged in the water. Before measuring a mass of the submergence aggregate, the vibrator is raised and put in a standby state, until a next measurement, in an upward location.

While the following has not been particularly noted in this embodiment, if the summation $\Sigma M_{awi}$ (i=1 to N), that is, the total mass of a plurality of aggregates of the i-th kind (i=1 to N) in wet condition is previously measured, an average percentage of surface moisture can be calculated from the following formula.

$$(\Sigma M_{awi}(i=1 \text{ to } N) - \Sigma M_{ai}(i=1 \text{ to } N))/\Sigma M_{ai}(i=1 \text{ to } N) \qquad (27)$$

Figure 39:
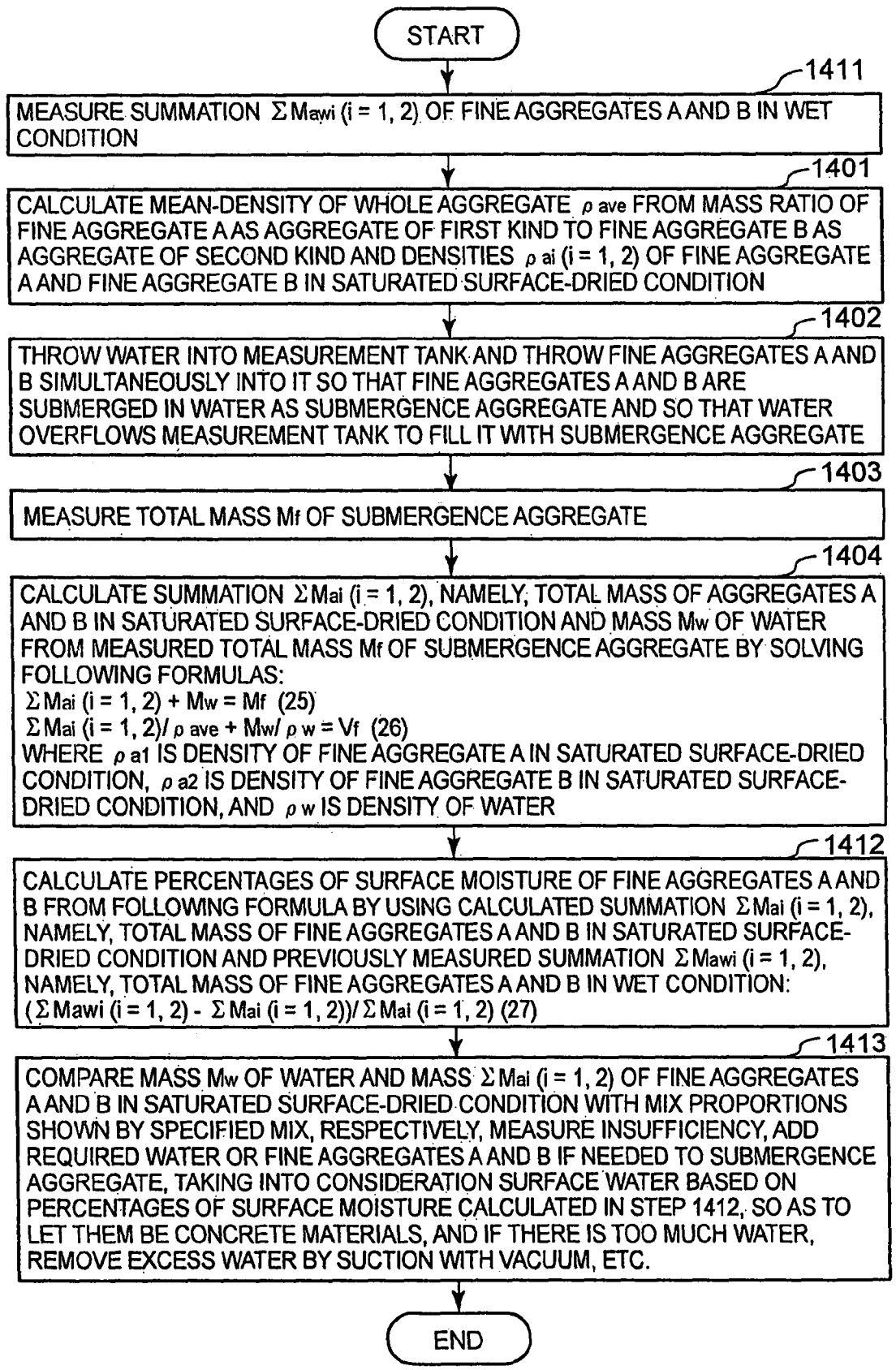
FIG. 39 is a flowchart of a preferable measuring method for concrete-forming materials according to a modification of the invention.

Referring to FIG. 39, there is shown a flowchart of a procedure for a measuring method according to this modification.

This modification shown in FIG. 39 is described by giving an example of using two fine aggregates A and B in the same manner as for the above embodiment. First, measurements are made previously on summation $\Sigma M_{awi}$ (i=1, 2) of the fine aggregates A and B in a wet condition (step 1411).

On the other hand, in the same manner as for the above embodiment, a mean-density of the entire aggregate $\rho_{ave}$ is calculated from a mass ratio of the fine aggregate A to the fine aggregate B and the densities $\rho_{ai}$ (i=1, 2) of the fine aggregate A and the fine aggregate B in a saturated surface-dried condition (step 1401).

Subsequently, water is thrown into the measurement tank, and the fine aggregates A and B are thrown at the same time into the measurement tank so that the aggregates A and B are submerged in water as submergence aggregate and so that the water overflows the measurement tank (step 1402).

Hereinafter, in the same manner as for the above embodiment, the total mass $M_f$ of the submergence aggregate is measured (step 1403). The summation $\Sigma M_{ai}$, that is, the total mass of the aggregates A and B in a saturated surface-dried condition and the mass $M_w$ of the water are calculated from the measured total mass $M_f$ of the submergence aggregate by using the formulas (25) and (26) (step 1404).

Percentages of surface moisture of the fine aggregates A and B are then calculated from the following formula by using the calculated summation $\Sigma M_{ai}$ (i=1, 2), that is, the total mass of the fine aggregates A and B in the saturated surface-dried condition and the previously measured summation $\Sigma M_{awi}$ (i=1, 2), that is, the total mass of the fine aggregates A and B in a wet condition (step 1412).

$$(\Sigma M_{awi}(i=1, 2) - \Sigma M_{ai}(i=1, 2)/\Sigma M_{ai}(i=1, 2) \qquad (27)$$

Subsequently, the calculated mass $M_w$ of the water and the mass $M_{ai}$ (i=1, 2) of the fine aggregates A and B in the saturated surface-dried condition are compared with mix proportions shown by the specified mix, respectively, and an insufficiency is measured. The submergence aggregate is supplemented with additional water if water is needed or with additional fine aggregates if fine aggregates are needed, taking into consideration the surface water on the basis of the percentages of surface moisture calculated in step 1412. The aggregates and the water are then treated as concrete materials. If there is too much water, excess water is sucked and removed with a vacuum or the like (step 1413).

Furthermore, if the amount of water $M_I$ supplied to the measurement tank and the amount of water $M_O$ discharged from the measurement tank are previously measured as accumulation values similarly, $\Sigma M_{awi}$ (i=1 to N) is calculated from the following formula.

$$\Sigma M_{awi}(i=1 \text{ to } N) = M_f - (M_I - M_O) \qquad (28)$$

An average percentage of surface moisture of the aggregate of the i-th kind (i=1 to N) can be calculated by substituting $\Sigma M_{awi}$ (i=1 to N) for the following formula.

$$(\Sigma M_{awi}(i=1 \text{ to } N) - M_{ai}(i=1 \text{ to } N))/\Sigma M_{ai}(i=1 \text{ to } N) \qquad (27)$$

Figure 40:
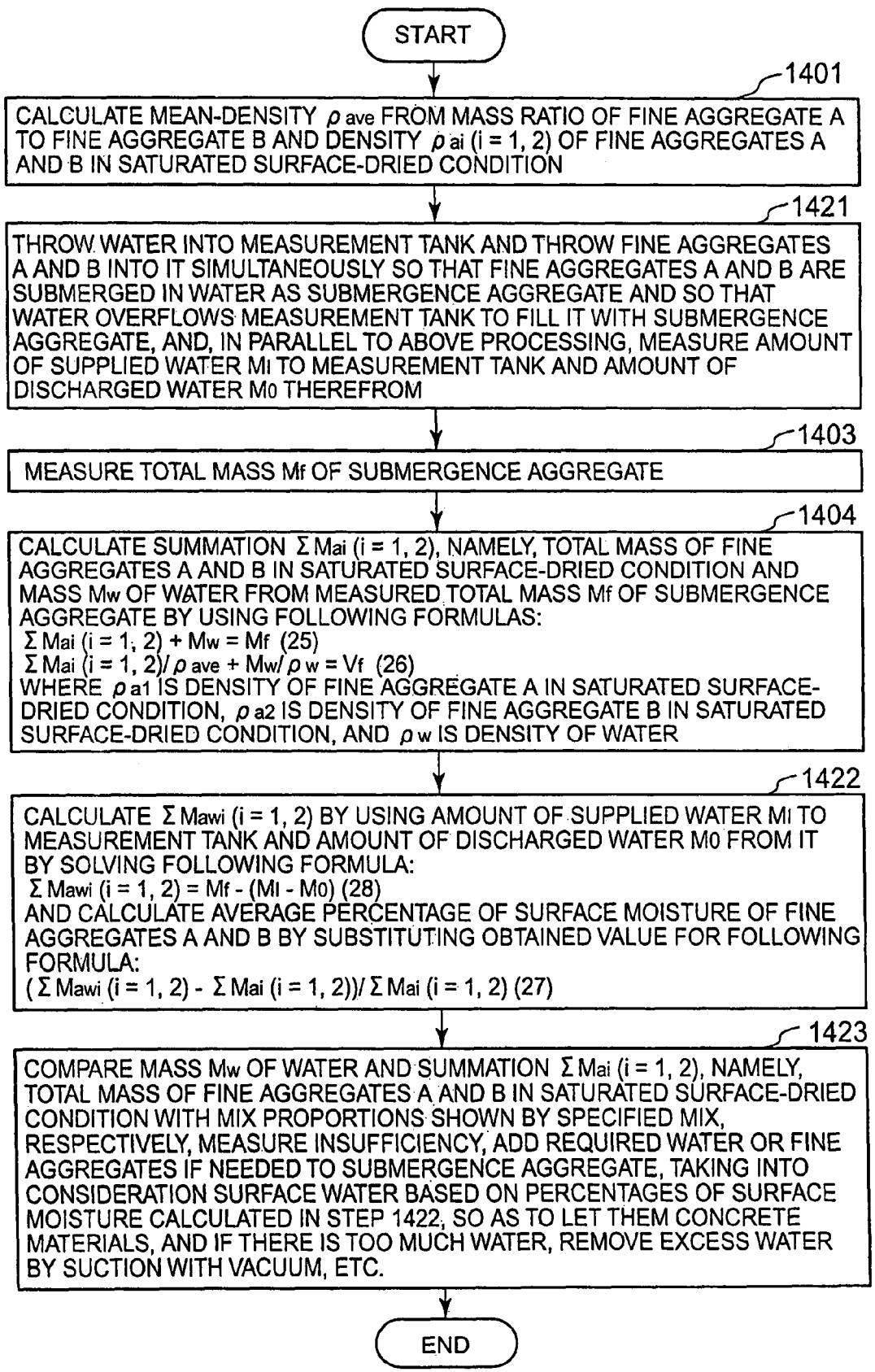
FIG. 40 is a flowchart of a preferable measuring method for concrete-forming materials according to another modification of the invention.

Referring to FIG. 40, there is shown a flowchart of a procedure for a measuring method according to this modification. In this measuring method, two fine aggregates A and B are used, for example. First, in the same manner as for the above embodiment, the mean-density $\rho_{ave}$ is calculated from the mass ratio of the fine aggregate A to the fine aggregate B and the density $\rho_{ai}$ (i=1, 2) of the fine aggregates A and B in a saturated surface-dried condition (step 1401).

Water is then thrown into the measurement tank, and the fine aggregates A and B are thrown into the measurement tank at the same time so that the fine aggregates A and B are submerged in water as submergence aggregate and so that the water overflows the measurement tank to fill the measurement tank with the submergence aggregate. In parallel to the above processing, the amount of water $M_I$ supplied to the measurement tank and the amount of water $M_O$ discharged from the measurement tank are measured (step 1421).

Thereafter, total mass $M_f$ of the submergence aggregate is measured in the same manner as for the above embodiment (step 1403) and the summation $\Sigma M_{ai}$ (i=1, 2), that is, the total mass of the fine aggregates A and B in the saturated surface-dried condition and the mass $M_w$ of the water are calculated from the measured total mass $M_f$ of the submergence aggregate by using the formulas (25) and (26) (step 1404).

Subsequently, $\Sigma M_{awi}$ (i=1, 2) is calculated by using the amount of water $M_I$ supplied to the measurement tank and the amount of water $M_O$ discharged from the measurement tank from the following formula.

$$\Sigma M_{awi}(i=1, 2)=M_I-(M_I-M_O) \qquad (28)$$

An average percentage of surface moisture of the fine aggregates A and B is calculated by substituting the $\Sigma M_{awi}$ for the following formula (step 1422).

$$(\Sigma M_{awi}(i=1, 2)-\Sigma M_{ai}(i=1, 2))/\Sigma M_{ai}(i=1, 2) \qquad (27)$$

Subsequently, the mass $M_w$ of the water and the summation $\Sigma M_{ai}$ (i=1, 2), that is, the total mass of the fine aggregates A and B in the saturated surface-dried condition are compared with mix proportions shown by a specified mix, respectively, and an insufficiency is measured. The submergence aggregate is supplemented with additional water if water is needed or with additional fine aggregates if fine aggregates are needed, taking into consideration surface water on the basis of the percentages of surface moisture calculated in step 1422. The aggregates and the water are then treated as concrete materials. If there is too much water, excess water is sucked and removed with a vacuum or the like (step 1423).

Ninth Embodiment

Figure 41:
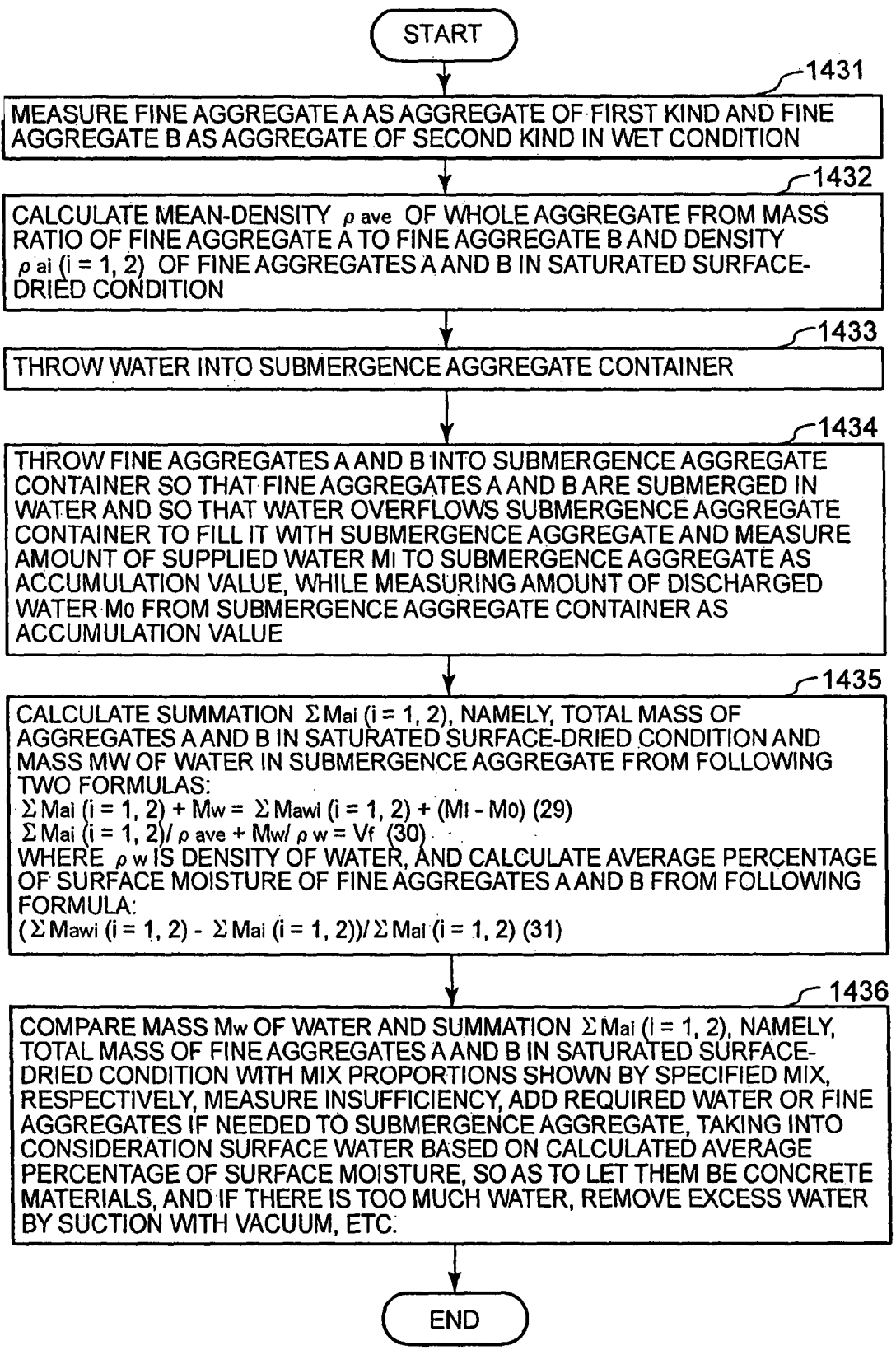
FIG. 41 is a flowchart of another preferable measuring method for concrete-forming materials according to the present invention.

Referring to FIG. 41, there is shown a flowchart of a procedure for a measuring method for concrete-forming materials according to a ninth embodiment. The embodiment will now be described by giving an example of using fine aggregate of two kinds A and B. The measuring method for concrete-forming materials according to this embodiment can be implemented by selecting an appropriate one from the above measuring apparatuses.

As apparent from FIG. 41, in the measuring method for concrete-forming materials according to this embodiment, the fine aggregate A as aggregate of a first kind and the fine aggregate B as aggregate of a second kind are measured in a wet condition, first (step 1431).

Subsequently, mean-density $\rho_{ave}$ of the entire aggregate is calculated from a mass ratio of the fine aggregate A to the fine aggregate B and density $\rho_{ai}$ (i=1, 2) of the fine aggregates A and B in a saturated surface-dried condition (step 1432).

The fine aggregates A and B can be stored in a predetermined storage hopper collectively in a condition where the mass ratio is known. Otherwise, two storage hoppers can be prepared to measure the fine aggregates A and B individually and to calculate the mass ratio at that time.

Water is then thrown into a submergence aggregate container (step 1433).

The submergence aggregate container may be formed, for example, in a shape of a hollow truncated cone so that a bore of the submergence aggregate container becomes larger in a downward direction. With this, when a measurement is finished, a free fall of the submergence aggregate in the submergence aggregate container can be achieved only by opening a bottom lid without a blockage of submergence aggregate in the submergence aggregate container even if no vibrating instrument such as a vibrator is used. Thereafter, the submergence aggregate can be thrown into a kneading mixer together with cement and coarse aggregate measured separately.

Subsequently, the fine aggregates A and B are thrown into the submergence aggregate container so that the fine aggregates A and B are submerged in water and so that the water overflows the submergence aggregate container to fill the submergence aggregate container with the submergence aggregate. In addition, an amount of water $M_I$ supplied to the submergence aggregate is measured as an accumulation value, while measuring an amount of water $M_O$ discharged from the submergence aggregate container as an accumulation value (step 1434).

If the water and the fine aggregate A are thrown into the submergence aggregate container in this manner, a water level at which the water overflows the submergence aggregate container is predetermined. Therefore, if the submergence aggregate container is filled with the submergence aggregate as mentioned above, total volume $V_f$ of the submergence aggregate equal to a known value is obtained without measurement.

When throwing the fine aggregates A and B into the submergence aggregate container at the same time, preferably the aggregates are conveyed to the submergence aggregate container by using a vibrating feeder having an electromagnetic vibrator, for example.

Subsequently, summation $\Sigma M_{ai}$ (i=1, 2), that is, total mass of the aggregates A and B in the saturated surface-dried condition and mass $M_w$ of water in the submergence aggregate are calculated from the following two formulas.

$$\Sigma M_{ai}(i=1, 2)+M_w=\Sigma M_{awi}(i=1, 2)+(M_I-M_O) \qquad (29)$$

$$\Sigma M_{ai}(i=1, 2)/\rho_{ave}+M_w/\rho_w=V_f \qquad (30)$$

where $\rho_w$ is the density of the water. In addition, an average percentage of surface moisture of the fine aggregates A and B is calculated from the following formula (step 1435).

$$(\Sigma M_{awi}(i=1, 2)-\Sigma M_{ai}(i=1, 2)/\Sigma M_{ai}(i=1, 2) \qquad (31)$$

By comparing the mass $M_w$ of the water and the summation $\Sigma M_{ai}$ (i=1, 2), that is, the total mass of the fine aggregates A and B in the saturated surface-dried condition calculated as mentioned above with mix proportions shown by a specified mix, respectively, an insufficiency is measured. The submergence aggregate is then supplemented with additional water if water is needed or with additional aggregate if aggregate is needed, taking into consideration surface water on the basis of the calculated average percentage of surface moisture, so as to let the aggregates and the water become concrete materials. If there is too much water, excess water is sucked and removed with a vacuum or the like (step 1436).

As set forth hereinabove, according to the measuring method of concrete materials of this embodiment, the surface water of the fine aggregates A and B can be indirectly calculated as a part of the mass $M_w$ of the water, even if a fine aggregate whose moisture state is not uniform is used, and the mass of the fine aggregate A and that of the fine aggregate B can be calculated as the summation $\Sigma M_{ai}$ (i=1, 2), that is, the total mass of the fine aggregates A and B in the saturated surface-dried condition. In other words, since the mass of the fine aggregates and the mass of the water are calculated on conditions equivalent to the specified mix, even if a humidity grade of the fine aggregates is not fixed at every measurement, it becomes possible to make concrete with water of the amount as shown by the specified mix.

In addition, even if the fine aggregates A and B differ from each other in density, grading, or the like, they can be measured in a single submergence aggregate container efficiently and very accurately.

Furthermore, the percentages of surface moisture of the fine aggregates A and B can also be calculated, by which it is possible to take into consideration the surface water by using the calculated percentages of surface moisture when the submergence aggregate is supplemented with the fine aggregates.

Furthermore, while this embodiment has been described by giving an example of fine aggregate of two kinds, naturally aggregates of an arbitrary number of kinds can be used. This method is applicable to a measurement of coarse aggregate and also applicable to a combination of fine aggregate and coarse aggregate.

A correction of air content has not been described particularly in this embodiment. If the air content a (%) of the submergence aggregate is considered, however, the known total volume Vf should be multiplied by (1−a/100).

This enables more accurate measurement since actual total volume is used for the measurement with the air content excluded.

Furthermore, the following should be noted though it has not been particularly noted in this embodiment. If there is a possibility that the aggregates thrown into the submergence aggregate container will emerge from the water and will not form submergence aggregate, a vibrator is lowered during or after throwing the fine aggregates A and B and operated in this condition. Thereby, the fine aggregates A and B thrown into the submergence aggregate container can be leveled by vibration of the vibrator, so that the fine aggregates A and B are submerged in the water. Before measuring a mass of the submergence aggregate, the vibrator is raised and put in a standby state, until a next measurement, in an upward location.

Tenth Embodiment

Figure 42:
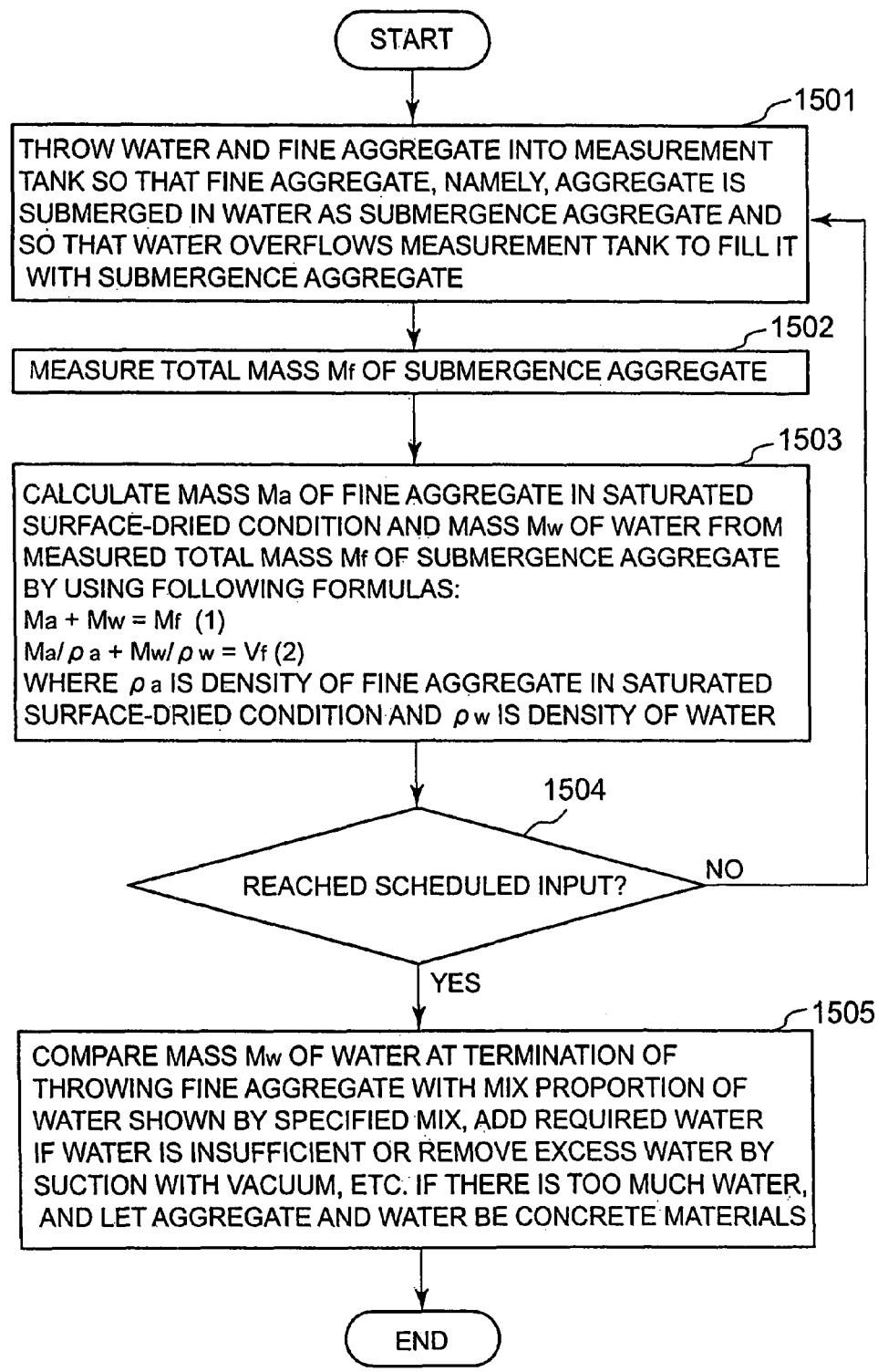
FIG. 42 is a flowchart of still another preferable measuring method for concrete-forming materials according to the present invention.

Referring to FIG. 42, there is shown a flowchart of a procedure for a measuring method for concrete-forming materials according to a tenth embodiment. The measuring method for concrete-forming materials according to this embodiment can be implemented by selecting an appropriate one from the above measuring apparatuses.

As apparent from FIG. 42, in the measuring method for concrete-forming materials according to this embodiment, water and fine aggregate are thrown into a measurement tank so that the fine aggregate, namely, aggregate is submerged in water as submergence aggregate and so that the water overflows the measurement tank to fill the measurement tank with the submergence aggregate (step 1501).

When throwing the fine aggregate and water into the measurement tank, preferably the water is thrown earlier and the fine aggregate is thrown later to prevent the submergence aggregate from being mixed with air bubbles. In addition, if the fine aggregate is not directly thrown into the measurement tank, but conveyed to the measurement tank by using a vibrating feeder having an electromagnetic vibrator, for example, it becomes possible to prevent granulation of the fine aggregate, and thus prevent air bubble mixing.

The measurement tank may be formed, for example, in a shape of a hollow truncated cone so that a bore of the measurement tank becomes larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

If the water and the fine aggregate are thrown into the measurement tank in this manner, a water level at which the water overflows the measurement tank is predetermined. Therefore, if the measurement tank is filled with the submergence aggregate as mentioned above, total volume $V_f$ of the submergence aggregate equal to a known value is obtained without measurement.

Subsequently, the total mass $M_f$ of the submergence aggregate is measured (step 1502). The total mass $M_f$ of the submergence aggregate can be obtained by subtracting a measurement value of an empty measurement tank, containing no submergence aggregate, from a measurement value of the measurement tank filled with the submergence aggregate.

Subsequently, mass $M_a$ of the fine aggregate in the saturated surface-dried condition and mass $M_w$ of the water are calculated from the measured total mass $M_f$ of the submergence aggregate by using the following formulas (step 1503).

$$M_a + M_w = M_f \quad (1)$$

$$M_a/\rho_a + M_w/\rho_w = V_f \quad (2)$$

where $\rho_a$ is the density of the fine aggregate in the saturated surface-dried condition and $\rho_w$ is the density of the water.

When measuring the fine aggregate in the procedure mentioned above, the aggregate is thrown into the measurement tank at a predetermined speed continuously or intermittently while measuring the total mass $M_f$ of the submergence aggregate in real time or at predetermined time intervals repeatedly (steps 1501 to 1503) until the mass $M_a$ of the aggregate in a saturated surface-dried condition reaches a scheduled input (step 1504, NO).

Thereafter, when the mass $M_a$ of the fine aggregate in the saturated surface-dried condition reaches the scheduled input (step 1504, YES), throwing the fine aggregate is terminated.

After measuring the fine aggregate of the scheduled input, the mass $M_w$ of the water at a termination of throwing the fine aggregate is compared with a mix proportion of water shown by a specified mix. If the amount of water is insufficient, required water is added. If there is too much water, excess water is sucked and removed with a vacuum or the like, for example. The aggregate and the water are then treated as concrete materials (step 1505).

As set forth hereinabove, according to the measuring method for concrete-forming materials of this embodiment, surface water of the fine aggregate can be indirectly calculated as a part of the mass $M_w$ of the water, even if a fine aggregate whose moisture state is not uniform is used, and the mass of the fine aggregate can be calculated as the mass $M_a$ of the fine aggregate in the saturated surface-dried condition. In other words, since the mass of the fine aggregate and the mass of the water are calculated on conditions equivalent to the specified mix, even if a humidity grade of the fine aggregate is not fixed at every measurement, it becomes possible to make concrete with water of the amount as shown by the specified mix.

Furthermore, the fine aggregate is thrown into the measurement tank at a predetermined speed continuously or intermittently while measuring the total mass $M_f$ of the submergence aggregate in real time or at predetermined time intervals, and throwing the fine aggregate is terminated when the mass $M_a$ of the fine aggregate in the saturated surface-dried condition reaches the scheduled input. Therefore, there is no possibility of excess or deficiency in the measurement of fine aggregate, thereby improving efficiency of measuring aggregate.

Still further, according to the measuring method for concrete-forming materials of this embodiment, the fine aggregate is thrown into the measurement tank so that the water overflows the measurement tank, and the total volume $V_f$ of the submergence aggregate is maintained at a steady value that is an internal volume of the measurement tank in an overflow condition, and therefore, the total volume $V_f$ of the submergence aggregate need not be measured every time.

While the total volume $V_f$ of the submergence aggregate is maintained at the steady value by causing the water to overflow the measurement tank in this embodiment as mentioned above, the total volume $V_f$ of the submergence aggregate can be measured by using an electrode-type displacement sensor or the like, instead.

The electrode-type displacement sensor can be one capable of measuring a water level of the submergence aggregate by monitoring a change in an energized condition when a lower end of a detection electrode contacts a water surface of the submergence aggregate in the measurement tank, for example.

A correction of an air content has not been described particularly in this embodiment. If the air content a (%) of the submergence aggregate is considered, however, the known total volume Vf should be multiplied by (1−a/100). For example, the following formula may be used instead of formula (2).

$$M_a/\rho_a + M_w/\rho_w = V_f(1-a/100)$$

This enables more accurate measurement since actual total volume is used for the measurement with the air content excluded.

Furthermore, the following should be noted though it has not been particularly noted in this embodiment. If there is a possibility that the aggregate thrown into the measurement tank will emerge from the water and will not be submergence aggregate, a vibrator is lowered during or after throwing the fine aggregate and operated in this condition. Thereby, the fine aggregate thrown into the measurement tank can be leveled by vibration of the vibrator, so that the fine aggregate is submerged in the water. Before measuring a mass of the submergence aggregate, the vibrator is raised and put in a standby state, until a next measurement, in an upward location.

While the following has not been particularly noted in this embodiment, the percentage of surface moisture of the fine aggregate can be calculated by measuring an amount of water $M_I$ supplied to the measurement tank and an amount of water $M_O$ discharged from the measurement tank as accumulation values.

Figure 43:
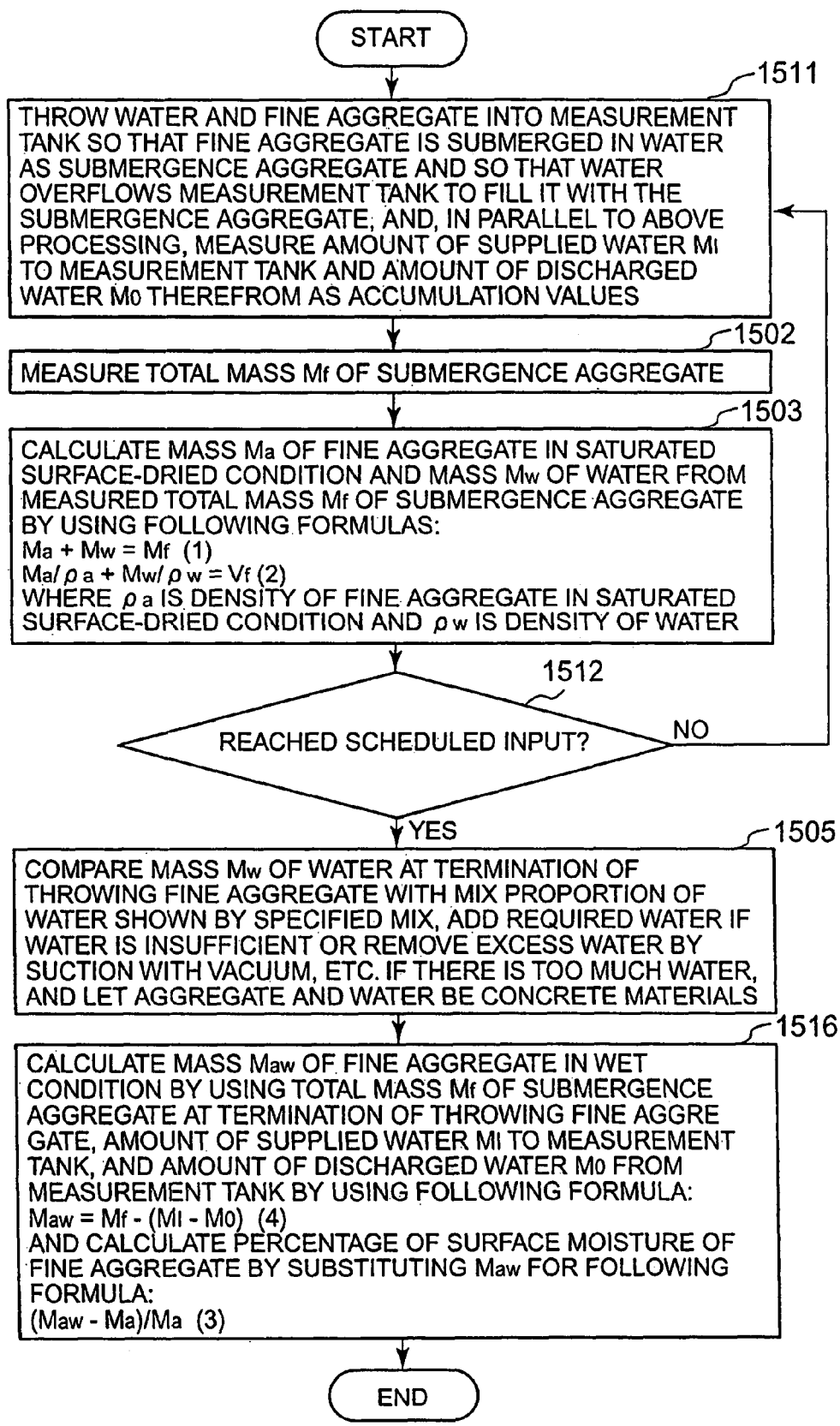
FIG. 43 is a flowchart of a preferable measuring method for concrete-forming materials according to a modification of the invention.

Referring to FIG. 43, there is shown a flowchart of a procedure for a measuring method according to this modification. In the measuring method, in the same manner as for the embodiment, water is thrown into the measurement tank, first, and fine aggregate is thrown into the measurement tank so that the fine aggregate is submerged in the water as submergence aggregate and so that the water overflows the measurement tank to fill the measurement tank with the submergence aggregate. In parallel to the above processing, the amount of water $M_I$ supplied to the measurement tank and the amount of water $M_O$ discharged from the measurement tank are measured as accumulation values (step 1511).

Thereafter, total mass $M_f$ of the submergence aggregate is measured in the same manner as for the above embodiment (step 1502) and the mass $M_a$ of the fine aggregate in a saturated surface-dried condition and the mass $M_w$ of the water are calculated from the measured total mass $M_f$ of the submergence aggregate by using the formulas (1) and (2) (step 1503). In measuring the fine aggregate in the above procedure, the fine aggregate is thrown into the measurement tank at a predetermined speed continuously or intermittently here, too, while measuring the total mass $M_f$ of the submergence aggregate in real time or at predetermined time intervals repeatedly (steps 1511, 1502, 1503), until the mass $M_a$ of the aggregate in the saturated surface-dried condition reaches a scheduled input (step 1512, NO).

When the mass $M_a$ of the fine aggregate in the saturated surface-dried condition reaches the scheduled input (step 1512, YES), throwing the fine aggregate is terminated.

After measuring the fine aggregate of the scheduled input, the mass $M_w$ of the water at termination of throwing the fine aggregate is compared with a mix proportion of water shown by a specified mix. If the amount of water is insufficient, required water is added. If there is too much water, excess water is sucked and removed with a vacuum or the like, for example. The aggregate and the water are then treated as concrete materials (step 1505).

On the other hand, mass $M_{aw}$ of the fine aggregate in a wet condition is calculated by using the total mass $M_f$ of the submergence aggregate at the termination of throwing the fine aggregate, the amount of water $M_I$ supplied to the measurement tank, and the amount of water $M_O$ discharged from the measurement tank from the following formula.

$$M_{aw} = M_f - (M_I - M_O) \qquad (4)$$

A percentage of surface moisture of the fine aggregate is calculated by substituting the above $M_{aw}$ into the following formula (step 1516).

$$(M_{aw} - M_a)/M_a \qquad (3)$$

In this constitution, the calculated percentage of surface moisture can be used as a measure of an amount of thrown water for a next measurement.

Eleventh Embodiment

Figure 44:
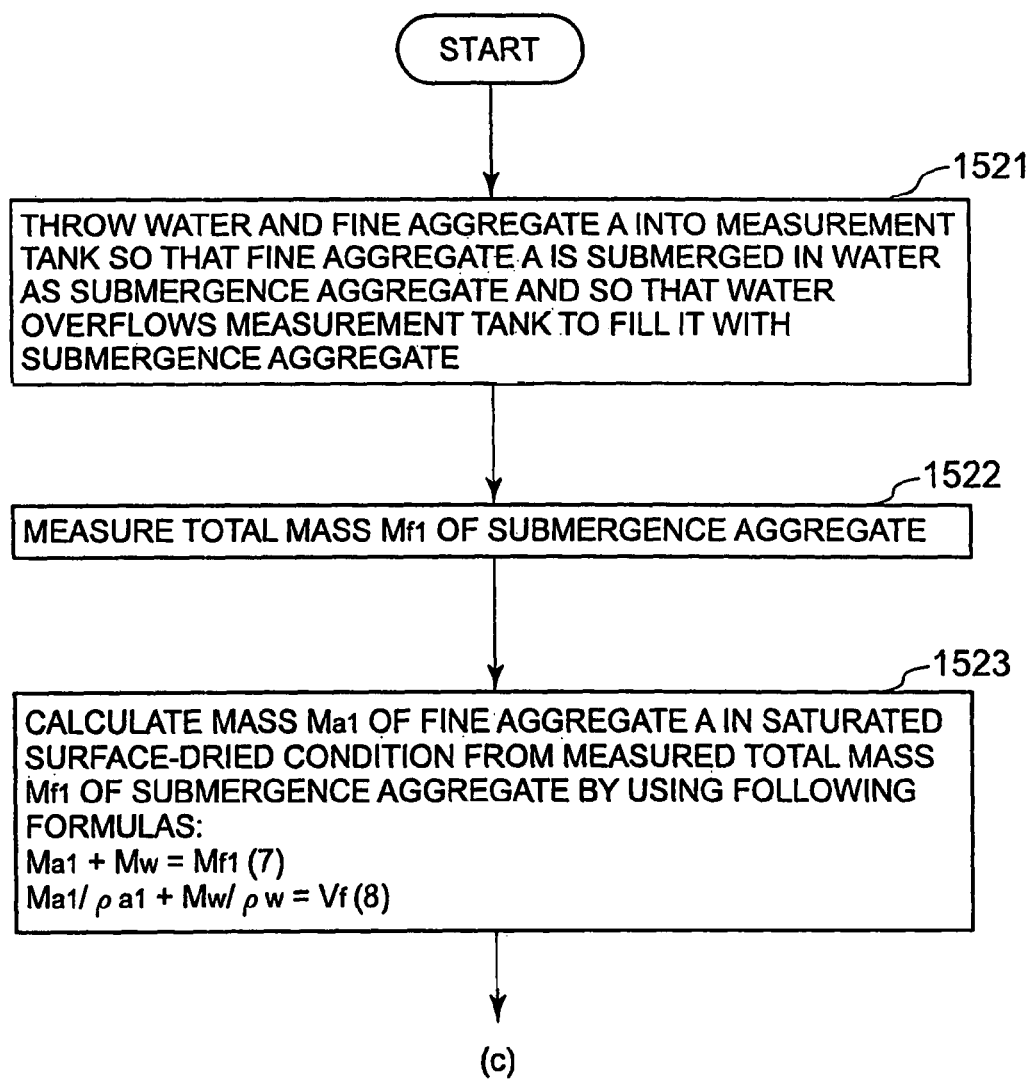
FIGS. 44 and 45 are a series of flowcharts of a preferable measuring method for concrete-forming materials according to the present invention.
Figure 45:
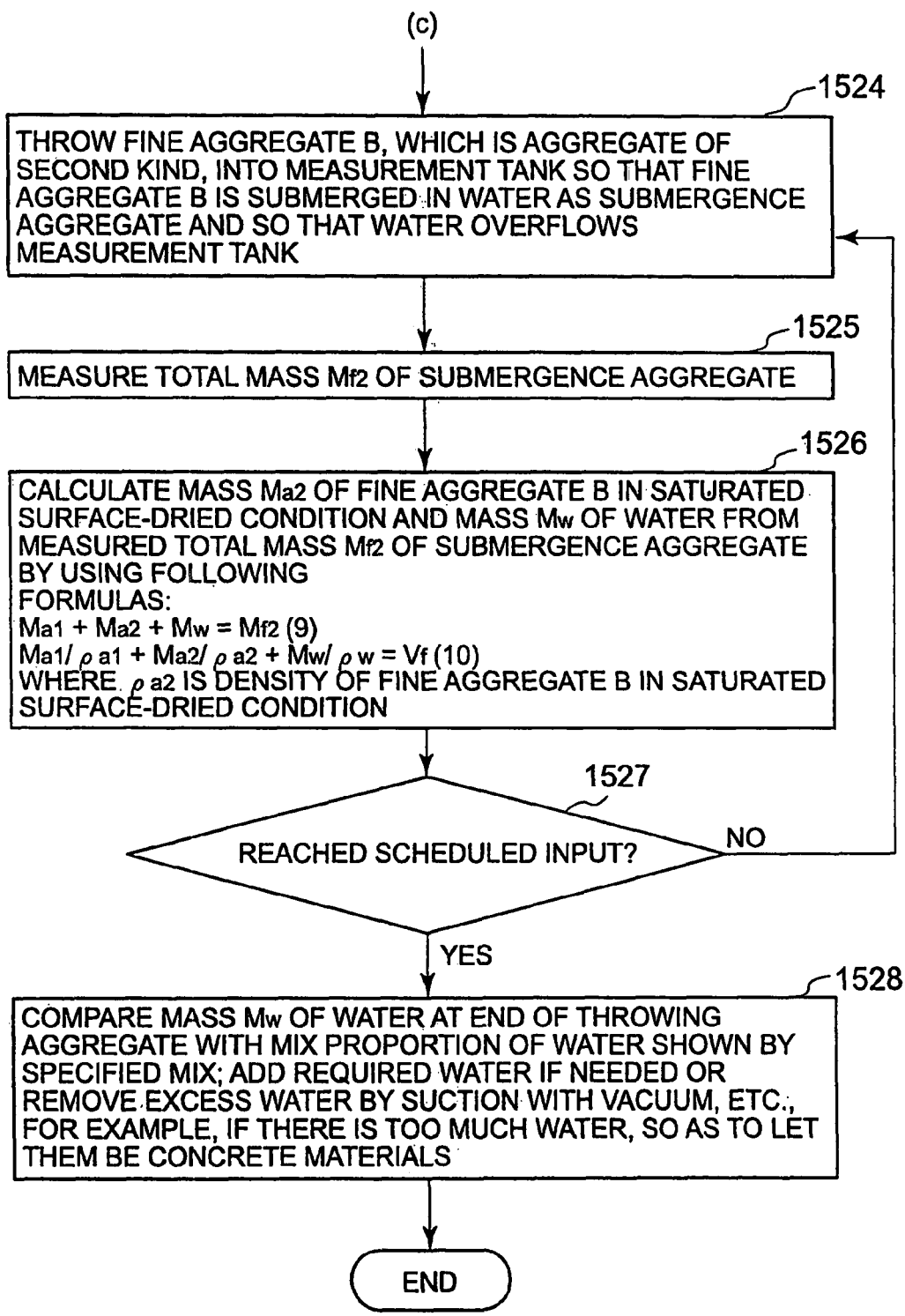

Referring to FIGS. 44 and 45, there is shown a flowchart a procedure for a measuring method for concrete-forming materials according to an eleventh embodiment. This embodiment will now be described on the assumption that two fine aggregates A and B are thrown cumulatively and that an aggregate input reaches a scheduled input during a throwing operation of the fine aggregate B. The measuring method for concrete-forming materials according to this embodiment can be implemented by selecting an appropriate one from the measuring apparatuses mentioned above.

As apparent from FIGS. 44 and 45, in the measuring method for concrete-forming materials according to this embodiment, water and the fine aggregate A are thrown into a measurement tank first so that the fine aggregate A is submerged in water as submergence aggregate and so that the water overflows the measurement tank to fill the measurement tank with the submergence aggregate (step 1521).

The measurement tank may be formed, for example, in a shape of a hollow truncated cone so that a bore of the measurement tank becomes larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

If the water and the fine aggregate A are thrown into the measurement tank in this manner, a water level at which the water overflows the measurement tank is predetermined. Therefore, if the measurement tank is filled with the submergence aggregate as mentioned above, total volume $V_f$ of the submergence aggregate equal to a known value is obtained without measurement.

Subsequently, the total mass $M_{f1}$ of the submergence aggregate is measured (step 1522). The total mass $M_{f1}$ of the submergence aggregate can be obtained by subtracting a measurement value of an empty measurement tank, containing no submergence aggregate, from a measurement value of the measurement tank filled with the submergence aggregate.

Subsequently, mass $M_{a1}$ of the fine aggregate A in a saturated surface-dried condition is calculated from the measured total mass $M_{f1}$ of the submergence aggregate by using the following formulas (step 1523).

$$M_{a1} + M_w = M_{f1} \quad (7)$$

$$M_{a1}/\rho_{a1} + M_w/\rho_w = V_f \quad (8)$$

where $\rho_{a1}$ is the density of the fine aggregate A in the saturated surface-dried condition and $\rho_w$ is the density of the water.

When measuring the fine aggregate A in the procedure mentioned above, the aggregate A is thrown into the measurement tank at a predetermined speed continuously or intermittently while measuring the total mass $M_{f1}$ of the submergence aggregate in real time or at predetermined time intervals repeatedly until the mass $M_{a1}$ of the aggregate A in the saturated surface-dried condition reaches a scheduled input. In this embodiment, however, it is assumed that the aggregate input will not reach the scheduled input even after a completion of throwing all the fine aggregate A. Therefore, an aggregate of a second kind, namely, the fine aggregate B is thrown into the measurement tank so that the fine aggregate B is submerged in water as submergence aggregate and so that the water overflows the measurement tank (step 1524).

When throwing the fine aggregates A and B and water into the measurement tank, preferably the water is thrown earlier and the fine aggregates A and B are thrown later to prevent the submergence aggregate from being mixed with air bubbles. In addition, if the fine aggregates A and B are not directly thrown into the measurement tank, but conveyed to the measurement tank by using a vibrating feeder having an electromagnetic vibrator, for example, it becomes possible to prevent granulation of the fine aggregates, and thus prevent air bubble mixing.

Total mass $M_{f2}$ of the submergence aggregate is then measured (step 1525).

Subsequently, mass $M_{a2}$ of the fine aggregate B in a saturated surface-dried condition and mass $M_w$ of the water are calculated from the measured total mass $M_{f2}$ of the submergence aggregate by using the following formulas (step 1526).

$$M_{a1} + M_{a2} + M_w = M_{f2} \quad (9)$$

$$M_{a1}/\rho_{a1} + M_{a2}/\rho_{a2} + M_w/\rho_w = V_f \quad (10)$$

where $\rho_{a2}$ is the density of the fine aggregate B in the saturated surface-dried condition.

In measuring the fine aggregate B in the above procedure, the fine aggregate B is thrown into the measurement tank at a predetermined speed continuously or intermittently, while measuring the total mass $M_f$ of the submergence aggregate in real time or at predetermined time intervals repeatedly (steps 1524 to 1526), until summation $\Sigma M_{ai}$ (i=1, 2), which is total mass of the fine aggregates A and B thrown by then in the saturated surface-dried condition, reaches the scheduled input (step 1527, NO).

When the summation $\Sigma M_{ai}$ (i=1, 2), which is the total mass of the thrown fine aggregates A and B in the saturated surface-dried condition, reaches the scheduled input (step 1527, YES), throwing the fine aggregate B is terminated in a middle of this throwing operation.

If measuring the aggregate of the scheduled input is accomplished in the middle of throwing the fine aggregate B as mentioned above, the mass $M_w$ of the water at a termination of throwing the aggregate is compared with a mix proportion of water shown by a specified mix. If the amount of water is insufficient, required water is added. If there is too much water, excess water is sucked and removed with a vacuum or the like, for example. The aggregate and the water are then treated as concrete materials (step 1528).

As set forth hereinabove, according to the measuring method for concrete materials of this embodiment, surface water of the fine aggregates A and B can be indirectly calculated as a part of the mass $M_w$ of the water, even if a fine aggregate whose moisture state is not uniform is used, and the mass of the fine aggregate A and the mass of the fine aggregate B can be calculated as the mass $M_{ai}$ (i=1, 2) of the fine aggregates A and B in the saturated surface-dried condition. In other words, since the mass of the fine aggregates and the mass of the water are calculated on conditions equivalent to the specified mix, even if a humidity grade of the fine aggregate is not fixed at every measurement, it becomes possible to make concrete with water of the amount as shown by the specified mix.

Furthermore, the fine aggregates A an B are thrown into the measurement tank at a predetermined speed continuously or intermittently while measuring the total mass $M_{fi}$ (i=1, 2) of the submergence aggregate in real time or at predetermined time intervals. In addition, throwing the fine aggregates is terminated when the mass $M_{ai}$ (i=1, 2) of the fine aggregates A and B in the saturated surface-dried condition reaches the scheduled input. Therefore, there is no possibility of excess or deficiency in the measurement of fine aggregates, thereby improving efficiency of measuring aggregate.

Even if the fine aggregates A and B differ from each other in density, grading, or the like, they can be measured in a single measurement tank efficiently and very accurately.

Still further, according to the measuring method for concrete-forming materials of this embodiment, the fine aggregates A and B are thrown into the measurement tank so that the water overflows the measurement tank, the total volume $V_{fi}$ (i=1, 2) of the submergence aggregate is maintained at a steady value $V_f$ that is an internal volume of the measurement tank in an overflow condition, and therefore, the total volume $V_{fi}$ (i=1, 2) of the submergence aggregate need not be measured every time.

While the total volume $V_{fi}$ (i=1, 2) of the submergence aggregate is maintained at the steady value $V_f$ by causing the water to overflow the measurement tank in this embodiment as mentioned above, the total volume $V_{fi}$ (i=1, 2) of the submergence aggregate can be measured by using an electrode-type displacement sensor or the like, instead.

The electrode-type displacement sensor can be one capable of measuring a water level of the submergence aggregate by monitoring a change in an energized condition when a lower end of a detection electrode contacts a water surface of the submergence aggregate in the measurement tank, for example.

Furthermore, while this embodiment has been described by giving an example of fine aggregate of two kinds, naturally aggregate of an arbitrary number of kinds can be used. This method is applicable to a measurement of coarse aggregate and also applicable to a combination of fine aggregate and coarse aggregate.

A correction of an air content has not been described particularly in this embodiment. If the air content a (%) of the submergence aggregate is considered, however, the known total volume $V_f$ should be multiplied by $(1-a/100)$. For example, the following formula may be used instead of formula (8).

$$M_{a1}/\rho_{a1}+M_w/\rho_w=V_f(1-a/100)$$

This enables more accurate measurement since actual total volume is used for the measurement with the air content excluded.

Furthermore, the following should be noted though it has not been particularly noted in this embodiment. If there is a possibility that the fine aggregate thrown into the measurement tank will emerge from the water and will not be submergence aggregate, a vibrator is lowered during or after throwing the fine aggregate A or B and operated in this condition. Thereby, the fine aggregate A or B thrown into the measurement tank can be leveled by vibration of the vibrator, so that the fine aggregate is submerged in the water. Before measuring a mass of the submergence aggregate, the vibrator is raised and put in a standby state, until the next measurement, in an upward location.

While the following has not been particularly noted in this embodiment, if an amount of water $M_I$ supplied to the measurement tank and an amount of water $M_O$ discharged from the measurement tank are previously measured as accumulation values, $\Sigma M_{awj}$ (j=1 to i) can be calculated from the following formula.

$$\Sigma M_{awj}(j=1 \text{ to } i)=M_{fi}-(M_I-M_O) \qquad (14)$$

Mawi is then calculated from the following formula.

$$\Sigma M_{awj}(j=1 \text{ to } i)-\Sigma M_{awj}(j=1 \text{ to } (i-1)) \qquad (15)$$

Thereafter, the percentages of surface moisture of the aggregate of the i-th kind (i=1 to N) can be calculated by substituting $M_{awi}$ for the following formula.

$$(M_{awi}-M_{ai})/M_{ai} \qquad (13)$$

Figure 46:
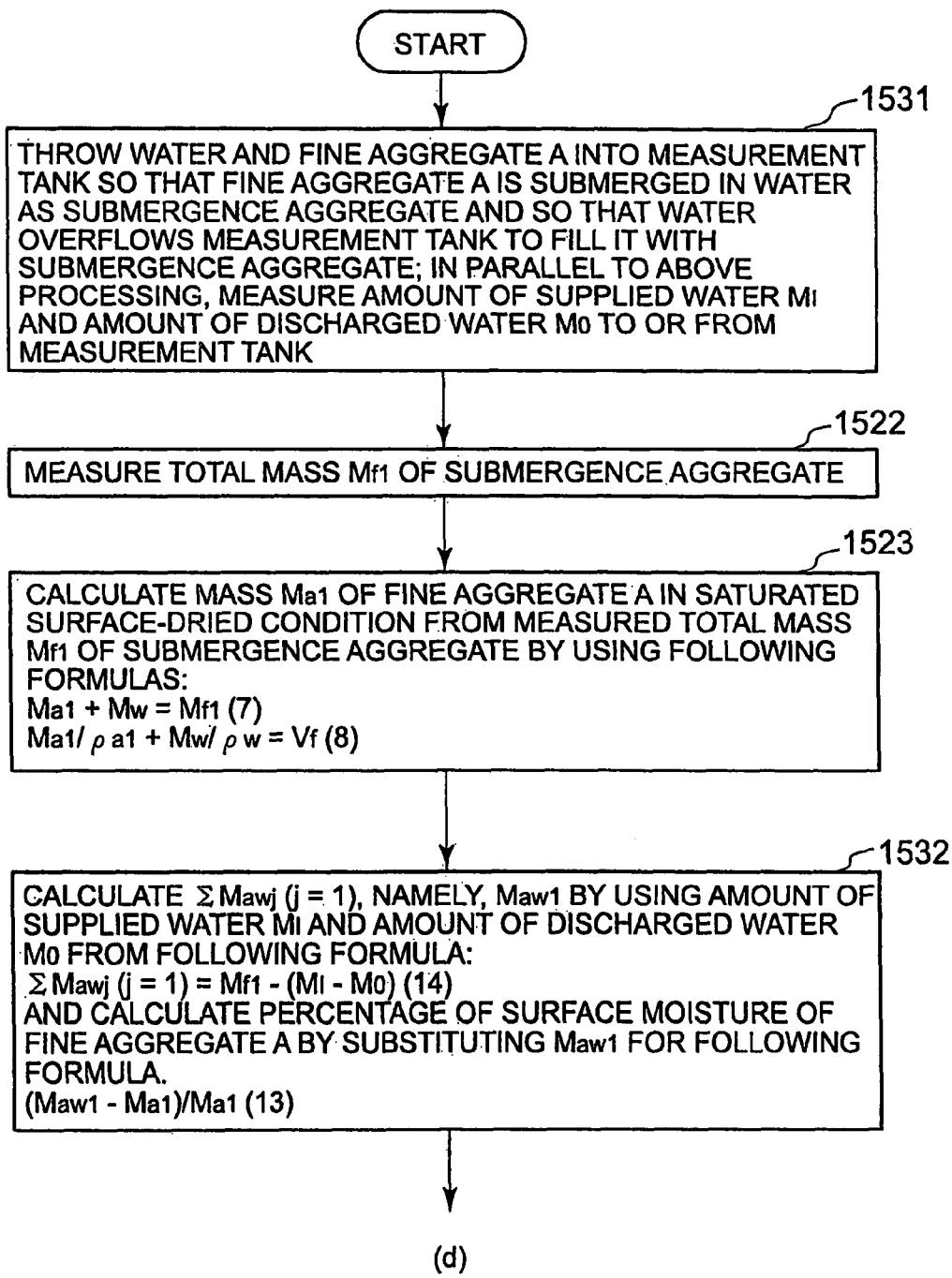
FIGS. 46 and 47 are a series of flowcharts of a preferable measuring method for concrete-forming materials according to a modification of the present invention.
Figure 47:
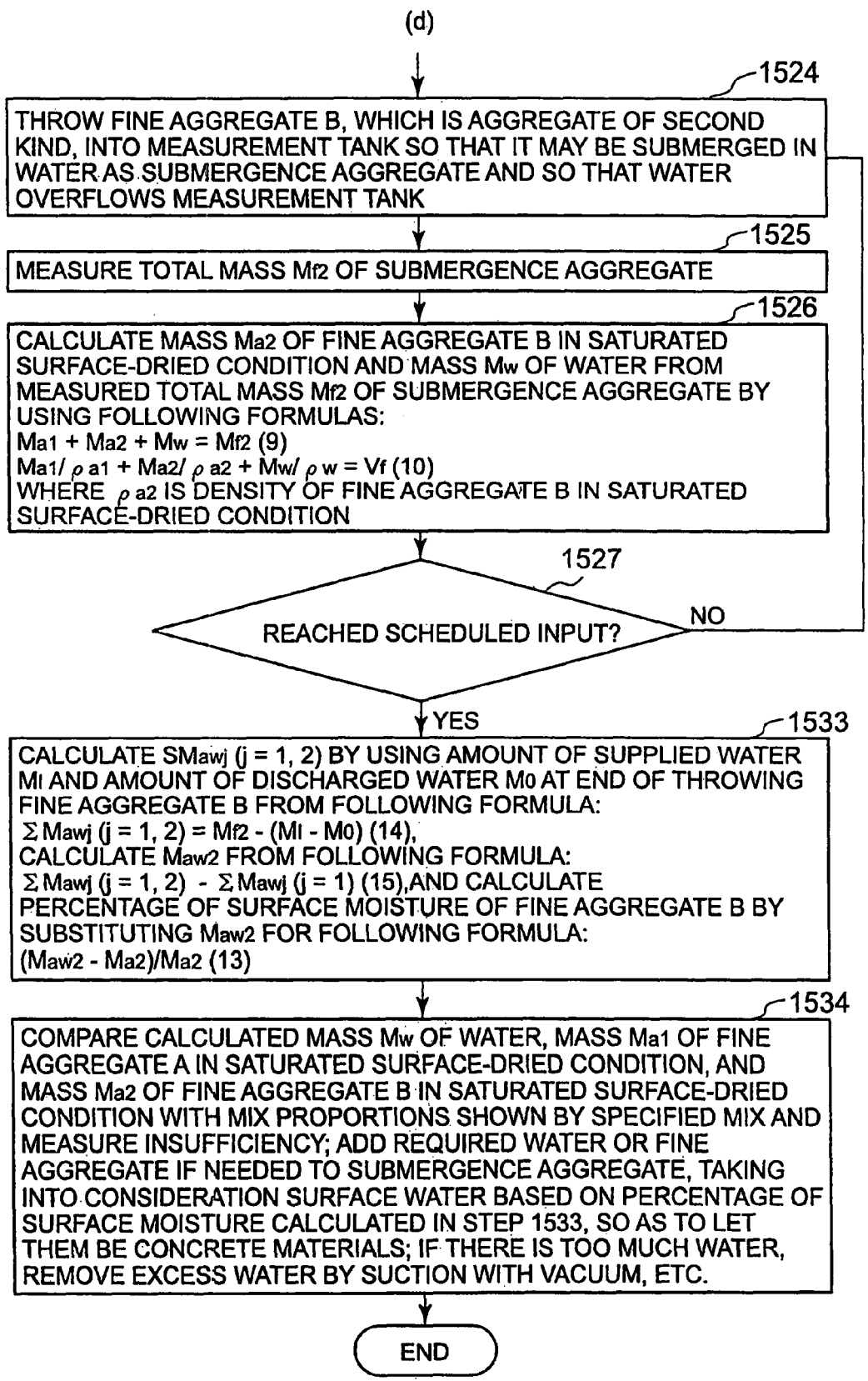

Referring to FIGS. 46 and 47, there is shown a flowchart of a procedure for a measuring method according to this modification. This measuring method will be described by giving an example of using fine aggregate of two kinds A and B on the assumption that an input of the fine aggregate B reaches a scheduled input in the same manner as for the embodiment.

In this modification, water is thrown into the measurement tank, first, and the fine aggregate A is then thrown into the measurement tank so that it is submerged in water as submergence aggregate and so that the water overflows the measurement tank to fill the measurement tank with the submergence aggregate. In parallel to the above processing, the amount of water $M_I$ supplied to the measurement tank and the amount of water $M_O$ discharged from the measurement tank are measured (step 1531).

Thereafter, total mass $M_{f1}$ of the submergence aggregate is measured in the same manner as for the above embodiment (step 1522). The mass $M_{a1}$ of the fine aggregate A in a saturated surface-dried condition is then calculated from the measured total mass $M_{f1}$ of the submergence aggregate by using the formulas (7) and (8) (step 1523).

Subsequently, $\Sigma M_{awj}$ (j=1), namely, $M_{aw1}$ is calculated by using the amount of supplied water $M_I$ and the amount of discharged water $M_O$ from the following formula.

$$\Sigma M_{awj}(j=1)=M_{f1}-(M_I-M_O) \qquad (14)$$

Thereafter, the percentage of surface moisture of the aggregate A is calculated by substituting $M_{aw1}$ into the following formula (step 1532).

$$(M_{aw1}-M_{a1})/M_{a1} \qquad (13)$$

Subsequently, the fine aggregate B is thrown into the measurement tank so that it is submerged in water as submergence aggregate and so that the water overflows the measurement tank in the same manner as for the embodiment (step 1524). Total mass $M_{f2}$ of the submergence aggregate is measured (step 1525). Then, mass $M_{a2}$ of the fine aggregate B in a saturated surface-dried condition and mass $M_w$ of the water are calculated from the measured total mass $M_{f2}$ of the submergence aggregate by using the formulas (9) and (10) (step 1526).

In measuring the fine aggregate B in the above procedure, the fine aggregate B is thrown into the measurement tank at a predetermined speed continuously or intermittently, while measuring the total mass $M_{f2}$ of the submergence aggregate in real time or at predetermined time intervals repeatedly (steps 1524 to 1526), until the summation $\Sigma M_{ai}$ (i=1, 2), which is the total mass of the fine aggregates A and B thrown by then in the saturated surface-dried condition, reaches the scheduled input (step 1527, NO).

When the summation $\Sigma M_{ai}$ (i=1, 2) of the thrown fine aggregates A and B in the saturated surface-dried condition reaches the scheduled input (step 1527, YES), throwing the fine aggregate B is terminated in a middle of this operation.

Subsequently, $\Sigma M_{awj}$ (j=1, 2) is calculated by using the amount of supplied water $M_I$ and the amount of discharged water $M_O$ at termination of throwing the fine aggregate B from the following formula.

$$\Sigma M_{awj}(j=1, 2)=M_{f2}-(M_I-M_O) \qquad (14)$$

$M_{aw2}$ is then calculated from the following formula.

$$\Sigma M_{awj}(j=1, 2)-\Sigma M_{awj}(j=1) \qquad (15)$$

Furthermore, a percentage of surface moisture of the fine aggregate B is calculated by substituting $M_{aw2}$ into the following formula (step 1533).

$$(M_{aw2}-M_{a2})/M_{a2} \qquad (13)$$

Thereafter, by comparing the mass $M_w$ of the water, the mass $M_{a1}$ of the fine aggregate A in the saturated surface-dried condition, and the mass $M_{a2}$ of the fine aggregate B in the saturated surface-dried condition calculated in the above with mix proportions shown by a specified mix, an insufficiency is measured. If the water is insufficient, required water is added. If the fine aggregate is insufficient, required fine aggregate is added to the above submergence aggregate, taking into consideration surface water on the basis of the percentage of surface moisture calculated in step 1533, so as to allow the water and the fine aggregates become concrete materials. If there is too much water, excess water is sucked and removed with a vacuum or the like, for example (step 1534).

Twelfth Embodiment

Figure 48:
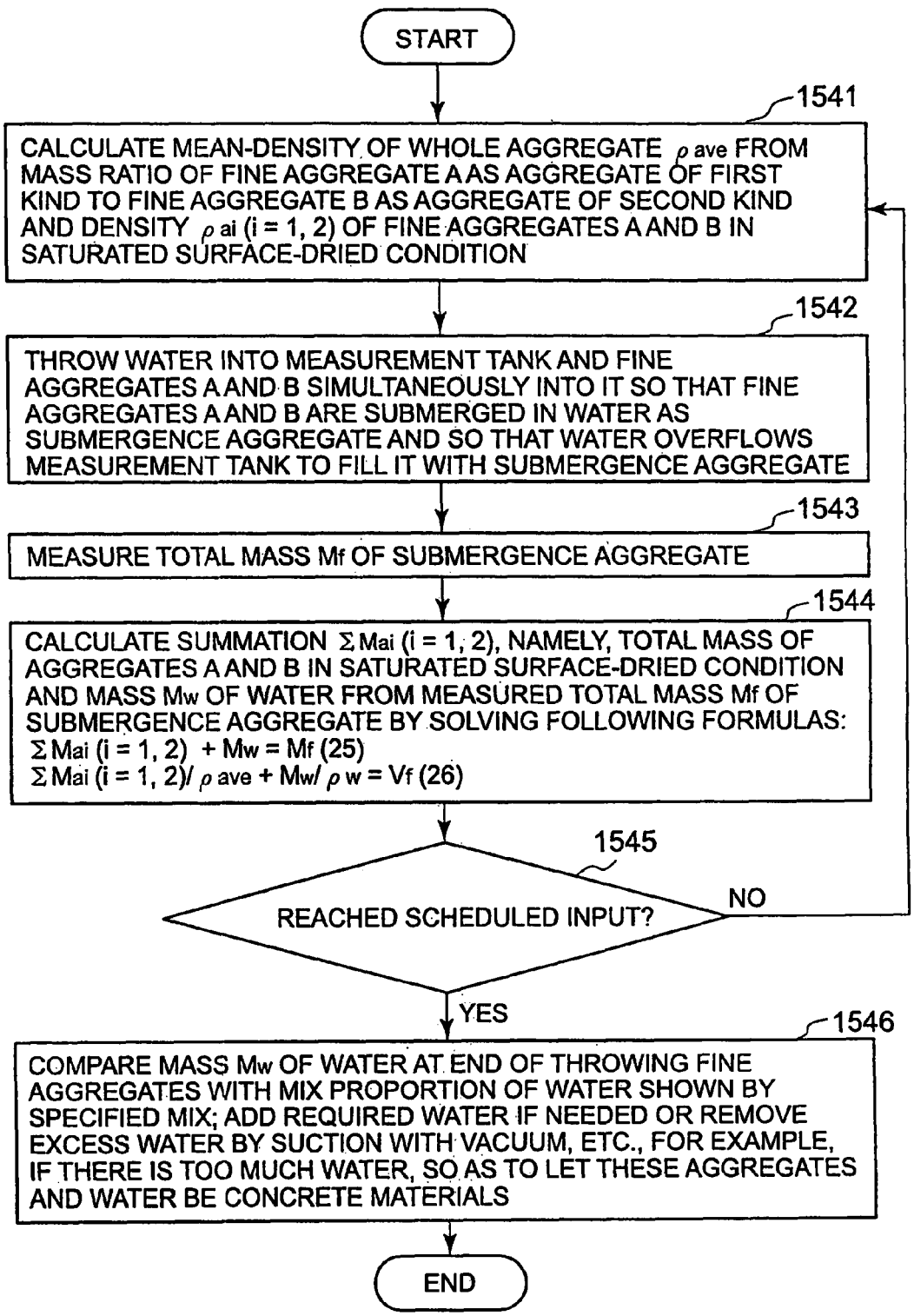
FIG. 48 is a flowchart of a preferable measuring method for concrete-forming materials according to the present invention.

Referring to FIG. 48, there is shown a flowchart of a procedure for a measuring method for concrete-forming materials according to a twelfth embodiment. The measuring method for concrete-forming materials according to this embodiment can be implemented by selecting an appropriate one from the above measuring apparatuses.

As apparent from FIG. 48, the embodiment will now be described by giving an example of using fine aggregate of two kinds A and B. Mean-density of the entire aggregate $\rho_{ave}$ is first calculated from a mass ratio of the fine aggregate A as aggregate of a first kind to the fine aggregate B as aggregate of a second kind and density $\rho_{ai}$ (i=1, 2) of the fine aggregates A and B in a saturated surface-dried condition (step 1541).

The fine aggregates A and B can be stored in a predetermined storage hopper collectively in a condition where the mass ratio is known. Otherwise, two storage hoppers can be prepared individually to calculate the mass ratio from a speed at which the aggregates are conveyed from a location beneath these hoppers to the measurement tank. Contrarily, a conveyance speed can be adjusted so as to achieve a target mass ratio.

Subsequently, water is thrown into the measurement tank, and the fine aggregates A and B are thrown at the same time into the measurement tank so that the fine aggregates A and B are submerged in the water as submergence aggregate and so that the water overflows the measurement tank to fill the measurement tank with the submergence aggregate (step 1542).

The measurement tank may be formed, for example, in a shape of a hollow truncated cone so that a bore of the measurement tank becomes larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

When throwing the fine aggregates A and B at the same time into the measurement tank, preferably the water is thrown earlier and the fine aggregates A and B are thrown later to prevent the submergence aggregate from being mixed with air bubbles. In addition, if the fine aggregates A and B are conveyed to the measurement tank by using a vibrating feeder having an electromagnetic vibrator, for example, it becomes possible to prevent granulation of the fine aggregates, and thus prevent air bubble mixing.

If the water and the fine aggregates A and B are thrown into the measurement tank in this manner, a water level at which the water overflows the measurement tank is predetermined. Therefore, if the measurement tank is filled with the submergence aggregate as mentioned above, total volume Vf of the submergence aggregate equal to a known value is obtained without measurement.

Subsequently, the total mass $M_f$ of the submergence aggregate is measured (step 1543). The total mass $M_f$ of the submergence aggregate can be obtained by subtracting a measurement value of an empty measurement tank, containing no submergence aggregate, from a measurement value of the measurement tank filled with the submergence aggregate.

Subsequently, summation $\Sigma M_{ai}$ (i=1, 2), that is, total mass of the aggregates A and B in a saturated surface-dried condition and mass $M_w$ of water are calculated from the measured total mass $M_f$ of the submergence aggregate by solving the following formulas (step 1544).

$$\Sigma M_{ai}(i=1, 2) + M_w = M_f \quad (25)$$

$$\Sigma M_{ai}(i=1, 2)/\rho_{ave} + M_w/\rho_w = V_f \quad (26)$$

When measuring the fine aggregates A and B in the procedure mentioned above, the aggregates are thrown into the measurement tank at a predetermined speed continuously or intermittently while measuring the total mass $M_f$ of the submergence aggregate in real time or at predetermined time intervals repeatedly (steps 1542 to 1544) until the summation $\Sigma M_{ai}$ (i=1, 2) of the fine aggregates A and B in the saturated surface-dried condition reaches a scheduled input (step 1545, NO).

Thereafter, when the summation $\Sigma M_{ai}$ (i=1, 2) of the fine aggregates A and B in the saturated surface-dried condition reaches the scheduled input (step 1545, YES), throwing the fine aggregates A and B is terminated.

After measuring the fine aggregate of the scheduled input, the mass $M_w$ of the water at termination of throwing the fine aggregates is compared with the mix proportion of water shown by a specified mix. If the water is insufficient, required water is added. If there is too much water, excess water is sucked and removed with a vacuum or the like, for example. The aggregates and the water are then treated as concrete materials (step 1546).

As set forth hereinabove, according to the measuring method for concrete-forming materials of this embodiment, the surface water of the fine aggregates A and B can be indirectly calculated as a part of the mass $M_w$ of the water, even if a fine aggregate whose moisture state is not uniform is used, and the mass of the fine aggregate can be calculated as the summation $\Sigma M_{ai}$ (i=1, 2) of the aggregates A and B in the saturated surface-dried condition. In other words, since the mass of the fine aggregates and the mass of the water are calculated on conditions equivalent to the specified mix, even if a humidity grade of the fine aggregate is not fixed at every measurement, it becomes possible to make concrete with water of the amount as shown by the specified mix.

Furthermore, the fine aggregate is thrown into the measurement tank at a predetermined speed continuously or intermittently while measuring the total mass $M_f$ of the submergence aggregate in real time or at predetermined time intervals, and throwing the fine aggregate is terminated when the summation $\Sigma M_{ai}$ (i=1, 2) of the aggregates A and B in the saturated surface-dried condition reaches the scheduled input. Therefore, there is no possibility of excess or deficiency in the measurement of fine aggregates, thereby improving efficiency of measuring aggregate.

Even if the fine aggregates A and B differ from each other in density, grading, or the like, they can be measured in a single measurement tank efficiently and very accurately.

Still further, according to the measuring method of concrete materials of this embodiment, the fine aggregates A and B are thrown into the measurement tank at a time so that the water overflows the measurement tank, and the total volume $V_f$ of the submergence aggregate is maintained at a steady value that is an internal volume of the measurement tank in an overflow condition, and therefore, the total volume $V_f$ of the submergence aggregate need not be measured every time.

While the total volume $V_f$ of the submergence aggregate is maintained at the steady value by causing the water to overflow the measurement tank in this embodiment as mentioned above, the total volume $V_f$ of the submergence aggregate can be measured by using an electrode-type displacement sensor or the like, instead.

The electrode-type displacement sensor can be one capable of measuring a water level of the submergence aggregate by monitoring a change in an energized condition when a lower end of a detection electrode contacts a water surface of the submergence aggregate in the measurement tank, for example.

Furthermore, while this embodiment has been described by giving an example of fine aggregate of two kinds, naturally aggregate of an arbitrary number of kinds can be used. This method is applicable to a measurement of coarse aggregate and also applicable to a combination of fine aggregate and coarse aggregate.

A correction of an air content has not been described particularly in this embodiment. If the air content a (%) of the submergence aggregate is considered, however, the known total volume $V_f$ should be multiplied by $(1-a/100)$. For example, the following formula may be used instead of formula (26).

$$\Sigma M_{ai}(i=1 \text{ to } N)/\rho_{ave}+M_w/\rho_w=V_f(1-a/100)$$

This enables more accurate measurement since actual total volume is used for the measurement with the air content excluded.

Furthermore, the following should be noted though it has not been particularly mentioned in this embodiment. If there is a possibility that the aggregates thrown into the measurement tank will emerge from the water and will not be submergence aggregate, a vibrator is lowered during or after throwing the fine aggregates A and B and operated in this condition. Thereby, the fine aggregates A and B thrown into the measurement tank can be leveled by vibration of the vibrator, so that the fine aggregates are submerged in the water. Before measuring a mass of the submergence aggregate, the vibrator is raised and put in a standby state, until a next measurement, in an upward location.

While the following has not been particularly mentioned in this embodiment, the percentage of surface moisture of the aggregates of the i-th kind (i=1 to N) can be calculated by measuring an amount of supplied water $M_I$ to the measurement tank and an amount of water $M_O$ discharged from the measurement tank as accumulation values.

Figure 49:
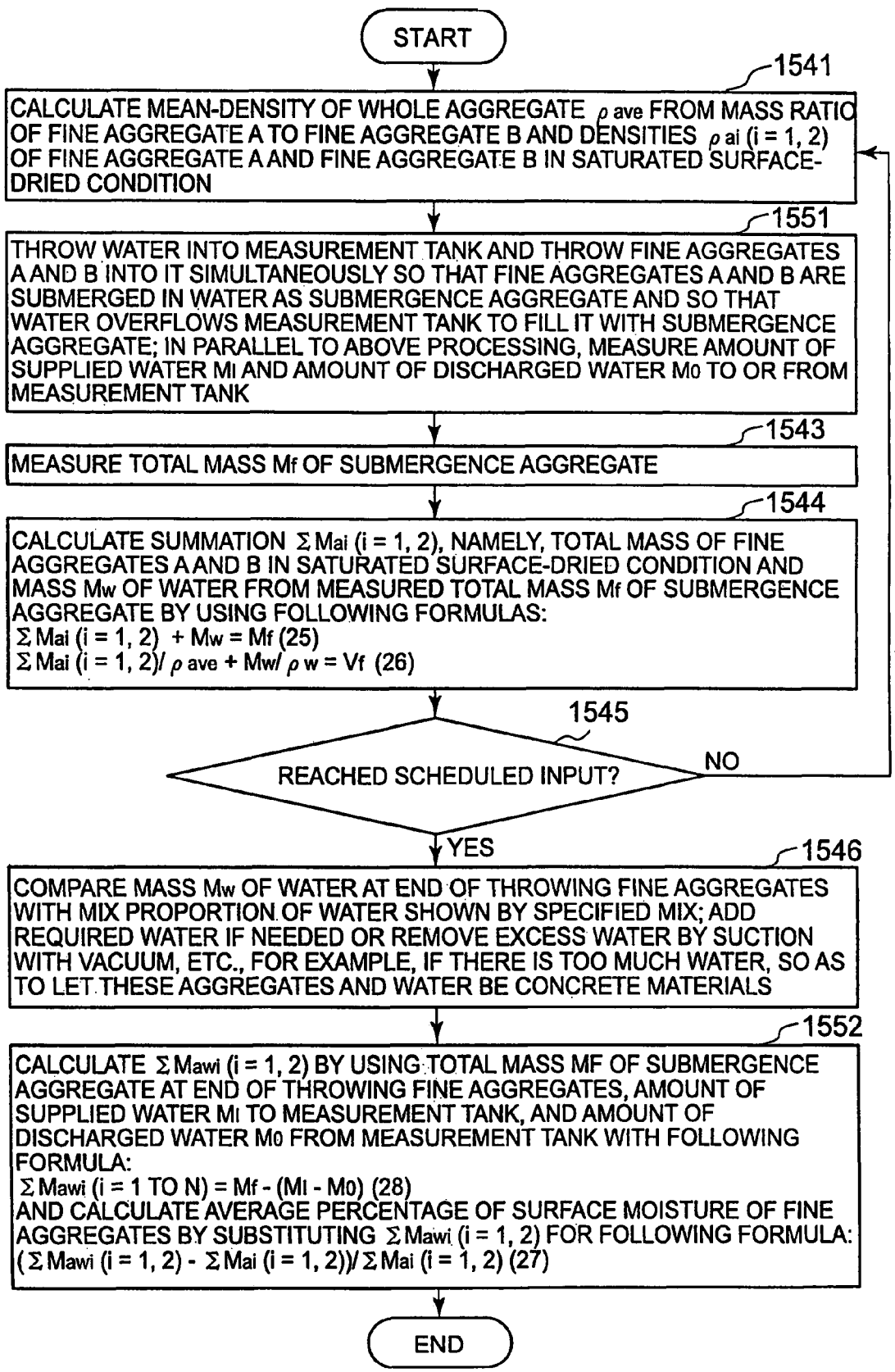
FIG. 49 is a flowchart of a preferable measuring method for concrete-forming materials according to a modification of the invention.

Referring to FIG. 49, there is shown a flowchart of a procedure for a measuring method according to this modification. The measuring method will be described by giving an example of using fine aggregate of two kinds A and B. In the same manner as for the above embodiment, a mean-density of the entire aggregate $\rho_{ave}$ is calculated from a mass ratio of the fine aggregate A to the fine aggregate B and the densities $\rho_{ai}$ (i=1, 2) of the fine aggregate A and the fine aggregate B in a saturated surface-dried condition (step 1541).

Subsequently, water is thrown into the measurement tank and the fine aggregates A and B are thrown into the measurement tank at the same time so that the fine aggregates A and B are submerged in the water as submergence aggregate and so that the water overflows the measurement tank to fill the measurement tank with the submergence aggregate. In parallel to the above processing, the amount of water $M_I$ supplied to the measurement tank and the amount of water $M_O$ discharged from the measurement tank are measured (step 1551).

Thereafter, total mass $M_f$ of the submergence aggregate is measured in the same manner as for the above embodiment (step 1543) and the summation $\Sigma M_{ai}$ (i=1, 2), that is, the total mass of the fine aggregates A and B in a saturated surface-dried condition and the mass $M_w$ of the water are calculated from the measured total mass $M_f$ of the submergence aggregate by using the formulas (25) and (26) (step 1544).

When measuring the fine aggregates A and B in the procedure mentioned above, the aggregates are thrown into the measurement tank at a predetermined speed continuously or intermittently while measuring the total mass $M_f$ of the submergence aggregate in real time or at predetermined time intervals repeatedly (steps 1551, 1543, and 1544) until the summation $\Sigma M_{ai}$ (i=1, 2) of the fine aggregates A and B in a saturated surface-dried condition reaches a scheduled input (step 1545, NO).

Thereafter, when the summation $\Sigma M_{ai}$ (i=1, 2) of the fine aggregates A and B in the saturated surface-dried condition reaches the scheduled input (step 1545, YES), throwing the fine aggregates A and B is terminated.

After measuring the fine aggregates of the scheduled input, the mass $M_w$ of the water at termination of throwing the fine aggregates is compared with a mix proportion of water shown by a specified mix. If the water is insufficient, required water is added. If there is too much water, excess water is sucked and removed with a vacuum or the like, for example. The aggregates and the water are then treated as concrete materials (step 1546).

On the other hand, $\Sigma M_{awi}$ (i=1, 2) is calculated by using the total mass $M_f$ of the submergence aggregate at termination of throwing the fine aggregates, the amount of water $M_I$ supplied to the measurement tank, and the amount of water $M_O$ discharged from the measurement tank with the following formula.

$$\Sigma M_{awi}(i=1,2)=M_f-(M_I-M_O) \tag{28}$$

Thereafter, an average percentage of surface moisture of the fine aggregates is calculated by substituting $\Sigma M_{awi}$ (i=1, 2) into the following formula (step 1552).

$$(\Sigma M_{awi}(i=1,2)-\Sigma M_{ai}(i=1,2)/M_{ai}(i=1,2) \tag{27}$$

According to this constitution, the calculated percentage of surface moisture can be used as a standard of water input for a subsequent measurement.

Thirteenth Embodiment

Figure 50:
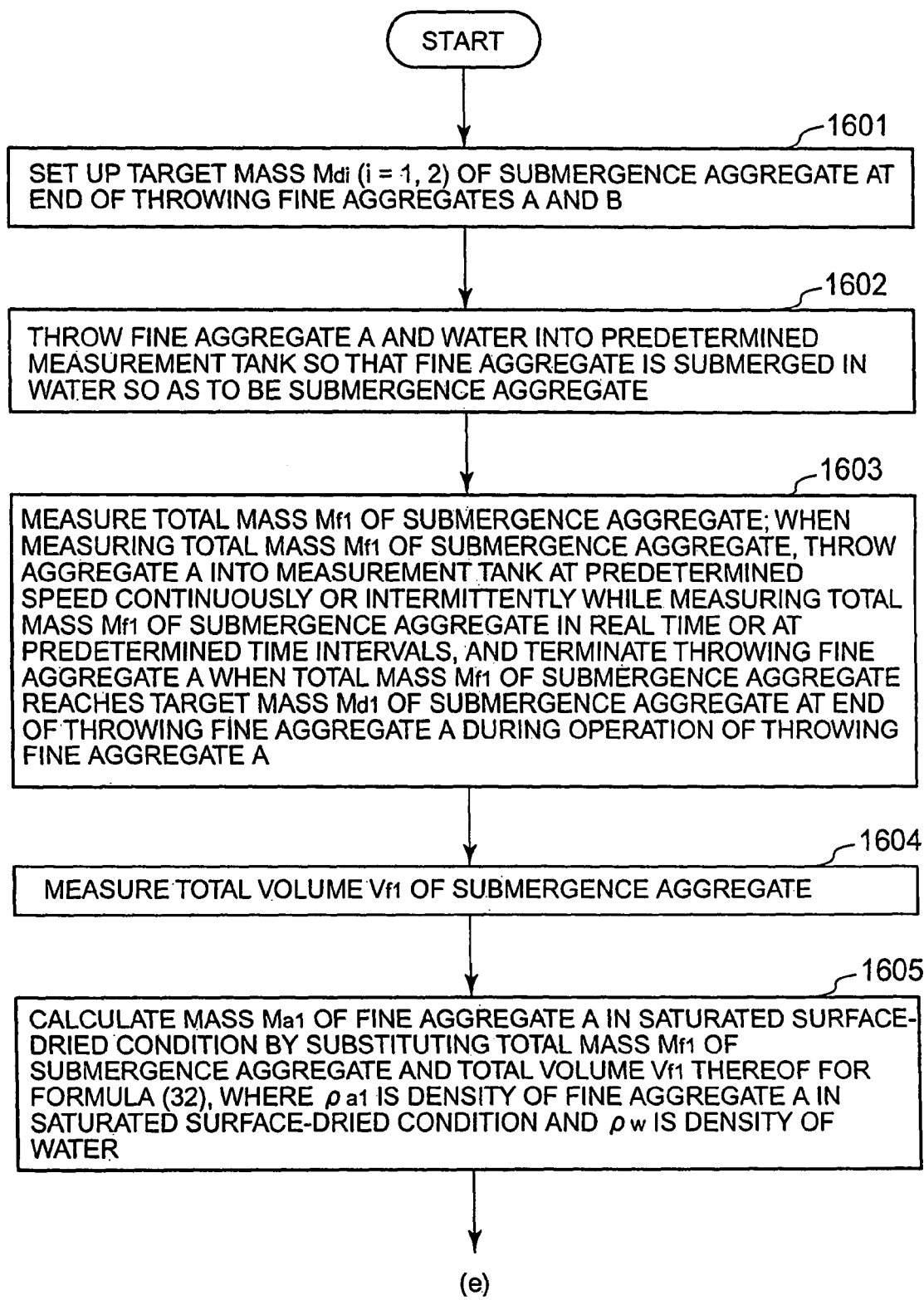
FIGS. 50 and 51 are a series of flowcharts of a preferable measuring method for concrete-forming materials according to the present invention.
Figure 51:
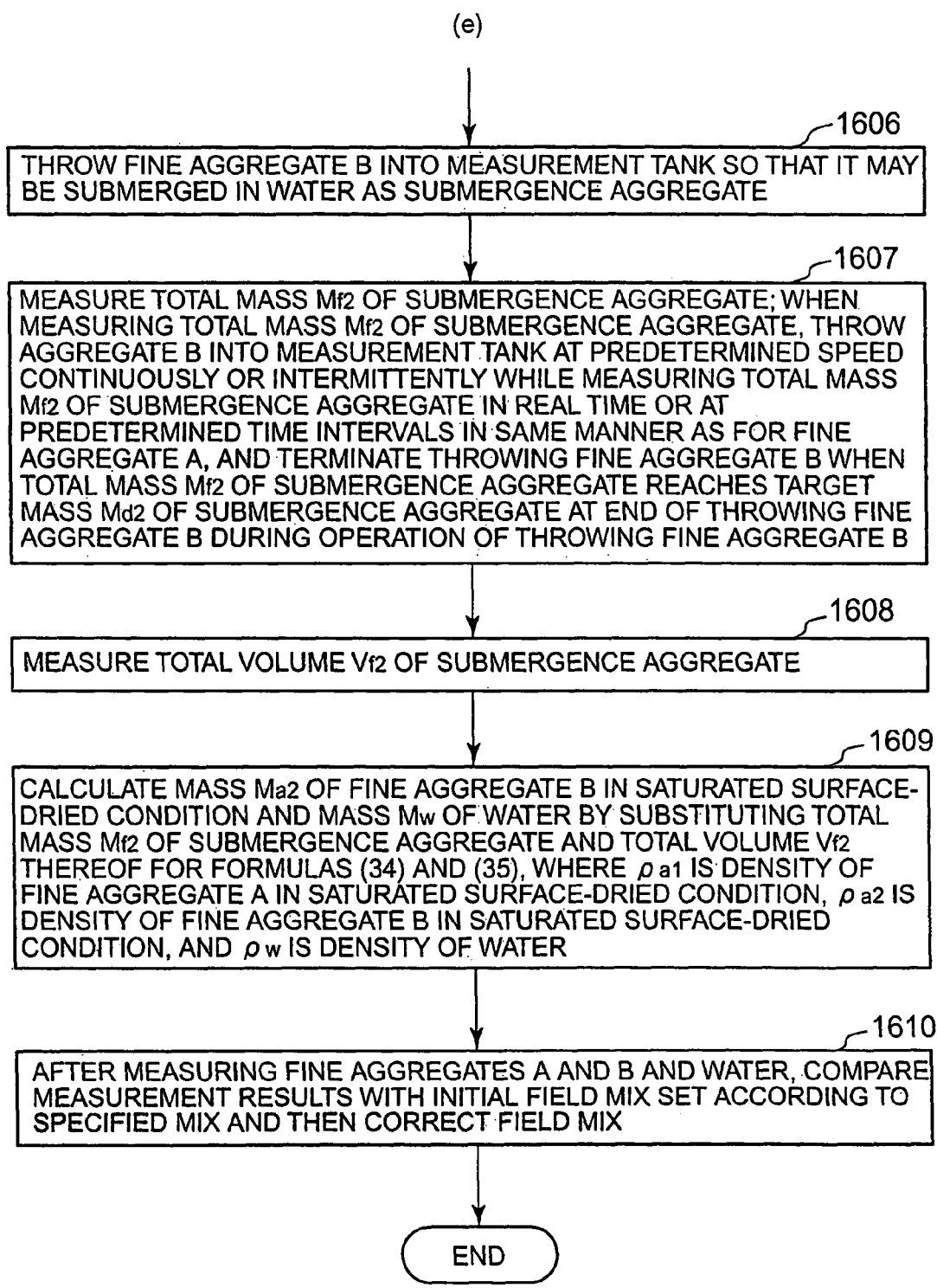

Referring to FIGS. 50 and 51, there is shown a flowchart of a procedure for a measuring method of concrete materials according to a thirteenth embodiment. The measuring method of concrete materials according to this embodiment can be implemented by selecting an appropriate one from the measuring apparatuses mentioned above.

As apparent from FIGS. 50 and 51, in the measuring method for concrete-forming materials according to this embodiment, there is set up a target mass $M_{di}$ (i=1, 2) of submergence aggregate at an end of throwing fine aggregates A and B, first (step 1601).

During setup of the target mass $M_{di}$ (i=1, 2) filling factor F of the submergence aggregate, which is a volume ratio of fine aggregate in the total volume of water and fine aggregate, is set up first. Then, a mixing volume $N_0$ of one batch is set up. A volume of the fine aggregate is set up on the basis of the filling factor F of the submergence aggregate and the mixing volume $N_0$ of one batch. Subsequently, a target input mass of the fine aggregates A and B in a saturated surface-dried condition is determined from a mixture ratio of the fine aggregates A and B and densities thereof in the saturated surface-dried condition. Then, a mass of water thrown first (primary measurement water) and the fine aggregate A thrown into the water may be considered to be target mass $M_{d1}$ of the submergence aggregate, and a mass of the submergence aggregate and the fine aggregate B thrown into the submergence aggregate may be considered to be target mass $M_{d2}$ of the submergence aggregate. When the target mass $M_{di}$ (i=1, 2) of the submergence aggregate is determined, a correction after measurement can be reduced by setting a most appropriate percentage of surface moisture and including it in the primary measurement water.

Subsequently, the fine aggregate A and the water are thrown into a predetermined measurement tank so that the fine aggregate is submerged in the water so as to be submergence aggregate (step 1602). When throwing the fine aggregate and the water into the measurement tank, preferably the water is thrown earlier and the fine aggregate is thrown later to prevent the submergence aggregate from being mixed with air bubbles. In addition, if the fine aggregate is not directly thrown into the measurement tank, but it is conveyed to the measurement tank by using a vibrating feeder having an electromagnetic vibrator, for example, it becomes possible to prevent granulation of the fine aggregate, and thus prevent air bubble mixing.

The measurement tank may be formed, for example, in a shape of a hollow truncated cone so that a bore of the measurement tank gets larger as it goes below. With this, when the measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

Subsequently, the total mass $M_{f1}$ of the submergence aggregate is measured (step 1603). The total mass $M_{f1}$ of the submergence aggregate can be measured by subtracting a measurement value of an empty measurement tank from the mass of the measurement tank filled with the submergence aggregate. This mass measurement can be performed with tension-type load cells, for example.

When measuring total mass $M_{f1}$ of the submergence aggregate, the aggregate A is thrown into the measurement tank at a predetermined speed continuously or intermittently while measuring the total mass $M_{f1}$ of the submergence aggregate in real time or at predetermined time intervals. Thereafter, when the total mass $M_{f1}$ of the submergence aggregate reaches the target mass $M_{d1}$ of the submergence aggregate at an end of throwing the fine aggregate A, during throwing the fine aggregate A, throwing the fine aggregate A is terminated.

Subsequently, total volume $V_{f1}$ of the submergence aggregate is measured (step 1604). The total volume $V_{f1}$ of the submergence aggregate can be measured with, for example, means for measuring a water level of the submergence aggregate, more specifically, an electrode-type displacement sensor.

Then, mass $M_{a1}$ of the fine aggregate A in a saturated surface-dried condition is calculated by substituting the total mass $M_{f1}$ of the submergence aggregate and the total volume $V_{f1}$ thereof into the following formula (step 1605).

$$M_{a1}=\rho_{a1}(M_{f1}-\rho_w V_{f1})/(\rho_{a1}-\rho_w) \tag{32}$$

where $\rho_{a1}$ is the density of the fine aggregate A in the saturated surface-dried condition and $\rho_w$ is the density of the water.

Subsequently, in the same manner as for the fine aggregate A, the fine aggregate B is thrown into the measurement tank so that it is submerged in the water so as to be submergence aggregate (step 1606). Then, the total mass $M_{f2}$ of the submergence aggregate is measured (step 1607). When measuring the total mass $M_{f2}$ of the submergence aggregate, the aggregate B is thrown into the measurement tank at a predetermined speed continuously or intermittently while measuring the total mass $M_{f2}$ of the submergence aggregate in real time or at predetermined time intervals in the same manner as for the fine aggregate A. Thereafter, when the total mass $M_{f2}$ of the submergence aggregate reaches the target mass $M_{d2}$ of the submergence aggregate at an end of throwing the fine aggregate B during throwing the fine aggregate B, throwing the fine aggregate B is terminated.

Subsequently, total volume $V_{f2}$ of the submergence aggregate is measured (step 1608). The total volume $V_{f2}$ of the submergence aggregate can be measured with, for example, means for measuring a water level of the submergence aggregate, more specifically, an electrode-type displacement sensor.

The electrode-type displacement sensor is configured so as to measure a water level of the submergence aggregate by monitoring a change in an energized condition when a lower end of typically, for example, a detection electrode contacts a water surface of the submergence aggregate.

Then, mass $M_{a2}$ of the fine aggregate B in a saturated surface-dried condition and mass $M_w$ of the water are calculated by substituting the total mass $M_{f2}$ of the submergence aggregate and the total volume $V_{f2}$ thereof into the following formulas (step 1609).

$$M_{a2}=\rho_{a2}((M_{f2}-\Sigma M_{ai}(i=1,2))-\rho_w(V_{f2}-\Sigma(M_{ai}/\rho_{ai})(i=1,2)))/(\rho_{a2}-\rho_w) \tag{34}$$

$$M_w=\rho_w(\rho_{a2}(V_{f2}-\Sigma(M_{ai}/\rho_{ai})(i=1,2))-(M_{f2}-\Sigma M_{ai}(i=1,2)))/(\rho_{a2}-\rho_w) \tag{35}$$

where $\rho_{a1}$ is the density of the fine aggregate A in the saturated surface-dried condition, $\rho_{a2}$ is the density of the fine aggregate B in the saturated surface-dried condition, and $\rho_w$ is the density of the water.

After measuring the fine aggregates A and B and the water as mentioned above, measurement results are compared with an initial field mix set according to a specified mix and then the field mix is corrected (step 1610).

In other words, the measured mass of the aggregate is compared with the mass of aggregate of an initially set field mix. Calculation is then made on a ratio of the measured total mass of the fine aggregates A and B in the saturated surface-dried condition to the preset total mass of the fine aggregates A and B in the saturated surface-dried condition. If it is 0.9, for example, the measured mass of the fine aggregates A and B is 10% less, and therefore, there is a need for decreasing the mixing volume $N_0$ of one batch by 10% so as to be $0.9N_0$. Accordingly, also regarding other concrete-forming materials such as cement and admixture, the initial field mix is corrected by using a corresponding ratio for measurement. Furthermore, regarding the water, an initially set amount of water is compared with a measured amount of water. Then, required water is added as secondary water or excess water is discharged. Thereafter, the concrete-forming materials are thrown into a kneading mixer for mixing.

As set forth hereinabove, according to the measuring method for concrete-forming materials of this embodiment, the surface water of the fine aggregates A and B can be indirectly calculated as a part of the mass $M_w$ of the water, even if a fine aggregate whose moisture state is not uniform is used, and the mass of the fine aggregate can be calculated as the mass $M_{ai}$ (i=1, 2) of the aggregates A and B in the saturated surface-dried condition. In other words, since the mass of the fine aggregates and the mass of the water are calculated on conditions equivalent to the specified mix, even if a humidity grade of the fine aggregate is not fixed at every measurement, it becomes possible to make concrete as shown by the specified mix.

Furthermore, the fine aggregates A and B are thrown into the measurement tank at a predetermined speed continuously or intermittently while measuring the total mass $M_{fi}$ (i=1, 2) of the submergence aggregate in real time or at predetermined time intervals, and throwing the fine aggregates is terminated when the total masses $M_{f1}$ and $M_{f2}$ of the submergence aggregate reaches the target masses $M_{d1}$ and $M_{d2}$, respectively, during throwing the fine aggregates A and B into the measurement tank. Thereby, it becomes possible to manage inputs of the fine aggregates A and B accurately and to correct the field mix, which results in making concrete as shown by the specified mix.

Furthermore, even if the plurality of fine aggregates differ from each other in density, grading, or the like, they can be measured in a single measurement tank efficiently and very accurately while calculating an effect of surface water caused by a difference in a moisture state as a part of the final amount of water.

The following should be noted though it has not been particularly mentioned in this embodiment. Mass $M_I$ of water supplied to the measurement tank and mass $M_O$ of water discharged from the measurement tank are measured as accumulation values. $\Sigma M_{awj}$ (j=1 to i) is calculated by substituting the mass $M_I$ of water supplied to the measurement tank, the mass $M_O$ of water discharged from the measurement tank, and the total mass $M_{fi}$ (i=1, 2) of the submergence aggregate into the following formula.

$$\Sigma M_{awj}(j=1 \text{ to } i)=M_{fi}-(M_I-M_O) \tag{14}$$

Thereafter, the following formula is calculated.

$$\Sigma M_{awj}(j=1 \text{ to } i)-\Sigma M_{awj}(j=1 \text{ to } (i-1)) \tag{15}$$

$M_{awi}$ is then substituted into the following formula.

$$(M_{awi}-M_{ai})/M_{ai} \tag{13}$$

Thereby, percentages of surface moisture of the fine aggregates A and B can be calculated and they can be used as setting values for a subsequent measurement.

Furthermore, the following should be noted though it has not been particularly mentioned in this embodiment. If $V_{fi}$ (i=1, 2)·(1−a/100) is used instead of $V_{fi}$ (i=1, 2) assuming that a (%) is air content of the submergence aggregate, more accurate measurement is achieved with the air content considered.

Still further, the following should be noted though it has not been particularly mentioned in this embodiment. If there is a possibility that the aggregates thrown into the measurement tank will emerge from the water and will not be submergence aggregate, a vibrator is lowered during or after throwing the fine aggregates A and B and operated in this condition. Thereby, the fine aggregates A and B thrown into the measurement tank can be leveled by vibration of the vibrator, so that the fine aggregates are submerged in the water. Before measuring a mass of the submergence aggregate, the vibrator is raised and put in a standby state, until a next measurement, in an upward location.

Fourteenth Embodiment

Figure 52:
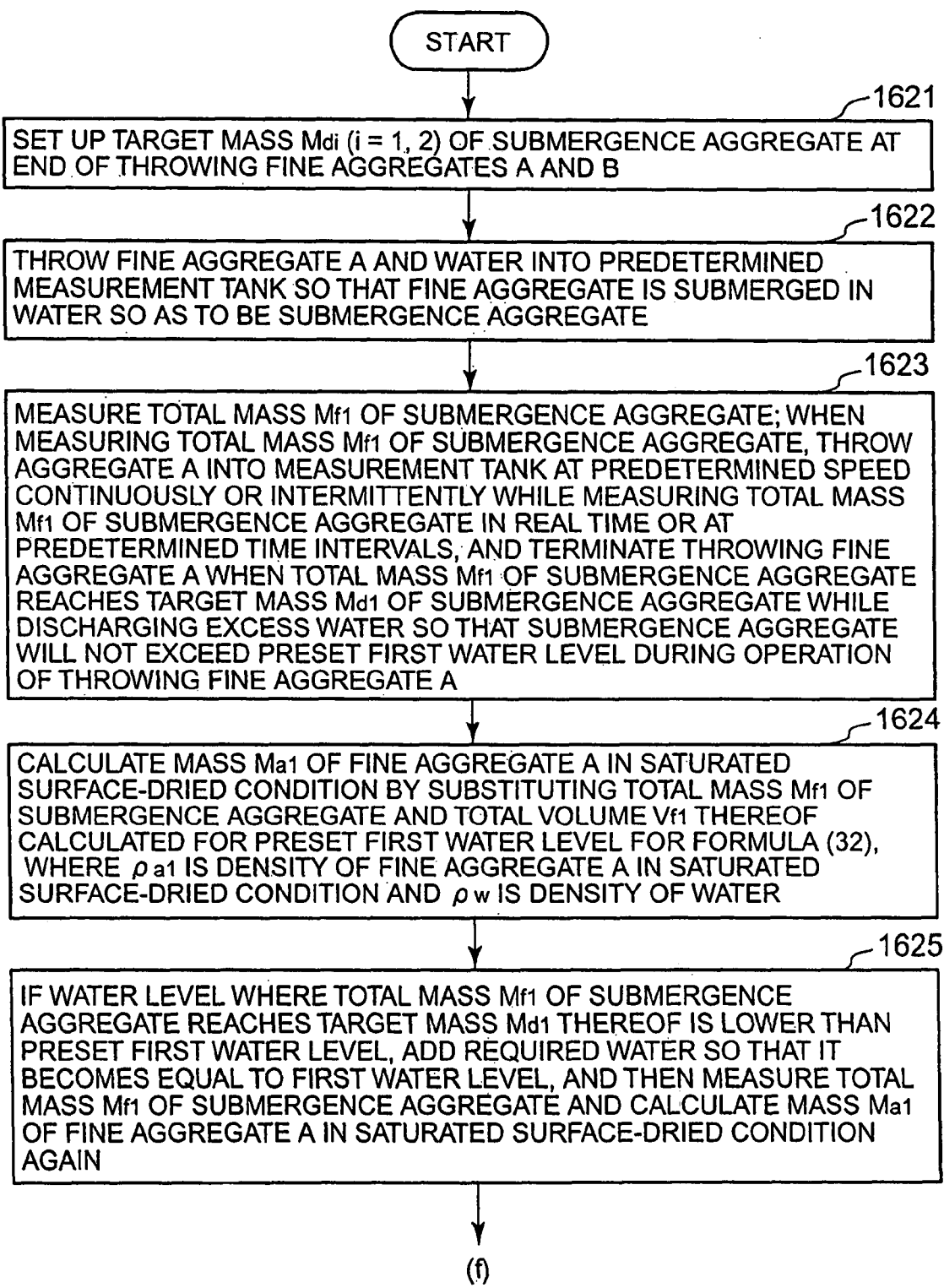
FIGS. 52 and 53 are a series of flowcharts of another preferable measuring method for concrete-forming materials according to the present invention.
Figure 53:
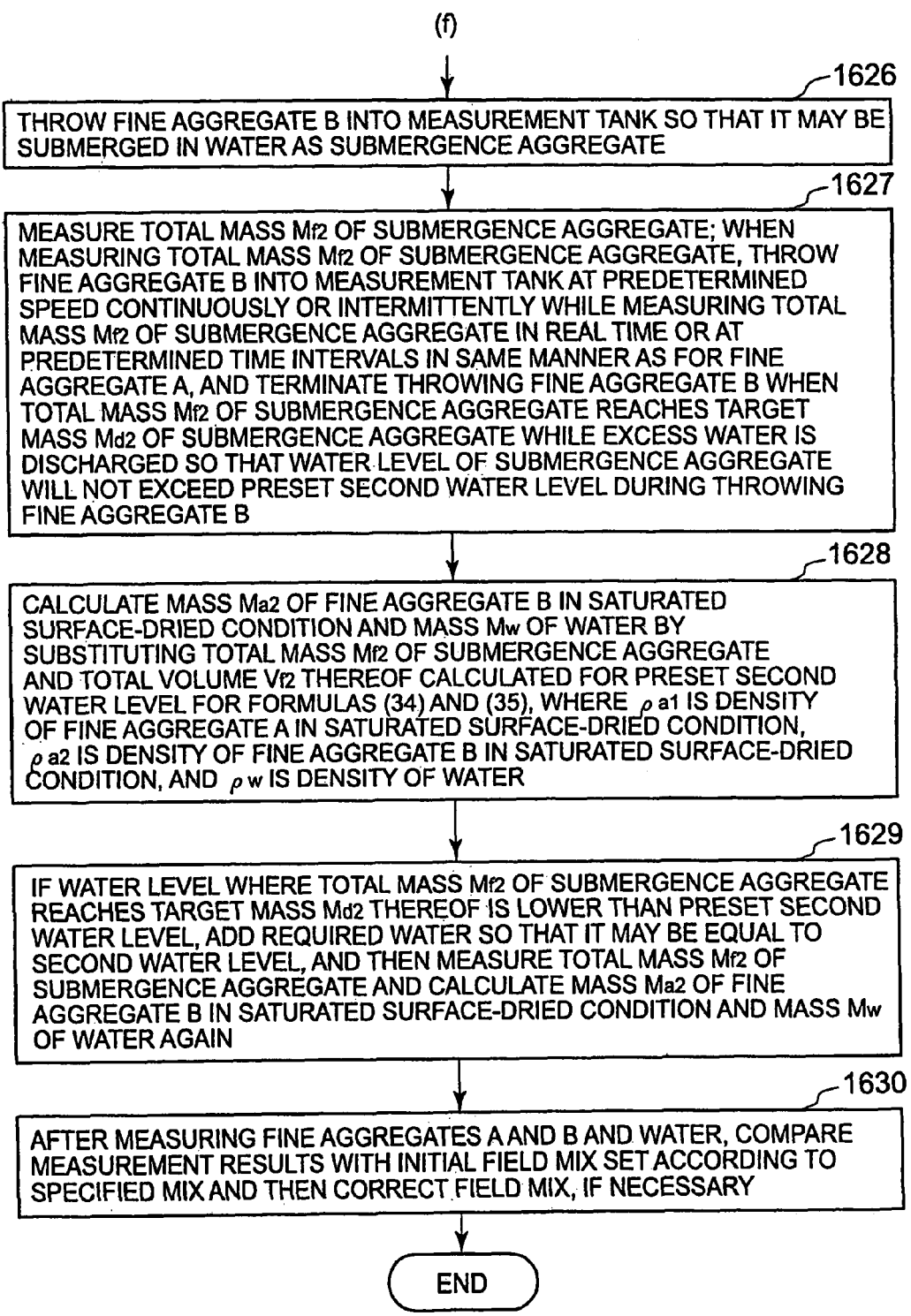

Referring to FIGS. 52 and 53, there is shown a flowchart of a procedure for a measuring method for concrete-forming materials according to a fourteenth embodiment. The measuring method for concrete-forming materials according to this embodiment can be implemented by selecting an appropriate one from the measuring apparatuses mentioned above.

As apparent from FIGS. 52 and 53, in the measuring method for concrete-forming materials according to this embodiment, there is set up a target mass $M_{di}$ (i=1, 2) of submergence aggregate at an end of throwing fine aggregates A and B, first (step 1621).

During setup of the target mass $M_{di}$ (i=1, 2) filling factor F of the submergence aggregate, which is a volume ratio of fine aggregate in the total volume of water and fine aggregate, is set up first. Then, a mixing volume $N_0$ of one batch is set up. A volume of the fine aggregate is set up on the basis of the filling factor F of the submergence aggregate and the mixing volume $N_0$ of one batch. Subsequently, a target input mass of the fine aggregates A and B in a saturated surface-dried condition is determined from a mixture ratio of the fine aggregates A and B and densities thereof in the saturated surface-dried condition. Then, a mass of water thrown first (primary measurement water) and the fine aggregate A thrown into the water may be considered to be target mass $M_{d1}$ of the submergence aggregate, and a mass of the submergence aggregate and the fine aggregate B thrown into the submergence aggregate may be considered to be target mass $M_{d2}$ of the submergence aggregate. When the target mass $M_{di}$ (i=1, 2) of the submergence aggregate is determined, a correction after measurement can be reduced by setting a most appropriate percentage of surface moisture and including it in the primary measurement water.

Subsequently, the fine aggregate A and the water are thrown into a predetermined measurement tank so that the fine aggregate is submerged in the water so as to be submergence aggregate (step 1622). When throwing the fine aggregate and the water into the measurement tank, preferably the water is thrown earlier and the fine aggregate is thrown later to prevent the submergence aggregate from being mixed with air bubbles. In addition, if the fine aggregate is not directly thrown into the measurement tank, but it is conveyed to the measurement tank by using a vibrating feeder having an electromagnetic vibrator, for example, it becomes possible to prevent granulation of the fine aggregate, and thus prevent air bubble mixing.

The measurement tank may be formed, for example, in a shape of a hollow truncated cone so that a bore of the measurement tank becomes larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

Subsequently, the total mass $M_{f1}$ of the submergence aggregate is measured (step 1623). The total mass $M_{f1}$ of the submergence aggregate can be measured by subtracting a measurement value of an empty measurement tank from the mass of the measurement tank filled with the submergence aggregate. This mass measurement can be performed with tension-type load cells, for example.

When measuring total mass $M_{f1}$ of the submergence aggregate, the aggregate A is thrown into the measurement tank at a predetermined speed continuously or intermittently while measuring the total mass $M_{f1}$ of the submergence aggregate in real time or at predetermined time intervals. Thereafter, when the total mass $M_{f1}$ of the submergence aggregate reaches the target mass $M_{d1}$ of the submergence aggregate while excess water is discharged so that the water level of the submergence aggregate does not exceed a preset first water level during throwing the fine aggregate A, throwing the fine aggregate A is terminated.

The first water level can be preset by causing the water in the submergence aggregate to overflow the measurement tank at a predetermined depth or by discharging the water with suction.

Subsequently, mass $M_{a1}$ of the fine aggregate A in the saturated surface-dried condition is calculated by substituting the total mass $M_{f1}$ of the submergence aggregate and the total volume $V_{f1}$ thereof calculated for the preset first water level into the following formula (step 1624).

$$M_{a1}=\rho_{a1}(M_{f1}-\rho_w V_{f1})/(\rho_{a1}-\rho_w) \tag{32}$$

where $\rho_{a1}$ is the density of the fine aggregate A in the saturated surface-dried condition and $\rho_w$ is the density of the water.

On the other hand, if the water level at which the total mass $M_{f1}$ of the submergence aggregate reaches the target mass $M_{d1}$ thereof is lower than the preset first water level, required water is added so that it is equal to the first water level. Then, the total mass $M_{f1}$ of the submergence aggregate is measured again and the mass $M_{a1}$ of the fine aggregate A in the saturated surface-dried condition is calculated again (step 1625).

Subsequently, in the same manner as for the fine aggregate A, the fine aggregate B is thrown into the measurement tank so that it is submerged in the water so as to be submergence aggregate (step 1626). Then, the total mass $M_{f2}$ of the submergence aggregate is measured (step 1627). When measuring the total mass $M_{f2}$ of the submergence aggregate, the fine aggregate B is thrown into the measurement tank at a predetermined speed continuously or intermittently while measuring the total mass $M_{f2}$ of the submergence aggregate in real time or at predetermined time intervals in the same manner as for the fine aggregate A. Thereafter, when the total mass $M_{f2}$ of the submergence aggregate reaches the target mass $M_{d2}$ of the submergence aggregate while excess water is discharged so that the water level of the submergence aggregate does not exceed a preset second water level during throwing the fine aggregate B, throwing the fine aggregate B is terminated.

The second water level can also be preset by causing the water in the submergence aggregate to overflow the measurement tank at a predetermined depth or by discharging the water with suction.

Subsequently, mass $M_{a2}$ of the fine aggregate B in a saturated surface-dried condition and mass $M_w$ of the water are calculated by substituting the total mass $M_{f2}$ of the submergence aggregate and the total volume $V_{f2}$ thereof calculated for the preset second water level into the following formulas (step 1628).

$$M_{a2}=\rho_{a2}((M_{f2}-\Sigma M_{ai}(i=1,2))-\rho_w(V_{f2}-\Sigma(M_{ai}/\rho_{ai})(i=1,2)))/(\rho_{a2}-\rho_w) \quad (34)$$

$$M_w=\rho_w(\rho_{a2}(V_{f2}-\Sigma(M_{ai}/\rho_{ai})(i=1,2))-(M_{f2}-\Sigma M_{ai}(i=1,2)))/(\rho_{a2}-\rho_w) \quad (35)$$

where $\rho_{a1}$ is the density of the fine aggregate A in the saturated surface-dried condition, $\rho_{a2}$ is the density of the fine aggregate B in the saturated surface-dried condition, and $\rho_w$ is the density of the water.

On the other hand, if the water level at which the total mass $M_{f2}$ of the submergence aggregate reaches the target mass $M_{d2}$ thereof is lower than the preset second water level, required water is added so that it becomes equal to the second water level. Then, the total mass $M_{f2}$ of the submergence aggregate is measured again and the mass $M_{a2}$ of the fine aggregate B in the saturated surface-dried condition and the mass $M_w$ of the water are calculated again (step 1629).

After measuring the fine aggregates A and B and the water as mentioned above, these measurement results are compared with an initial field mix set according to a specified mix and then the field mix is corrected, if necessary (step 1630).

In other words, excess water is discharged so that the water level of the submergence aggregate does not exceed the first and second water levels. If the total mass $M_{fi}$ (i=1, 2) of the submergence aggregate reaches the target mass $M_{d2}$ during discharging the water, the total mass $M_{fi}$ (i=1, 2) of the submergence aggregate and the total volume $V_{fi}$ (i=1, 2) of the submergence aggregate are equal to initial setting values. Therefore, the field mix need not be corrected and the submergence aggregate is thrown into the kneading mixer together with other concrete-forming materials for mixing.

On the other hand, unless the water level of the submergence aggregate reaches the first or second water level, required water is added so that the water level reaches the first or second water level. Therefore, the total mass $M_{fi}$ (i=1, 2) of the submergence aggregate measured again, and thus the masses of the fine aggregates A and B in the saturated surface-dried condition derived from the total mass result in values different from the initial setting values.

Therefore, if so, in the same manner as for the above embodiment, the measured masses of the aggregates A and B are compared with the masses of the aggregates A and B of the initially set field mix. Calculation is then made on a ratio of the measured total mass of the fine aggregates A and B in the saturated surface-dried condition to a preset total mass of the fine aggregates A and B in the saturated surface-dried condition. If it is 0.9, for example, the measured mass of the fine aggregates A and B is 10% less, and therefore, there is a need for decreasing the mixing volume $N_0$ of one batch by 10% so as to be $0.9N_0$. Accordingly, also regarding other concrete-forming materials such as cement and admixture, the initial field mix is corrected by using a corresponding ratio for measurement. Furthermore, regarding the water, an initially set amount of water is compared with a measured amount of water. Then, required water is added as secondary water or excess water is discharged. Thereafter, the concrete-forming materials are thrown into the kneading mixer for mixing.

As set forth hereinabove, according to the measuring method for concrete-forming materials of this embodiment, the surface water of the fine aggregates A and B can be indirectly calculated as a part of the mass $M_w$ of the water, even if a fine aggregate whose moisture state is not uniform is used, and the mass of the aggregate can be calculated as the mass $M_{ai}$ (i=1 to N) of the aggregate in the saturated surface-dried condition. In other words, since the mass of the aggregate and the mass of the water are calculated on conditions equivalent to the specified mix, even if a humidity grade of the aggregate is not fixed at every measurement, it becomes possible to make concrete as shown by the specified mix.

Furthermore, according to the measuring method for concrete-forming materials of this embodiment, if the total mass $M_{fi}$ (i=1, 2) of the submergence aggregate reaches the target mass $M_{d2}$ thereof while discharging excess water so that the water level of the submergence aggregate does not exceed the first and second water levels, not only the total volume $V_{fi}$ (i=1, 2) of the submergence aggregate need not be measured, but also the total mass $M_{fi}$ (i=1, 2) of the submergence aggregate and the total volume $V_{fi}$ (i=1, 2) thereof become equal to initial setting values. Therefore, the field mix need not be corrected and the submergence aggregate can be thrown into the kneading mixer together with other concrete-forming materials for mixing.

Still further, according to the measuring method for concrete-forming materials of this embodiment, if the water level of the submergence aggregate does not reach the preset first or second water level, required water need be added so that it reaches the first or second water level, but the total volume $V_{fi}$ (i=1, 2) of the submergence aggregate need not be measured in the same manner as for the above. By measuring the total mass $M_{fi}$ (i=1, 2) of the submergence aggregate again, it becomes possible to manage inputs of the fine aggregates A and B accurately and to correct the field mix, which results in making concrete as shown by the specified mix.

Furthermore, even if the plurality of fine aggregates differ from each other in density, grading, or the like, they can be measured in a single measurement tank efficiently and very accurately while calculating an effect of surface water caused by a difference in a moisture state as a part of the final amount of water.

The following should be noted though it has not been particularly mentioned in this embodiment. Mass $M_I$ of water supplied to the measurement tank and mass $M_O$ of water discharged from the measurement tank are measured as accumulation values. $\Sigma M_{awj}$ (j=1 to i) is calculated by substituting the mass $M_I$ of water supplied to the measurement tank, the mass $M_O$ of water discharged from the measurement tank, and the total mass $M_{fi}$ (i=1, 2) of the submergence aggregate into the following formula.

$$\Sigma M_{awj}(j=1 \text{ to } i) = M_{fi} - (M_I - M_O) \quad (14)$$

Thereafter, the following formula is calculated.

$$\Sigma M_{awj}(j=1 \text{ to } i) - \Sigma M_{awj}(j=1 \text{ to } (i-1)) \quad (15)$$

$M_{awi}$ is then substituted into the following formula.

$$(M_{awi} - M_{ai})/M_{ai} \quad (13)$$

Thereby, percentages of surface moisture of the fine aggregates A and B can be calculated and they can be used as setting values for a subsequent measurement.

Furthermore, the following should be noted though it has not been particularly mentioned in this embodiment. If $V_{fi}$ (i=1, 2)·(1−a/100) is used instead of $V_{fi}$ (i=1, 2) assuming that a (%) is the air content of the submergence aggregate, more accurate measurement is achieved with the air content considered.

Still further, the following should be noted though it has not been particularly mentioned in this embodiment. If there is a possibility that the aggregates thrown into the measurement tank will emerge from the water and will not be submergence aggregate, a vibrator is lowered during or after throwing the fine aggregates A and B and operated in this condition. Thereby, the fine aggregates A and B thrown into the measurement tank can be leveled by vibration of the vibrator, so that the fine aggregates are submerged in the water. Before measuring a mass of the submergence aggregate, the vibrator is raised and put in a standby state, until a next measurement, in an upward location.

Fifteenth Embodiment

The following describes a program for an execution of measuring and calculating concrete-forming materials according to a fifteenth embodiment, and a computer-readable recording medium where the program is recorded.

Figure 54:
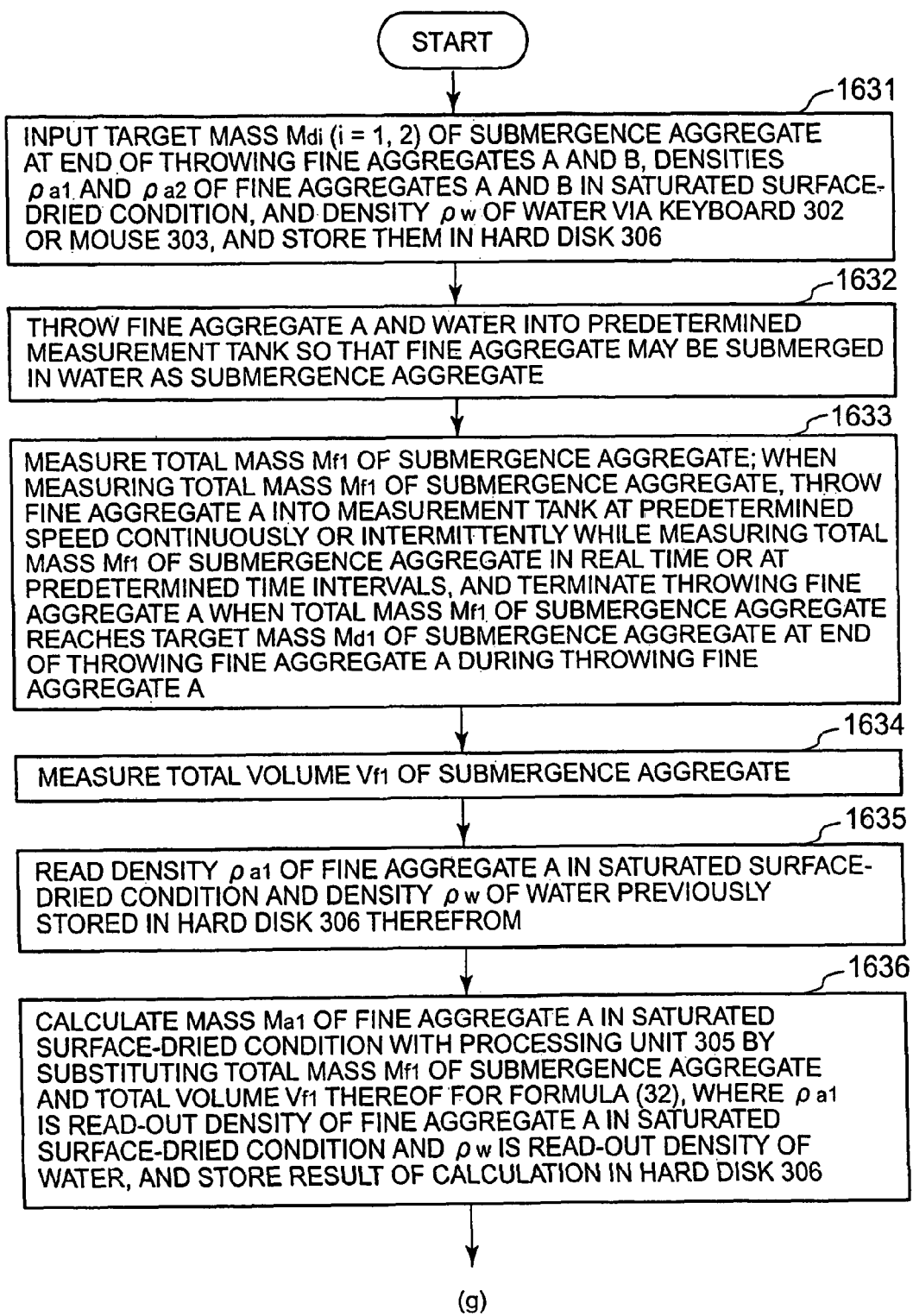
FIGS. 54 and 55 are a series of flowcharts of a processing procedure of a program for enabling concrete-forming materials to be measured and calculated according to the present invention.
Figure 55:
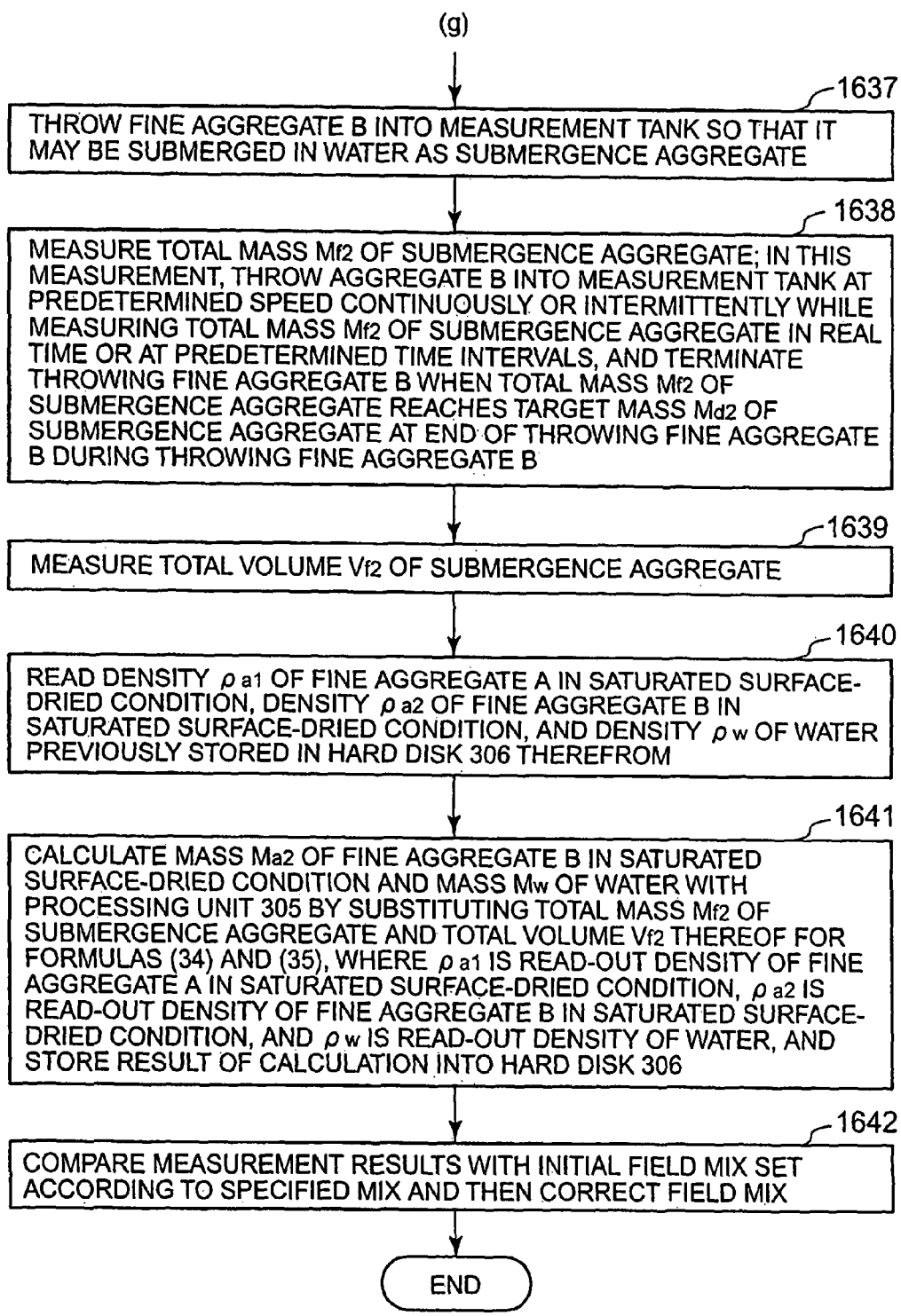
Figure 56:
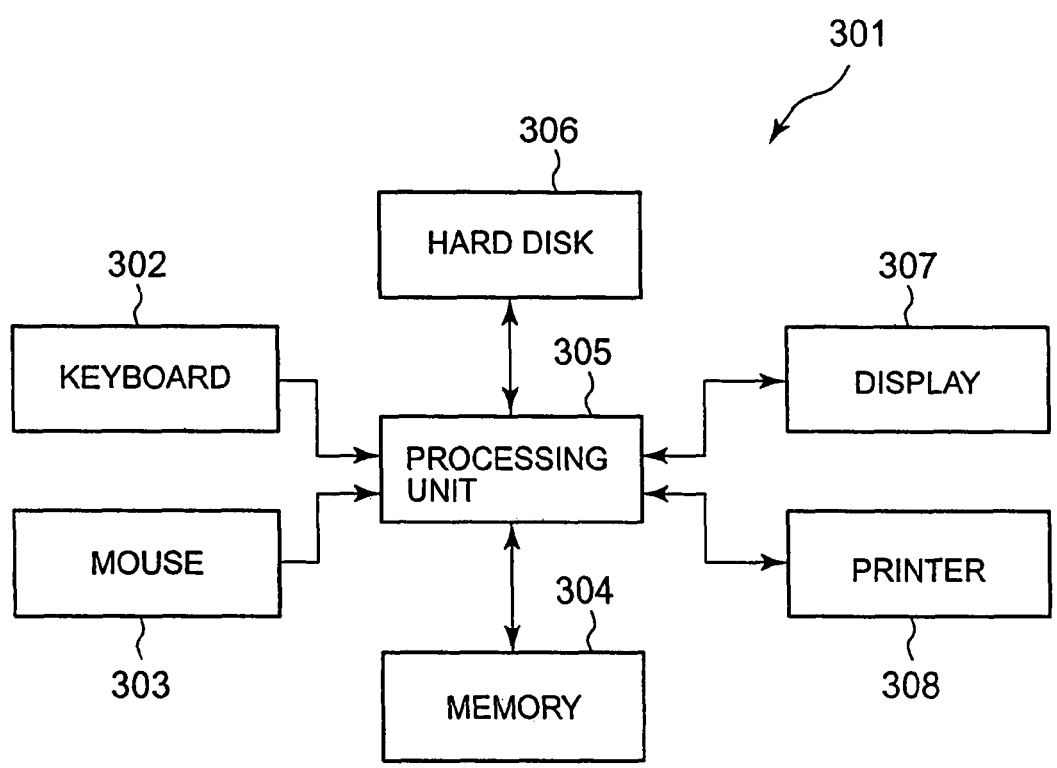
FIG. 56 is a block diagram showing a hardware configuration for executing the program mentioned above.

Referring to FIGS. 54 and 55, there is shown a flowchart of a processing procedure of the program for an execution of measuring and calculating concrete-forming materials according to this embodiment. Referring to FIG. 56, there is shown a block diagram of a hardware configuration for executing the program. As apparent from FIG. 56, a personal computer 301 for processing a program for an execution of measuring and calculating concrete-forming materials according to this embodiment comprises a keyboard 302 as input means, a mouse 303, a memory 304 incorporated in a body of the personal computer, a processing unit 305 for performing various kinds of arithmetic processing, a hard disk 306 as storage means for storing input data or a result of processing, a display 307 for displaying a setting input screen or a result of processing, and a printer 308 for printing setting values and a result of processing.

The program for an execution of measuring and calculating concrete-forming materials according to this embodiment may be previously recorded into a computer-readable recording medium such as, for example, the hard disk 306, a CD-ROM not shown, an MO disk, a CDR or the like, and may be loaded into the memory 304 in the personal computer 301 for executing the program.

In the program for an execution of measuring and calculating concrete materials according to this embodiment, an input operation is performed first via the keyboard 302 or the mouse 303 by entering target mass $M_{di}$ (i=1, 2) of submergence aggregate at an end of throwing fine aggregates A and B, densities $\rho_{a1}$ and $\rho_{a2}$ of the fine aggregates A and B in a saturated surface-dried condition, and density $\rho_w$ of water, and these values are stored in the hard disk 306 (step 1631).

During setup of the target mass $M_{di}$ (i=1, 2) filling factor F of the submergence aggregate, which is a volume ratio of fine aggregate in the total volume of water and fine aggregate, is set up first. Then, mixing volume $N_0$ of one batch is set up. A volume of the fine aggregate is set up on the basis of the filling factor F of the submergence aggregate and the mixing volume $N_0$ of one batch. Subsequently, a target input mass of the fine aggregates A and B in a saturated surface-dried condition is determined from a mixture ratio of the fine aggregates A and B and densities thereof in the saturated surface-dried condition. Then, a mass of water thrown first (primary measurement water) and the fine aggregate A thrown into the water may be considered to be target mass $M_{d1}$ of the submergence aggregate, and a mass of the submergence aggregate and the fine aggregate B thrown into the submergence aggregate may be considered to be target mass $M_{d2}$ of the submergence aggregate.

An input operation should be appropriately performed, if necessary, by entering a percentage of surface moisture of fine aggregate obtained by the previous measurement, presence or absence of compaction with vibration at measurement, physical-properties values of various materials, a mixing volume of one batch, a percentage of surface moisture of coarse aggregate, and other data related to a specified mix and a field mix. By entering the percentages of surface moisture obtained by the previous measurement as initial values as mentioned above, a correction can be reduced after measurement.

Subsequently, the fine aggregate A and the water are thrown into a predetermined measurement tank so that the fine aggregate is submerged in the water so as to be submergence aggregate (step 1632). When throwing the fine aggregate and the water into the measurement tank, preferably the water is thrown earlier and the fine aggregate is thrown later to prevent the submergence aggregate from being mixed with air bubbles. In addition, if the fine aggregate is not directly thrown into the measurement tank, but it is conveyed to the measurement tank by using a vibrating feeder having an electromagnetic vibrator, for example, it becomes possible to prevent granulation of the fine aggregate, and thus prevent air bubble mixing.

The measurement tank may be formed, for example, in a shape of a hollow truncated cone so that a bore of the measurement tank becomes larger in a downward direction. With this, when the measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

Subsequently, the total mass $M_{f1}$ of the submergence aggregate is measured (step 1633). The total mass $M_{f1}$ of the submergence aggregate can be measured by subtracting a measurement value of an empty measurement tank from the mass of the measurement tank filled with the submergence aggregate. This mass measurement can be performed with tension-type load cells, for example. The measured total mass $M_{f1}$ of the submergence aggregate is preferably written onto the hard disk 306, if necessary.

When measuring total mass $M_{f1}$ of the submergence aggregate, the fine aggregate A is thrown into the measurement tank at a predetermined speed continuously or intermittently while measuring the total mass $M_{f1}$ of the submergence aggregate in real time or at predetermined time intervals. Thereafter, when the total mass $M_{f1}$ of the submergence aggregate reaches the target mass $M_{d1}$ of the submergence aggregate at an end of throwing the fine aggregate A, during throwing the fine aggregate A, throwing the fine aggregate A is terminated.

Subsequently, the total volume $V_{f1}$ of the submergence aggregate is measured (step 1634). The total volume $V_{f1}$ of the submergence aggregate may be measured by using the electrode-type displacement sensor mentioned above. The measured total volume $V_{f1}$ of the submergence aggregate is preferably written onto the hard disk 306, if necessary.

Then, the density $\rho_{a1}$ of the fine aggregate A in the saturated surface-dried condition and the density $\rho_w$ of the water previously stored on the hard disk 306 are read from the hard disk (step 1635).

Subsequently, the processing unit 305 is operated to calculate the mass $M_{a1}$ of the fine aggregate A in the saturated surface-dried condition by substituting the total mass $M_{f1}$ of the submergence aggregate and the total volume $V_{f1}$ thereof into the following formula.

$$M_{a1}=\rho_{a1}(M_{f1}-\rho_w V_{f1})/(\rho_{a1}-\rho_w) \tag{32}$$

where $\rho_{a1}$ is a read-out density of the fine aggregate A in the saturated surface-dried condition and $\rho_w$ is a read-out density of the water. In addition, a result of this calculation is stored on the hard disk 306 (step 1636).

Subsequently, in the same manner as for the fine aggregate A, the fine aggregate B is thrown into the measurement tank so that it is submerged in the water so as to be submergence aggregate (step 1637). Then, the total mass $M_{f2}$ of the submergence aggregate is measured (step 1638). When measuring the total mass $M_{f2}$ of the submergence aggregate, the aggregate B is thrown into the measurement tank at a predetermined speed continuously or intermittently while measuring the total mass $M_{f2}$ of the submergence aggregate in real time or at predetermined time intervals in the same manner as for the fine aggregate A. Thereafter, when the total mass $M_{f2}$ of the submergence aggregate reaches the target mass $M_{d2}$ of the submergence aggregate at an end of throwing the fine aggregate B, during throwing the fine aggregate B, throwing the fine aggregate B is terminated. The measured total mass $M_{f2}$ of the submergence aggregate is preferably written onto the hard disk 306, if necessary.

Subsequently, total volume $V_{f2}$ of the submergence aggregate is measured (step 1639). The total volume $V_{f2}$ of the submergence aggregate can be measured with, for example, an electrode-type displacement sensor mentioned above.

Then, the density $\rho_{a1}$ of the fine aggregate A in the saturated surface-dried condition, the density $\rho_{a2}$ of the fine aggregate B in the saturated surface-dried condition, and the density $\rho_w$ of the water previously stored on the hard disk 306 are read from the hard disk (step 1640).

Then, mass $M_{a2}$ of the fine aggregate B in the saturated surface-dried condition and mass $M_w$ of the water are calculated with processing unit 305 by substituting the total mass $M_{f2}$ of the submergence aggregate and the total volume $V_{f2}$ thereof into the following formulas.

$$M_{a2}=\rho_{a2}((M_{f2}-\Sigma M_{ai}(i=1,2))-\rho_w(V_{f2}-\Sigma(M_{ai}/\rho_{ai})(i=1,2)))/(\rho_{a2}-\rho_w) \tag{34}$$

$$M_w=\rho_w(\rho_{a2}(V_{f2}-\Sigma(M_{ai}/\rho_{ai})(i=1,2))-(M_{f2}-\Sigma M_{ai}(i=1,2)))/(\rho_{a2}-\rho_w) \tag{35}$$

where $\rho_{a1}$ is a read-out density of the fine aggregate A in the saturated surface-dried condition, $\rho_{a2}$ is a read-out density of the fine aggregate B in the saturated surface-dried condition, and $\rho_w$ is a read-out density of the water. In addition, a result of this calculation is stored on the hard disk 306 (step 1641).

After measuring the fine aggregates A and B and the water as mentioned above, these measurement results are compared with an initial field mix set according to a specified mix, and then the field mix is corrected (step 1642).

In other words, the measured mass of the aggregate is compared with the mass of aggregate of an initially set field mix. Calculation is then made on a ratio of the measured total mass of the fine aggregates A and B in the saturated surface-dried condition to the preset total mass of the fine aggregates A and B in the saturated surface-dried condition. If it is 0.9, for example, the measured mass of the fine aggregates A and B is 10% less, and therefore, there is a need for decreasing the mixing volume $N_0$ of one batch by 10% so as to be $0.9N_0$. Accordingly, also regarding other concrete-forming materials such as cement and admixture, the initial field mix is corrected by using a corresponding ratio for measurement. Furthermore, regarding the water, an initially set amount of water is compared with a measured amount of water. Then, required water is added as secondary water or excess water is discharged. Thereafter, the concrete-forming materials are thrown into a kneading mixer for mixing.

As set forth hereinabove, according to the program for an execution of measuring and calculating concrete-forming materials of this embodiment, surface water of the fine aggregates A and B can be indirectly calculated as a part of the mass $M_w$ of the water, even if a fine aggregate whose moisture state is not uniform is used, and the mass of the fine aggregate can be calculated as the mass $M_{ai}$ (i=1, 2) of the aggregates A and B in the saturated surface-dried condition. In other words, since the mass of the fine aggregates and the mass of the water are calculated on conditions equivalent to the specified mix, even if a humidity grade of the fine aggregate is not fixed at every measurement, it becomes possible to make concrete as shown by the specified mix.

Furthermore, the fine aggregates A and B are thrown into the measurement tank at a predetermined speed continuously or intermittently while measuring the total mass $M_{fi}$ (i=1, 2) of the submergence aggregate in real time or at predetermined time intervals, and throwing the fine aggregates A and B are terminated when the total masses $M_{f1}$ and $M_{f2}$ of the submergence aggregate reach the target masses $M_{d1}$ and $M_{d2}$ thereof, respectively, during throwing the fine aggregates A and B into the measurement tank. Thereby, it becomes possible to manage inputs of the fine aggregates A and B accurately and to correct the field mix, which results in making concrete as shown by the specified mix.

Furthermore, even if the plurality of fine aggregates differ from each other in density, grading, or the like, they can be measured in a single measurement tank efficiently and very accurately while calculating an effect of surface water caused by a difference in a moisture state as a part of the final amount of water.

The following should be noted though it has not been particularly mentioned in this embodiment. Mass $M_I$ of water supplied to the measurement tank and mass $M_O$ of water discharged from the measurement tank are measured as accumulation values. In addition, a result of the calculation is stored on the hard disk 306. Then, $\Sigma M_{awj}$ (j=1 to i) is calculated with the processing unit 305 by reading the mass $M_I$ of water supplied to the measurement tank, the mass $M_O$ of water discharged from the measurement tank, and the total mass $M_{fi}$ (i=1, 2) of the submergence aggregate from the hard disk 306 and substituting them into the following formula.

$$\Sigma M_{awj}(j=1 \text{ to } i) = M_{fi} - (M_I - M_O) \qquad (14)$$

In addition, a result of this calculation is stored on the hard disk 306. Thereafter, the following formula is calculated to obtain $M_{awi}$.

$$\Sigma M_{awj}(j=1 \text{ to } i) - \Sigma M_{awj}(j=1 \text{ to } (i-1)) \qquad (15)$$

$M_{awi}$ is then substituted into the following formula to obtain percentages of surface moisture of the fine aggregates A and B with the processing unit 305.

$$(M_{awi} - M_{ai})/M_{ai} \qquad (13)$$

Thereby, the percentages of surface moisture can be calculated.

Furthermore, the following should be noted though it has not been particularly mentioned in this embodiment. If $V_{fi}$ (i=1, 2)·(1−a/100) is used instead of $V_{fi}$ (i=1, 2) assuming that a (%) is air content of the submergence aggregate, more accurate measurement is achieved with the air content considered.

Sixteenth Embodiment

The following describes a program for an execution of measuring and calculating concrete-forming materials according to a sixteenth embodiment, and a computer-readable recording medium where the program is recorded.

Figure 57:
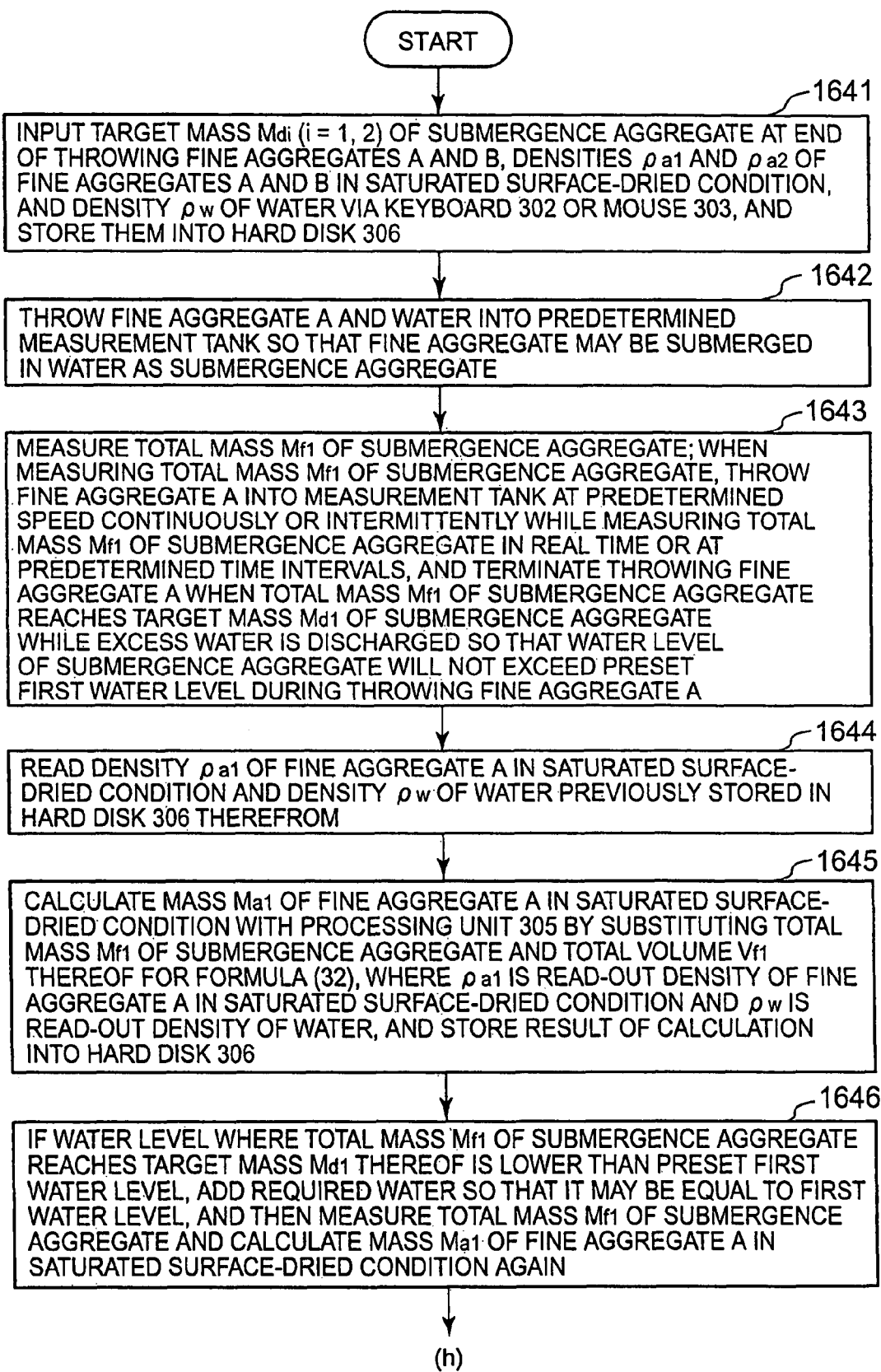
FIGS. 57 and 58 are a series of flowcharts of a processing procedure of another program for enabling concrete-forming materials to be measured and calculated according to the present invention.
Figure 58:
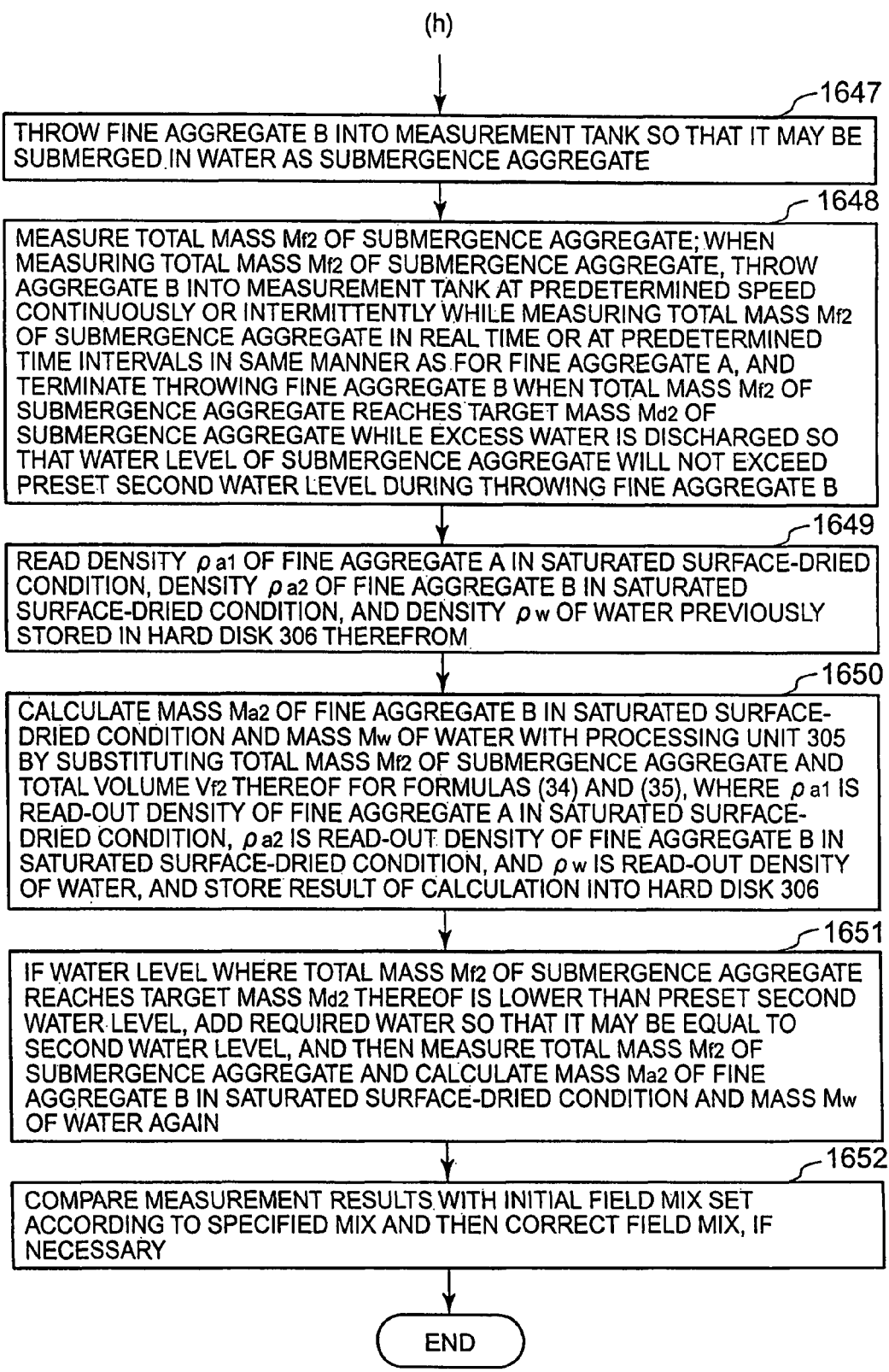

Referring to FIGS. 57 and 58, there is shown a flowchart of a processing procedure of the program for an execution of measuring and calculating concrete-forming materials according to this embodiment. It is assumed that the personal computer 301 described in the fifteenth embodiment is used for executing the program according to this embodiment and its description is omitted here.

The program for an execution of measuring and calculating concrete-forming materials according to this embodiment may be previously recorded onto a computer-readable recording medium such as, for example, a hard disk 306, a CD-ROM not shown, an MO disk, a CDR or the like and may be loaded into a memory 304 in the personal computer 301 for executing the program.

In the program for an execution of measuring and calculating concrete-forming materials according to this embodiment, an input operation is performed first via a keyboard 302 or a mouse 303 by entering target mass $M_{di}$ (i=1, 2) of submergence aggregate at an end of throwing fine aggregates A and B, densities $\rho_{a1}$ and $\rho_{a2}$ of the fine aggregates A and B in a saturated surface-dried condition, and density $\rho_w$ of water, and these values are stored on the hard disk 306 (step 1641).

During setup of the target mass $M_{di}$ (i=1, 2) filling factor F of the submergence aggregate, which is a volume ratio of fine aggregate in the total volume of water and fine aggregate, is set up first. Then, mixing volume $N_0$ of one batch is set up. A volume of the fine aggregate is set up on the basis of the filling factor F of the submergence aggregate and the mixing volume $N_0$ of one batch. Subsequently, a target input mass of the fine aggregates A and B in the saturated surface-dried condition is determined from a mixture ratio of the fine aggregates A and B and densities thereof in the saturated surface-dried condition. Then, a mass of water thrown first (primary measurement water) and the fine aggregate A thrown into the water may be considered to be target mass $M_{d1}$ of the submergence aggregate and a mass of the submergence aggregate and the fine aggregate B thrown into the submergence aggregate may be considered to be target mass $M_{d2}$ of the submergence aggregate.

An input operation should be appropriately performed, if necessary, by entering a percentage of surface moisture of fine aggregate obtained by the previous measurement, presence or absence of compaction with vibration at measurement, physical-properties values of various materials, a mixing volume of one batch, a percentage of surface moisture of coarse aggregate, and other data related to a specified mix and a field mix. By entering the percentages of surface moisture obtained by the previous measurement as initial values as mentioned above, a correction can be reduced after measurement.

Subsequently, the fine aggregate A and the water are thrown into a predetermined measurement tank so that the fine aggregate is submerged in the water so as to be submergence aggregate (step 1642). When throwing the fine aggregate and the water into the measurement tank, preferably the water is thrown earlier and the fine aggregate is thrown later to prevent the submergence aggregate from being mixed with air bubbles. In addition, if the fine aggregate is not directly thrown into the measurement tank, but it is conveyed to the measurement tank by using a vibrating feeder having an electromagnetic vibrator, for example, it becomes possible to prevent granulation of the fine aggregate, and thus prevent air bubble mixing.

The measurement tank may be formed, for example, in a shape of a hollow truncated cone so that a bore of the measurement tank becomes larger in a downward direction. With this, when a measurement is finished, a free fall of the submergence aggregate in the measurement tank can be achieved only by opening a bottom lid without a blockage of submergence aggregate in the measurement tank even if no vibrating instrument such as a vibrator is used. Thereafter, the submergence aggregate can be thrown into a kneading mixer together with cement and coarse aggregate measured separately.

Subsequently, the total mass $M_{f1}$ of the submergence aggregate is measured (step 1643). The total mass $M_{f1}$ of the submergence aggregate can be measured by subtracting a measurement value of an empty measurement tank from the mass of the measurement tank filled with the submergence aggregate. The mass measurement can be performed with tension-type load cells, for example. The measured total mass $M_{f1}$ of the submergence aggregate is preferably written onto the hard disk 306, if necessary.

When measuring total mass $M_{f1}$ of the submergence aggregate, the fine aggregate A is thrown into the measurement tank at a predetermined speed continuously or intermittently while measuring the total mass $M_{f1}$ of the submergence aggregate in real time or at predetermined time intervals. Thereafter, when the total mass $M_{f1}$ of the submergence aggregate reaches the target mass $M_{d1}$ of the submergence aggregate while excess water is discharged so that the water level of the submergence aggregate does not exceed a preset first water level during throwing the fine aggregate A, throwing the fine aggregate A is terminated.

The first water level can be preset by causing the water in the submergence aggregate to overflow the measurement tank at a predetermined depth or by discharging the water with suction.

Then, the density $\rho_{a1}$ of the fine aggregate A in the saturated surface-dried condition and the density $\rho_w$ of the water previously stored on the hard disk 306 are read from the hard disk (step 1644).

Subsequently, the processing unit 305 is operated to calculate the mass $M_{a1}$ of the fine aggregate A in the saturated surface-dried condition by substituting the total mass $M_{f1}$ of the submergence aggregate and the total volume $V_{f1}$ thereof into the following formula.

$$M_{a1}=\rho_{a1}(M_{f1}-\rho_w V_{f1})/(\rho_{a1}-\rho_w) \tag{32}$$

where $\rho_{a1}$ is a read-out density of the fine aggregate A in the saturated surface-dried condition and $\rho_w$ is a read-out density of the water. In addition, a result of this calculation is stored on the hard disk 306 (step 1645).

On the other hand, if the water level at which the total mass $M_{f1}$ of the submergence aggregate reaches the target mass $M_{d1}$ thereof is lower than the preset first water level, required water is added so that it is equal to the first water level. Then, the total mass $M_{f1}$ of the submergence aggregate is measured again and the mass $M_{a1}$ of the fine aggregate A in the saturated surface-dried condition is calculated again (step 1646).

Subsequently, in the same manner as for the fine aggregate A, the fine aggregate B is thrown into the measurement tank so that it is submerged in the water so as to be submergence aggregate (step 1647). Then, the total mass $M_{f2}$ of the submergence aggregate is measured (step 1648). When measuring the total mass $M_{f2}$ of the submergence aggregate, the aggregate B is thrown into the measurement tank at a predetermined speed continuously or intermittently while measuring the total mass $M_{f2}$ of the submergence aggregate in real time or at predetermined time intervals in the same manner as for the fine aggregate A. Thereafter, when the total mass $M_{f2}$ of the submergence aggregate reaches the target mass $M_{d2}$ of the submergence aggregate while excess water is discharged so that the water level of the submergence aggregate does not exceed a preset second water level during throwing the fine aggregate B, throwing the fine aggregate B is terminated. The measured total mass $M_{f2}$ of the submergence aggregate is preferably written onto the hard disk 306, if necessary.

The second water level can also be preset by causing the water in the submergence aggregate to overflow the measurement tank at a predetermined depth or by discharging the water with suction.

Then, the density $\rho_{a1}$ of the fine aggregate A in the saturated surface-dried condition, the density $\rho_{a2}$ of the fine aggregate B in the saturated surface-dried condition, and the density $\rho_w$ of the water previously stored on the hard disk 306 are read from the hard disk (step 1649).

Then, mass $M_{a2}$ of the fine aggregate B in the saturated surface-dried condition and mass $M_w$ of the water are calculated with the processing unit 305 by substituting the total mass $M_{f2}$ of the submergence aggregate and the total volume $V_{f2}$ thereof into the following formulas.

$$M_{a2}=\rho_{a2}((M_{f2}-\Sigma M_{ai}(i=1,2))-\rho_w(V_{f2}-\Sigma(M_{ai}/\rho_{ai})\\(i==1,2)))/(\rho_{a2}-\rho_w) \tag{34}$$

$$M_w=\rho_w(\rho_{a2}(V_{f2}-\Sigma(M_{ai}/\rho_{ai})(i=1,2))-(M_{f2}-\Sigma M_{ai}(i=1,\\2)))/(\rho_{a2}-\rho_w) \tag{35}$$

where $\rho_{a1}$ is a read-out density of the fine aggregate A in the saturated surface-dried condition, $\rho_{a2}$ is a read-out density of the fine aggregate B in the saturated surface-dried condition, and $\rho_w$ is a read-out density of the water. In addition, a result of this calculation is stored on the hard disk 306 (step 1650).

On the other hand, if the water level at which the total mass $M_{f2}$ of the submergence aggregate reaches the target mass $M_{d2}$ thereof is lower than the preset second water level, required water is added so that it is equal to the second water level. Then, the total mass $M_{f2}$ of the submergence aggregate is measured again and the mass $M_{a2}$ of the fine aggregate B in the saturated surface-dried condition and the mass $M_w$ of the water are calculated again (step 1651).

After measuring the fine aggregates A and B and the water as mentioned above, these measurement results are compared with an initial field mix set according to the specified mix and then the field mix is corrected, if necessary (step 1652).

In other words, if the total mass $M_{fi}$ (i=1, 2) of the submergence aggregate reaches the target mass $M_{d2}$ while excess water is discharged so that the water level of the submergence aggregate does not exceed the first and second water levels, the total mass $M_{fi}$ (i=1, 2) of the submergence aggregate and the total volume $V_{fi}$ (i=1, 2) of the submergence aggregate are equal to initial setting values. Therefore, the field mix need not be corrected and the submergence aggregate is thrown into the kneading mixer together with other concrete-forming materials for mixing.

On the other hand, unless the water level of the submergence aggregate reaches the first or second water level, required water is added so that the water level reaches the first or second water level. Therefore, the total mass $M_{fi}$ (i=1, 2) of the submergence aggregate measured again, i.e. the masses of the fine aggregates A and B in the saturated surface-dried condition derived from the total mass, result in values different from the initial setting values.

Therefore, if so, in the same manner as for the above embodiment, the measured masses of the aggregates A and B are compared with the masses of the aggregates A and B of an initially set field mix. Calculation is then made on a ratio of the measured total mass of the fine aggregates A and B in the saturated surface-dried condition to the preset total mass of the fine aggregates A and B in the saturated surface-dried condition. If it is 0.9, for example, the measured mass of the fine aggregates A and B is 10% less and therefore there is a need for decreasing the mixing volume $N_0$ of one batch by 10% so as to be $0.9N_0$. Accordingly, also regarding other concrete-forming materials such as cement and admixture, the initial field mix is corrected by using a corresponding ratio for measurement. Furthermore, regarding the water, an initially set amount of water is compared with a measured amount of water. Then, required water is added as secondary water or excess water is discharged. Thereafter, the concrete-forming materials are thrown into the kneading mixer for mixing.

As set forth hereinabove, according to the program for an execution of measuring and calculating the concrete-forming materials of this embodiment, surface water of the fine aggregates A and B can be indirectly calculated as a part of the mass $M_w$ of the water, even if a fine aggregate whose moisture state is not uniform is used, and the mass of the aggregate can be calculated as the mass $M_{ai}$ (i=1, 2) of the aggregate in the saturated surface-dried condition. In other words, since the mass of the aggregate and the mass of the water are calculated on conditions equivalent to the specified mix, even if a humidity grade of the aggregate is not fixed at every measurement, it becomes possible to make concrete as shown by the specified mix.

Furthermore, according to the program for an execution of measuring and calculating the concrete-forming materials of this embodiment, if the total mass $M_{fi}$ (i=1, 2) of the submergence aggregate reaches the target mass $M_{d2}$ thereof while excess water is discharged so that the water level of the submergence aggregate does not exceed the first and second water levels, not only the total volume $V_{fi}$ (i=1, 2) of the submergence aggregate need not be measured, but also the total mass $M_{fi}$ (i=1, 2) of the submergence aggregate and the total volume $V_{fi}$ (i=1, 2) thereof become equal to the initial setting values. Therefore, the field mix need not be corrected and the submergence aggregate can be thrown into the kneading mixer together with other concrete-forming materials for mixing.

Still further, according to the program for an execution of measuring and calculating concrete-forming materials of this embodiment, if the water level of the submergence aggregate does not reach the preset first or second water level, required water need be added so that it reaches the first or second water level, but the total volume $V_{fi}$ (i=1, 2) of the submergence aggregate need not be measured in the same manner as for the above. By measuring the total mass $M_{fi}$ (i=1, 2) of the submergence aggregate again, it becomes possible to manage inputs of the fine aggregates A and B accurately and to correct the field mix, which results in making concrete as shown by the specified mix.

Furthermore, even if the plurality of fine aggregates differ from each other in density, grading, or the like, they can be measured in a single measurement tank efficiently and very accurately while calculating an effect of surface water caused by a difference in a moisture state as a part of the final amount of water.

The following should be noted though it has not been particularly mentioned in this embodiment. Mass $M_I$ of water supplied to the measurement tank and mass $M_O$ of water discharged from the measurement tank are measured as accumulation values. In addition, a result of this calculation is stored on the hard disk 306. Then, $\Sigma M_{awj}$ (j=1 to i) is calculated with the processing unit 305 by reading the mass $M_I$ of water supplied to the measurement tank, the mass $M_O$ of water discharged from the measurement tank, and the total mass $M_{fi}$ (i=1, 2) of the submergence aggregate from the hard disk 306 and substituting these values into the following formula.

$$\Sigma M_{awj}(j=1 \text{ to } i) = M_{fi} - (M_I - M_O) \quad (14)$$

In addition, a result of this calculation is stored on the hard disk 306. Thereafter, the following formula is calculated to obtain $M_{awi}$.

$$\Sigma M_{awj}(j=1 \text{ to } i) - \Sigma M_{awj}(j=1 \text{ to } (i-1)) \quad (15)$$

$M_{awi}$ is then substituted into the following formula to obtain percentages of surface moisture of the fine aggregates A and B with the processing unit 305.

$$(M_{awi} - M_{ai})/M_{ai} \quad (13)$$

Thereby, the percentages of surface moisture can be calculated.

Furthermore, the following should be noted though it has not been particularly mentioned in this embodiment. If $V_{fi}$ (i=1, 2)·(1−a/100) is used instead of $V_{fi}$ (i=1, 2) assuming that a (%) is air content of the submergence aggregate, more accurate measurement is achieved with the air content considered.

Seventeenth Embodiment

Figure 59:
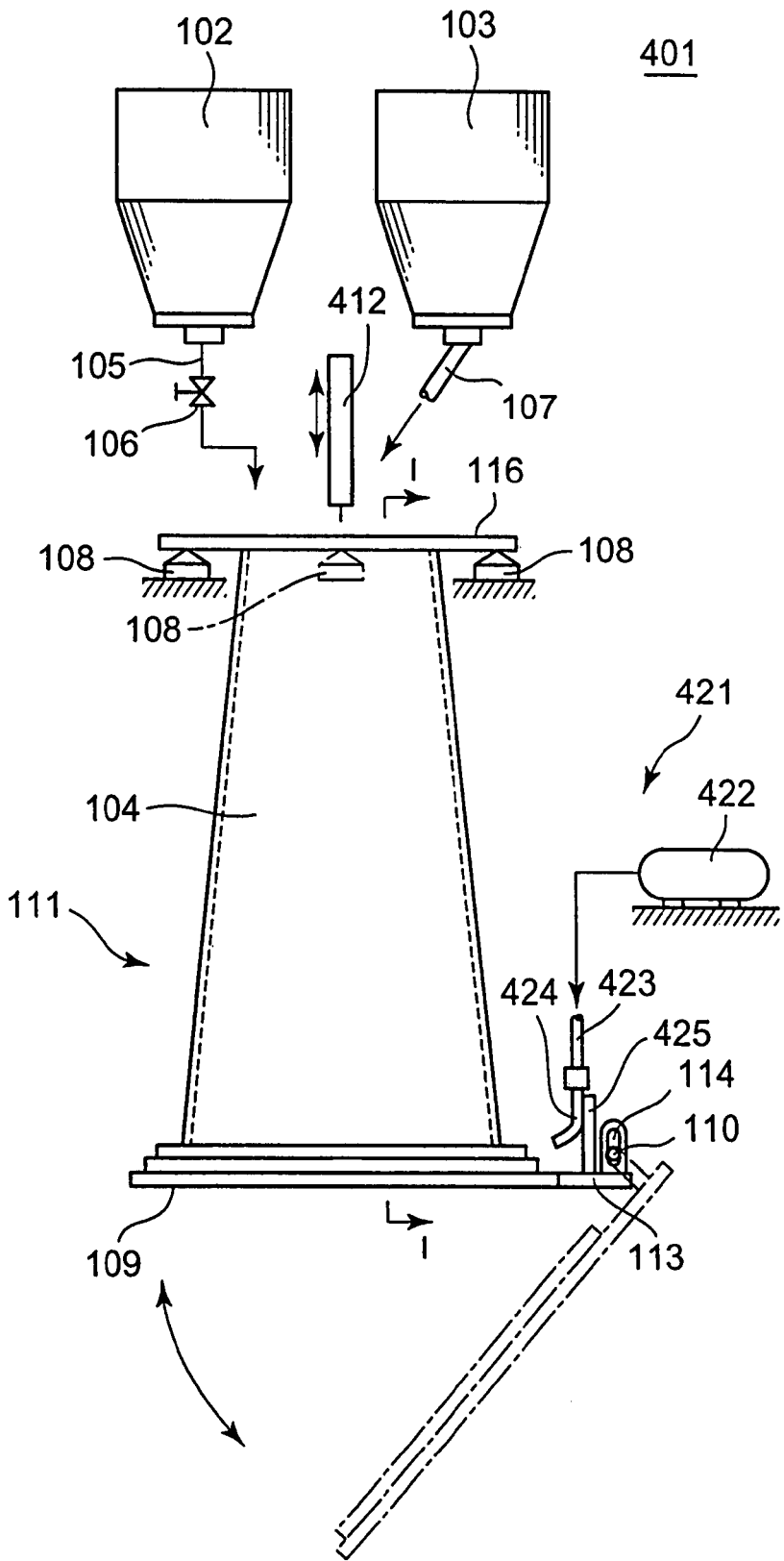
FIG. 59 is a general view of a discharge mechanism of a preferable measurement container according to the present invention, and a measuring apparatus to which it is applied.
Figure 60:
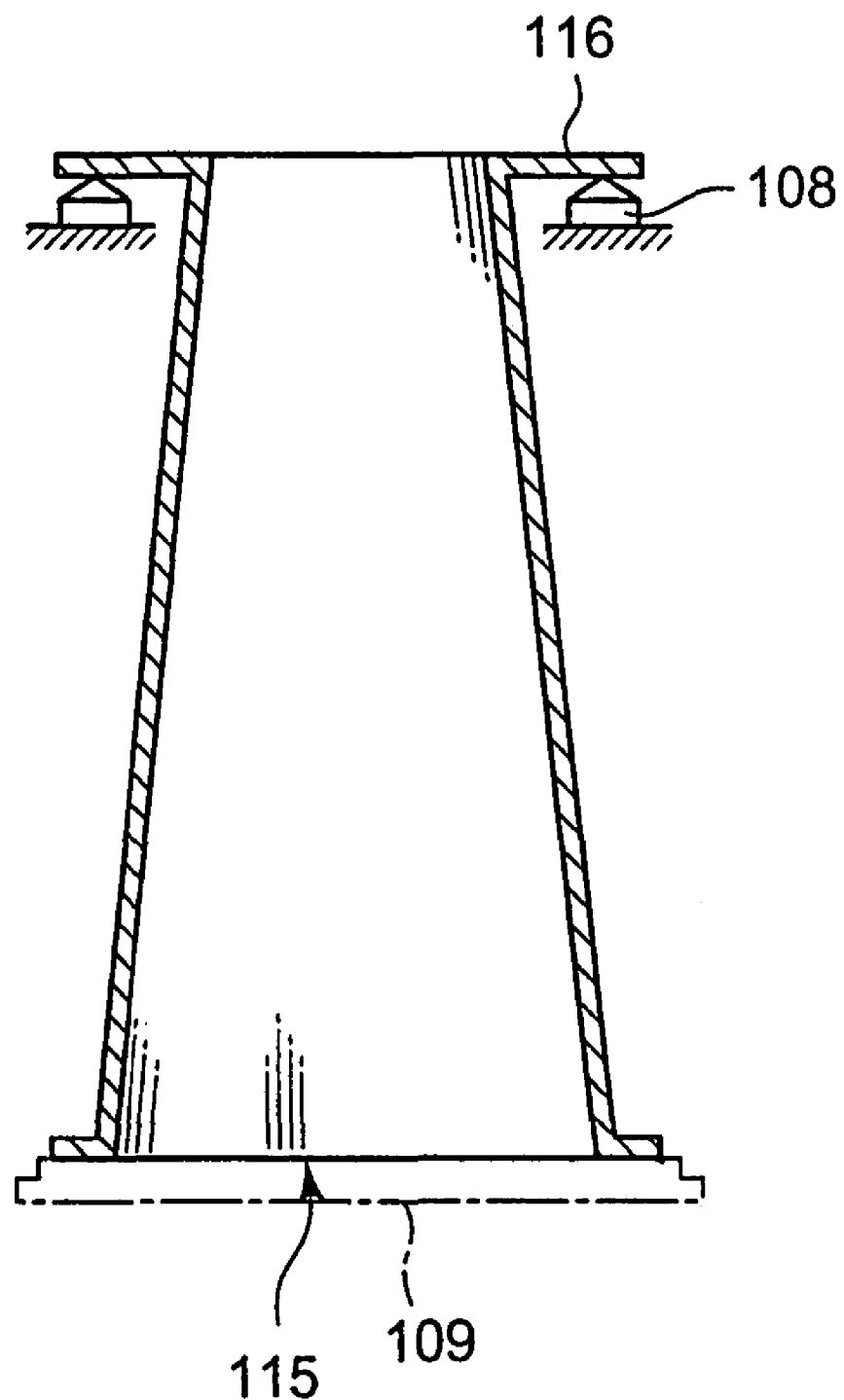
FIG. 60 is a vertical sectional view taken along line I-I of FIG. 59.

Referring to FIG. 59, there is shown a general view of a discharge mechanism 421 of a measurement container with a measuring apparatus 401 to which the discharge mechanism is applied. Referring to FIG. 60, there is shown a sectional view taken along line I-I in FIG. 59.

First, the measuring apparatus 401 to which the discharge mechanism 421 of the measurement container is applied according to a seventeenth embodiment comprises a water storage hopper 102 for storing water, a fine aggregate storage hopper 103 for storing fine aggregate as aggregate, a measurement container 111 for containing water and fine aggregate supplied from the water storage hopper 102 and the fine aggregate storage hopper 103 as submergence aggregate, respectively, load cells 108 for measuring a mass of submergence aggregate in the measurement container, and an electrode-type displacement sensor 412 for measuring a water level in the measurement container 111. The water storage hopper 102 forms means for supplying water in conjunction with a water feed pipe 105 connected to the water storage hopper 102 at a bottom thereof and whose discharge opening is located above the measurement container 111, and a closing valve 106 arranged in a predetermined position of the water feed pipe 105. The fine aggregate storage hopper 103 forms means for feeding aggregate in conjunction with a fine aggregate feed pipe 107 whose discharge opening is located above the measurement container 111.

The measurement container 111 comprises a body of the container 104 and a bottom lid 109 attachable so as to be free to open or close at a bottom opening 115 of the body of the container. The body of the container 104 is formed in a shape of a hollow truncated cone so that a bore of the container becomes larger in a downward direction. With this, when a measurement is finished, a free fall of the submergence aggregate in the container can be achieved only by opening the bottom lid 109 without a blockage of submergence aggregate in the container even if no vibrating instrument such as a vibrator is used. Thereafter, the submergence aggregate can be thrown into a kneading mixer, which is not shown, together with cement and coarse aggregate measured separately. At abutting portions of the bottom lid 109 and the bottom opening 115 of the body of the container 104, sealing members, which are not shown, are appropriately attached so that watertightness is secured between the bottom lid 109 and the body of the container 104 when the bottom lid 109 is closed.

A volume of the measurement container 111 is arbitrary. The volume may be made in agreement with a total amount required for a unit of concrete mixing, i.e., one batch. Otherwise, the volume can be divided into some amounts for measurement.

The electrode-type displacement sensor 412 is capable of measuring a water level of submergence aggregate by monitoring a change in an energized condition when a lower end of a detection electrode contacts a water surface of the submergence aggregate in the measurement container 111.

The water storage hopper 102, the fine aggregate storage hopper 103, and the load cells 108 are attached to a stand, which is not shown, and a collar circular ring 116 of the measurement container 111 is put on the load cells 108 to hold the measurement container 111 in a suspended condition. Thereby, the mass of the measurement container 111 can be measured with the load cells 108. The load cells 108 are preferably placed, for example, in three places at 120° intervals on the same level surface so that the measurement container 111 can be held stably in a suspended condition during measurement.

On the other hand, the discharge mechanism 421 of the measurement container according to this embodiment causes the measurement container 111 to contain fine aggregate as submergence aggregate with water when the bottom lid 109 is closed to measure the submergence aggregate, and causes the submergence aggregate to be discharged from below when this measurement is finished by opening the bottom lid 109.

The bottom lid 109 is made of a circular plate having an outside diameter substantially equivalent to or slightly larger than an outside diameter of the bottom opening of the body of the container 104. Furthermore, a long hole 114 is formed at a tip of an L-shaped mounting arm 113 provided as an extension from a rim of the circular plate, and a pin 110 fixed to a stand not shown is passed through the long hole 114, by which it becomes possible to rotate the bottom lid 109 around the pin 110 so as to open or close the bottom opening 115 of the body of the container 104. Furthermore, in a condition where the bottom lid 109 is closed, the long hole 114 is oriented vertically, thereby preventing a reaction force from being generated at the pin 110 by a load of the measurement container 111. In fixing the bottom lid 109 to the bottom opening 115 of the body of the container 104, an appropriate method can be selected out of known methods such as fastening with a bolt or a clamp.

In the discharge mechanism 421 of the body of the container, an air spray nozzle 424 as a gas spray mechanism connected in communication with an air compressor 422 is fixed to a nozzle holding part 425 arranged in a standing condition on an L-shaped mounting arm 113 in the vicinity of the bottom lid 109. In a condition where the bottom lid 109 is opened, air can be blown against an upper surface of the bottom lid 109 from a tip of the air spray nozzle 424.

Figure 61:
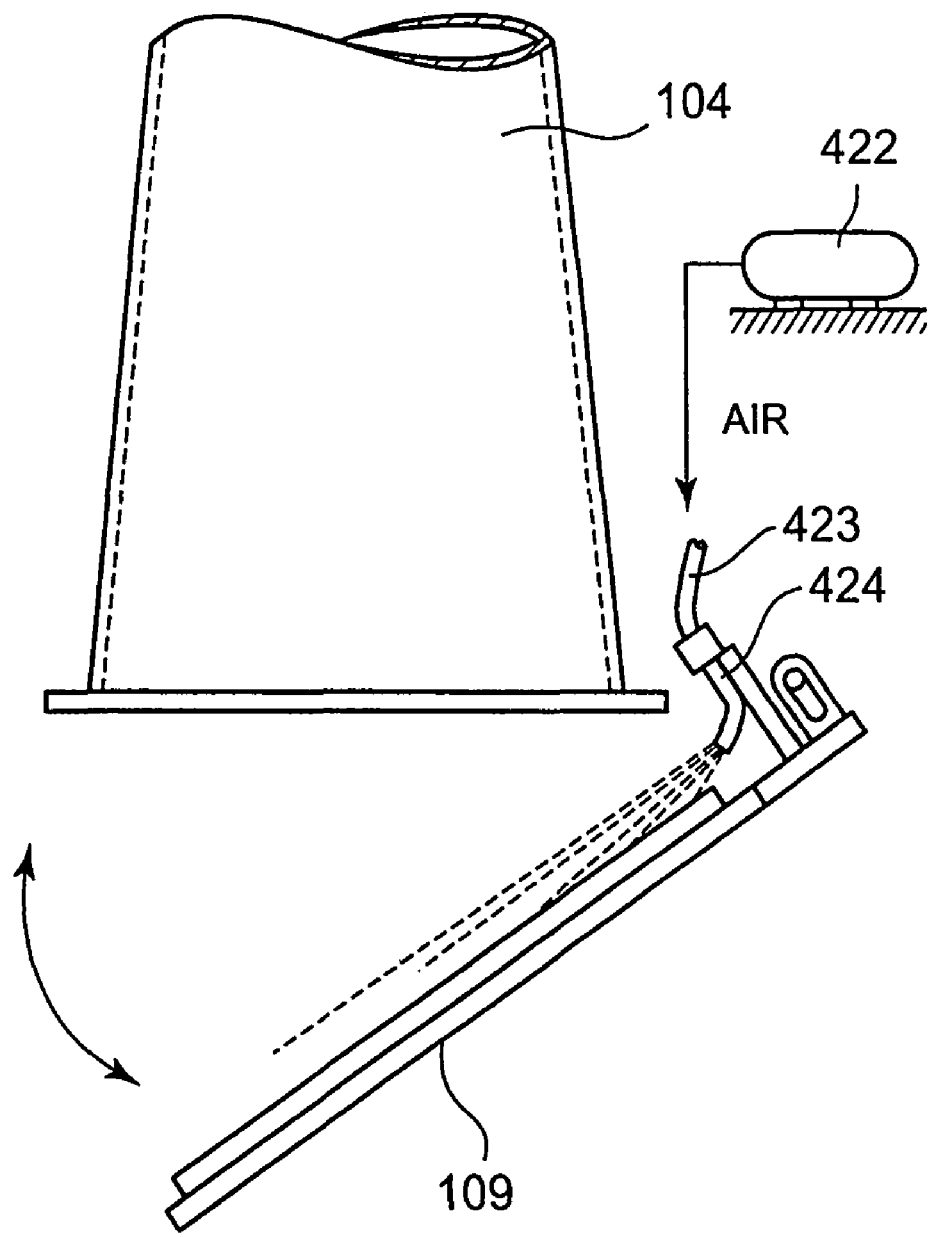
FIG. 61 is a diagram showing an action of the discharge mechanism of the preferable measurement container according to the present invention.

In the discharge mechanism 421 of the measurement container according to this embodiment, the bottom lid 109 is opened to achieve a free fall of submergence aggregate for discharging it after measurement of the submergence aggregate is finished. Thereafter, the air compressor 422 is operated in the condition where the bottom lid 109 is opened as shown in FIG. 61 to blow air against the upper surface of the bottom lid 109 from the tip of the air spray nozzle 424.

With this, even if fine aggregate is adhering to the upper surface of the bottom lid 109 at discharging of the submergence aggregate, the fine aggregate is blown off by the air, thereby preventing the fine aggregate from being caught between the body of the container 104 and the bottom lid 109 when the bottom lid 109 is closed for a subsequent measurement.

Figure 62:
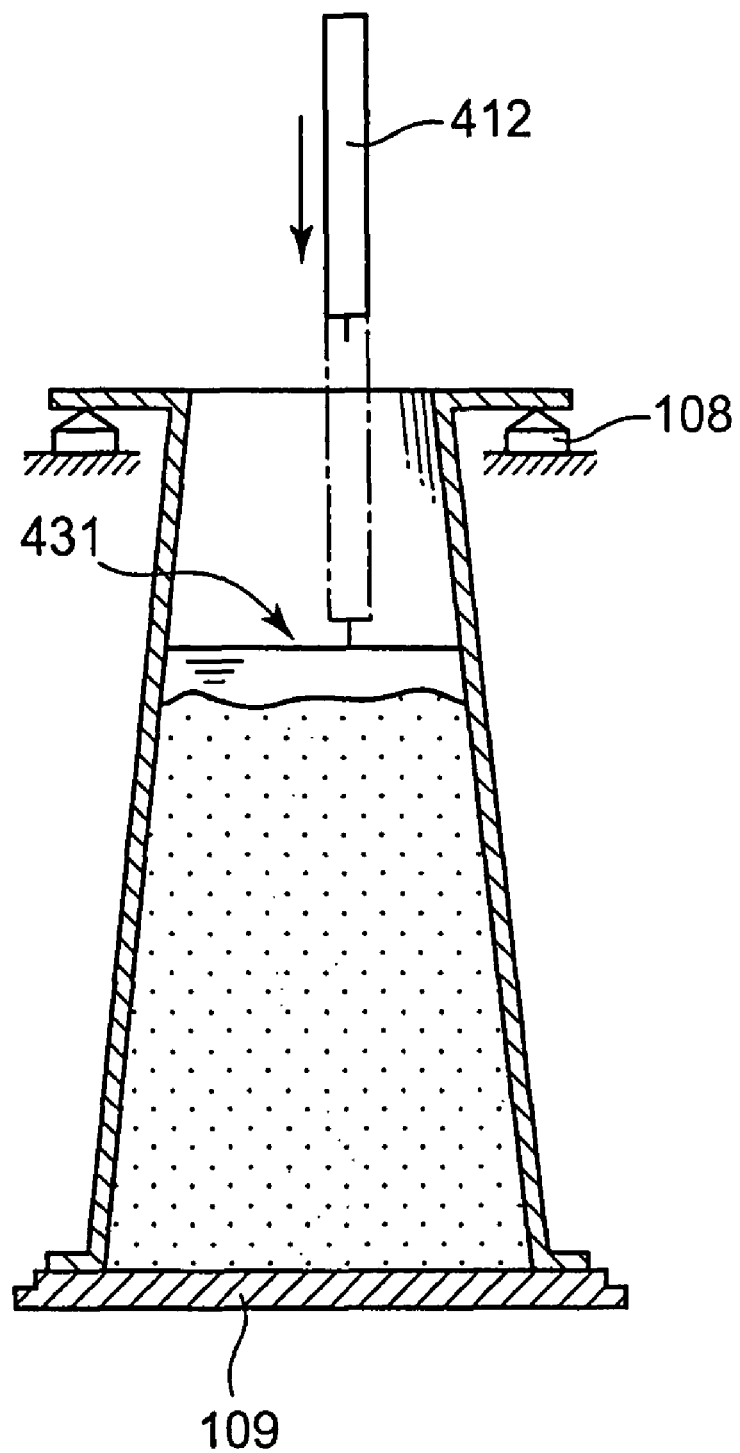
FIG. 62 is a diagram showing a condition where submergence aggregate is measured by using measuring apparatus 401.

In the discharge mechanism 421 of the measurement container according to this embodiment, the bottom opening 115 of the body of the container 104 is closed by the bottom lid 109 to put the inside of the measurement container 111 in a watertightness condition, first. The closing valve 106 is opened in the above condition. Water is then thrown from the water storage hopper 102 to the measurement container 111 and the fine aggregate stored in the fine aggregate storage hopper 103 is thrown into the measurement container 111 so that it is put in the submergence condition to fill the measurement container 111 with submergence aggregate 431 as shown in FIG. 62. Thereafter, a water level of the submergence aggregate 431 is measured with the electrode-type displacement sensor 412, and total volume Vf of the submergence aggregate 431 is measured from the water level. In addition, total mass Mf of the submergence aggregate is measured with the load cells 108. Regarding this measuring method of the submergence aggregate, however, an arbitrary method can be selected out of the various measuring methods as mentioned above. Therefore, its detailed description is omitted here.

As set forth hereinabove, according to the discharge mechanism 421 of the measurement container of this embodiment, the air compressor 422 is operated in the condition where the bottom lid 109 is opened to blow air against the upper surface of the bottom lid 109 from the tip of the air spray nozzle 424, so that fine aggregate is blown off by the air even if it is adhering to the upper surface of the bottom lid 109 at discharging of the submergence aggregate. Thereby, there is no possibility of inclusions of fine aggregate between the body of the container 104 and the bottom lid 109 when the bottom lid 109 is closed for a subsequent measurement.

Therefore, it becomes possible to prevent an occurrence of an error in measurement that may be caused by water leakage from a clearance gap generated by inclusions of fine aggregate, and to prevent seal members provided on the body of the container 104 or on the bottom lid 109 from being damaged.

While the discharge mechanism of the measurement container according to the invention is applied to the measuring apparatus 401 as an example in this embodiment, the discharge mechanism of the measurement container according to the invention is characterized in that a gas is blown against an upper surface of a bottom lid from a gas spraying mechanism in a condition where the bottom lid is opened. Therefore, the discharge mechanism is applicable to all kinds of measuring apparatuses as well as the measuring apparatuses mentioned above if only the apparatus is capable of containing submergence aggregate in a measurement container or a container having a bottom lid attached so as to be free to open or close at a bottom opening of a body of the container.

Furthermore, while the air compressor 422 is connected in communication with the air spray nozzle 424 so as to blow air from the tip of the air spray nozzle 424 by supplying air from the air compressor with pressure in this embodiment, the invention is not always limited to air compressor 422, but any configuration is applicable if only it enables gas supply with pressure. For example, a bottle of compressed nitrogen can be used instead of the air compressor 422.

Still further, while fine aggregate is used as aggregate in this embodiment, naturally the invention is applicable to coarse aggregate.

Eighteenth Embodiment

The following describes another preferable embodiment of a discharge mechanism of measurement container according to the preset invention. Like reference characters indicate parts substantially identical to the discharge mechanism 421 of the measurement container and the measuring apparatus 401 mentioned above. Therefore, their description is omitted here.

Figure 63A:
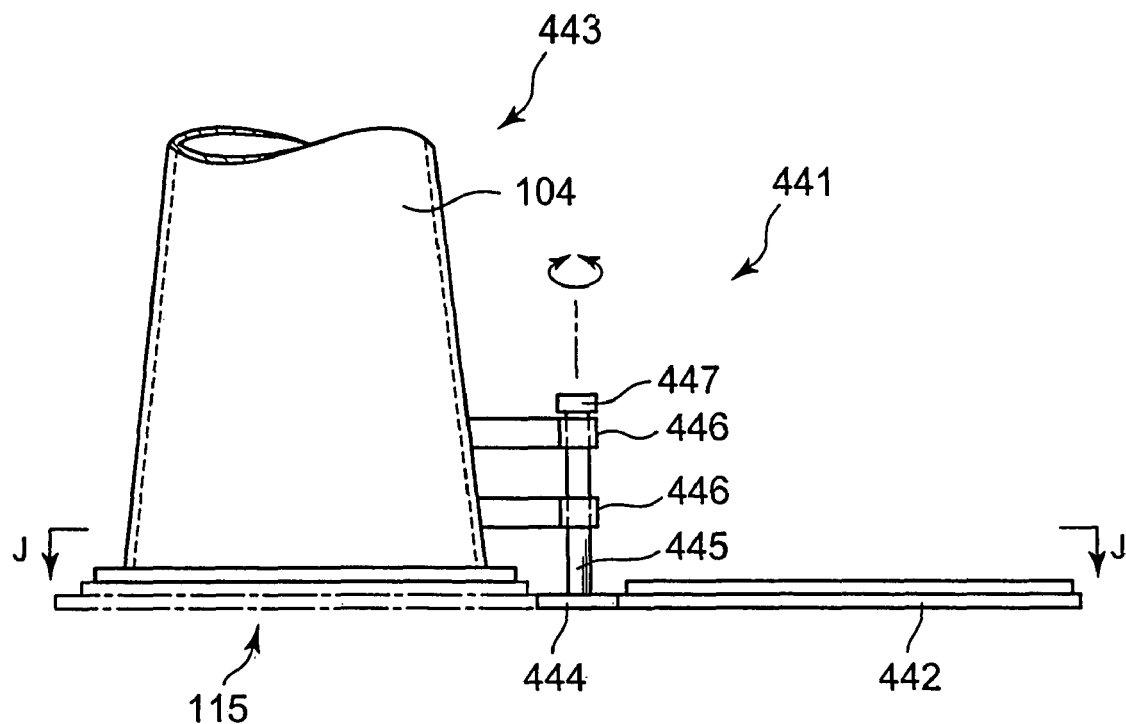
FIGS. 63A and 63B are diagrams of a discharge mechanism of another preferable measurement container according to the present invention, with FIG. 63A being a side view and FIG. 63B being a horizontal sectional view taken along line J-J of FIG. 63A.
Figure 63B:
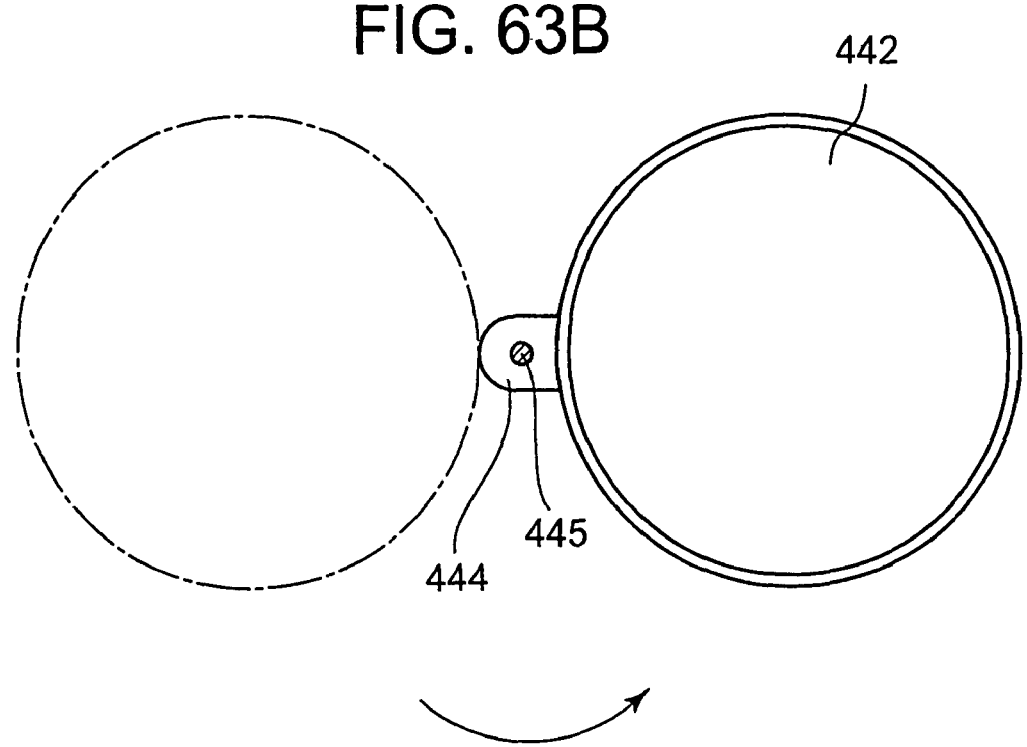

Referring to FIGS. 63A and 63B, there is shown a discharge mechanism 441 of a measurement container according to this embodiment. As apparent from FIG. 63A, on the assumption that there is used a measurement container 443 comprising a body of container 104 and a bottom lid 442 attachable so as to be free to open or close at a bottom opening 115 of the body of the container, the discharge mechanism 441 of the measurement container according to this embodiment is configured to contain fine aggregate, which is aggregate, with water as submergence aggregate in the measurement container 443 when the bottom lid is closed for measuring the submergence aggregate and to discharge the submergence aggregate downward by opening the bottom lid 442 after a measurement is finished.

The bottom lid 442 is made of a circular plate having an outside diameter substantially equivalent to or slightly larger than an outside diameter of the bottom opening of the body of the container 104. A protrusion 444 is then provided as an extension from a rim of the circular plate.

At this point, a rotational axle 445 is arranged in a standing condition in a protrusion 444, with the rotational axle inserted into a hollow of hinge members 446, 446 having a two-stage structure provided in a protruding condition in a horizontal direction on a circumferential surface of the body of the container 104 and with the rotational axle 445 clamped at the top by a nut 447. With this constitution, the discharge mechanism 441 of the measurement container according to this embodiment can rotate the bottom lid 442 around a vertical axis; in other words, in a plane to open or close the bottom lid 442 while supporting an empty weight of the bottom lid 442 by means of a locking action between the nut 447 and the hinge members 446 in the upper stage.

In the discharge mechanism 441 of the measurement container according to this embodiment, after completing measurement of the submergence aggregate, fall discharge of the submergence aggregate is performed by opening the bottom lid 442. When being opened, the bottom lid 442 is not rotated around a horizontal axis, but it is rotated in a plane and then the aggregate in the measurement container 443 is dropped and discharged.

In other words, the bottom lid 442 is moved by a rotation in the plane toward the body of the container 104, first. Thereafter, the bottom opening 115 of the body of the container 104 is closed to put the inside of the measurement container in a watertightness condition. After measuring the submergence aggregate in this condition, the bottom lid 442 is rotated in the plane in an opposite direction and then the submergence aggregate in the measurement container 443 is dropped downward and thrown into a kneading mixer.

A measuring method of the submergence aggregate can be arbitrarily chosen from various measuring methods as mentioned above. Therefore, its detailed description is omitted here.

As set forth hereinabove, according to the discharge mechanism 441 of the measurement container of this embodiment, the bottom lid 442 is rotated in the plane, by which there is no need to secure an opening-and-closing space in a height direction up to the kneading mixer, but it is only necessary to secure a space in the plane, while the bottom lid will hang down if it is opened and therefore an opening-and-closing space of the bottom lid need be secured by a distance up to the kneading mixer in a conventional opening-and-closing mechanism.

Therefore, the bottom opening 115 of the body of the container 104 can be lowered up to just above an inlet of the kneading mixer by a distance equivalent to an opening-and-closing height that has been conventionally indispensable, by which the submergence aggregate can be thrown into the kneading mixer reliably after a measurement is finished.

While the discharge mechanism of the measurement container according to the present invention is applied to the measuring apparatus 401 as an example, the discharge mechanism of the measurement container according to the present invention is characterized in that the bottom lid is moved in a translational direction or rotated in the plane to open or close the bottom lid. Therefore, the discharge mechanism is applicable to all kinds of measuring apparatuses as well as the measuring apparatuses mentioned above if only the apparatus is capable of containing submergence aggregate in a measurement container or a container having a bottom lid attached so as to be free to open or close a bottom opening of a body of the container.

Furthermore, while fine aggregate is used as aggregate in this embodiment, naturally the invention is applicable to coarse aggregate.

Nineteenth Embodiment

The following describes still another preferable embodiment of a discharge mechanism of a measurement container according to the preset invention. Like reference characters indicate parts substantially identical to the discharge mechanism 421 of the measurement container and the measuring apparatus 401 mentioned above. Therefore, their description is omitted here.

Figure 64:
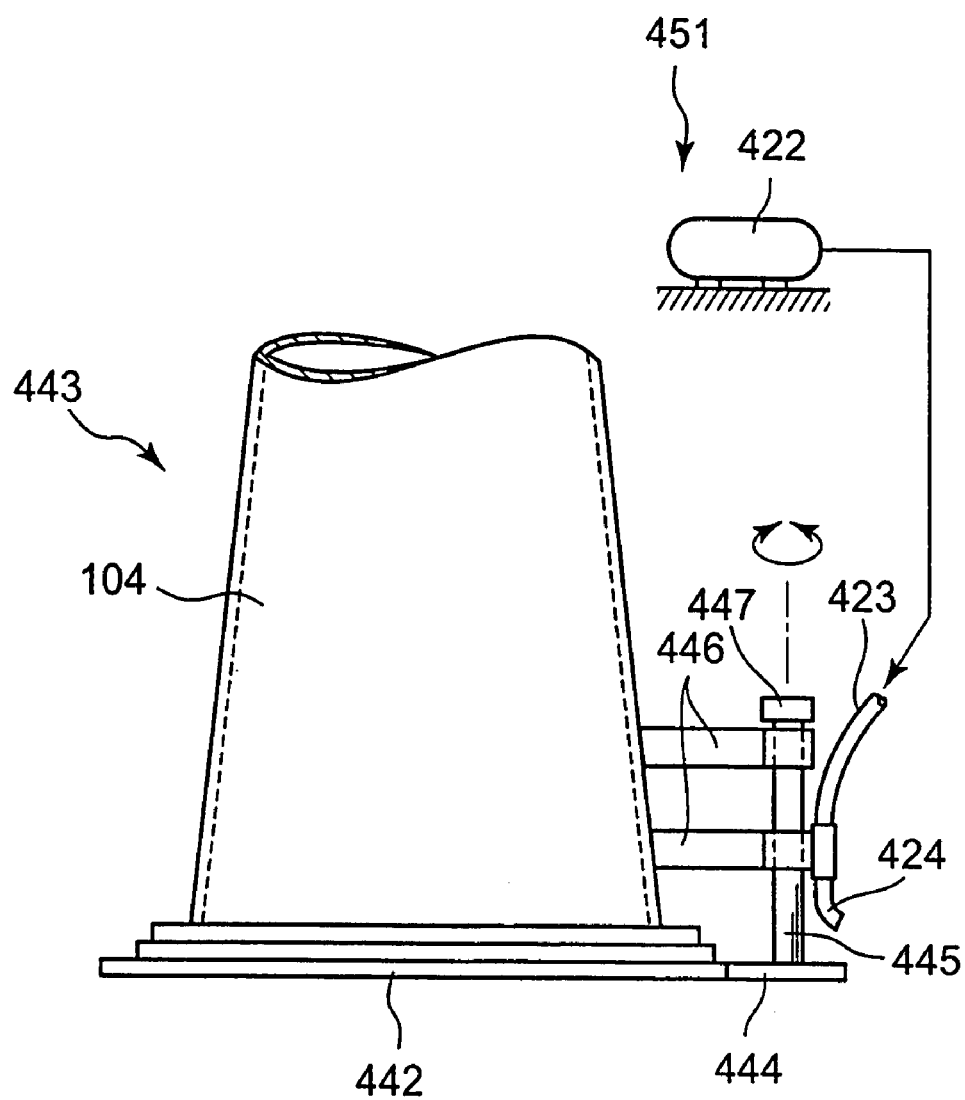
FIG. 64 is a general view of a discharge mechanism of still another preferable measurement container according to the present invention.
Figure 65A:
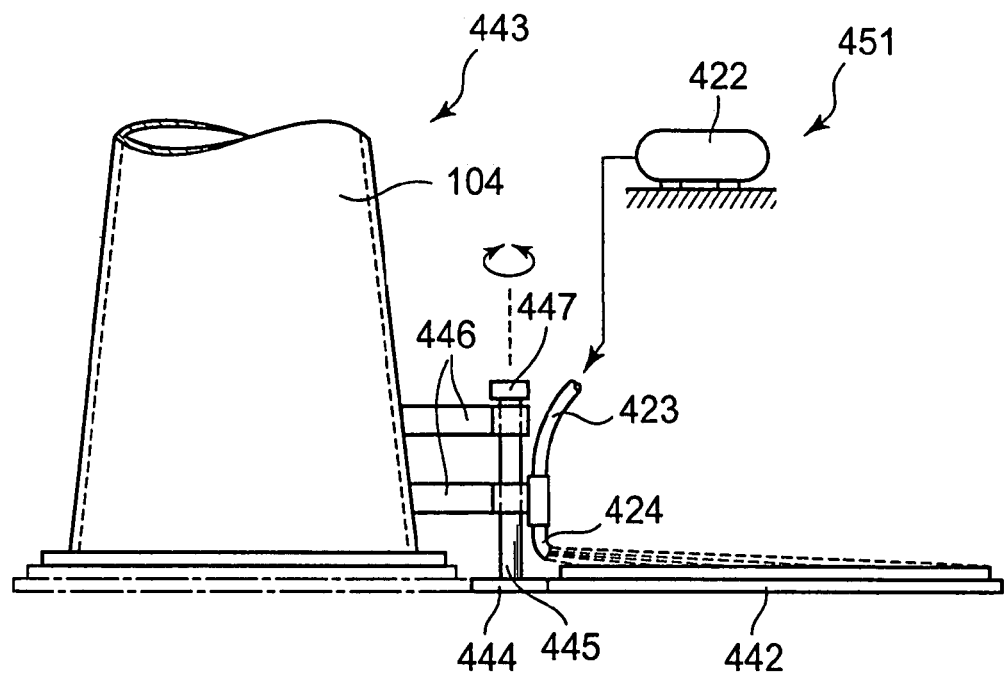
FIGS. 65A and 65B are diagrams showing an action of the discharge mechanism of the measurement container shown in FIG. 64.
Figure 65B:
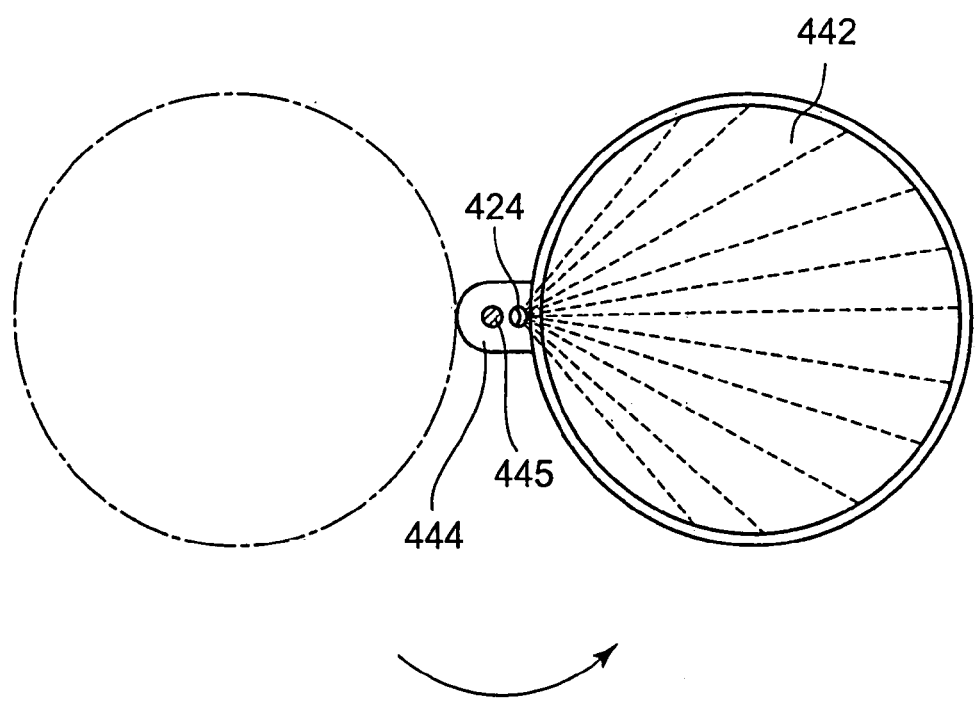

Referring to FIG. 64, there is shown a discharge mechanism 451 of a measurement container according to this embodiment. As apparent from FIG. 64, on the assumption that there is used a measurement container 443 comprising a body of container 104 and a bottom lid 442 attachable so as to be free to open or close a bottom opening 115 of the body of the container, the discharge mechanism 451 of the measurement container according to this embodiment is configured to contain fine aggregate, which is aggregate, with water as submergence aggregate in the measurement container 443 when the bottom lid is closed for measuring the submergence aggregate, and to discharge the submergence aggregate downward by opening the bottom lid 442 after a measurement is finished.

The bottom lid 442 is made of a circular plate having an outside diameter substantially equivalent to or slightly larger than an outside diameter of the bottom opening of the body of the container 104. A protrusion 444 is then provided as an extension from a rim of the circular plate.

At this point, a rotational axle 445 is arranged in a standing condition in a protrusion 444, with the rotational axle inserted into a hollow of hinge members 446, 446 having a two-stage structure provided in a protruding condition in a horizontal direction on the circumferential surface of the body of the container 104, and with the rotational axle 445 clamped at the top by a nut 447. With this constitution, the discharge mechanism 451 of the measurement container according to this embodiment can rotate the bottom lid 442 around a vertical axis, in other words, in a plane to open or close the bottom lid 442 while supporting an empty weight of the bottom lid 442 by means of a locking action between the nut 447 and the hinge members 446 in the upper stage.

In the discharge mechanism 451 of the body of the container according to this embodiment, an air spray nozzle 424, as a gas spraying mechanism connected in communication with an air compressor 422 via a hose 423, is fixed aside the lower-stage hinge member 446 provided in a protruding condition in a horizontal direction from the body of the container 104 in the vicinity of the bottom lid 442. In a condition where the bottom lid 442 is opened, air can be blown against an upper surface of the bottom lid 442 from a tip of the air spray nozzle 424.

In the discharge mechanism 451 of the measurement container according to this embodiment, after completing measurement of the submergence aggregate, fall discharge of the submergence aggregate is performed by opening the bottom lid 442. When being opened, the bottom lid 442 is not rotated around a horizontal axis, but it is rotated in a plane and then the aggregate in the measurement container 443 is dropped and discharged.

In other words, the bottom lid 442 is moved by a rotation in the plane toward the body of the container 104, first. Thereafter, the bottom opening 115 of the body of the container 104 is closed to put the inside of the measurement container in a watertightness condition. After measuring the submergence aggregate in this condition, the bottom lid 442 is rotated in the plane in an opposite direction and then the submergence aggregate in the measurement container 443 is dropped downward and thrown into a kneading mixer.

Subsequently, the air compressor 422 is operated in a condition where the bottom lid 442 is opened as shown in FIG.

65A to blow air against the upper surface of the bottom lid 442 from the tip of the air spray nozzle 424.

With this, even if fine aggregate is adhering to the upper surface of the bottom lid 442 at discharging of the submergence aggregate, the fine aggregate is blown off by the air, thereby preventing the fine aggregate from being caught between the body of the container 104 and the bottom lid 442 when the bottom lid 442 is closed for a subsequent measurement.

As set forth hereinabove, according to the discharge mechanism 451 of the measurement container of this embodiment, the bottom lid 442 is rotated in the plane, by which there is no need to secure an opening-and-closing space in a height direction up to the kneading mixer, but it is only necessary to secure a space in the plane, while the bottom lid will hang down if it is opened and therefore an opening-and-closing space of the bottom lid need be secured by a distance up to the kneading mixer in the conventional opening-and-closing mechanism.

Therefore, the bottom opening 115 of the body of the container 104 can be lowered up to just above an inlet of the kneading mixer by a distance equivalent to an opening-and-closing height that has been conventionally indispensable, by which the submergence aggregate can be thrown into the kneading mixer reliably after a measurement is finished.

As set forth hereinabove, according to the discharge mechanism 451 of the measurement container of this embodiment, the air compressor 422 is operated in the condition where the bottom lid 109 is opened to blow air against the upper surface of the bottom lid 442 from the tip of the air spray nozzle 424, so that fine aggregate is blown off by the air even if the fine aggregate is adhering to the upper surface of the bottom lid 442 at discharging of the submergence aggregate. Thereby, there is no possibility of inclusions of fine aggregate between the body of the container 104 and the bottom lid 442 when the bottom lid 442 is closed for a subsequent measurement.

Therefore, it becomes possible to prevent an occurrence of an error in measurement that may be caused by water leakage from a clearance gap generated by inclusion of fine aggregate, and to prevent seal members provided on the body of the container 104 or on the bottom lid 442 from being damaged.

While the discharge mechanism of the measurement container according to the invention is applied to the measuring apparatus 401 as an example in this embodiment, the discharge mechanism of the measurement container according to the invention is characterized in that the bottom lid is moved in a translational direction or rotated in a plane to open or close the bottom lid and in that a gas spraying mechanism is provided in the vicinity of the bottom lid so as to blow a gas flow against an upper surface of the bottom lid from the gas spraying mechanism in the condition where the bottom lid is opened. Therefore, the discharge mechanism is applicable to all kinds of measuring apparatuses as well as the measuring apparatuses mentioned above so long as the apparatus is capable of containing submergence aggregate in a measurement container or a container having a bottom lid attached so as to be free to open or close a bottom opening of a body of the container.

Furthermore, while fine aggregate is used as aggregate in this embodiment, naturally the invention is applicable to coarse aggregate.

Twentieth Embodiment

Figure 66:
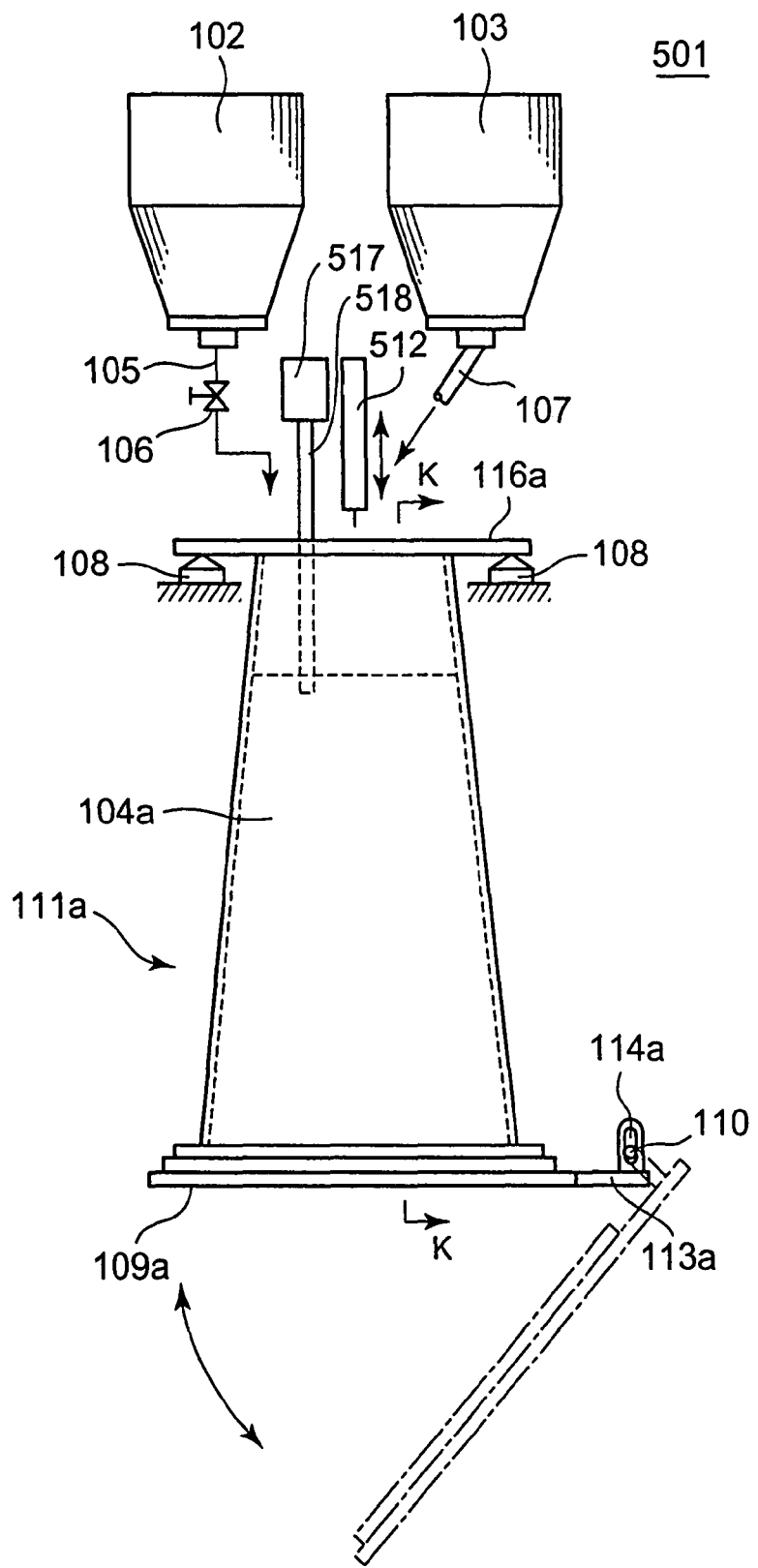
FIG. 66 is a general view of a preferable measuring apparatus of concrete-forming materials according to the present invention.

Referring to FIG. 66, there is shown a general view of a measuring apparatus 501 according to a twentieth embodiment. As apparent from FIG. 66 and FIGS. 67A-67C, a measuring apparatus 501 according to a twentieth embodiment comprises a water storage hopper 102 for storing water, a fine aggregate storage hopper 103 for storing fine aggregate as aggregate, three measurement containers 111a, 111b, and 111c for containing water and fine aggregate supplied from the water storage hopper 102 and the fine aggregate storage hopper 103 as submergence aggregate, respectively, load cells 108 as submergence aggregate mass measurement means for measuring a mass of submergence aggregate in the measurement containers, an electrode-type displacement sensor 512 as water level measurement means for measuring water levels in the measurement containers 111a, 111b, and 111c, and a suction unit 517 as water level regulation means for regulating water levels of the submergence aggregates. The water storage hopper 102 forms means for supplying water in conjunction with a water feed pipe 105 connected to the water storage hopper 102 at a bottom thereof and whose discharge opening is located above the measurement containers 111a, 111b, and 111c, and a closing valve 106 arranged in a predetermined position of the water feed pipe 105. The fine aggregate storage hopper 103 forms means for feeding aggregate in conjunction with a fine aggregate feed pipe 107 whose discharge opening is located above the measurement containers 111a, 111b, and 111c. In FIG. 66, there is shown only the measurement container 111a of the measurement containers for convenience. Other measurement containers 111b and 111c are shown with the measurement container 111a in FIGS. 67A-67C.

Figure 68:
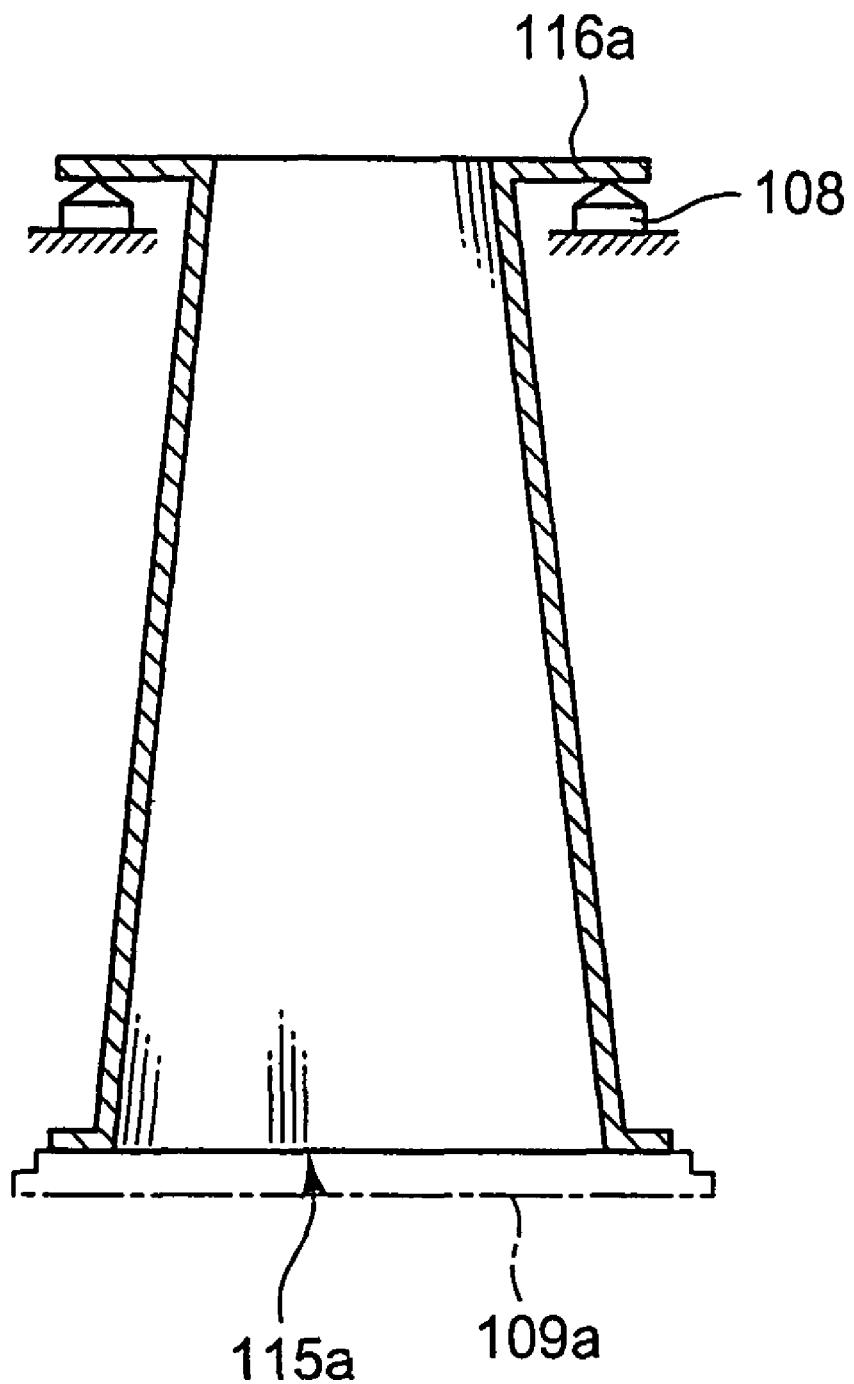
FIG. 68 is a cross section taken along line K-K of FIG. 66.

As apparent from a cross section shown in FIG. 68, the measurement container 111a comprises a body of container 104a and a bottom lid 109a attachable so as to be free to open or close a bottom opening 115a of the body of the container. The measurement container is configured so as to contain fine aggregate as submergence aggregate with water when the bottom lid 109a is closed to measure the submergence aggregate and causes the submergence aggregate to be discharged downward by opening the bottom lid 109a when this measurement is finished. In the same manner as for the measurement container 111a, each of the measurement containers 111b and 111c comprises a body of the container 104b or 104c and a bottom lid 109b or 109c attachable so as to be free to open or close a bottom opening of the body of the container. Each of the measurement containers is configured so as to contain fine aggregate as submergence aggregate with water when the bottom lid 109b or 109c is closed to measure the submergence aggregate, and causes the submergence aggregate to be discharged downward by opening the bottom lid 109b or 109c when this measurement is finished.

Each of the body of the container 104a, 104b, and 104c is formed in a shape of a hollow truncated cone so that a bore of the container becomes larger in a downward direction. With this, when a measurement is finished, a free fall of the submergence aggregate in the body of the container can be achieved only by opening the bottom lid 109a, 109b, or 109c without a blockage of submergence aggregate in the body of the container even if no vibrating instrument such as a vibrator is used. Thereafter, the submergence aggregate can be thrown into a kneading mixer, which is not shown, together with cement and coarse aggregate measured separately.

Each of the bottom lid 109a, 109b, and 109c is made of a circular plate having an outside diameter substantially equivalent to or slightly larger than an outside diameter of the bottom opening of the body of the container 104a, 104b, or 104c. Furthermore, a long hole 114a, 114b, or 114c is formed at a tip of an L-shaped mounting arm 113a, 113b, or 113c provided as an extension from a rim of the circular plate and a pin 110 fixed to a stand not shown is passed through the long hole 114a, 114b, or 114c, by which it becomes possible to rotate the bottom lid 109a, 109b, or 109c around the pin 110 so as to open or close the bottom opening of the body of the container 104a, 104b, or 104c. Furthermore, in a condition where the bottom lid 109a, 109b, or 109c is closed, the long hole 114a, 114b, or 114c is oriented vertically, thereby preventing a reaction force from being generated at the pin 110 by a load of the measurement container 111a, 111b, or 111c. In fixing the bottom lid 109a to the bottom opening 115a of the body of the container 104a, an appropriate method can be selected out of known methods such as fastening with a bolt or a clamp. The same is equally true of the bottom lids 109b and 109c.

The electrode-type displacement sensor 512 is capable of measuring a water level of submergence aggregate by monitoring a change in an energized condition when a lower end of a detection electrode contacts a water surface of the submergence aggregate in the measurement container 111a, 111b, or 111c by moving the detection electrode up and down.

The water storage hopper 102, the fine aggregate storage hopper 103, and the load cells 108 are attached to a stand, which is not shown, and collar circular rings 116a, 116b, and 116c of the measurement containers 111a, 111b, and 111c are put on the load cells 108 to hold the measurement containers 111a, 111b, and 111c in a suspended condition. Thereby, the mass of each measurement container can be measured with the load cells 108. The load cells 108 are preferably placed, for example, in three places at 120° intervals on the same plane so that the measurement containers 111a, 111b, and 111c can be held stably in a suspended condition during measurement.

As apparent from FIGS. 67A-67C, volumes of the measurement containers 111a, 111b, and 111c differ from each other at the same depth $h_1$ that is a normal water level. More specifically, the measurement container 111a is configured so that the volume at the normal water level mentioned above matches a volume (hereinafter, referred to as normal volume) of submergence aggregate necessary for mixing concrete materials of a given amount determined from a specification of a kneading mixer, which is not shown. The measurement container 111b is configured so that the volume at the normal water level matches a volume corresponding to two-thirds of the normal volume. Similarly, the measurement container 111c is configured so that the volume at the normal water level matches a volume corresponding to one-half of the normal volume.

It should be noted that the water level at the same depth $h_1$ is previously input as a control value into a control unit (not shown) for driving and controlling the electrode-type displacement sensor 512.

The suction unit 517 can be used to suck and remove water in the measurement containers 111a, 111b, and 111c via a rubber hose 518. In addition, the suction unit is configured to suck and remove water so that there is always no difference between the measurement water level of submergence aggregate transmitted from the control unit of the electrode-type displacement sensor 512 and the normal water level.

Measurement of submergence aggregate with the measuring apparatus 501 for concrete-forming materials according to this embodiment will be described below, by giving an example of a case of measuring three kinds of aggregate; submergence aggregate (fine aggregate A+water A) necessary for mixing concrete materials corresponding to a given amount of a kneading mixer, submergence aggregate (fine aggregate B+water B) necessary for mixing concrete materials corresponding to two-thirds of the given amount of the kneading mixer, and submergence aggregate (fine aggregate C+water C) necessary for mixing concrete materials corresponding to one-half of the given amount of the kneading mixer.

Figure 69:
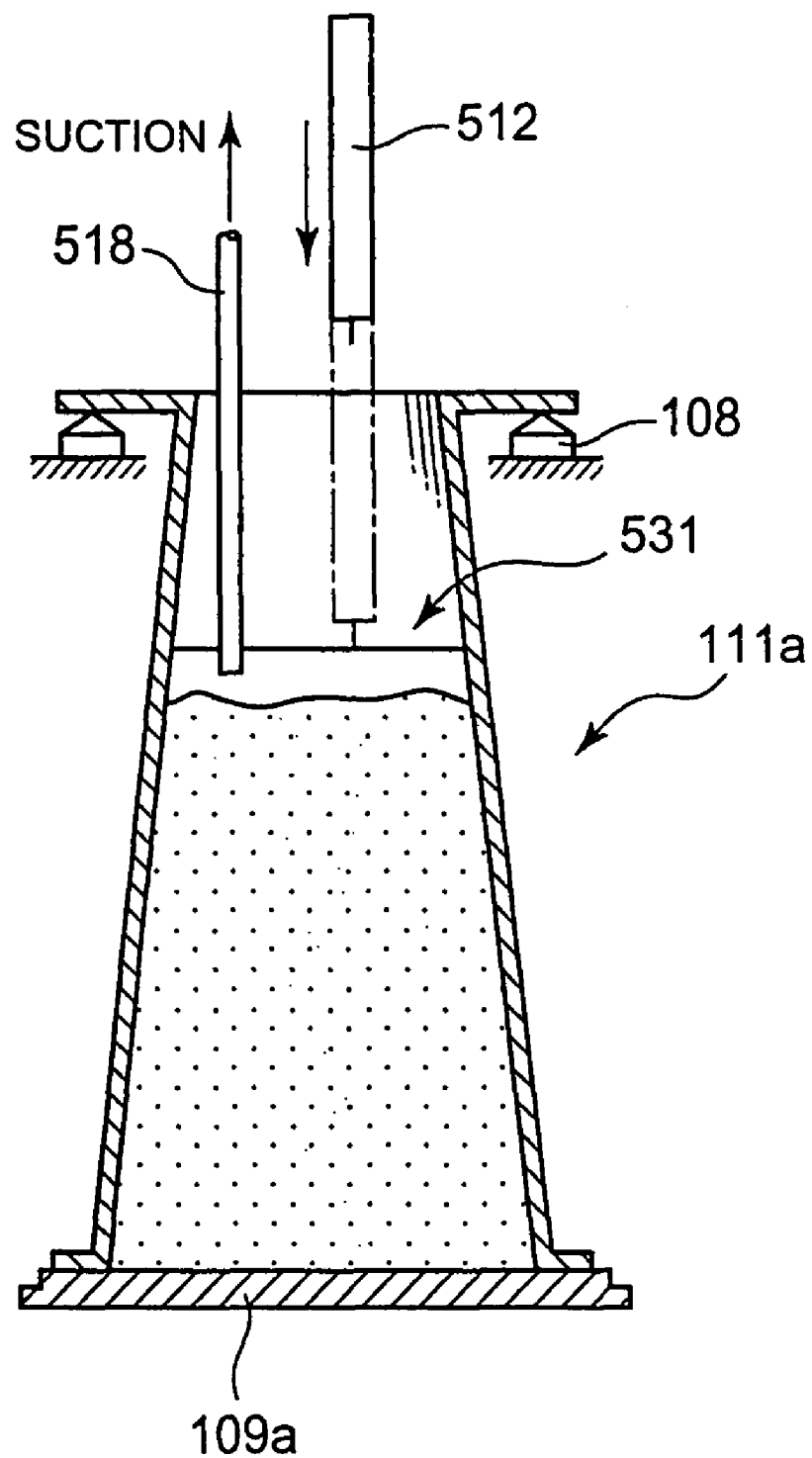
FIG. 69 is a diagram showing an action of a measuring apparatus of concrete-forming materials.

First, to measure the fine aggregate A and the water A, the bottom opening 115a of the body of the container 104a is closed by the bottom lid 109a to put the inside of the measurement container 111a in a watertightness condition. The closing valve 106 is opened in the above condition. The water A is then thrown from the water storage hopper 102 to the measurement container 111a and the fine aggregate A stored in the fine aggregate storage hopper 103 is thrown into the measurement container 111a so that it is put in a submergence condition to fill the measurement container 111a with submergence aggregate 531 as shown in FIG. 69.

When throwing the fine aggregate A and the water A into the measurement container 111a, preferably the water A is thrown earlier and the fine aggregate A is thrown later to prevent the submergence aggregate 531 from being mixed with air bubbles. In addition, if the fine aggregate A is not directly thrown into the measurement container 111a from the fine aggregate storage hopper 103, but it is conveyed from just under the fine aggregate storage hopper 103 to an upper opening of the measurement container 111a by using a vibrating feeder having an electromagnetic vibrator, for example, it becomes possible to prevent granulation of the fine aggregate, and thus prevent air bubble mixing.

Subsequently, a water level of the submergence aggregate 531 is measured with the electrode-type displacement sensor 512 to calculate total volume $V_f$ of the submergence aggregate 531 by using the water level. When the total volume $V_f$ is calculated, the suction unit 517 is operated, as needed so that there is always no difference between the measurement water level of the submergence aggregate 531 transmitted from the control unit of the electrode-type displacement sensor 512 and the normal water level, to suck and remove excess water via the rubber hose 518.

With this, the water level used for calculating the total volume $V_f$ of the submergence aggregate 531 is always kept at the normal water level.

On the other hand, total mass $M_f$ of the submergence aggregate 531 is measured with the load cells 108. The total mass $M_f$ of the submergence aggregate is obtained by subtracting a mass of an empty measurement container 111a, with the submergence aggregate 531 not contained therein, from a value measured by the load cells 108.

In the following, an appropriate measuring method is selected from the measuring methods mentioned above and then the measuring method is used to measure the fine aggregate A and the water A corresponding to the normal volume.

After measuring the fine aggregate A and the water A, they are thrown into the kneading mixer with cement and other concrete-forming materials for mixing a given amount of materials.

Subsequently, the measurement container 111a is detached once to measure the fine aggregate B and the water B and the measurement container 111b is mounted on the load cells 108 instead. In the same manner as for the measuring method of the fine aggregate A and the water A, measurement is then made on the fine aggregate B and the water B corresponding to two-thirds of the normal volume. Thereafter, water B and fine aggregate B are thrown into the kneading mixer with cement and other concrete-forming materials for mixing two-thirds of the given amount of materials.

Subsequently, the measurement container 111b is detached once to measure the fine aggregate C and the water C, and the measurement container 111c is mounted on the load cells 108 instead. In the same manner as for the measuring method of the fine aggregate A and the water A, measurement is then made on the fine aggregate C and the water C corresponding to one-half of the normal volume. Thereafter, water C and fine aggregate C are thrown into the kneading mixer with cement and other concrete-forming materials for mixing one-half of the given amount of materials.

As set forth hereinabove, according to the measuring apparatus 501 for concrete-forming materials of this embodiment, the normal water level at which the depth is identical is equal to the measured water level even if any of the measurement containers 111a, 111b, and 111c is used for the measurement. Therefore, an accuracy of water measurement is identical in any of the measurement containers 111a, 111b, and 111c. In other words, a different depth in the water level measurement varies an accuracy thereof. More specifically, on the assumption that the water level is measured with an error of ±1 mm, for example, the accuracy is 1/1000 if the depth is 1 m, while the accuracy is 1/500 if the depth is 50 cm.

On the other hand, according to the measuring apparatus 501 for concrete-forming materials of this embodiment, a measured water level always matches the normal water level at an identical depth even if any of the measurement containers 111a, 111b, and 111c is used for measurement. Therefore, accuracy of a measured water level, and thus the accuracy of the total volume of submergence aggregate calculated from the measured water level, can be identical. Thereby, even if required aggregate amounts are different from each other, it becomes possible to find a common accuracy of the total volume, and thus of the aggregate measurement.

Furthermore, according to the measuring apparatus 501 for concrete-forming materials of this embodiment, surface water of fine aggregate can be indirectly calculated as a part of mass $M_w$ of water, even if a fine aggregate whose moisture state is not uniform is used, and the mass of the fine aggregate can be calculated as mass $M_a$ of the fine aggregate in a saturated surface-dried condition. In other words, since the mass of the fine aggregate and the mass of the water are calculated on conditions equivalent to a specified mix, even if a humidity grade of the fine aggregate is not fixed at every measurement, it becomes possible to make concrete as shown by the specified mix.

While the present invention is applied to measurement of fine aggregate in this embodiment, it is applicable to measurement of coarse aggregate instead. If a plurality of aggregates is mixed as concrete-forming materials, measurement values of the aggregates often differ from each other. The measuring apparatus according to the present invention is also applicable to this case.

Furthermore in this embodiment, for convenience of description, the volumes of the measurement containers are assumed to be the given amount, the given amount multiplied by two-thirds, and the given amount multiplied by one-half of the kneading mixer, respectively, when the volumes are at the normal water level where they have the same depth. It is apparent, however, that the volumes are not limited to the above.

Still further, while three measurement containers are used as the plurality of measurement containers in this embodiment, it is apparent that the number of measurement containers is not limited to the above.

Twenty-first Embodiment

Figure 70:
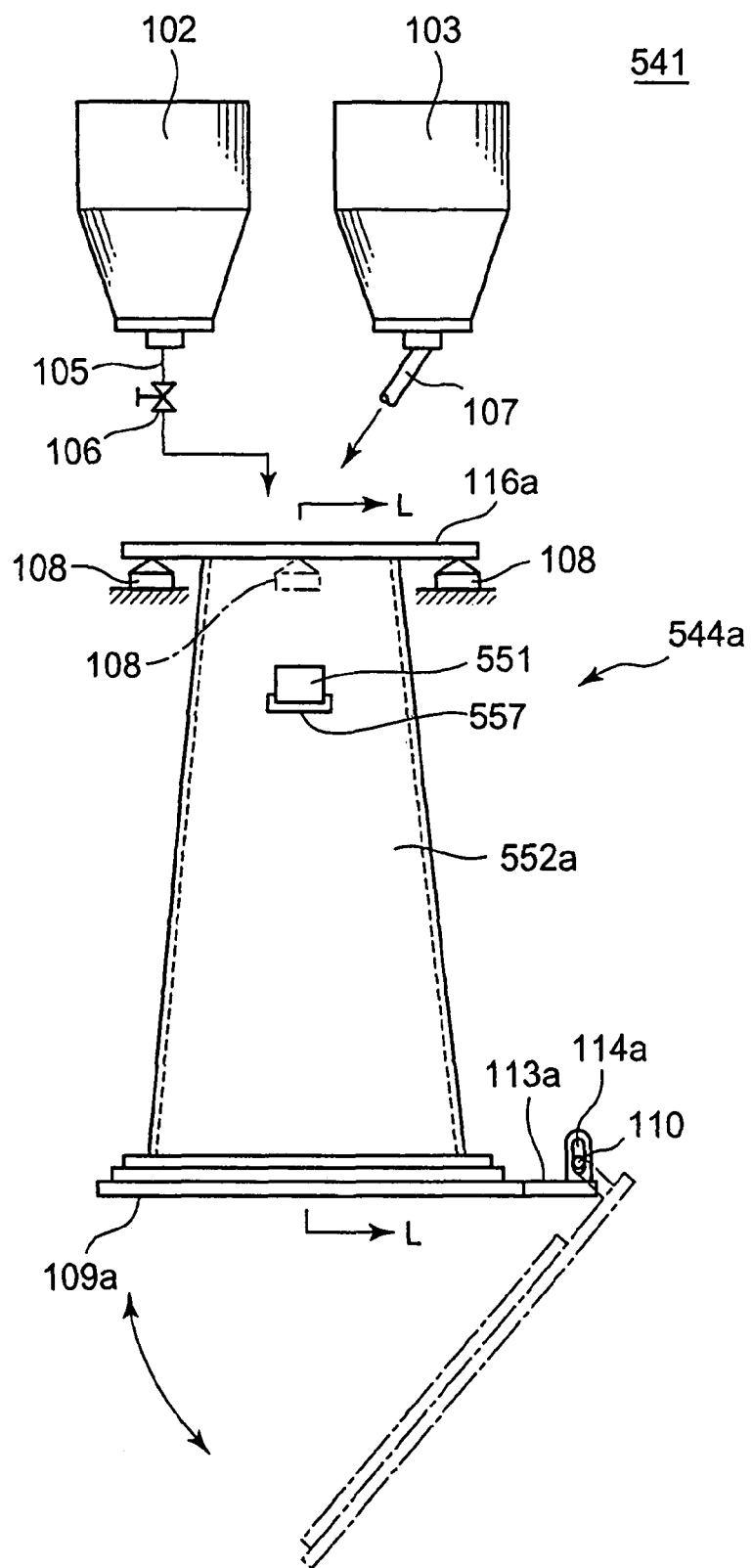
FIG. 70 is a general view of a preferable measuring apparatus of concrete-forming materials according to the present invention.

Referring to FIG. 70, there is shown a general view of a measuring apparatus 541 according to a twenty-first embodiment. As apparent from FIG. 70 and FIGS. 71A-71C, the measuring apparatus 541 according to this embodiment generally comprises a water storage hopper 102 for storing water, a fine aggregate storage hopper 103 for storing fine aggregate as aggregate, three measurement containers 544a, 544b, and 544c for containing water and fine aggregate supplied from the water storage hopper 102 and the fine aggregate storage hopper 103 as submergence aggregate, respectively, and load cells 108 as submergence aggregate mass measurement means for measuring a mass of submergence aggregate in the measurement containers. The water storage hopper 102 forms means for supplying water in conjunction with a water feed pipe 105 connected to the water storage hopper 102 at a bottom thereof and whose discharge opening is located above the measurement containers 544a, 544b, and 544c, and a closing valve 106 arranged in a predetermined position of the water feed pipe 105. The fine aggregate storage hopper 103 forms means for feeding aggregate in conjunction with a fine aggregate feed pipe 107 whose discharge opening is located above the measurement containers 544a, 544b, and 544c. In FIG. 70, there is shown only the measurement container 544a of the measurement containers for convenience. Other measurement containers 544b and 544c are shown with the measurement container 544a in FIGS. 71A-71C.

Figure 72:
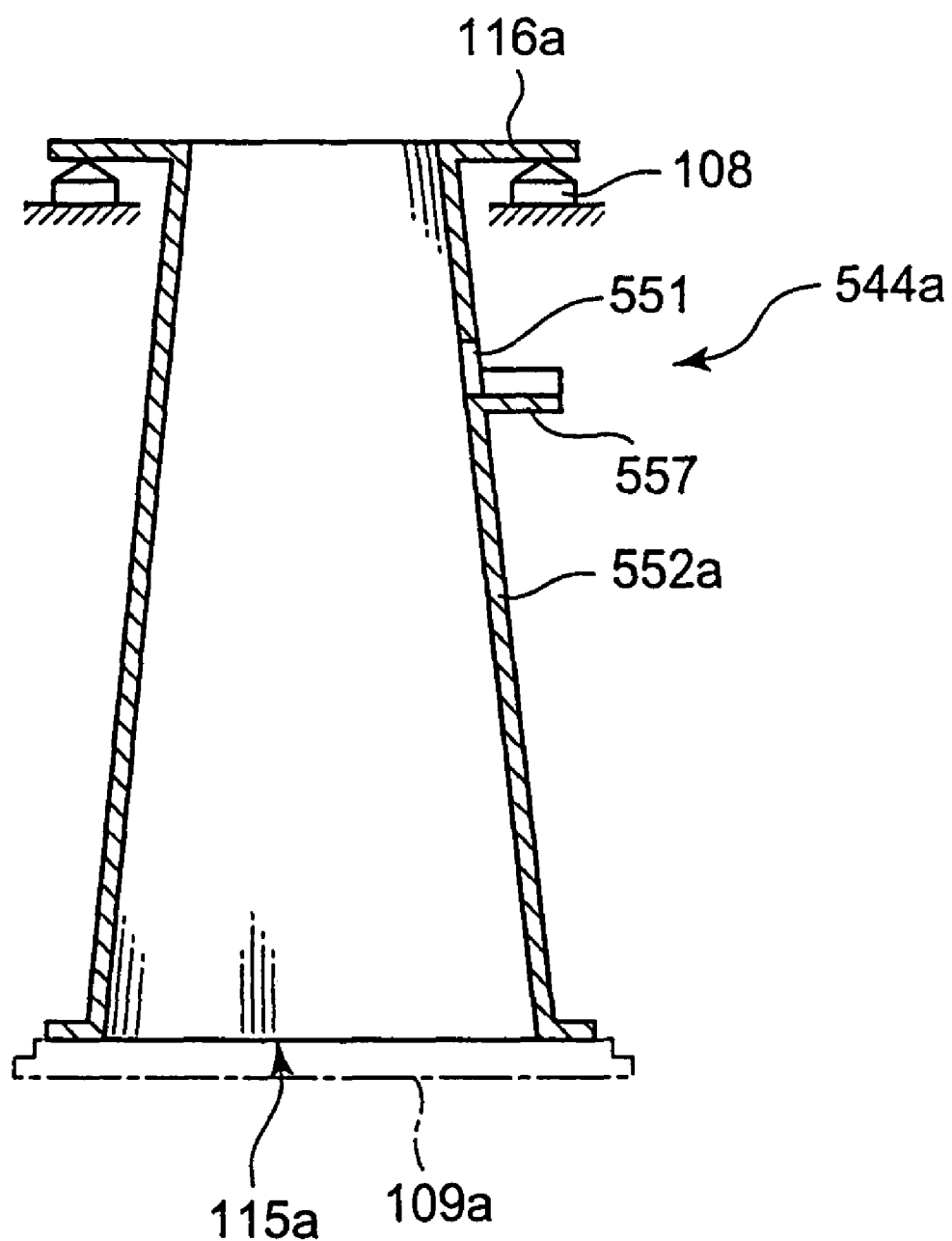
FIG. 72 is a cross section taken along line L-L of FIG. 70.

As apparent from a cross section shown in FIG. 72, the measurement container 544a comprises a body of container 552a and a bottom lid 109a attachable so as to be free to open or close a bottom opening 115a of the body of the container. This measurement container is configured so as to contain fine aggregate as submergence aggregate with water in a watertightness condition when the bottom lid 109a is closed to measure the submergence aggregate, and causes the submergence aggregate to be discharged downward by opening the bottom lid 109a when this measurement is finished. In the same manner as for the measurement container 544a, each of the measurement containers 544b and 544c comprises a body of the container 552b or 552c and a bottom lid 109b or 109c attachable so as to be free to open or close a bottom opening of the body of the container. Each of the measurement containers is configured so as to contain fine aggregate as submergence aggregate with water when the bottom lid 109b or 109c is closed to measure the submergence aggregate and causes the submergence aggregate to be discharged downward by opening the bottom lid 109b or 109c when this measurement is finished.

Each of the body of the container 552a, 552b, and 552c is formed in a shape of a hollow truncated cone so that a bore of the container becomes larger in a downward direction. With this, when the measurement is finished, a free fall of the submergence aggregate in the body of the container can be achieved only by opening the bottom lid 109a, 109b, or 109c without a blockage of submergence aggregate in the body of the container even if no vibrating instrument such as a vibrator is used. Thereafter, the submergence aggregate can be thrown into a kneading mixer, which is not shown, together with cement and coarse aggregate measured separately. The bottom lids 109a, 109b, and 109c are the same as those of the above embodiment. Therefore, their description is omitted here.

The water storage hopper 102, the fine aggregate storage hopper 103, and the load cells 108 are attached to a stand, which is not shown, and collar circular rings 116a, 116b, and 116c of the measurement containers 544a, 544b, and 544c are put on the load cells 108 to hold the measurement containers 544a, 544b, and 544c in a suspended condition. Thereby, the mass of each measurement container can be measured with the load cells 108. The load cells 108 are preferably placed, for example, in three places at 120° intervals on the same plane so that the measurement containers 544a, 544b, and 544c can be held stably in a suspended condition during measurement.

Figure 71:
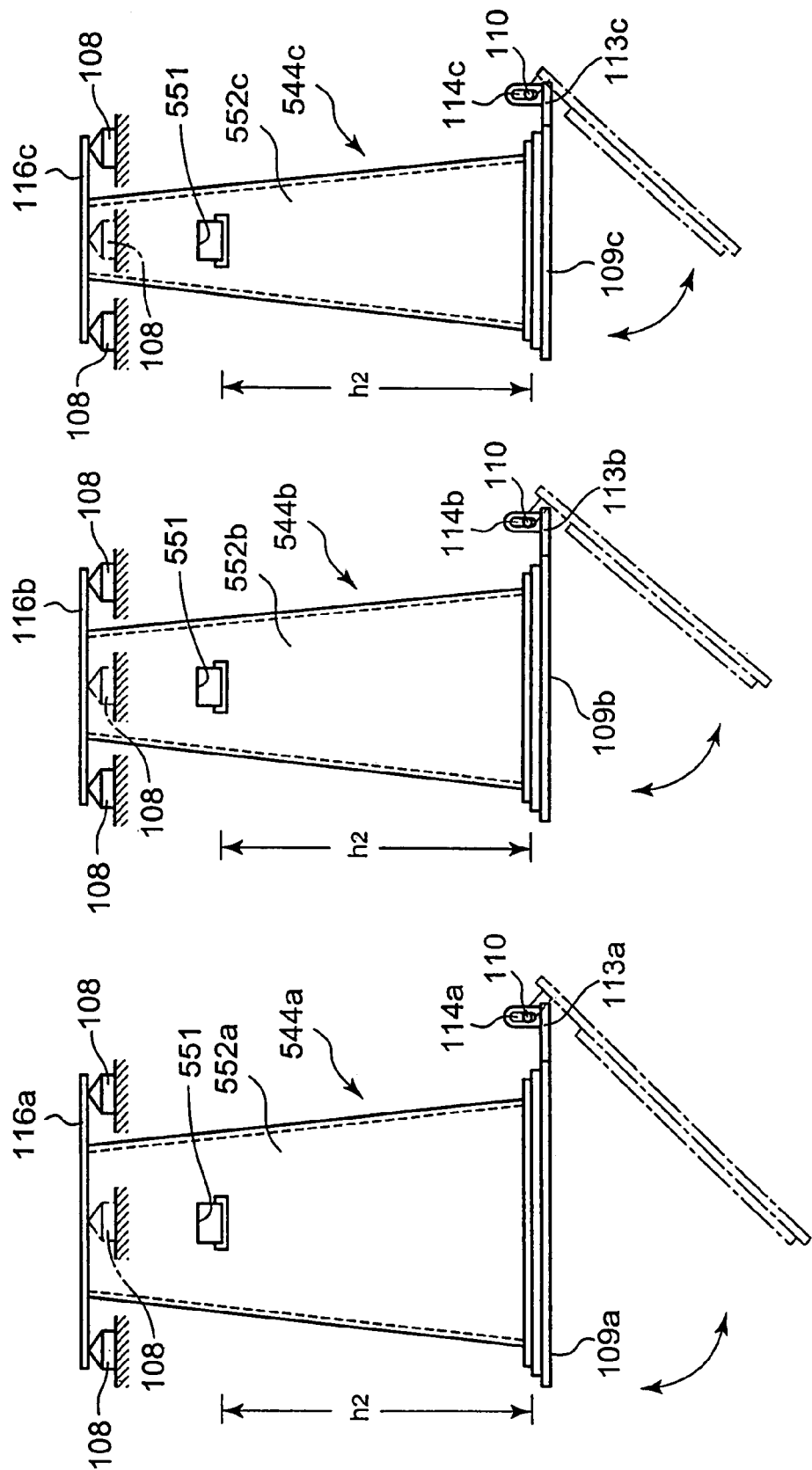
FIGS. 71A-71C are side views of measurement containers.

At this point, as apparent from FIGS. 70 to 72, a rectangular opening for overflow 551 is formed in a wall of each body of the containers 552a, 552b, and 552c so that water of the submergence aggregate in the measurement containers overflows outside. In addition, a grooved guide 557 is provided in a horizontally protruding condition along a lower edge of the opening for overflow 551. Overflow water flows on the guide and falls from a tip thereof, thereby enabling water to overflow smoothly from the opening for overflow 551 without a flow on a circumferential surface of the measurement containers 544a, 544b, and 544c.

The openings for overflow 551 are provided so that their lower edges match a normal water level at the same depth $h_2$ of the measurement containers. Therefore, the openings for overflow function as water level maintaining means for maintaining water levels of the submergence aggregates in the measurement containers 544a, 544b, and 544c at the normal water level.

At this point, volumes of the measurement containers 544a, 544b, and 544c differ from each other when the depths are at the normal water level. More specifically, the measurement container 544a is configured so that the volume at the normal water level in the above matches a volume (hereinafter, referred to as normal volume) of submergence aggregate necessary for mixing concrete-forming materials of a given amount determined from a specification of a kneading mixer, which is not shown. The measurement container 544b is configured so that the volume at the normal water level matches a volume corresponding to two-thirds of the normal volume. Similarly, the measurement container 544c is configured so that the volume at the normal water level matches a volume corresponding to one-half of the normal volume.

Measurement of submergence aggregate with the measuring apparatus 541 for concrete-forming materials according to this embodiment will be described below, by giving an example of a case of measuring three kinds of aggregate; submergence aggregate (fine aggregate A+water A) necessary for mixing concrete-forming materials corresponding to a given amount of the kneading mixer, submergence aggregate (fine aggregate B+water B) necessary for mixing concrete-forming materials corresponding to two-thirds of the given amount of the kneading mixer, and submergence aggregate (fine aggregate C+water C) necessary for mixing concrete-forming materials corresponding to one-half of the given amount of the kneading mixer.

First, to measure the fine aggregate A and the water A, the bottom opening 115a of the body of the container 552a is closed by the bottom lid 109a to put the inside of the measurement container 544a in a watertightness condition. The closing valve 106 is opened in the above condition. The water A is then thrown from the water storage hopper 102 into the measurement container 544a and the fine aggregate A stored in the fine aggregate storage hopper 103 is thrown into the measurement container 544a so that it is put in a submergence condition to fill the measurement container 544a with submergence aggregate 561 as shown in FIG. 73.

When throwing the fine aggregate A and the water A into the measurement container 544a, preferably the water A is thrown earlier and the fine aggregate A is thrown later to prevent the submergence aggregate 561 from being mixed with air bubbles. In addition, if the fine aggregate A is not directly thrown into the measurement container 544a from the fine aggregate storage hopper 103, but it is conveyed from just under the fine aggregate storage hopper 103 to an upper opening of the measurement container 544a by using a vibrating feeder having an electromagnetic vibrator, for example, it becomes possible to prevent granulation of the fine aggregate, and thus prevent air bubble mixing.

Figure 73:
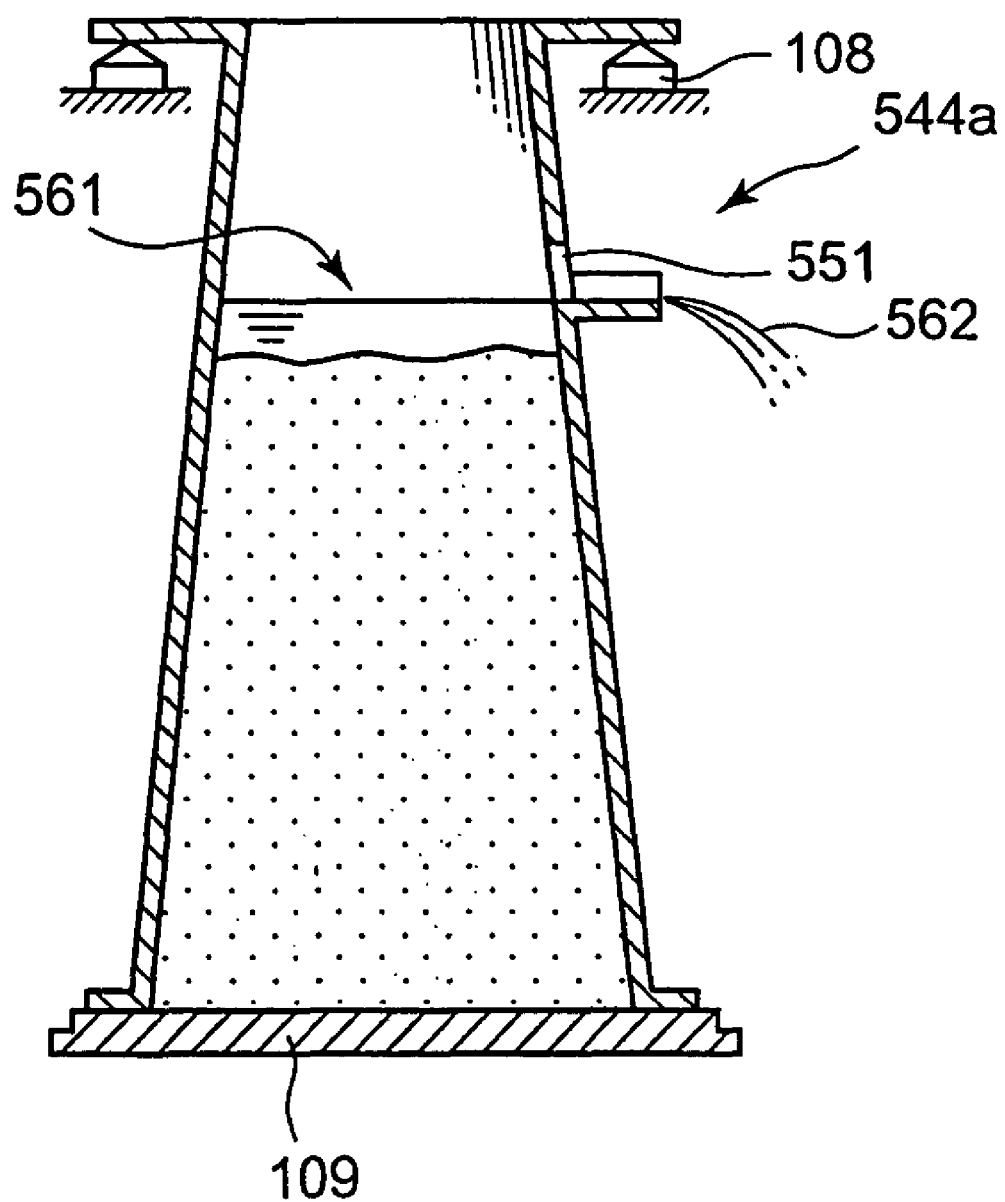
FIG. 73 is a diagram showing an action of a measuring apparatus of concrete-forming materials.

At this point, apparent from FIG. 73, the measurement container 544a is filled with the submergence aggregate 561 by throwing the water A and the fine aggregate A so that the fine aggregate is submerged in the water and that the water overflows from the opening for overflow 551.

With this, the water level at which water 562 overflows from the opening for overflow 551 is kept to the normal water level. Therefore, if the measurement container is filled with the submergence aggregate 561 as mentioned above, the water level used for calculating total volume $V_f$ of the submergence aggregate 561 is always equal to the normal water level. If the total volume $V_f$ is measured once at calibration in an initial stage, subsequent measurements of the total volume can be omitted and the value can be treated as a known value.

On the other hand, total mass $M_f$ of the submergence aggregate 561 is measured with the load cells 108. The total mass $M_f$ of the submergence aggregate 561 is obtained by subtracting a mass of empty measurement container 544a with the submergence aggregate 561 not contained therein from a value measured with the load cells 108.

In the following, an appropriate measuring method is selected out of the measuring methods mentioned above, and then the measuring method is used to measure the fine aggregate A and the water A corresponding to the normal volume.

After measuring the fine aggregate A and the water A, they are thrown into the kneading mixer with cement and other concrete-forming materials for mixing the given amount of materials.

Subsequently, the measurement container 544a is detached once to measure the fine aggregate B and the water B, and the measurement container 544b is mounted on the load cells 108 instead. In the same manner as for the measuring method of the fine aggregate A and the water A, measurement is then made of the fine aggregate B and the water B corresponding to two-thirds of the normal volume. Thereafter, water B and fine aggregate B are thrown into the kneading mixer with cement and other concrete-forming materials for mixing two-thirds of the given amount of materials.

Subsequently, the measurement container 544b is detached once to measure the fine aggregate C and the water C, and the measurement container 544c is mounted on the load cells 108 instead. In the same manner as for the measuring method of the fine aggregate A and the water A, measurement is then made of the fine aggregate C and the water C corresponding to one-half of the normal volume. Thereafter, water C and fine aggregate C are thrown into the kneading mixer with cement and other concrete-forming materials for mixing one-half of the given amount of materials.

As set forth hereinabove, according to the measuring apparatus 541 for concrete-forming materials of this embodiment, water overflows from the opening for overflow 551 at the normal water level at which the depth is identical even if any of the measurement containers 544a, 544b, and 544c is used for measurement. Thereby, accuracy of the water level is identical in any of the measurement containers 544a, 544b, and 544c.

Therefore, accuracy of the water level, and thus accuracy of the total volume of submergence aggregate calculated from the water level, can be identical. Thereby, even if required aggregate amounts are different from each other, it becomes possible to find a common accuracy of the total volume, and thus of the aggregate measurement.

Furthermore, according to the measuring apparatus 541 for concrete-forming materials of this embodiment, surface water of fine aggregate can be indirectly calculated as a part of mass $M_w$ of water, even if a fine aggregate whose moisture state is not uniform is used, and the mass of the fine aggregate can be calculated as mass $M_a$ of the fine aggregate in a saturated surface-dried condition. In other words, since the mass of the fine aggregate and the mass of the water are calculated on conditions equivalent to a specified mix, even if a humidity grade of the fine aggregate is not fixed at every measurement, it becomes possible to make concrete as shown by the specified mix.

While the present invention is applied to measurement of fine aggregate in this embodiment, it is applicable to measurement of coarse aggregate instead. If a plurality of aggregates are mixed as concrete-forming materials, measurement values of the aggregates often differ from each other. The measuring apparatus according to the present invention is also applicable to this case.

Furthermore in this embodiment, for convenience of description, the volumes of the measurement containers are assumed to be the given amount, the given amount multiplied by two-thirds, and the given amount multiplied by one-half of the kneading mixer, respectively, when the volumes are at the normal water level where they have the same depth. It is apparent, however, that the volumes are not limited to the above.

Still further, while three measurement containers are used as the plurality of measurement containers in this embodiment, it is apparent that the number of measurement containers is not limited to the above.

Twenty-second Embodiment

Figure 74:
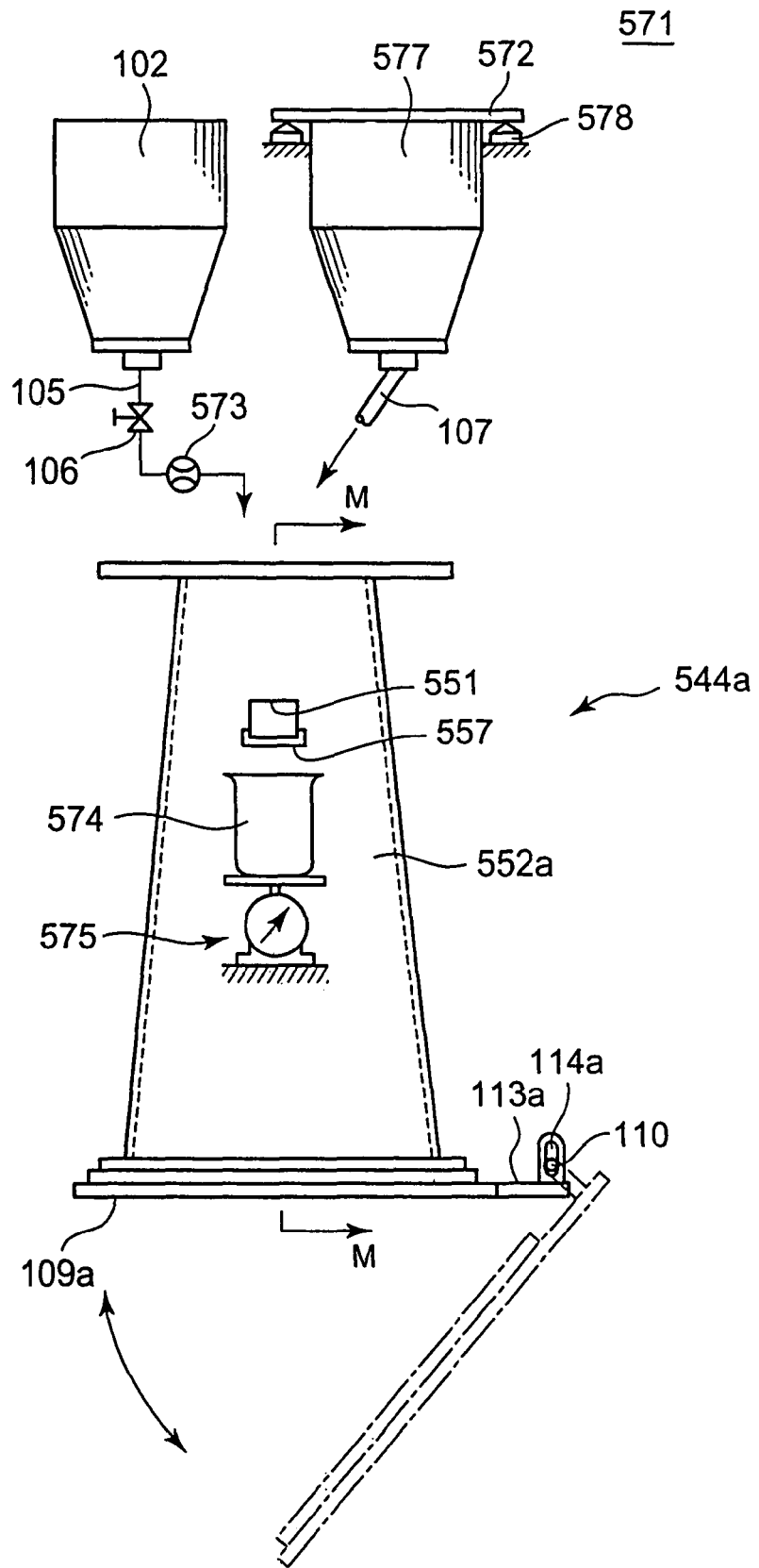
FIG. 74 is a general view of a preferable measuring apparatus of concrete-forming materials according to the present invention.

Referring to FIG. 74, there is shown a general view of a measuring apparatus 571 according to a twenty-second embodiment. As apparent from FIG. 74 and FIGS. 75A-75C, the measuring apparatus 571 according to this embodiment generally comprises a water storage hopper 102 for storing water, a fine aggregate measurement container 577 as an aggregate measurement container for storing fine aggregate to be measured, three measurement containers 544a, 544b, and 544c for containing water and fine aggregate supplied from the water storage hopper 102 and the fine aggregate measurement container 577 as submergence aggregate, respectively, and load cells 578 as aggregate mass measurement means for measuring a mass of fine aggregate in the fine aggregate measurement container 577. The water storage hopper 102 forms means for supplying water in conjunction with a water feed pipe 105 connected to the water storage hopper 102 at a bottom thereof and whose discharge opening is located above the measurement containers 544a, 544b, and 544c, a closing valve 106 arranged in a predetermined position of the water feed pipe 105, and a flowmeter 573 as means for measuring an amount of supplied or discharged water.

The fine aggregate measurement container 577 is configured so as to be provided as needed with fine aggregate from a stock bin, which is not shown, and is connected at its bottom to a fine aggregate feed pipe 107 whose discharge opening is located above the measurement containers 544a, 544b, and 544c.

In FIG. 74, there is shown only the measurement container 544a of the measurement containers for convenience. Other measurement containers 544b and 544c are shown with the measurement container 544a in FIGS. 75A-75C.

At this point, the water storage hopper 102, the measurement containers 544a, 544b, and 544c, and the load cells 578 are attached to a stand, which is not shown, and a collar circular portion 572 that is attached to an upper-end opening edge of the fine aggregate measurement container 577 is put on the load cells 578 to hold the measurement container 577 in a suspended condition. Thereby, the mass of fine aggregate stored in the fine aggregate measurement container can be measured with the load cells 578. The load cells 578 are preferably placed, for example, in three places at 120° intervals on the same plane so that the fine aggregate measurement container 577 can be held stably in a suspended condition during measurement.

Figure 76:
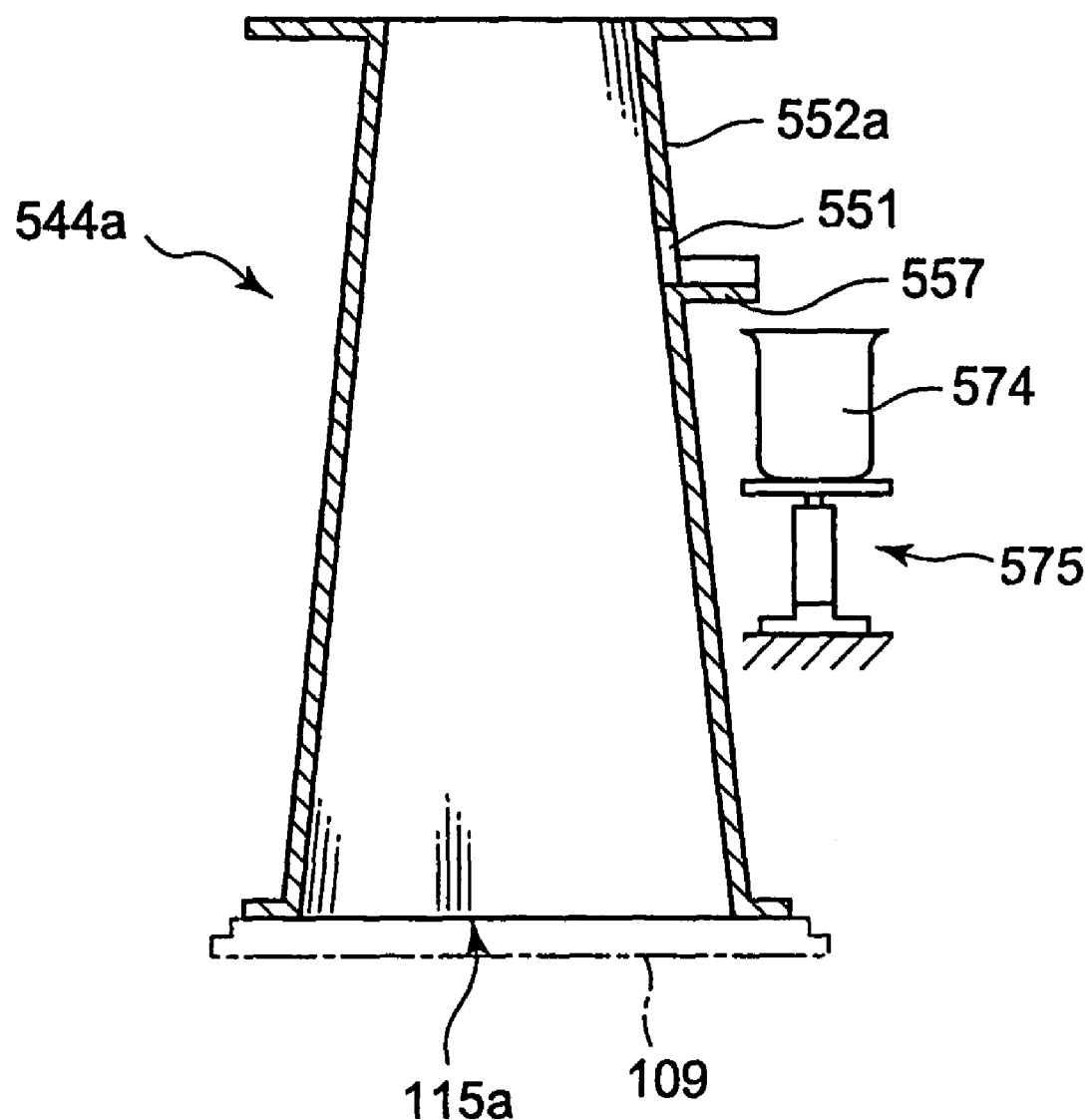
FIG. 76 is a cross section taken along line M-M of FIG. 74.

As apparent from a cross section shown in FIG. 76, the measurement container 544a comprises a body of container 552a and a bottom lid 109a attachable so as to be free to open or close a bottom opening 115a of the body of the container. This measuring container is configured so as to contain fine aggregate as submergence aggregate with water in a water-tightness condition when the bottom lid 109a is closed to measure the submergence aggregate and causes the submergence aggregate to be discharged downward by opening the bottom lid 109a when this measurement is finished. In the same manner as for the measurement container 544a, each of the measurement containers 544b and 544c comprises a body of the container 552b or 552c and a bottom lid 109b or 109c attachable so as to be free to open or close a bottom opening of the body of the container. Each of the measurement containers is configured so as to contain fine aggregate as submergence aggregate with water when the bottom lid 109b or 109c is closed to measure the submergence aggregate, and causes the submergence aggregate to be discharged downward by opening the bottom lid 109b or 109c when this measurement is finished.

Each of the body of the container 552a, 552b, and 552c is formed in a shape of a hollow truncated cone so that a bore of the container becomes larger in a downward direction. With this, when a measurement is finished, a free fall of the submergence aggregate in the body of the container can be achieved only by opening the bottom lid 109a, 109b, or 109c without a blockage of submergence aggregate in the body of the container even if no vibrating instrument such as a vibrator is used. Thereafter, the submergence aggregate can be thrown into a kneading mixer, which is not shown, together with cement and coarse aggregate measured separately. The bottom lids 109a, 109b, and 109c are the same as those of the above embodiment. Therefore, their description is omitted here.

At this point, as apparent from FIGS. 74 to 77, a rectangular opening for overflow 551 is formed in a wall of each body of the containers 552a, 552b, and 552c so that water of the submergence aggregate in the measurement containers overflows outside. In addition, a grooved guide 557 is provided in a horizontally protruding condition along a lower edge of the opening for overflow 551. Overflow water flows on the guide and falls from a tip thereof, thereby enabling water to overflow smoothly from the opening for overflow 551 without a flow on a circumferential surface of the measurement containers 544a, 544b, and 544c.

The openings for overflow 551 are provided so that their lower edges match a normal water level at the same depth $h_3$ of the measurement containers. Therefore, the openings for overflow function as water level maintaining means for maintaining water levels of the submergence aggregates in the measurement containers 544a, 544b, and 544c at the normal water level.

At this point, volumes of the measurement containers 544a, 544b, and 544c differ from each other when the depths are at the normal water level. More specifically, the measurement container 544a is configured so that the volume at the normal water level in the above matches a volume (hereinafter, referred to as normal volume) of submergence aggregate necessary for mixing concrete-forming materials of a given amount determined from a specification of a kneading mixer, which is not shown. The measurement container 544b is configured so that the volume at the normal water level matches a volume corresponding to two-thirds of the normal volume. Similarly, the measurement container 544c is configured so that the volume at the normal water level matches a volume corresponding to one-half of the normal volume.

On the other hand, as apparent from the cross section shown in FIG. 76, the measuring apparatus 571 of concrete materials according to this embodiment further comprises a storage container 574 for storing overflow water overflowing from the opening for overflow 551 and running down from a tip of the guide 557 and a massmeter 575 for measuring a mass of overflow water stored in the storage container. The flowmeter 573 mentioned above can be used to measure amounts of water thrown into the measurement containers 544a, 544b, and 544c, and the massmeter 575 can be used to measure amounts of overflow water from the measurement containers 544a, 544b, and 544c.

Measurement of submergence aggregate with the measuring apparatus 571 for concrete-forming materials according to this embodiment will be described below, by giving an example of a case of measuring three kinds of aggregate; submergence aggregate (fine aggregate A+water A) necessary for mixing concrete materials corresponding to a given amount of a kneading mixer, submergence aggregate (fine aggregate B+water B) necessary for mixing concrete materials corresponding to two-thirds of the given amount of the kneading mixer, and submergence aggregate (fine aggregate C+water C) necessary for mixing concrete materials corresponding to one-half of the given amount of the kneading mixer.

To measure the fine aggregate A and the water A, mass $M_{aw}$ of the fine aggregate in a wet condition stored in the fine aggregate measurement container 577 is measured with the load cells 578, first.

The mass $M_{aw}$ of the fine aggregate in a wet condition in the fine aggregate measurement container 577 is obtained by subtracting a mass of an empty fine aggregate measurement container 577, containing no fine aggregate, from the value measured by the load cells 578.

Figure 77:
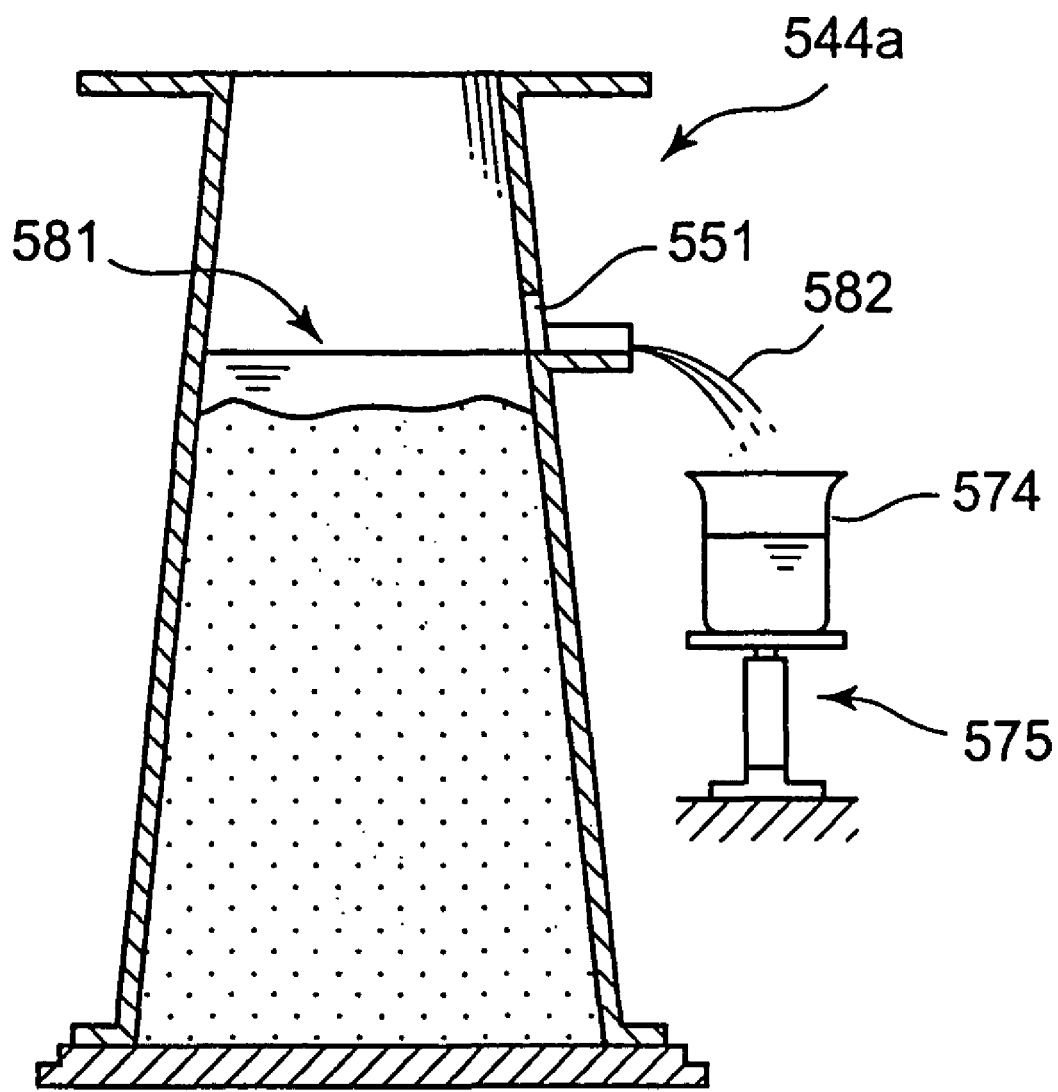
FIG. 77 is a diagram showing an action of a measuring apparatus of concrete-forming materials.

Subsequently, the bottom opening 115a of the body of the container 552a is closed by the bottom lid 109a to put the inside of the measurement container 544a in a watertightness condition. The closing valve 106 is opened in the above condition. The water A is then thrown from the water storage hopper 102 into the measurement container 544a and the fine aggregate A stored in the fine aggregate measurement container 577 is thrown into the measurement container 544a so that it is put in a submergence condition to fill the measurement container 544a with submergence aggregate 581 as shown in FIG. 77. In addition, mass $M_I$ of water supplied from the water storage hopper 102 is measured as an accumulation value with the flowmeter 573. On the other hand, water overflowing from the opening for overflow 551 is stored once in the storage container 574 and then mass $M_O$ of overflow water therefrom is measured as an accumulation value with the massmeter 575.

When throwing the fine aggregate A and the water A into the measurement container 544a, preferably the water A is thrown earlier and the fine aggregate A is thrown later to prevent the submergence aggregate 581 from being mixed with air bubbles. In addition, if the fine aggregate A is not directly thrown into the measurement container 544a from the fine aggregate measurement container 577, but it is conveyed from just under the fine aggregate measurement container 577 to an upper opening of the measurement container 544a by using a vibrating feeder having an electromagnetic vibrator, for example, it becomes possible to prevent granulation of the fine aggregate, and thus prevent air bubble mixing.

At this point, apparent from FIG. 77, the measurement container 544a is filled with the submergence aggregate 581 by throwing the water A and the fine aggregate A so that the fine aggregate is submerged in the water and that the water overflows from the opening for overflow 551.

With this, the water level at which the water 582 overflows from the opening for overflow 551 is kept at the normal water level. Therefore, if the measurement container is filled with the submergence aggregate 581 as mentioned above, the water level used for calculating total volume $V_f$ of the submergence aggregate 581 is always equal to the normal water level. If the total volume $V_f$ is measured once at calibration in an initial stage, subsequent measurements of the total volume can be omitted and the value can be treated as a known value.

In the following, an appropriate measuring method is selected out of the measuring methods mentioned above and then the measuring method is used to measure the fine aggregate A and the water A corresponding to the normal volume.

After measuring the fine aggregate A and the water A, they are thrown into the kneading mixer with cement and other concrete-forming materials for mixing a given amount of materials.

Subsequently, the measurement container 544a is detached once to measure the fine aggregate B and the water B and the measurement container 544b is mounted on the stand instead. In the same manner as for the measuring method of the fine aggregate A and the water A, measurement is then made of the fine aggregate B and the water B corresponding to two-thirds of the normal volume. Thereafter, water B and fine aggregate B are thrown into the kneading mixer with cement and other concrete-forming materials for mixing two-thirds of the given amount of materials.

Subsequently, the measurement container 544b is detached once to measure the fine aggregate C and the water C and the measurement container 544c is mounted on the stand instead. In the same manner as for the measuring method of the fine aggregate A and the water A, measurement is then made of the fine aggregate C and the water C corresponding to one-half of the normal volume. Thereafter, water C and fine aggregate C are thrown into the kneading mixer with cement and other concrete-forming materials for mixing one-half of the given amount of materials.

As set forth hereinabove, according to the measuring apparatus 571 for concrete-forming materials of this embodiment, water overflows from the opening for overflow 551 at the normal water level at which the depth is identical even if any of the measurement containers 544a, 544b, and 544c is used for measurement. Thereby, accuracy of the water level is identical in any of the measurement containers 544a, 544b, and 544c.

Therefore, accuracy of the water level, and thus accuracy of the total volume of submergence aggregate calculated from the water level, can be identical. Thereby, even if required aggregate amounts are different from each other, it becomes possible to find a common accuracy of the total volume, and thus of the aggregate measurement.

Furthermore, according to the measuring apparatus 571 for concrete-forming materials of this embodiment, surface water of fine aggregate can be indirectly calculated as a part of mass $M_w$ of water, even if a fine aggregate whose moisture state is not uniform is used, and the mass of the fine aggregate can be calculated as mass Ma of the fine aggregate in a saturated surface-dried condition. In other words, since the mass of the fine aggregate and the mass of the water are calculated on conditions equivalent to a specified mix, even if a humidity grade of the fine aggregate is not fixed at every measurement, it becomes possible to make concrete as shown by the specified mix.

While the present invention is applied to measurement of fine aggregate in this embodiment, it is applicable to measurement of coarse aggregate instead. If a plurality of aggregates are mixed as concrete-forming materials, measurement values of the aggregates often differ from each other. The measuring apparatus according to the present invention is also applicable to this case.

Furthermore in this embodiment, for convenience of description, the volumes of the measurement containers are assumed to be the given amount, the given amount multiplied by two-thirds, and the given amount multiplied by one-half of the kneading mixer, respectively, when the volumes are at the normal water level where they have the same depth. It is apparent, however, that the volumes are not limited to the above.

Still further, while three measurement containers are used as the plurality of measurement containers in this embodiment, it is apparent that the number of measurement containers is not limited to the above.

Furthermore, the masses $M_I$ of water thrown into the measurement containers 544a, 544b, and 544c are measured as an accumulation value with the flowmeter 573. Instead of it, however, if water is thrown earlier into the measurement containers 544a, 544b, and 544c so that the water overflows the measurement containers, the water level at which the water overflows from the opening for overflow is previously determined to be the normal water level as mentioned above, by which the mass $M_I$ of supplied water is a known value without a need for measurement. Therefore, in this constitution, there is no need to have means for supplying water comprising the flowmeter 573, the water storage hopper 102, the water feed pipe 105, and the closing valve 106.

In this case, water may overflow due to throwing aggregate in a subsequent step, but the water level will never decrease. Therefore, an accumulation value of the mass $M_I$ of supplied water is fixed during measurement.

INDUSTRIAL APPLICABILITY

Surface water of aggregate is indirectly calculated as a part of mass $M_w$ of water, even if an aggregate whose moisture state is not uniform is used, and the mass of the aggregate is calculated as mass Ma of the aggregate in a saturated surface-dried condition. In other words, since the mass of the aggregate and the mass of the water are calculated on conditions equivalent to a specified mix, even if a humidity grade of the fine aggregate is not fixed at every measurement, it becomes possible to make concrete as shown by the specified mix.

Practically, both fine aggregate and coarse aggregate are needed as materials for construction of concrete. Furthermore, there is assumed a case of using a plurality of fine or coarse aggregates that differ from each other in density, grading, or the like. It is often important to make new aggregate having desired grading particularly by mixing a plurality of aggregates, different from each other in grading, at appropriate percentages.

A measuring method for concrete-forming materials according to the present invention is a very effective measuring method for measuring a plurality of aggregates different from each other in at least one of density and grading as mentioned above.

What is claimed is:

1. A discharge mechanism of a concrete-material-measurement container comprising:
    a bottom lid; and
    a gas spraying mechanism provided in the vicinity of said bottom lid,
    wherein, the bottom lid, when closed, contains aggregate with water as submergence aggregate in the measurement container for measuring the submergence aggregate,
    wherein, the bottom lid, when opened, discharges the submergence aggregate downward after the measurement is finished, and
    wherein said gas spraying mechanism is configured to spray a top face of the bottom lid with a gas flow when the bottom lid is opened.

2. The discharge mechanism of the measurement container according to claim 1, wherein said gas spraying mechanism is an air spray nozzle connected in communication with an air compressor.

3. A discharge mechanism of a concrete-material-measurement container comprising:
    a bottom lid; and
    a gas spraying mechanism provided in the vicinity of said bottom lid,
    wherein, the bottom lid, when closed, contains aggregate with water as submergence aggregate in the measurement container for measuring the submergence aggregate,
    wherein, the bottom lid, when opened, discharges the submergence aggregate downward after the measurement is finished,
    wherein said bottom lid is opened or closed by moving it in a translation direction or rotating it within a level surface, and
    wherein said gas spraying mechanism is configured to spray a top face of the bottom lid with a gas flow when the bottom lid is opened.

4. The discharge mechanism of the measurement container according to claim 3, wherein said gas spraying mechanism is an air spray nozzle connected in communication with an air compressor.

5. A discharge mechanism of a concrete-material-measurement container for measuring concrete material, comprising:
    a bottom lid; and
    a gas spraying mechanism provided in the vicinity of said bottom lid,
    wherein, the bottom lid is configured to contain, when closed, concrete aggregate with water as submergence aggregate concrete material in the measurement container for measuring the submergence aggregate concrete material,
    wherein, the bottom lid, when opened, discharges the submergence aggregate downward after the measurement is finished, and
    wherein said bottom lid is opened or closed by moving it in a translation direction or rotating it within a level surface.

* * * * *